US011261457B2

(12) United States Patent
Rajani

(10) Patent No.: US 11,261,457 B2
(45) Date of Patent: Mar. 1, 2022

(54) TRANSGENIC PLANTS WITH ENHANCED TRAITS

(71) Applicant: Monsanto Technology LLC, St. Louis, MO (US)

(72) Inventor: Monnanda Somaiah Rajani, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 51 days.

(21) Appl. No.: 16/539,635

(22) Filed: Aug. 13, 2019

(65) Prior Publication Data

US 2019/0367935 A1 Dec. 5, 2019

Related U.S. Application Data

(63) Continuation of application No. 15/027,777, filed as application No. PCT/US2014/059253 on Oct. 6, 2014, now abandoned.

(60) Provisional application No. 61/932,899, filed on Jan. 29, 2014, provisional application No. 61/887,545, filed on Oct. 7, 2013.

(51) Int. Cl.

| | |
|---|---|
| ***C12N 15/82*** | (2006.01) |
| ***A01H 1/02*** | (2006.01) |
| ***C12N 15/113*** | (2010.01) |

(52) U.S. Cl.

CPC ........... *C12N 15/8241* (2013.01); *A01H 1/02* (2013.01); *C12N 15/113* (2013.01); *C12N 15/8261* (2013.01); *C12N 15/8271* (2013.01); *C12N 2310/141* (2013.01)

(58) Field of Classification Search

None

See application file for complete search history.

(56) References Cited

U.S. PATENT DOCUMENTS

| | | | |
|---|---|---|---|
| 4,761,373 | A | 8/1988 | Anderson et al. |
| 4,810,648 | A | 5/1989 | Stalker |
| 5,013,659 | A | 5/1991 | Bedbrook et al. |
| 5,015,580 | A | 5/1991 | Christou et al. |
| 5,094,945 | A | 3/1992 | Comai |
| 5,141,870 | A | 8/1992 | Bedbrook et al. |
| 5,159,135 | A | 10/1992 | Umbeck |
| 5,188,642 | A | 2/1993 | Shah et al. |
| 5,250,515 | A | 10/1993 | Fuchs et al. |
| 5,273,894 | A | 12/1993 | Strauch et al. |
| 5,276,268 | A | 1/1994 | Strauch et al. |
| 5,378,824 | A | 1/1995 | Bedbrook et al. |
| 5,420,034 | A | 5/1995 | Kridl et al. |
| 5,463,174 | A | 10/1995 | Moloney et al. |
| 5,463,175 | A | 10/1995 | Barry et al. |
| 5,538,880 | A | 7/1996 | Lindquist et al. |
| 5,550,318 | A | 8/1996 | Adams et al. |
| 5,561,236 | A | 10/1996 | Leemans et al. |
| 5,591,616 | A | 1/1997 | Hiei et al. |
| 5,605,011 | A | 2/1997 | Bedbrook et al. |
| 5,627,061 | A | 5/1997 | Barry et al. |
| 5,633,435 | A | 5/1997 | Barry et al. |
| 5,633,437 | A | 5/1997 | Bernasconi et al. |
| 5,637,489 | A | 6/1997 | Strauch et al. |
| 5,646,024 | A | 7/1997 | Leemans et al. |
| 5,728,925 | A | 3/1998 | Herrera-Estrella et al. |
| 5,767,366 | A | 6/1998 | Sathasivan et al. |
| 5,780,708 | A | 7/1998 | Lundquist et al. |
| 5,824,877 | A | 10/1998 | Hichee et al. |
| 5,846,797 | A | 12/1998 | Strickland |
| 5,880,275 | A | 3/1999 | Fischhoff et al. |
| 5,914,451 | A | 6/1999 | Martinell et al. |
| 5,986,175 | A | 11/1999 | Jilka et al. |
| 6,040,497 | A | 3/2000 | Spencer et al. |
| 6,090,627 | A | 7/2000 | Kemp et al. |
| 6,118,047 | A | 9/2000 | Anderson et al. |
| 6,153,812 | A | 11/2000 | Fry et al. |
| 6,160,208 | A | 12/2000 | Lundquist et al. |
| 6,225,105 | B1 | 5/2001 | Sathasivan et al. |
| 6,329,571 | B1 | 12/2001 | Hiei |
| 6,365,807 | B1 | 4/2002 | Christou et al. |
| 6,376,754 | B1 | 4/2002 | Schillinger et al. |
| 6,384,301 | B1 | 5/2002 | Martinell et al. |
| 6,399,861 | B1 | 6/2002 | Anderson et al. |
| 6,414,222 | B1 | 7/2002 | Gengenbach et al. |
| 6,433,252 | B1 | 8/2002 | Kriz et al. |
| 6,506,599 | B1 | 1/2003 | Yoon |
| 6,613,963 | B1 | 9/2003 | Gingera et al. |

(Continued)

FOREIGN PATENT DOCUMENTS

| | | |
|---|---|---|
| WO | WO 2009/073069 | 6/2009 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*
Nishimura et al. (Plant Cell Physiol., 41(5):583-590, 2000).*
Yang et al. (PNAS, 98:11438-11443, 2001).*

(Continued)

*Primary Examiner* — Vinod Kumar

(74) *Attorney, Agent, or Firm* — Morrison & Foerster LLP

(57) ABSTRACT

This disclosure provides transgenic plants having enhanced traits such as increased yield, increased nitrogen use efficiency and enhanced drought tolerance; propagules, progeny and field crops of such transgenic plants; and methods of making and using such transgenic plants. This disclosure also provides methods of producing hybrid seed from such transgenic plants, growing such seed and selecting progeny plants with enhanced traits. Also disclosed are transgenic plants with altered phenotypes which are useful for screening and selecting transgenic event for the desired enhanced trait.

13 Claims, No Drawings

Specification includes a Sequence Listing.

(56) References Cited

U.S. PATENT DOCUMENTS

| | | | | |
|---|---|---|---|---|
| 7,026,528 | B2 | 4/2006 | Cheng et al. | |
| 7,112,721 | B2 | 9/2006 | Fabijanski | |
| 2001/0042257 | A1 | 11/2001 | Connor-Ward et al. | |
| 2002/0112260 | A1 | 8/2002 | Schillinger et al. | |
| 2002/0192813 | A1 | 12/2002 | Conner et al. | |
| 2003/0010609 | A1 | 1/2003 | Kaneko | |
| 2003/0083480 | A1 | 5/2003 | Castle et al. | |
| 2003/0115626 | A1 | 6/2003 | Weeks et al. | |
| 2003/0150017 | A1 | 8/2003 | Mesa et al. | |
| 2004/0087030 | A1 | 5/2004 | Armstrong et al. | |
| 2006/0107345 | A1 | 5/2006 | Alexandrov | |
| 2007/0006337 | A1 | 1/2007 | Cook et al. | |
| 2007/0271633 | A9* | 11/2007 | Kovalic | C12N 15/82 800/284 |
| 2009/0070898 | A1 | 3/2009 | Allen et al. | |
| 2009/0087878 | A9* | 4/2009 | La Rosa | C07K 14/415 435/69.1 |
| 2009/0138985 | A1 | 5/2009 | Martinell et al. | |
| 2010/0186106 | A1 | 7/2010 | Creelman et al. | |
| 2011/0047659 | A1 | 2/2011 | Daley et al. | |
| 2011/0135161 | A1 | 6/2011 | Koutsky et al. | |
| 2011/0214199 | A1* | 9/2011 | Coffin | C12N 15/1079 800/275 |
| 2011/0296555 | A1 | 12/2011 | Ivashuta et al. | |
| 2012/0137382 | A1 | 5/2012 | Repetti et al. | |
| 2017/0037426 | A1 | 2/2017 | Alexnadrov | |

OTHER PUBLICATIONS

McConnell et al. (Nature, 411:709-713, 2001).*

Hanzawa et al. (PNAS, 102:7748-7753, 2005).*

Gang et al. (The Plant Cell, 14:505-519, 2002).*

Schroder et al. (Phytochemistry, 59:1-8, 2002).*

Balenger et al., "Molecular Basis for Allelic Polymorphism of the Maize Globulin-1 Gene," *Genetics Society of America* 129:763-872 (1991).

Biochemistry pp. 140-141 (Mathews, van Holde, and Ahern eds., Benjamin Cummings) (3rd edition, 2000).

Bork et al., "Go hunting in sequence databases but watch out for the traps," *Trends in Genetics*, 12:425-427 (1996).

DeBlock et al., "Engineering herbicide resistance in plants by expression of a detoxifying enzyme," *The EMBO Journal* 6(9):2513-2519 (1987).

Doerks et al., "Protein Annotation: Detective Work for Function Prediction," *Trends Genet*, 14:248-250 (1998).

Fraley et al., "Expression of bacterial genes in plant cells," *Proc. Natl. Acad. Sci. USA* 80:4803-4807 (1983).

Genbank Accession No. AAO63403, Atlg70560 [*Arabidopsis thaliana*], pp. 1-2 (2003).

Genbank Accession No. AC010796.15, putative alliinase; 54807-57232 [*Arabidopsis thaliana*], pp. 1-2 (2016).

Genbank Accession No. AC011663.27, putative alliinase; 99695-97270 [*Arabidopsis thaliana*], pp. 1-5 (2016).

Genbank Accession No. AEE35079, tryptophan aminotransferase of *Arabidopsis* 1 [*Arabidopsis thaliana*], pp. 1-3 (2017).

Genbank Accession No. BAC41884.1, "putative alliinase [*Arabidopsis thaliana*]," pp. 1-2 (2004).

Guo et al., "Proteins tolerance to random amino acid change," *PNAS*, 101:9205-9210 (2004).

Ingelbrecht et al., "Different 3' End Regions Strongly Influence the Level of Gene Expression in Plant Cells," *The Plant Cell* 1:671-680 (1989).

International Search Report dated Mar. 19, 2015, in International Application No. PCT/US2014/059253.

Keskin et al., "A new, structurally nonredundant, diverse data set of protein-protein interfaces and its implication," *Protein Science*, 13:1043-1055 (2004).

Klee et al., "Agrobacterium-Mediated Plant Transformation and its Further Application to Plant Biology," *Ann. Rev. Plant Physiol* 38:467-486 (1987).

Mashiguchi et al., "The main auxin biosynthesis pathway in *Arabidopsis*," *PNAS*, 108(45):18512-18517 (2011).

Milano et al., "Type I pyridoxal 5'-phosphate dependent enzymatic domains embedded within multimodular nonribosomal peptide synthetase and polyketide synthase assembly lines," *BMC Structural Biology*, 13(26):13-26 (2013).

Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal* 6:481-489 (1994).

Misawa et al., "Functional expression of the *Erwinia uredovora* carotenoid biosynthesis gene crtl in transgenic plants showing an increase of β-carotene biosynthesis activity and resistance to the bleaching herbicide norflurazon," *The Plant Journal* 4:833-840 (1993).

Ngo et al., "The Protein Folding Problem and Teitiary Structure Prediction," pp. 492-495 (1994).

Russell et al., "Tissue-specific expression in transgenic maize of four endosperm promoters from maize and rice," *Transgenic Research* 6:157-168 (1997).

Sathasiivan et al., "Nucleotide sequence of a mutant acetolactate synthase gene from an imidazolinone-resistant *Arabidopsis thaliana* var. Columbia," *Nucleic Acids Research* 18:2188-2193 (1990).

Singh et al., "Improved Nutrient Use Efficiency Increases Plant Growth of Rice with the Use of IAA-Overproducing Strains of Endophytic *Burkholderia cepacian* Strain $RRE_{25}$," *Plant Microbe Interactions*, 66:375-384 (2013).

Smith et al., The challenges of genome sequence annotation or "The devil is in the details," *Nature Biotechnology*, 15:1222-1223 (1997).

Stacy et al., "A peroxiredoxin antioxidant is encoded by a dormancy-related gene, *Perl*, expressed during late development in the aleurone and embryo of barley grains," *Plant Molecular Biology* 36(6):1205-1216 (1996).

Stepanova et al., "TAA1-Mediated Auxin Biosynthesis Is Essential for Hormone Crosstalk and Plant Development," *Cell*, 133:177-191 (2008).

Theologis et al., (NCBI, GenBank Sequence Accession No. Q9S7N2; published Nov. 30, 2010).

Thornton et al., "From structure to function: Approaches and limitations," *Nature structure Biology*, 991-994 (2000).

Wells, "Additivity of Mutational Effects in Proteins," *Biochemistry*, 29:8509-8517 (1990).

Zhou et al., "Functional characterization of the CKRC1/TAA1 gene and dissection of hormonal actions in the *Arabidopsis* root," *The Plant Journal*, 66:516-527 (2011).

* cited by examiner

SEQUENCE LISTING

```
<160> NUMBER OF SEQ ID NOS: 116

<210> SEQ ID NO 1
<211> LENGTH: 507
<212> TYPE: DNA
<213> ORGANISM: Arabidopsis thaliana

<400> SEQUENCE: 1

atgttggtgt accaagatct tctcaccggt gatgagcttc tgtctgactc tttcccttac      60

aaggagattg agaatggaat cctctgggaa gtagaaggaa agtgggttac tgtgggagct     120

gtagatgtta acattggtgc caatccatct gctgaagaag gtggtgagga tgaaggtgtt     180

gatgactcta ctcaaaaggt tgttgacatt gtcgacacct tcagacttca ggagcaacca     240

acttatgaca agaagggatt catcgcttac attaagaaat acattaagct tttgacaccc     300

aagctcagcg aagaagatca agctgtcttc aagaagggta ttgagggagc taccaagttt     360

ttgctcccca ggctcagtga cttccaattc tttgttgggg agggtatgca tgatgacagc     420

actttggtct ttgcttacta caaggagggt tcaactaacc caacattttt gtacttcgct     480

catggtttga aggaggtcaa gtgctag                                         507
```

<210> SEQ ID NO 2
<211> LENGTH: 168
<212> TYPE: PRT
<213> ORGANISM: Arabidopsis thaliana

<400> SEQUENCE: 2

```
Met Leu Val Tyr Gln Asp Leu Leu Thr Gly Asp Glu Leu Leu Ser Asp
1               5                   10                  15

Ser Phe Pro Tyr Lys Glu Ile Glu Asn Gly Ile Leu Trp Glu Val Glu
            20                  25                  30

Gly Lys Trp Val Thr Val Gly Ala Val Asp Val Asn Ile Gly Ala Asn
        35                  40                  45

Pro Ser Ala Glu Glu Gly Gly Glu Asp Glu Gly Val Asp Asp Ser Thr
    50                  55                  60

Gln Lys Val Val Asp Ile Val Asp Thr Phe Arg Leu Gln Glu Gln Pro
65                  70                  75                  80

Thr Tyr Asp Lys Lys Gly Phe Ile Ala Tyr Ile Lys Lys Tyr Ile Lys
                85                  90                  95

Leu Leu Thr Pro Lys Leu Ser Glu Glu Asp Gln Ala Val Phe Lys Lys
            100                 105                 110

Gly Ile Glu Gly Ala Thr Lys Phe Leu Leu Pro Arg Leu Ser Asp Phe
        115                 120                 125

Gln Phe Phe Val Gly Glu Gly Met His Asp Asp Ser Thr Leu Val Phe
    130                 135                 140

Ala Tyr Tyr Lys Glu Gly Ser Thr Asn Pro Thr Phe Leu Tyr Phe Ala
145                 150                 155                 160

His Gly Leu Lys Glu Val Lys Cys
                165
```

<210> SEQ ID NO 3
<211> LENGTH: 4497
<212> TYPE: DNA
<213> ORGANISM: Zea mays

<400> SEQUENCE: 3

```
atggcgtcgg gcagccgcgc cacgcccacg cgctccccct cctccgcgcg gcccgaggcg      60

ccgcgtcacg cgcaccacca ccaccactcc cagtcgtcgg gcgggagcac gtcccgcgcg     120

ggcgggggag ccgcggccac ggagtcggtc tccaaggccg tcgcccagta caccctagac     180

gcgcgcctac acgcggtgtt cgagcaatcg ggcgcgtcgg gccgcagctt cgactactcc     240

caatcgctgc gcgcgccgcc cacgccgtcc tccgagcagc agatcgccgc ctacctctcc     300

cgcatccagc gcggcggcca catccagccc ttcggctgca cgctcgctgt tgccgacgac     360

tcctccttcc gcctcctcgc cttctccgag aactcccccg acctgctcga cctgtcgcct     420

caccactccg ttccctcgct ggactcctct gcgccgcccc acgtttccct gggtgccgac     480

gcgcgcctcc tcttctcccc ctcgtccgcg gtcctcctag agcgcgcctt cgccgcgcgc     540

gagatctcgc tgctcaaccc gatatggatc cactccaggg tctcctccaa gccgttctac     600

gccatcctcc accgcatcga cgtcggcgtc gtcatcgacc tcgagcccgc ccgcaccgag     660

gaccccgctc tctccatcgc cggtgcagtc cagtcccaga aactggcggt ccgcaccatc     720

tcccgcctcc aggcgctacc cggcggggac gtcaagcttc tctgcgacac agtcgtggag     780

catgttcgcg agctcacggg ttatgaccgt gtcatggtgt acaggttcca tgaagacgag     840

cacggggaag ttgtcgccga gagccggcgc gacaaccttg agccttacct cggattgcat     900
```

-continued

```
tatcccgcca cagatatccc ccaggcgtcg cgcttcctgt tccggcagaa ccgcgtgcga    960
atgattgccg attgccatgc caccccggtg agagttattc aagatcctgg gctgtcgcag   1020
cctctgtgtt tggtaggctc cacgctacgc gctccacacg ggtgtcatgc acagtacatg   1080
gcgaacatgg ggtcaattgc gtcgcttgtt atggcagtca tcattagcag tggcggtgac   1140
gatgagcaaa caggtcgggg tggcatctcc tcggcaatga agttgtgggg gttagtggtg   1200
tgccaccata catcaccacg gtgtatccct tttccattga ggtatgcttg cgagtttctc   1260
atgcaggtat ttgggttgca gctcaacatg gagttgcagc ttgcgcacca gctgtcagag   1320
aagcacattc tgcgaactca gacgctattg tgtgacatgc tactacgaga ttcaccaact   1380
ggcatcgtca cgcagagccc cagcatcatg gaccttgtga agtgcgacgg ggctgcactg   1440
tattatcatg ggaaatacta tccattgggt gtcactccca ctgagtctca gattaaggat   1500
atcatcgagt ggttgacggt gtttcatggg gactcaacag ggctcagcac agatagcctg   1560
gctgatgcag gctaccttgg tgctgctgca ctaggggagg ctgtgtgtgg aatggcggtg   1620
gcttatatta caccgagtga ttacttgttt tggtttcggt cacacacagc taaagagatc   1680
aaatggggtg gcgcaaagca tcaccctgag gataaggatg atggtcagag gatgcaccca   1740
cggtcgtcat tcaaggcatt tcttgaagtg gttaaaagca gaagcctacc atgggagaat   1800
gcagaaatgg acgcaataca ttccttgcag ctcatattgc gtgactcctt cagggatgct   1860
gcagagggca ccaacaactc aaaagccatt gtcaatggac aagttcagct tcgggagcta   1920
gaattgcggg ggataaatga gcttagttcc gtagcaagag agatggttcg gttgatagag   1980
acagcaacag tacccatatt tgcagtagat actgatgggt gtataaatgg ttggaatgca   2040
aagattgctg agttgacagg gctttcagtt gaggaggcaa tggcaaatc tctggtaaat   2100
gatcttatct tcaaggaatc tgaggcgaca gttgaaaaac tactctcacg agctttaaga   2160
ggtatttcca tttctgtttc ttatatggat gctattgcct ttatactacg tttcatgaaa   2220
actgcggagt gctgttgagg aaaatattat gttcttggtt gtatctctta aggtatatgg   2280
cataacagaa gcttatggac atgatgtaca catgtttatt agaccaaata tggaaatgtg   2340
tggtaatata ctcctggaaa atggatattt gaaggagctg agcctatctc agtttgttga   2400
cagtgtggat gtatgcctag acccagaccc ccaagttcaa gtccttgtcg aggcgatttt   2460
tttgcatatt tcttctaatt aaaaagccct tctatgttgg tcaaggtttt ttaatagata   2520
tactcagttt cttaggcgga cttctttttg tgcacaaata tatagaaaat gggggatcaa   2580
ctagagacta ccaacaaatt cattcaacca tttctagagt atttttagaa cctggtgctt   2640
ataactagca gacatgaata ctcattagtc atatgtgaaa agtaagcata tgaaacttat   2700
aaaaaaggtc atgttagttg ttgaagtgta tgagtggatt aactatcttt tcccatcagc   2760
ttaagctttt gggttcaact ggttagcgcg tccactccaa catggtacca aagacaaagg   2820
tctcgaattc gaattctggc aaaggcttta tttatgcctc cacccattta tttccacgtt   2880
tgcgcccctc tctctctctc tggctgcatt tgcgcctttc tctctggcta cacgtaagtg   2940
ggggtgttga agtgtataag tggattgact accttctccc atcagcttaa gcttttgggt   3000
tgaactgttt agtgcgttca ctctaacatt agctactcac aggagtacaa tgtttctccc   3060
caggctgttt gaactatttt aatgtacttc ccaatgcatg tagctaagct atgttagctt   3120
taatggatgt gagattggag agtgctaatt tgtgaagttg cttcccatac aggtgaggaa   3180
gacaaaaatg tggagataaa gctgaagaca tttgggtcag agcaatctaa gggaccaata   3240
tttgttgttg tcaatgcttg ttctagtaga gattacacac aaaatattgt tggtgtctgt   3300
```

```
tttgttggac aagatgtcac aggacaaaag gtggtcatgg ataaatttgt taacatacaa   3360
ggggactaca aagctattgt acacaatcct aatcctctga taccaccaat ttttgcatca   3420
gatgagaaca cttcttgttc agaatggaat acagccatgg aaaaacttac aggatggtcg   3480
agaggtgaag ttgttggtaa gtttcttatt ggagaggtgt ttggaaattg ttgtcgactc   3540
aagggcccag atgcattgac aaaattcatg gttattattc acaacgctat aggagggcag   3600
gattatgaga agttcccttt ttcatttttt gacaagaatg gaaagtatgt gcaggcctta   3660
ttgaccgcca atacaaggag caaaatggat ggtaaatcca ttggagcctt ttgtttcctg   3720
cagattgcaa gcgctgaaat acagcaagcc attgagattc agagacaaca agaaaagaag   3780
tgttacgcaa ggatgaaaga attggcctat atttgccagg agataaagaa tcctcttagt   3840
ggcatccgat ttaccaactc tctgttgcag atgactgatt taaatgatga ccagaggcag   3900
ttccttgaaa ctagctctgc ttgtgagaaa cagatgtcca agattgttaa ggacgccagt   3960
ctccaaagta tcgaggacgg ctctttggtg cttgagcaaa gtgagttttc tcttggagac   4020
gttatgaatg ctgttgtcag ccaagcaatg ttattgttga gagagaggga tttacaactt   4080
attcgggaca tccctgatga aatcaaggat gcgtcagcgt atggtgatca atgtagaatt   4140
caacaagttt tggctgactt cttgctaagc atggtgcggt ctgctccatc cgagaatggt   4200
tgggtagaaa tacaagtcag accaaatgta aaacagaatt ctgatggaac aaatacagaa   4260
cttttcatat tcaggtttgc ctgccctggt gagggcctcc ctgctgacgt cgtccaggat   4320
atgttcagca attcccaatg gtcaacacaa gaaggcgtag gactaagcac atgcaggaag   4380
atcctcaaat tgatgggtgg cgaggtccaa tacatcagag agtcagagcg gagtttcttc   4440
ctcatcgtcc tcgagcagcc ccaacctcgt ccagcagctg gtagagaaat cgtctag      4497
```

<210> SEQ ID NO 4
<211> LENGTH: 745
<212> TYPE: PRT
<213> ORGANISM: Zea mays

<400> SEQUENCE: 4

```
Met Ala Ser Gly Ser Arg Ala Thr Pro Thr Arg Ser Pro Ser Ser Ala
1               5                   10                  15

Arg Pro Glu Ala Pro Arg His Ala His His His His His Ser Gln Ser
            20                  25                  30

Ser Gly Gly Ser Thr Ser Arg Ala Gly Gly Gly Ala Ala Ala Thr Glu
        35                  40                  45

Ser Val Ser Lys Ala Val Ala Gln Tyr Thr Leu Asp Ala Arg Leu His
    50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Ser Glu Gln Gln Ile Ala
                85                  90                  95

Ala Tyr Leu Ser Arg Ile Gln Arg Gly Gly His Ile Gln Pro Phe Gly
            100                 105                 110

Cys Thr Leu Ala Val Ala Asp Asp Ser Ser Phe Arg Leu Leu Ala Phe
        115                 120                 125

Ser Glu Asn Ser Pro Asp Leu Leu Asp Leu Ser Pro His His Ser Val
    130                 135                 140

Pro Ser Leu Asp Ser Ser Ala Pro Pro His Val Ser Leu Gly Ala Asp
145                 150                 155                 160
```

```
Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
            180                 185                 190

Arg Val Ser Ser Lys Pro Phe Tyr Ala Ile Leu His Arg Ile Asp Val
        195                 200                 205

Gly Val Val Ile Asp Leu Glu Pro Ala Arg Thr Glu Asp Pro Ala Leu
    210                 215                 220

Ser Ile Ala Gly Ala Val Gln Ser Gln Lys Leu Ala Val Arg Thr Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
            260                 265                 270

Val Tyr Arg Phe His Glu Asp Glu His Gly Glu Val Val Ala Glu Ser
        275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
                325                 330                 335

Gly Leu Ser Gln Pro Leu Cys Leu Val Gly Ser Thr Leu Arg Ala Pro
            340                 345                 350

His Gly Cys His Ala Gln Tyr Met Ala Asn Met Gly Ser Ile Ala Ser
        355                 360                 365

Leu Val Met Ala Val Ile Ile Ser Ser Gly Gly Asp Asp Glu Gln Thr
    370                 375                 380

Gly Arg Gly Gly Ile Ser Ser Ala Met Lys Leu Trp Gly Leu Val Val
385                 390                 395                 400

Cys His His Thr Ser Pro Arg Cys Ile Pro Phe Pro Leu Arg Tyr Ala
                405                 410                 415

Cys Glu Phe Leu Met Gln Val Phe Gly Leu Gln Leu Asn Met Glu Leu
            420                 425                 430

Gln Leu Ala His Gln Leu Ser Glu Lys His Ile Leu Arg Thr Gln Thr
        435                 440                 445

Leu Leu Cys Asp Met Leu Leu Arg Asp Ser Pro Thr Gly Ile Val Thr
    450                 455                 460

Gln Ser Pro Ser Ile Met Asp Leu Val Lys Cys Asp Gly Ala Ala Leu
465                 470                 475                 480

Tyr Tyr His Gly Lys Tyr Tyr Pro Leu Gly Val Thr Pro Thr Glu Ser
                485                 490                 495

Gln Ile Lys Asp Ile Ile Glu Trp Leu Thr Val Phe His Gly Asp Ser
            500                 505                 510

Thr Gly Leu Ser Thr Asp Ser Leu Ala Asp Ala Gly Tyr Leu Gly Ala
        515                 520                 525

Ala Ala Leu Gly Glu Ala Val Cys Gly Met Ala Val Ala Tyr Ile Thr
    530                 535                 540

Pro Ser Asp Tyr Leu Phe Trp Phe Arg Ser His Thr Ala Lys Glu Ile
545                 550                 555                 560

Lys Trp Gly Gly Ala Lys His His Pro Glu Asp Lys Asp Asp Gly Gln
                565                 570                 575

Arg Met His Pro Arg Ser Ser Phe Lys Ala Phe Leu Glu Val Val Lys
```

```
            580                 585                 590

Ser Arg Ser Leu Pro Trp Glu Asn Ala Glu Met Asp Ala Ile His Ser
        595                 600                 605

Leu Gln Leu Ile Leu Arg Asp Ser Phe Arg Asp Ala Ala Glu Gly Thr
    610                 615                 620

Asn Asn Ser Lys Ala Ile Val Asn Gly Gln Val Gln Leu Arg Glu Leu
625                 630                 635                 640

Glu Leu Arg Gly Ile Asn Glu Leu Ser Ser Val Ala Arg Glu Met Val
                645                 650                 655

Arg Leu Ile Glu Thr Ala Thr Val Pro Ile Phe Ala Val Asp Thr Asp
            660                 665                 670

Gly Cys Ile Asn Gly Trp Asn Ala Lys Ile Ala Glu Leu Thr Gly Leu
        675                 680                 685

Ser Val Glu Glu Ala Met Gly Lys Ser Leu Val Asn Asp Leu Ile Phe
    690                 695                 700

Lys Glu Ser Glu Ala Thr Val Glu Lys Leu Leu Ser Arg Ala Leu Arg
705                 710                 715                 720

Gly Ile Ser Ile Ser Val Ser Tyr Met Asp Ala Ile Ala Phe Ile Leu
                725                 730                 735

Arg Phe Met Lys Thr Ala Glu Cys Cys
            740                 745
```

<210> SEQ ID NO 5
<211> LENGTH: 888
<212> TYPE: DNA
<213> ORGANISM: Zea mays

<400> SEQUENCE: 5

```
atggctcctc tgtctcctag actggtagtg cccgtagacg tgaagaagct gccgcgggag      60

caaaaggtcc ctctccacaa ccgctggcac ccggatatcc ctcctgttgc tgatgtaacc     120

gaaggggaat tgttccgcgt tgagatggtc gattggagtg gagggcgggt tagggatgat     180

aactctgcag atgatctgaa attcatggat ttcacaattg ctcattatct tagtgggccc     240

ctaagaatag ttgattctga aggggttcca gcttcaccag gtgatcttct cgcggtagaa     300

atctgcaacc ttggcccact tcctggcgac gagtggggtt acaccgcaat acttgaaagg     360

gagaatggag gtggattctt aactgaccac ttccctagcg caagaaaagc catctggtat     420

ttcgaaggaa tttacgcatg ctccccgcag ataccaggtg ttcgttttcc aggattgact     480

catcctggtg ttgtgggaac tgcaccgtca cttgagctcc taaatatatg gaatgaaaga     540

gagaaaagtt tgtctgagac aagcctagag actattaaac tgtgtgaagt tctacaccag     600

aggccccttg ctcatttacc gaccccctgaa aattgcttac ttgggaaggt ccaagaaggg     660

actgctgaat ggcacataat tgcaaacgaa gcggccagaa ctattgctgg aagggaaaat     720

ggcgggaatt gcgacataaa gaacctaagc agaggctcca gaatttatct accagtgttt     780

gtcgaaggag caaacctcag cactggtgac atgcacttct cccaggggga cggcgagatt     840

tcgctgtgtg gagcaattga aatgagcggg ttccttgagc tcaagtag                  888
```

<210> SEQ ID NO 6
<211> LENGTH: 295
<212> TYPE: PRT
<213> ORGANISM: Zea mays

<400> SEQUENCE: 6

```
Met Ala Pro Leu Ser Pro Arg Leu Val Val Pro Val Asp Val Lys Lys
```

```
1               5                   10                  15

Leu Pro Arg Glu Gln Lys Val Pro Leu His Asn Arg Trp His Pro Asp
            20                  25                  30

Ile Pro Pro Val Ala Asp Val Thr Glu Gly Glu Leu Phe Arg Val Glu
        35                  40                  45

Met Val Asp Trp Ser Gly Gly Arg Val Arg Asp Asp Asn Ser Ala Asp
    50                  55                  60

Asp Leu Lys Phe Met Asp Phe Thr Ile Ala His Tyr Leu Ser Gly Pro
65                  70                  75                  80

Leu Arg Ile Val Asp Ser Glu Gly Val Pro Ala Ser Pro Gly Asp Leu
                85                  90                  95

Leu Ala Val Glu Ile Cys Asn Leu Gly Pro Leu Pro Gly Asp Glu Trp
            100                 105                 110

Gly Tyr Thr Ala Ile Leu Glu Arg Glu Asn Gly Gly Gly Phe Leu Thr
        115                 120                 125

Asp His Phe Pro Ser Ala Arg Lys Ala Ile Trp Tyr Phe Glu Gly Ile
    130                 135                 140

Tyr Ala Cys Ser Pro Gln Ile Pro Gly Val Arg Phe Pro Gly Leu Thr
145                 150                 155                 160

His Pro Gly Val Val Gly Thr Ala Pro Ser Leu Glu Leu Leu Asn Ile
                165                 170                 175

Trp Asn Glu Arg Glu Lys Ser Leu Ser Glu Thr Ser Leu Glu Thr Ile
            180                 185                 190

Lys Leu Cys Glu Val Leu His Gln Arg Pro Leu Ala His Leu Pro Thr
        195                 200                 205

Pro Glu Asn Cys Leu Leu Gly Lys Val Gln Glu Gly Thr Ala Glu Trp
    210                 215                 220

His Ile Ile Ala Asn Glu Ala Ala Arg Thr Ile Ala Gly Arg Glu Asn
225                 230                 235                 240

Gly Gly Asn Cys Asp Ile Lys Asn Leu Ser Arg Gly Ser Arg Ile Tyr
                245                 250                 255

Leu Pro Val Phe Val Glu Gly Ala Asn Leu Ser Thr Gly Asp Met His
            260                 265                 270

Phe Ser Gln Gly Asp Gly Glu Ile Ser Leu Cys Gly Ala Ile Glu Met
        275                 280                 285

Ser Gly Phe Leu Glu Leu Lys
    290                 295


<210> SEQ ID NO 7
<211> LENGTH: 1398
<212> TYPE: DNA
<213> ORGANISM: Arabidopsis thaliana

<400> SEQUENCE: 7

atgatgaaag tggtgtcacc tcgtacacgg tcggattcaa tcactgagaa ggtgtttcga      60

cgagtctata gcaattttaa catctcaaca gtagaagatg agtatatcca tcgtcagaga     120

tcaagtgatt atgagaagga gagtcgtcta aggaagagag ggttagaaga caaagaagaa     180

gttatggaga tggagcagat gggagcagag aggatcaaaa ctgttcttat tctcatgagt     240

gataccggcg gtggccaccg tgcttcagcc gaggccatcc gcgacgcttt caagatcgaa     300

ttcggagatg actatcggat aatcataaaa gatgtttgga aagaatacac tggatggcca     360

ttgaacgaca tggagagaca gtacaagttc atggtgaaac atgttggtct ttggtctgtt     420

gcgtttcatg gtacttctcc caaatggatc cacaaaagct atctaagtgc tcttgccgct     480
```

```
tattatgcca aagaaataga ggccggttta atggagtaca aaccggacat tattattagc    540
gtgcatcctc tgatgcaaca cataccattg tgggtaatga aatggcaagg acttcacaag    600
aaagttattt tcgttacggt catcactgat ctaaacactt gccaccgtac atggttccat    660
catggagtca gcagatgtta ttgtccgtcc aaagaggttg caaagagagc attagtagac    720
ggccttgatg actctcaaat ccgtgtcttt ggcttacctg tccgcccatc tttccctcgc    780
actattctca acaagaatga actaaggaag gaacttgaaa tagacttaaa tttacctgcg    840
gttctattaa tgggaggggg tgaaggaatg ggtccggttc aaaaaacagc tctagccctt    900
ggagattctt tatacaactc taaagaaagt aatccaatag gacaattgat tgtcatatgc    960
ggccggaaca aagtccttgc ttctacatta gcatctcatg aatggaagat tccggtcaag   1020
gttcgagggt ttgaaacaca aatggaaaaa tggatgggag cttgtgattg tatcatcact   1080
aaggctggtc cgggtacgat tgcggaagca ctgatttgcg gcctcccaat tatcctcaat   1140
gactatattc ctggacagga aaaaggcaac gtgccgtatg ttgtggacaa tggggctgga   1200
gttttcaccc gaagtcccaa agaaactgcg aaaatcgtgg cggattggtt tagcaacaat   1260
aaagaggaat taaagaaaat gtcagagaat gctctaaagt tgtcgcaacc tgaagccgtg   1320
ttcgacattg tgaaggatat ccatcatcta tcccaacaac aacaacgtat tccacttttt   1380
aatgaatttt cctattag                                                 1398
```

<210> SEQ ID NO 8
<211> LENGTH: 465
<212> TYPE: PRT
<213> ORGANISM: Arabidopsis thaliana

<400> SEQUENCE: 8

```
Met Met Lys Val Val Ser Pro Arg Thr Arg Ser Asp Ser Ile Thr Glu
1               5                   10                  15

Lys Val Phe Arg Arg Val Tyr Ser Asn Phe Asn Ile Ser Thr Val Glu
            20                  25                  30

Asp Glu Tyr Ile His Arg Gln Arg Ser Ser Asp Tyr Glu Lys Glu Ser
        35                  40                  45

Arg Leu Arg Lys Arg Gly Leu Glu Asp Lys Glu Glu Val Met Glu Met
    50                  55                  60

Glu Gln Met Gly Ala Glu Arg Ile Lys Thr Val Leu Ile Leu Met Ser
65                  70                  75                  80

Asp Thr Gly Gly Gly His Arg Ala Ser Ala Glu Ala Ile Arg Asp Ala
                85                  90                  95

Phe Lys Ile Glu Phe Gly Asp Asp Tyr Arg Ile Ile Ile Lys Asp Val
            100                 105                 110

Trp Lys Glu Tyr Thr Gly Trp Pro Leu Asn Asp Met Glu Arg Gln Tyr
        115                 120                 125

Lys Phe Met Val Lys His Val Gly Leu Trp Ser Val Ala Phe His Gly
    130                 135                 140

Thr Ser Pro Lys Trp Ile His Lys Ser Tyr Leu Ser Ala Leu Ala Ala
145                 150                 155                 160

Tyr Tyr Ala Lys Glu Ile Glu Ala Gly Leu Met Glu Tyr Lys Pro Asp
                165                 170                 175

Ile Ile Ile Ser Val His Pro Leu Met Gln His Ile Pro Leu Trp Val
            180                 185                 190

Met Lys Trp Gln Gly Leu His Lys Lys Val Ile Phe Val Thr Val Ile
        195                 200                 205
```

```
Thr Asp Leu Asn Thr Cys His Arg Thr Trp Phe His His Gly Val Ser
    210                 215                 220

Arg Cys Tyr Cys Pro Ser Lys Glu Val Ala Lys Arg Ala Leu Val Asp
225                 230                 235                 240

Gly Leu Asp Asp Ser Gln Ile Arg Val Phe Gly Leu Pro Val Arg Pro
                245                 250                 255

Ser Phe Pro Arg Thr Ile Leu Asn Lys Asn Glu Leu Arg Lys Glu Leu
            260                 265                 270

Glu Ile Asp Leu Asn Leu Pro Ala Val Leu Leu Met Gly Gly Gly Glu
        275                 280                 285

Gly Met Gly Pro Val Gln Lys Thr Ala Leu Ala Leu Gly Asp Ser Leu
    290                 295                 300

Tyr Asn Ser Lys Glu Ser Asn Pro Ile Gly Gln Leu Ile Val Ile Cys
305                 310                 315                 320

Gly Arg Asn Lys Val Leu Ala Ser Thr Leu Ala Ser His Glu Trp Lys
                325                 330                 335

Ile Pro Val Lys Val Arg Gly Phe Glu Thr Gln Met Glu Lys Trp Met
            340                 345                 350

Gly Ala Cys Asp Cys Ile Ile Thr Lys Ala Gly Pro Gly Thr Ile Ala
        355                 360                 365

Glu Ala Leu Ile Cys Gly Leu Pro Ile Ile Leu Asn Asp Tyr Ile Pro
    370                 375                 380

Gly Gln Glu Lys Gly Asn Val Pro Tyr Val Val Asp Asn Gly Ala Gly
385                 390                 395                 400

Val Phe Thr Arg Ser Pro Lys Glu Thr Ala Lys Ile Val Ala Asp Trp
                405                 410                 415

Phe Ser Asn Asn Lys Glu Glu Leu Lys Lys Met Ser Glu Asn Ala Leu
            420                 425                 430

Lys Leu Ser Gln Pro Glu Ala Val Phe Asp Ile Val Lys Asp Ile His
        435                 440                 445

His Leu Ser Gln Gln Gln Gln Arg Ile Pro Leu Phe Asn Glu Phe Ser
    450                 455                 460

Tyr
465
```

```
<210> SEQ ID NO 9
<211> LENGTH: 2160
<212> TYPE: DNA
<213> ORGANISM: Arabidopsis thaliana

<400> SEQUENCE: 9

atggatggga tgaagctttc gttcccaccg gaaagtccac cactttcagt catcgttgct      60

ctttctctct cagcttctcc ggtgacgatt gattcttccg ccgctgcaac aaccgtccct     120

tcttttgtct tctccgacgg gaggaaattg aatggagcca ccgttcttct tcgctatgtt     180

ggtcgatcag cgaaaaagct tcctgatttc tatggcaaca atgcttttga ttcttctcag     240

attgatgagt gggtagatta cgcatctgtc ttctcttctg gttcagagtt tgagaatgct     300

tgtggtcgtg ttgataagta tctcgagagt agcacgtttc ttgttggcca ttctctttcc     360

attgctgatg tcgctatttg gtcagctctt gctggaactg gtcaaagatg ggaaagtttg     420

aggaaatcta aaaagtatca gagtcttgtt agatggttca attcgatatt agacgagtac     480

agtgaggtgc ttaacaaggt tctagcaact tatgttaaga aaggatcagg gaagcctgtt     540

gctgcaccta agtctaaaga tagccaacaa gctgtgaaag gagatggtca ggataaaggt     600
```

```
aagcctgaag tggacttgcc ggaagcggag attggaaagg ttaaactccg gtttgctcca    660

gagccaagtg gttatcttca cataggacat gctaaggctg cgttgctgaa caagtatttc    720

gctgagcgtt accaagggga agtgattgtg cgttttgatg atactaaccc tgctaaagaa    780

agcaatgagt ttgtggataa tcttgtgaag gatattggga ccttggggat caagtatgag    840

aaagtgacat acacttcgga ctattttcct gaattgatgg atatggcgga aaaactgatg    900

cgtgagggta aggcatatgt tgatgacaca ccgagggagc agatgcagaa agagaggatg    960

gatgggattg attcgaaatg taggaatcat agcgtcgagg agaatttgaa gctatggaag   1020

gaaatgattg caggaagtga gagaggatta cagtgctgtg ttcgtgggaa attcaacatg   1080

caagatccca acaaagccat gcgtgacccg gtttattacc gatgcaatcc tatgtctcac   1140

caccgtatcg ggataagta taagatatat ccaacatatg actttgcttg cccgtttgtt   1200

gattcccttg aaggtataac gcatgctctt cggtctagtg agtatcatga ccgaaatgct   1260

cagtacttta aagttctgga ggatatggga ctgcgacagg ttcagcttta cgaattcagc   1320

cggttaaacc tagtttttac acttctcagt aagcgcaagc ttctctggtt tgtccaaact   1380

ggattggttg acgggtggga tgatccacgt ttcccgacag tccaaggaat tgttcgtaga   1440

ggtttgaaaa tcgaggctct gattcaattc attctcgagc agggggcttc gaagaatcta   1500

aatttgatgg aatgggacaa actttggtct ataaataaga gaataattga tcctgtgtgc   1560

cctagacaca ctgctgtggt tgcagaacgt cgtgtactat ttaccttaac ggatggtcct   1620

gatgagccgt ttgttcgcat gataccaaag cacaagaaat tcgaaggtgc tggagaaaag   1680

gcgaccactt tcactaagag catttggctc gaggaagctg atgcgagtgc catatccgtt   1740

ggtgaggaag taactttgat ggattgggga aatgctatcg taaaggaaat cacaaaggac   1800

gaggagggtc gtgtcactgc cttatctggt gtcttgaatc tccaaggttc tgtaaagact   1860

acaaagctga agctgacatg gcttcctgat actaatgaat tggtcaatct cacattaaca   1920

gagtttgatt atctaatcac caagaagaag ctggaagatg atgatgaagt tgctgatttt   1980

gtgaatccta acacaaagaa ggaaacattg gcacttggtg attcgaatat gaggaatctg   2040

aaatgtggag atgtgattca gcttgagagg aaaggctatt tcagatgtga tgtgcctttt   2100

gtcaaatctt caaagcccat tgtcttattc tccattccag atggaagagc cgctaagtag   2160
```

<210> SEQ ID NO 10
<211> LENGTH: 719
<212> TYPE: PRT
<213> ORGANISM: Arabidopsis thaliana

<400> SEQUENCE: 10

```
Met Asp Gly Met Lys Leu Ser Phe Pro Pro Glu Ser Pro Pro Leu Ser
1               5                   10                  15

Val Ile Val Ala Leu Ser Leu Ser Ala Ser Pro Val Thr Ile Asp Ser
            20                  25                  30

Ser Ala Ala Ala Thr Thr Val Pro Ser Phe Val Phe Ser Asp Gly Arg
        35                  40                  45

Lys Leu Asn Gly Ala Thr Val Leu Leu Arg Tyr Val Gly Arg Ser Ala
    50                  55                  60

Lys Lys Leu Pro Asp Phe Tyr Gly Asn Asn Ala Phe Asp Ser Ser Gln
65                  70                  75                  80

Ile Asp Glu Trp Val Asp Tyr Ala Ser Val Phe Ser Ser Gly Ser Glu
                85                  90                  95
```

```
Phe Glu Asn Ala Cys Gly Arg Val Asp Lys Tyr Leu Glu Ser Ser Thr
            100                 105                 110

Phe Leu Val Gly His Ser Leu Ser Ile Ala Asp Val Ala Ile Trp Ser
        115                 120                 125

Ala Leu Ala Gly Thr Gly Gln Arg Trp Glu Ser Leu Arg Lys Ser Lys
    130                 135                 140

Lys Tyr Gln Ser Leu Val Arg Trp Phe Asn Ser Ile Leu Asp Glu Tyr
145                 150                 155                 160

Ser Glu Val Leu Asn Lys Val Leu Ala Thr Tyr Val Lys Lys Gly Ser
                165                 170                 175

Gly Lys Pro Val Ala Ala Pro Lys Ser Lys Asp Ser Gln Gln Ala Val
            180                 185                 190

Lys Gly Asp Gly Gln Asp Lys Gly Lys Pro Glu Val Asp Leu Pro Glu
        195                 200                 205

Ala Glu Ile Gly Lys Val Lys Leu Arg Phe Ala Pro Glu Pro Ser Gly
    210                 215                 220

Tyr Leu His Ile Gly His Ala Lys Ala Ala Leu Leu Asn Lys Tyr Phe
225                 230                 235                 240

Ala Glu Arg Tyr Gln Gly Glu Val Ile Val Arg Phe Asp Asp Thr Asn
                245                 250                 255

Pro Ala Lys Glu Ser Asn Glu Phe Val Asp Asn Leu Val Lys Asp Ile
            260                 265                 270

Gly Thr Leu Gly Ile Lys Tyr Glu Lys Val Thr Tyr Thr Ser Asp Tyr
        275                 280                 285

Phe Pro Glu Leu Met Asp Met Ala Glu Lys Leu Met Arg Glu Gly Lys
    290                 295                 300

Ala Tyr Val Asp Asp Thr Pro Arg Glu Gln Met Gln Lys Glu Arg Met
305                 310                 315                 320

Asp Gly Ile Asp Ser Lys Cys Arg Asn His Ser Val Glu Glu Asn Leu
                325                 330                 335

Lys Leu Trp Lys Glu Met Ile Ala Gly Ser Glu Arg Gly Leu Gln Cys
            340                 345                 350

Cys Val Arg Gly Lys Phe Asn Met Gln Asp Pro Asn Lys Ala Met Arg
        355                 360                 365

Asp Pro Val Tyr Tyr Arg Cys Asn Pro Met Ser His His Arg Ile Gly
    370                 375                 380

Asp Lys Tyr Lys Ile Tyr Pro Thr Tyr Asp Phe Ala Cys Pro Phe Val
385                 390                 395                 400

Asp Ser Leu Glu Gly Ile Thr His Ala Leu Arg Ser Ser Glu Tyr His
                405                 410                 415

Asp Arg Asn Ala Gln Tyr Phe Lys Val Leu Glu Asp Met Gly Leu Arg
            420                 425                 430

Gln Val Gln Leu Tyr Glu Phe Ser Arg Leu Asn Leu Val Phe Thr Leu
        435                 440                 445

Leu Ser Lys Arg Lys Leu Leu Trp Phe Val Gln Thr Gly Leu Val Asp
    450                 455                 460

Gly Trp Asp Asp Pro Arg Phe Pro Thr Val Gln Gly Ile Val Arg Arg
465                 470                 475                 480

Gly Leu Lys Ile Glu Ala Leu Ile Gln Phe Ile Leu Glu Gln Gly Ala
                485                 490                 495

Ser Lys Asn Leu Asn Leu Met Glu Trp Asp Lys Leu Trp Ser Ile Asn
            500                 505                 510

Lys Arg Ile Ile Asp Pro Val Cys Pro Arg His Thr Ala Val Val Ala
```

```
        515                 520                 525

Glu Arg Arg Val Leu Phe Thr Leu Thr Asp Gly Pro Asp Glu Pro Phe
    530                 535                 540

Val Arg Met Ile Pro Lys His Lys Lys Phe Glu Gly Ala Gly Glu Lys
545                 550                 555                 560

Ala Thr Thr Phe Thr Lys Ser Ile Trp Leu Glu Glu Ala Asp Ala Ser
                565                 570                 575

Ala Ile Ser Val Gly Glu Glu Val Thr Leu Met Asp Trp Gly Asn Ala
            580                 585                 590

Ile Val Lys Glu Ile Thr Lys Asp Glu Glu Gly Arg Val Thr Ala Leu
        595                 600                 605

Ser Gly Val Leu Asn Leu Gln Gly Ser Val Lys Thr Thr Lys Leu Lys
    610                 615                 620

Leu Thr Trp Leu Pro Asp Thr Asn Glu Leu Val Asn Leu Thr Leu Thr
625                 630                 635                 640

Glu Phe Asp Tyr Leu Ile Thr Lys Lys Lys Leu Glu Asp Asp Asp Glu
                645                 650                 655

Val Ala Asp Phe Val Asn Pro Asn Thr Lys Lys Glu Thr Leu Ala Leu
            660                 665                 670

Gly Asp Ser Asn Met Arg Asn Leu Lys Cys Gly Asp Val Ile Gln Leu
        675                 680                 685

Glu Arg Lys Gly Tyr Phe Arg Cys Asp Val Pro Phe Val Lys Ser Ser
    690                 695                 700

Lys Pro Ile Val Leu Phe Ser Ile Pro Asp Gly Arg Ala Ala Lys
705                 710                 715
```

<210> SEQ ID NO 11
<211> LENGTH: 912
<212> TYPE: DNA
<213> ORGANISM: Arabidopsis thaliana

<400> SEQUENCE: 11

```
atggtgacga aaacggagga gatacagtta aaccaactcg agaatcaagt tgagaatgga      60

ggaggaggtg tttgggagta tctgtgcctc gttcgtaagc tcaaggttcg ccgatcagag     120

attgtgctca agcatggtct ctcgatcttg aacgattcgg gaaagcgatc cgctcttggt     180

ccagatgaat ggaccctgta tgagcaggta gcaattgcag ctatggactg tcaatctctc     240

ggtgttgcac agaattgcat caaggttcta aagaagaaat ttccggagag caaacgtgtt     300

ggcaagctgg aggctctgct gctagaagca aagggaatgt gggaagaggc tgaaaaagca     360

tatacaagcc ttttggagga taatccactt gatcaagtaa ttcacaaaag aaaggtggct     420

atggccaagg cacaaggcaa atcttcctta gccattgaac atctgaacaa gtatcttgaa     480

gtattcatgg ctgatcatga tgcctggaga gaacttgcag aaatttatgt ttccttgcaa     540

atgtacaagc aagcagcttt ctgctacgag gagctcatac taactcagcc tactcttcca     600

ttgtaccact tagcatatgc cgatgttctc tacacaatag gtggactaga aaacctcatc     660

gcagcaagaa agtactatgc agcaactata gacttgacag gtggtaaaag cacaagagca     720

cttctcggaa tatgcttgtg tggatcagca atcgcacaga tctcaaaagg caggaacaaa     780

gaggacaagg acatggctgc accagagctt cagtctttgg ctgcaactgc attggagcga     840

gagtacaagc aaaaagctcc cgctaagctc aacctcctca cttctgcctt gagaaacttg     900

aaaatcgctt ag                                                        912
```

<210> SEQ ID NO 12
<211> LENGTH: 303
<212> TYPE: PRT
<213> ORGANISM: Arabidopsis thaliana

<400> SEQUENCE: 12

```
Met Val Thr Lys Thr Glu Glu Ile Gln Leu Asn Gln Leu Glu Asn Gln
1               5                   10                  15

Val Glu Asn Gly Gly Gly Gly Val Trp Glu Tyr Leu Cys Leu Val Arg
            20                  25                  30

Lys Leu Lys Val Arg Arg Ser Glu Ile Val Leu Lys His Gly Leu Ser
        35                  40                  45

Ile Leu Asn Asp Ser Gly Lys Arg Ser Ala Leu Gly Pro Asp Glu Trp
    50                  55                  60

Thr Leu Tyr Glu Gln Val Ala Ile Ala Ala Met Asp Cys Gln Ser Leu
65                  70                  75                  80

Gly Val Ala Gln Asn Cys Ile Lys Val Leu Lys Lys Lys Phe Pro Glu
                85                  90                  95

Ser Lys Arg Val Gly Lys Leu Glu Ala Leu Leu Leu Glu Ala Lys Gly
            100                 105                 110

Met Trp Glu Glu Ala Glu Lys Ala Tyr Thr Ser Leu Leu Glu Asp Asn
        115                 120                 125

Pro Leu Asp Gln Val Ile His Lys Arg Lys Val Ala Met Ala Lys Ala
    130                 135                 140

Gln Gly Lys Ser Ser Leu Ala Ile Glu His Leu Asn Lys Tyr Leu Glu
145                 150                 155                 160

Val Phe Met Ala Asp His Asp Ala Trp Arg Glu Leu Ala Glu Ile Tyr
                165                 170                 175

Val Ser Leu Gln Met Tyr Lys Gln Ala Ala Phe Cys Tyr Glu Glu Leu
            180                 185                 190

Ile Leu Thr Gln Pro Thr Leu Pro Leu Tyr His Leu Ala Tyr Ala Asp
        195                 200                 205

Val Leu Tyr Thr Ile Gly Gly Leu Glu Asn Leu Ile Ala Ala Arg Lys
    210                 215                 220

Tyr Tyr Ala Ala Thr Ile Asp Leu Thr Gly Gly Lys Ser Thr Arg Ala
225                 230                 235                 240

Leu Leu Gly Ile Cys Leu Cys Gly Ser Ala Ile Ala Gln Ile Ser Lys
                245                 250                 255

Gly Arg Asn Lys Glu Asp Lys Asp Met Ala Ala Pro Glu Leu Gln Ser
            260                 265                 270

Leu Ala Ala Thr Ala Leu Glu Arg Glu Tyr Lys Gln Lys Ala Pro Ala
        275                 280                 285

Lys Leu Asn Leu Leu Thr Ser Ala Leu Arg Asn Leu Lys Ile Ala
    290                 295                 300
```

<210> SEQ ID NO 13
<211> LENGTH: 2130
<212> TYPE: DNA
<213> ORGANISM: Arabidopsis thaliana

<400> SEQUENCE: 13

```
atggtgggag gaggaggagg tagtagtggt cgtggtggtg gtagtggtag tggtagtagt      60

aagcagcaga gaggtttctc tatgaatcct aaagactata agctaatgga agaaataggc     120

catggagcta gcgctgttgt ctatcgagcg atctatctcc ctactaatga agtcgtcgcc     180

atcaagtgtt tggatctcga tcgctgcaat agcaatctgg atgatattag gagggaatct     240
```

```
cagactatga gtttgataga ccatcccaac gttataaagt cgttttgttc attctctgtc    300

gaccatagtc tttgggttgt tatgccattc atggctcaag gttcgtgttt gcatcttatg    360

aagactgcgt attcagacgg atttgaagag tctgctatat gttgtgtatt aaaagaaact    420

cttaaagctc ttgattatct tcatagacaa ggccatatcc atcgggatgt taaggctgga    480

aacatacttc ttgatgacaa tggtgagatt aagcttggcg attttggtgt ctctgcttgc    540

ttgtttgata acggtgatag gcaacgtgct agaaacacat ttgttggtac tccttgctgg    600

atggcaccgg aagttttgca gccgggaaat ggatacaatt ccaaggctga tatctggtca    660

tttggtataa cagcacttga attggcccat ggtcatgcac ctttctcaaa atatcctccc    720

atgaaggtgc tcctaatgac tattcaaaac gcacctcctg gccttgatta tgaccgtgat    780

aagaaatttt ctaagtcctt taaagaaatg gttgcaatgt gtttggtgaa agatcaaaca    840

aaaaggccaa ctgctgaaaa actgctgaag cactcctgtt tcaaacacac gaagcctcca    900

gagcaaactg tgaaaatttt attttccgat ttaccacctc tttggacacg tgtaaaatct    960

cttcaggata aggatgctca acagcttgca ttaaagagaa tggccactgc tgacgaggaa   1020

gctatatcac agagcgaata ccaaagagga gtgagcgctt ggaactttga cgtcagagac   1080

ttgaaaacac aagcatcttt gttaattgat gatgatgatc tagaagagag taaggaagat   1140

gaagaaatat tatgtgcaca gtttaataag gtgaatgaca gagagcaagt atttgatagt   1200

ctgcaactat atgaaaacat gaacggaaaa gaaaaggttt ccaatactga ggtggaagaa   1260

ccaacctgca aagagaaatt cactttcgtt acaactactt cttctttaga acgaatgtca   1320

ccaaattcag agcatgacat tcccgaggcc aaggttaagc cattaagacg ccaaagtcag   1380

agtggaccac ttacaagcag gactgtatta agccactcgg cttcagagaa aagtcatatc   1440

tttgaaagat ccgagagtga accgcagacg gcaccaacag tccgaagagc acccagcttt   1500

agtggtcctt tgaatctttc aacccgtgct tcttcaaaca gtttgtctgc tcccatcaaa   1560

tactcaggag gattccgtga ttctctggat gataagtcaa aggctaatct ggttcagaaa   1620

ggacgatttt cagtaacatc aggaaatgta gatcttgcga aggatgttcc attaagtata   1680

gtccctcgtc gatctccaca ggcgaccccc ctgagaaaat ctgcaagtgt gggtaactgg   1740

atacttgagc ccaaaatgcc aacagctcag cctcagacga tcaaggagca tagtagccat   1800

cctacgtctt cctcacccat catgcctcaa cttcaacatc tattccagca aaactcaata   1860

caacaggatc ttattatgaa tttactaaat agcttacaac ccgtggaggc aacagaaggt   1920

tctcaatctg ggaagttacc acctttgcct cgctcagaca gtaatggaaa cgttgaacct   1980

gtggcttcag agagggagag gttacttctt agcagtatct ccgacctccg tgctaggctg   2040

gacgacttaa cggaggaact cgatatagag aaatcaaaat acagccaact gcaacagaaa   2100

ttgaaagcat tcacgggtcg cgaacactag                                    2130
```

<210> SEQ ID NO 14
<211> LENGTH: 709
<212> TYPE: PRT
<213> ORGANISM: Arabidopsis thaliana

<400> SEQUENCE: 14

```
Met Val Gly Gly Gly Gly Gly Ser Ser Gly Arg Gly Gly Gly Ser Gly
1               5                   10                  15

Ser Gly Ser Ser Lys Gln Gln Arg Gly Phe Ser Met Asn Pro Lys Asp
            20                  25                  30
```

```
Tyr Lys Leu Met Glu Glu Ile Gly His Gly Ala Ser Ala Val Val Tyr
        35                  40                  45

Arg Ala Ile Tyr Leu Pro Thr Asn Glu Val Val Ala Ile Lys Cys Leu
    50                  55                  60

Asp Leu Asp Arg Cys Asn Ser Asn Leu Asp Asp Ile Arg Arg Glu Ser
65                  70                  75                  80

Gln Thr Met Ser Leu Ile Asp His Pro Asn Val Ile Lys Ser Phe Cys
                85                  90                  95

Ser Phe Ser Val Asp His Ser Leu Trp Val Val Met Pro Phe Met Ala
            100                 105                 110

Gln Gly Ser Cys Leu His Leu Met Lys Thr Ala Tyr Ser Asp Gly Phe
        115                 120                 125

Glu Glu Ser Ala Ile Cys Cys Val Leu Lys Glu Thr Leu Lys Ala Leu
    130                 135                 140

Asp Tyr Leu His Arg Gln Gly His Ile His Arg Asp Val Lys Ala Gly
145                 150                 155                 160

Asn Ile Leu Leu Asp Asp Asn Gly Glu Ile Lys Leu Gly Asp Phe Gly
                165                 170                 175

Val Ser Ala Cys Leu Phe Asp Asn Gly Asp Arg Gln Arg Ala Arg Asn
            180                 185                 190

Thr Phe Val Gly Thr Pro Cys Trp Met Ala Pro Glu Val Leu Gln Pro
        195                 200                 205

Gly Asn Gly Tyr Asn Ser Lys Ala Asp Ile Trp Ser Phe Gly Ile Thr
    210                 215                 220

Ala Leu Glu Leu Ala His Gly His Ala Pro Phe Ser Lys Tyr Pro Pro
225                 230                 235                 240

Met Lys Val Leu Leu Met Thr Ile Gln Asn Ala Pro Pro Gly Leu Asp
                245                 250                 255

Tyr Asp Arg Asp Lys Lys Phe Ser Lys Ser Phe Lys Glu Met Val Ala
            260                 265                 270

Met Cys Leu Val Lys Asp Gln Thr Lys Arg Pro Thr Ala Glu Lys Leu
        275                 280                 285

Leu Lys His Ser Cys Phe Lys His Thr Lys Pro Pro Glu Gln Thr Val
    290                 295                 300

Lys Ile Leu Phe Ser Asp Leu Pro Pro Leu Trp Thr Arg Val Lys Ser
305                 310                 315                 320

Leu Gln Asp Lys Asp Ala Gln Gln Leu Ala Leu Lys Arg Met Ala Thr
                325                 330                 335

Ala Asp Glu Glu Ala Ile Ser Gln Ser Glu Tyr Gln Arg Gly Val Ser
            340                 345                 350

Ala Trp Asn Phe Asp Val Arg Asp Leu Lys Thr Gln Ala Ser Leu Leu
        355                 360                 365

Ile Asp Asp Asp Leu Glu Glu Ser Lys Glu Asp Glu Glu Ile Leu
    370                 375                 380

Cys Ala Gln Phe Asn Lys Val Asn Asp Arg Glu Gln Val Phe Asp Ser
385                 390                 395                 400

Leu Gln Leu Tyr Glu Asn Met Asn Gly Lys Glu Lys Val Ser Asn Thr
                405                 410                 415

Glu Val Glu Glu Pro Thr Cys Lys Glu Lys Phe Thr Phe Val Thr Thr
            420                 425                 430

Thr Ser Ser Leu Glu Arg Met Ser Pro Asn Ser Glu His Asp Ile Pro
        435                 440                 445

Glu Ala Lys Val Lys Pro Leu Arg Arg Gln Ser Gln Ser Gly Pro Leu
```

```
    450                 455                 460

Thr Ser Arg Thr Val Leu Ser His Ser Ala Ser Glu Lys Ser His Ile
465                 470                 475                 480

Phe Glu Arg Ser Glu Ser Glu Pro Gln Thr Ala Pro Thr Val Arg Arg
                485                 490                 495

Ala Pro Ser Phe Ser Gly Pro Leu Asn Leu Ser Thr Arg Ala Ser Ser
            500                 505                 510

Asn Ser Leu Ser Ala Pro Ile Lys Tyr Ser Gly Gly Phe Arg Asp Ser
        515                 520                 525

Leu Asp Asp Lys Ser Lys Ala Asn Leu Val Gln Lys Gly Arg Phe Ser
    530                 535                 540

Val Thr Ser Gly Asn Val Asp Leu Ala Lys Asp Val Pro Leu Ser Ile
545                 550                 555                 560

Val Pro Arg Arg Ser Pro Gln Ala Thr Pro Leu Arg Lys Ser Ala Ser
                565                 570                 575

Val Gly Asn Trp Ile Leu Glu Pro Lys Met Pro Thr Ala Gln Pro Gln
            580                 585                 590

Thr Ile Lys Glu His Ser Ser His Pro Thr Ser Ser Ser Pro Ile Met
        595                 600                 605

Pro Gln Leu Gln His Leu Phe Gln Gln Asn Ser Ile Gln Gln Asp Leu
    610                 615                 620

Ile Met Asn Leu Leu Asn Ser Leu Gln Pro Val Glu Ala Thr Glu Gly
625                 630                 635                 640

Ser Gln Ser Gly Lys Leu Pro Pro Leu Pro Arg Ser Asp Ser Asn Gly
                645                 650                 655

Asn Val Glu Pro Val Ala Ser Glu Arg Glu Arg Leu Leu Leu Ser Ser
            660                 665                 670

Ile Ser Asp Leu Arg Ala Arg Leu Asp Asp Leu Thr Glu Glu Leu Asp
        675                 680                 685

Ile Glu Lys Ser Lys Tyr Ser Gln Leu Gln Gln Lys Leu Lys Ala Phe
    690                 695                 700

Thr Gly Arg Glu His
705


<210> SEQ ID NO 15
<211> LENGTH: 1686
<212> TYPE: DNA
<213> ORGANISM: Arabidopsis thaliana

<400> SEQUENCE: 15

atgaaagaat cattcaaagt gtgtttctgt tgtgtaagaa acttcaaggt gaaatcaagt      60

gagccacctg aagaaatcaa gaaccttttc catgattact ctcaagacga caggatgtct     120

gctgatgaga tgctcagatt cgtgatccaa gttcaaggag aaacacacgc tgatatcaac     180

tacgtgaagg atatcttcca cagacttaaa catcacggcg tttttcatcc tcgtggaatt     240

catcttgaag gattctaccg ttatcttctt agtgatttca actctccatt gcctctgacc     300

cgcgaggttt ggcaagatat gaatcagcca ttatcgcatt acttcttgta cacgggacat     360

aactcttact tgactgggaa tcagttgaac agtaatagca gcatcgaacc gattgtgaaa     420

gctctgagaa atggagttcg tgtcattgag cttgatttat ggcctaactc ttcaggaaaa     480

gaagctgaag ttcgtcatgg agggacgtta acgagtcgtg aagatctgca gaaatgtctt     540

aacgtggtta aggagaacgc gtttcaggtg tctgcttatc ctgttgtgct tactttagaa     600

gaccatttaa ctccaattct tcagaagaaa gtcgctaaga tggtgagtaa gacgtttggg     660
```

```
ggatcattgt ttcaatgtac ggacgaaact acagagtgct ttccttcacc agaatcactc    720

aagaataaga tcttgatctc aacaaagcca ccaaaagagt atcttcagac ccaaatctca    780

aaaggttcaa caacggatga atccactaga gctaaaaaaa tttcggatgc agaagaacaa    840

gttcaagaag aagatgagga gagtgtagcg attgaataca gagacttaat ctcgattcac    900

gctgggaacc gcaaaggagg gttgaagaat tgcttgaatg gagatcctaa ccgagtcata    960

cggttaagca tgagtgagca gtggcttgag actctggcaa aaacccgtgg acccgattta   1020

gtaaagttca cgcagcggaa tcttttgagg atatttccca agactacacg gtttgactca   1080

tctaactatg atcctctcgt tgggtggatt catggggctc aaatggttgc cttcaatatg   1140

caaagccatg ggaggtatct gtggatgatg caaggaatgt ttaaagccaa tggtggatgt   1200

ggctatgtga aaaagcctga tgttttgctc tccaatggtc ctgaaggtga aatctttgac   1260

ccttgtagtc aaaacctccc gatcaagaca actcttaagg tgaagatcta cactggagaa   1320

ggatggaata tggactttcc tttagatcac tttgaccgat actctcctcc tgatttctac   1380

gcaaaggtcg gaatcgcagg ggttccattg gacacagcaa gttacagaac agaaatagat   1440

aaagacgaat ggtttccaat ttgggacaag gagtttgagt tcccattacg tgttcctgag   1500

ttatctcttc tgtgtatcac agtcaaagat tacgacagta acactcagaa cgatttcgct   1560

ggccagacat gttttccgtt gtcggaggta aggccaggta ttcgtgccgt tcggctccac   1620

gatcgtgccg gagaggtcta caagcacgtg agactgctca tgcggtttgt cttggagcct   1680

cgttag                                                              1686
```

```
<210> SEQ ID NO 16
<211> LENGTH: 561
<212> TYPE: PRT
<213> ORGANISM: Arabidopsis thaliana

<400> SEQUENCE: 16

Met Lys Glu Ser Phe Lys Val Cys Phe Cys Cys Val Arg Asn Phe Lys
1               5                   10                  15

Val Lys Ser Ser Glu Pro Pro Glu Glu Ile Lys Asn Leu Phe His Asp
            20                  25                  30

Tyr Ser Gln Asp Asp Arg Met Ser Ala Asp Glu Met Leu Arg Phe Val
        35                  40                  45

Ile Gln Val Gln Gly Glu Thr His Ala Asp Ile Asn Tyr Val Lys Asp
    50                  55                  60

Ile Phe His Arg Leu Lys His His Gly Val Phe His Pro Arg Gly Ile
65                  70                  75                  80

His Leu Glu Gly Phe Tyr Arg Tyr Leu Leu Ser Asp Phe Asn Ser Pro
                85                  90                  95

Leu Pro Leu Thr Arg Glu Val Trp Gln Asp Met Asn Gln Pro Leu Ser
            100                 105                 110

His Tyr Phe Leu Tyr Thr Gly His Asn Ser Tyr Leu Thr Gly Asn Gln
        115                 120                 125

Leu Asn Ser Asn Ser Ser Ile Glu Pro Ile Val Lys Ala Leu Arg Asn
    130                 135                 140

Gly Val Arg Val Ile Glu Leu Asp Leu Trp Pro Asn Ser Ser Gly Lys
145                 150                 155                 160

Glu Ala Glu Val Arg His Gly Gly Thr Leu Thr Ser Arg Glu Asp Leu
                165                 170                 175

Gln Lys Cys Leu Asn Val Val Lys Glu Asn Ala Phe Gln Val Ser Ala
```

```
            180                 185                 190

Tyr Pro Val Val Leu Thr Leu Glu Asp His Leu Thr Pro Ile Leu Gln
        195                 200                 205

Lys Lys Val Ala Lys Met Val Ser Lys Thr Phe Gly Gly Ser Leu Phe
    210                 215                 220

Gln Cys Thr Asp Glu Thr Thr Glu Cys Phe Pro Ser Pro Glu Ser Leu
225                 230                 235                 240

Lys Asn Lys Ile Leu Ile Ser Thr Lys Pro Pro Lys Glu Tyr Leu Gln
                245                 250                 255

Thr Gln Ile Ser Lys Gly Ser Thr Thr Asp Glu Ser Thr Arg Ala Lys
            260                 265                 270

Lys Ile Ser Asp Ala Glu Glu Gln Val Gln Glu Glu Asp Glu Glu Ser
        275                 280                 285

Val Ala Ile Glu Tyr Arg Asp Leu Ile Ser Ile His Ala Gly Asn Arg
    290                 295                 300

Lys Gly Gly Leu Lys Asn Cys Leu Asn Gly Asp Pro Asn Arg Val Ile
305                 310                 315                 320

Arg Leu Ser Met Ser Glu Gln Trp Leu Glu Thr Leu Ala Lys Thr Arg
                325                 330                 335

Gly Pro Asp Leu Val Lys Phe Thr Gln Arg Asn Leu Leu Arg Ile Phe
            340                 345                 350

Pro Lys Thr Thr Arg Phe Asp Ser Ser Asn Tyr Asp Pro Leu Val Gly
        355                 360                 365

Trp Ile His Gly Ala Gln Met Val Ala Phe Asn Met Gln Ser His Gly
    370                 375                 380

Arg Tyr Leu Trp Met Met Gln Gly Met Phe Lys Ala Asn Gly Gly Cys
385                 390                 395                 400

Gly Tyr Val Lys Lys Pro Asp Val Leu Leu Ser Asn Gly Pro Glu Gly
                405                 410                 415

Glu Ile Phe Asp Pro Cys Ser Gln Asn Leu Pro Ile Lys Thr Thr Leu
            420                 425                 430

Lys Val Lys Ile Tyr Thr Gly Glu Gly Trp Asn Met Asp Phe Pro Leu
        435                 440                 445

Asp His Phe Asp Arg Tyr Ser Pro Pro Asp Phe Tyr Ala Lys Val Gly
    450                 455                 460

Ile Ala Gly Val Pro Leu Asp Thr Ala Ser Tyr Arg Thr Glu Ile Asp
465                 470                 475                 480

Lys Asp Glu Trp Phe Pro Ile Trp Asp Lys Glu Phe Glu Phe Pro Leu
                485                 490                 495

Arg Val Pro Glu Leu Ser Leu Leu Cys Ile Thr Val Lys Asp Tyr Asp
            500                 505                 510

Ser Asn Thr Gln Asn Asp Phe Ala Gly Gln Thr Cys Phe Pro Leu Ser
        515                 520                 525

Glu Val Arg Pro Gly Ile Arg Ala Val Arg Leu His Asp Arg Ala Gly
    530                 535                 540

Glu Val Tyr Lys His Val Arg Leu Leu Met Arg Phe Val Leu Glu Pro
545                 550                 555                 560

Arg
```

```
<210> SEQ ID NO 17
<211> LENGTH: 549
<212> TYPE: DNA
<213> ORGANISM: Arabidopsis thaliana
```

<400> SEQUENCE: 17

```
atggcaacac actcttcctt caccgcaaca acacctctct ttctcatcgt tcttctatcc      60

ctatcctccg tctcagttct cggcgcatct caccaccacg caacggcgcc ggctccgtct     120

gtagactgtt cgactctcat actcaacatg gctgactgtt tatccttcgt ttcgagcgga     180

ggcacggtgg cgaaaccgga aggtacatgt tgctctggtc ttaagacggt gcttaaagct     240

gactctcagt gtctatgtga agcgtttaag agcagtgctt ctcttggagt tactttgaat     300

atcactaagg cttctactct tcccgccgca tgcaagcttc acgctccttc tatcgctact     360

tgtggattgt ctgttgctcc aagtactgct ccaggtcttg ctccaggagt agctgctgct     420

ggacctgaga cagccggatt tctagctcca aatccttctt cagggaacga tggatcttct     480

ttgattccga cctcgttcac aactgtactc agtgccgtac tgttcgtttt gttcttctct     540

agtgcgtag                                                             549
```

<210> SEQ ID NO 18
<211> LENGTH: 182
<212> TYPE: PRT
<213> ORGANISM: Arabidopsis thaliana

<400> SEQUENCE: 18

```
Met Ala Thr His Ser Ser Phe Thr Ala Thr Thr Pro Leu Phe Leu Ile
1               5                   10                  15

Val Leu Leu Ser Leu Ser Ser Val Ser Val Leu Gly Ala Ser His His
            20                  25                  30

His Ala Thr Ala Pro Ala Pro Ser Val Asp Cys Ser Thr Leu Ile Leu
        35                  40                  45

Asn Met Ala Asp Cys Leu Ser Phe Val Ser Ser Gly Gly Thr Val Ala
    50                  55                  60

Lys Pro Glu Gly Thr Cys Cys Ser Gly Leu Lys Thr Val Leu Lys Ala
65                  70                  75                  80

Asp Ser Gln Cys Leu Cys Glu Ala Phe Lys Ser Ser Ala Ser Leu Gly
                85                  90                  95

Val Thr Leu Asn Ile Thr Lys Ala Ser Thr Leu Pro Ala Ala Cys Lys
            100                 105                 110

Leu His Ala Pro Ser Ile Ala Thr Cys Gly Leu Ser Val Ala Pro Ser
        115                 120                 125

Thr Ala Pro Gly Leu Ala Pro Gly Val Ala Ala Ala Gly Pro Glu Thr
    130                 135                 140

Ala Gly Phe Leu Ala Pro Asn Pro Ser Ser Gly Asn Asp Gly Ser Ser
145                 150                 155                 160

Leu Ile Pro Thr Ser Phe Thr Thr Val Leu Ser Ala Val Leu Phe Val
                165                 170                 175

Leu Phe Phe Ser Ser Ala
            180
```

<210> SEQ ID NO 19
<211> LENGTH: 3579
<212> TYPE: DNA
<213> ORGANISM: Arabidopsis thaliana

<400> SEQUENCE: 19

```
atggaagagg acgatgagtt cggagatcta tattccgacg ttctccagcc gtttcaacct      60

cccgttgttc tccctcctcc gcctcctctt cctcaccgtt caatcgacct caacctccga     120

tcccaagatc aagatgtctc agaacctaat tcagctccaa tctctagggt ttcggacaac     180
```

```
gatgccgtaa aattatctac tcaggacgcg actcgtcaag caattgtcga tggtggcggc    240
gacgataagg atatgagctt tgatatcgaa gaacccgatg ccgattctac acctacgatt    300
cctggtcttt tcgttactgg agcgttacct ggtttggcta cagatcgagg cgtttcgcaa    360
gttacgacaa gaattgagca gcaggttggt ggtggtggcg atggaggcta tggaggacaa    420
ggagaaggag atgattggga tagcgacagt gaagatgatt tgcagatagt gttgaatgat    480
agtagccgta acgtcatgat cggaggagct gatagaagat caaggatggg agataatgaa    540
gatgacgatg atgaagatga tgaagaccca cttgttatag tggccgacac ggatccaaat    600
caacctatgg aggagcagat gtggggagaa gatggtcttc aagggattga aggagatggc    660
aaagacggag gagaagctgg caagggaagt ggaccaggag gtgctactgg accgcccaaa    720
gcagggtata gcagtcatgg gtatcatccg tttcattctc agtttaagta tgtaagaccg    780
ggggcagctc ccattcctgg aggtgctgca tctgttggtg gaccctcctc aggtcaagtt    840
cgtccacccg ccaaccttgg tcctatggct ggtcgtggca gaggagattg gcgtccactg    900
ggaatgagga atgcttctgc tgcacagaaa gggttccacc agccttgggg tagtaataca    960
gcagggcgtg gactggactt cactcttccc tctcacaaga ctatatttga ggtcgacata   1020
gatagttttg aagaaaagcc ctggagatat ccaggagttg agatgacaga ctacttcaac   1080
tttggactaa atgaggagag ctggaaagac tattgcaaac agctggacca acaccgtata   1140
cagactacga tgcaaagcag aatacgtgtt tatgaaagcg gtagaacgga tcagggttat   1200
gatccagatc tacccccaga gttagctgca gcaacagggg cacagggtgt tcccgttgat   1260
tcttcaaatt tagtgaagcc agactctgtt caaggtgatt cagcgaaagt gccagccaat   1320
gttagaccga cactaccccc tggaagacca atacctgtgg agactggttc tggtgaacgt   1380
cttccgtcca ttgatacacg tgctcctcgg atgcgtgatc tagatgctat cattgaggat   1440
tcacatgagg atgaaccctc gggtgaaaat ggcacagatc aagctgatag tagccttcct   1500
ggagaaaatg taccagttga gactagttat gttaacaaca aaagacctga cacggaatct   1560
gctgaacata gtcctgcaca ggatgagcca cataaaaatc ttctcaaaaa gcaagacgat   1620
gagatctcta gaagcacaga tagtggccag agttttcgtt catcgtctcc tgttggagac   1680
agaggcacaa ggtcatcaag tgttgaccgc gaagatgtgg gaggtgaagc tggcaaagat   1740
gctgagatgg gggaggagct taaaatgagt tttacatccc ctcagtcagc agtgcaagaa   1800
gatgatggag gggagtcaaa gacggagagg agtagtgaaa gcagcaaagc aagatctgga   1860
agtcacagag attttcagca agaagaggac gttattcaag ataagcattc ttctcgacca   1920
gctaacaata ggaaacagta cgataacaat gcacctcatc agagcagaaa gaatcaggac   1980
agagggaagg aaatggaaag aacacgagcg gcgagcaaag gtggtagaga gaactctaat   2040
ccacatatgg agcttgattc tacttatatc tactcaattg caagtcgcga ggattttgat   2100
aaaagaaaag agcgagatgt tgatggcgca gtctggcgca ggaaagaaga tgacccatac   2160
agtagaagag gtggggatga agggtctaga aaaagggatc gtgaagatga tccaggcttt   2220
aggcagaggg gtaaaatgcg cgagaatgaa atacgcagca aagatgatca ggttccttcc   2280
agaaaacata tggatgatgc tggtatgaga aatatttatg aaccggatga tcacattaac   2340
aagaggagga aggatgaaga atacttgaga agaagccggc ctgaaaaaaa tgaaatctca   2400
tatggtcaaa gggaatcaat gagccgcgtg aaacgagaac gtgatgatag gttggagcat   2460
caaaagagag atgtccaaca taagatcaga gatgattttg acgaccacgg ttctctcagg   2520
```

```
cagagagatg atatctatat gcagagggat ggaaacgaga ggttgaggga gcgtgatgtt   2580

ttggataaat tgaagctgcc tcacgaggat ggtatatcag cacgaggaag agagaggcag   2640

gtggcagtaa ggggccacag aggttccgaa gatcgatcat caaggatgaa ggatgagtat   2700

aaagcttctg acaaagagca tgtcacgaaa gatacattaa ggcatgctaa acagacaaag   2760

agaagggact accctggtga agaaagttct tcccatcata gaggacatga agacttctct   2820

gcacggacag acaacatagt taacaatgag aaaaaaccaa ggcaggagag gacaggtgct   2880

aaaattgata agtttattga tactttggat ggccagcgat tgcaagacag aaaacataaa   2940

gattctagac gaaagattaa agaacagcga gagggcacag aatcacttag caagcaaggg   3000

gagcaaaatg gcagttccgt agtgacagga tcaaaaggaa ccaacgacgc aaggaattgc   3060

aggagtgaga tcccacatca gcctaacacc gccaaaagac acaaggaaaa tgcatcctct   3120

ggtgatgaga tacacgattc aaagagagga cgtacaaaac tggagcgttg ggcaagccac   3180

aaagagagag aagatgctgt ctctgccaag tcatcatcca tttcctcaaa actagaagaa   3240

aaggaaaaca acactaatgg ccgtcttagt gaacctgttc atggttctat tggaaagagc   3300

cgggatgtaa ctgaagagaa aattggccat gatcttgcag acacaaaaga tggaagcgag   3360

aagggaccag gagaccggca cttggatacg gttgagaaac tcaagaaacg cagtgaaagg   3420

ttcaagcttc caatgcccac ggagaaagac accacgggag taaagaaaat ggagtctgag   3480

acactgccct ccgcaaaaat tgaaggccct gtggattcag agggagagta tgtgtgggat   3540

gagcgaagtt gtgtaagaat agggagggaa tacgcatag                           3579
```

```
<210> SEQ ID NO 20
<211> LENGTH: 1192
<212> TYPE: PRT
<213> ORGANISM: Arabidopsis thaliana

<400> SEQUENCE: 20

Met Glu Glu Asp Asp Glu Phe Gly Asp Leu Tyr Ser Asp Val Leu Gln
1               5                   10                  15

Pro Phe Gln Pro Pro Val Val Leu Pro Pro Pro Pro Pro Leu Pro His
            20                  25                  30

Arg Ser Ile Asp Leu Asn Leu Arg Ser Gln Asp Gln Asp Val Ser Glu
        35                  40                  45

Pro Asn Ser Ala Pro Ile Ser Arg Val Ser Asp Asn Asp Ala Val Lys
    50                  55                  60

Leu Ser Thr Gln Asp Ala Thr Arg Gln Ala Ile Val Asp Gly Gly Gly
65                  70                  75                  80

Asp Asp Lys Asp Met Ser Phe Asp Ile Glu Glu Pro Asp Ala Asp Ser
                85                  90                  95

Thr Pro Thr Ile Pro Gly Leu Phe Val Thr Gly Ala Leu Pro Gly Leu
            100                 105                 110

Ala Thr Asp Arg Gly Val Ser Gln Val Thr Thr Arg Ile Glu Gln Gln
        115                 120                 125

Val Gly Gly Gly Gly Asp Gly Gly Tyr Gly Gly Gln Gly Glu Gly Asp
    130                 135                 140

Asp Trp Asp Ser Asp Ser Glu Asp Asp Leu Gln Ile Val Leu Asn Asp
145                 150                 155                 160

Ser Ser Arg Asn Val Met Ile Gly Gly Ala Asp Arg Arg Ser Arg Met
                165                 170                 175

Gly Asp Asn Glu Asp Asp Asp Asp Glu Asp Asp Glu Asp Pro Leu Val
            180                 185                 190
```

```
Ile Val Ala Asp Thr Asp Pro Asn Gln Pro Met Glu Glu Gln Met Trp
        195                 200                 205

Gly Glu Asp Gly Leu Gln Gly Ile Glu Gly Asp Gly Lys Asp Gly Gly
    210                 215                 220

Glu Ala Gly Lys Gly Ser Gly Pro Gly Gly Ala Thr Gly Pro Pro Lys
225                 230                 235                 240

Ala Gly Tyr Ser Ser His Gly Tyr His Pro Phe His Ser Gln Phe Lys
                245                 250                 255

Tyr Val Arg Pro Gly Ala Ala Pro Ile Pro Gly Gly Ala Ala Ser Val
            260                 265                 270

Gly Gly Pro Ser Ser Gly Gln Val Arg Pro Pro Ala Asn Leu Gly Pro
        275                 280                 285

Met Ala Gly Arg Gly Arg Gly Asp Trp Arg Pro Leu Gly Met Arg Asn
    290                 295                 300

Ala Ser Ala Ala Gln Lys Gly Phe His Gln Pro Trp Gly Ser Asn Thr
305                 310                 315                 320

Ala Gly Arg Gly Leu Asp Phe Thr Leu Pro Ser His Lys Thr Ile Phe
                325                 330                 335

Glu Val Asp Ile Asp Ser Phe Glu Glu Lys Pro Trp Arg Tyr Pro Gly
            340                 345                 350

Val Glu Met Thr Asp Tyr Phe Asn Phe Gly Leu Asn Glu Glu Ser Trp
        355                 360                 365

Lys Asp Tyr Cys Lys Gln Leu Asp Gln His Arg Ile Gln Thr Thr Met
    370                 375                 380

Gln Ser Arg Ile Arg Val Tyr Glu Ser Gly Arg Thr Asp Gln Gly Tyr
385                 390                 395                 400

Asp Pro Asp Leu Pro Pro Glu Leu Ala Ala Ala Thr Gly Ala Gln Gly
                405                 410                 415

Val Pro Val Asp Ser Ser Asn Leu Val Lys Pro Asp Ser Val Gln Gly
            420                 425                 430

Asp Ser Ala Lys Val Pro Ala Asn Val Arg Pro Thr Leu Pro Pro Gly
        435                 440                 445

Arg Pro Ile Pro Val Glu Thr Gly Ser Gly Glu Arg Leu Pro Ser Ile
    450                 455                 460

Asp Thr Arg Ala Pro Arg Met Arg Asp Leu Asp Ala Ile Ile Glu Asp
465                 470                 475                 480

Ser His Glu Asp Glu Pro Ser Gly Glu Asn Gly Thr Asp Gln Ala Asp
                485                 490                 495

Ser Ser Leu Pro Gly Glu Asn Val Pro Val Glu Thr Ser Tyr Val Asn
            500                 505                 510

Asn Lys Arg Pro Asp Thr Glu Ser Ala Glu His Ser Pro Ala Gln Asp
        515                 520                 525

Glu Pro His Lys Asn Leu Leu Lys Lys Gln Asp Asp Glu Ile Ser Arg
    530                 535                 540

Ser Thr Asp Ser Gly Gln Ser Phe Arg Ser Ser Ser Pro Val Gly Asp
545                 550                 555                 560

Arg Gly Thr Arg Ser Ser Ser Val Asp Arg Glu Asp Val Gly Gly Glu
                565                 570                 575

Ala Gly Lys Asp Ala Glu Met Gly Glu Glu Leu Lys Met Ser Phe Thr
            580                 585                 590

Ser Pro Gln Ser Ala Val Gln Glu Asp Asp Gly Gly Glu Ser Lys Thr
        595                 600                 605
```

```
Glu Arg Ser Ser Glu Ser Ser Lys Ala Arg Ser Gly Ser His Arg Asp
    610                 615                 620

Phe Gln Gln Glu Glu Asp Val Ile Gln Asp Lys His Ser Ser Arg Pro
625                 630                 635                 640

Ala Asn Asn Arg Lys Gln Tyr Asp Asn Asn Ala Pro His Gln Ser Arg
                645                 650                 655

Lys Asn Gln Asp Arg Gly Lys Glu Met Glu Arg Thr Arg Ala Ala Ser
            660                 665                 670

Lys Gly Gly Arg Glu Asn Ser Asn Pro His Met Glu Leu Asp Ser Thr
        675                 680                 685

Tyr Ile Tyr Ser Ile Ala Ser Arg Glu Asp Phe Asp Lys Arg Lys Glu
    690                 695                 700

Arg Asp Val Asp Gly Ala Val Trp Arg Arg Lys Glu Asp Asp Pro Tyr
705                 710                 715                 720

Ser Arg Arg Gly Gly Asp Glu Gly Ser Arg Lys Arg Asp Arg Glu Asp
                725                 730                 735

Asp Pro Gly Phe Arg Gln Arg Gly Lys Met Arg Glu Asn Glu Ile Arg
            740                 745                 750

Ser Lys Asp Asp Gln Val Pro Ser Arg Lys His Met Asp Asp Ala Gly
        755                 760                 765

Met Arg Asn Ile Tyr Glu Pro Asp Asp His Ile Asn Lys Arg Arg Lys
    770                 775                 780

Asp Glu Glu Tyr Leu Arg Arg Ser Arg Pro Glu Lys Asn Glu Ile Ser
785                 790                 795                 800

Tyr Gly Gln Arg Glu Ser Met Ser Arg Val Lys Arg Glu Arg Asp Asp
                805                 810                 815

Arg Leu Glu His Gln Lys Arg Asp Val Gln His Lys Ile Arg Asp Asp
            820                 825                 830

Phe Asp Asp His Gly Ser Leu Arg Gln Arg Asp Asp Ile Tyr Met Gln
        835                 840                 845

Arg Asp Gly Asn Glu Arg Leu Arg Glu Arg Asp Val Leu Asp Lys Leu
    850                 855                 860

Lys Leu Pro His Glu Asp Gly Ile Ser Ala Arg Gly Arg Glu Arg Gln
865                 870                 875                 880

Val Ala Val Arg Gly His Arg Gly Ser Glu Asp Arg Ser Ser Arg Met
                885                 890                 895

Lys Asp Glu Tyr Lys Ala Ser Asp Lys Glu His Val Thr Lys Asp Thr
            900                 905                 910

Leu Arg His Ala Lys Gln Thr Lys Arg Arg Asp Tyr Pro Gly Glu Glu
        915                 920                 925

Ser Ser Ser His His Arg Gly His Glu Asp Phe Ser Ala Arg Thr Asp
    930                 935                 940

Asn Ile Val Asn Asn Glu Lys Lys Pro Arg Gln Glu Arg Thr Gly Ala
945                 950                 955                 960

Lys Ile Asp Lys Phe Ile Asp Thr Leu Asp Gly Gln Arg Leu Gln Asp
                965                 970                 975

Arg Lys His Lys Asp Ser Arg Arg Lys Ile Lys Glu Gln Arg Glu Gly
            980                 985                 990

Thr Glu Ser Leu Ser Lys Gln Gly  Glu Gln Asn Gly Ser  Ser Val Val
        995                 1000                1005

Thr Gly  Ser Lys Gly Thr Asn  Asp Ala Arg Asn Cys  Arg Ser Glu
    1010                1015                1020

Ile Pro  His Gln Pro Asn Thr  Ala Lys Arg His Lys  Glu Asn Ala
```

```
    1025                1030                1035

Ser Ser  Gly Asp Glu Ile His  Asp Ser Lys Arg Gly  Arg Thr Lys
    1040                1045                1050

Leu Glu  Arg Trp Ala Ser His  Lys Glu Arg Glu Asp  Ala Val Ser
    1055                1060                1065

Ala Lys  Ser Ser Ser Ile Ser  Ser Lys Leu Glu Glu  Lys Glu Asn
    1070                1075                1080

Asn Thr  Asn Gly Arg Leu Ser  Glu Pro Val His Gly  Ser Ile Gly
    1085                1090                1095

Lys Ser  Arg Asp Val Thr Glu  Glu Lys Ile Gly His  Asp Leu Ala
    1100                1105                1110

Asp Thr  Lys Asp Gly Ser Glu  Lys Gly Pro Gly Asp  Arg His Leu
    1115                1120                1125

Asp Thr  Val Glu Lys Leu Lys  Lys Arg Ser Glu Arg  Phe Lys Leu
    1130                1135                1140

Pro Met  Pro Thr Glu Lys Asp  Thr Thr Gly Val Lys  Lys Met Glu
    1145                1150                1155

Ser Glu  Thr Leu Pro Ser Ala  Lys Ile Glu Gly Pro  Val Asp Ser
    1160                1165                1170

Glu Gly  Glu Tyr Val Trp Asp  Glu Arg Ser Cys Val  Arg Ile Gly
    1175                1180                1185

Arg Glu  Tyr Ala
    1190


<210> SEQ ID NO 21
<211> LENGTH: 675
<212> TYPE: DNA
<213> ORGANISM: Arabidopsis thaliana

<400> SEQUENCE: 21

atggcggact ctgttttgaa ggaggttaac tgtggccggc ctgaaaagat cccgaagttg     60

gacaaagctt gcgaaggatc gaaatcgtcc tggaaacatc tcaagctagg aaacgtggaa    120

gatgatgagt atcttcgaca gtattgtttg tttcactacg aattccataa atccgagggt    180

ttcacggttg attgggagaa atatgactac atgttccata taaggccgtt ggaaaattca    240

ccacctatca gcgatatacg aaccaatgct gatgtgatcc gtgatgtgac actctttgcc    300

attgagaaac acaatgaagc tcatggatct aaacttgtgt ttgtcgagca tgtctcagct    360

aatttcaaat ttgccaatgg tctcctctgc tggttaacat tctgggctac cgatatggcc    420

tcatccgctc ctacatcgca gatctatcaa gtcgaacttt ggcgtcgcgg aaaacagttt    480

gaaattccca tcttcagggt caagcctaag gacgaagaga tggatgatgt tgaagtgaaa    540

ccaccctctc ccatgcctta tgatgactat gataaaccac cggttgtctt tgttcgagct    600

gctcctgaag atggtgtccc tttcgtcttt gatcgaactg gagctcttta tgatctctat    660

cggtctggtt tgtag                                                     675


<210> SEQ ID NO 22
<211> LENGTH: 224
<212> TYPE: PRT
<213> ORGANISM: Arabidopsis thaliana

<400> SEQUENCE: 22

Met Ala Asp Ser Val Leu Lys Glu Val Asn Cys Gly Arg Pro Glu Lys
1               5                   10                  15

Ile Pro Lys Leu Asp Lys Ala Cys Glu Gly Ser Lys Ser Ser Trp Lys
```

```
            20                  25                  30

His Leu Lys Leu Gly Asn Val Glu Asp Asp Glu Tyr Leu Arg Gln Tyr
        35                  40                  45

Cys Leu Phe His Tyr Glu Phe His Lys Ser Glu Gly Phe Thr Val Asp
    50                  55                  60

Trp Glu Lys Tyr Asp Tyr Met Phe His Ile Arg Pro Leu Glu Asn Ser
65                  70                  75                  80

Pro Pro Ile Ser Asp Ile Arg Thr Asn Ala Asp Val Ile Arg Asp Val
                85                  90                  95

Thr Leu Phe Ala Ile Glu Lys His Asn Glu Ala His Gly Ser Lys Leu
            100                 105                 110

Val Phe Val Glu His Val Ser Ala Asn Phe Lys Phe Ala Asn Gly Leu
        115                 120                 125

Leu Cys Trp Leu Thr Phe Trp Ala Thr Asp Met Ala Ser Ser Ala Pro
    130                 135                 140

Thr Ser Gln Ile Tyr Gln Val Glu Leu Trp Arg Arg Gly Lys Gln Phe
145                 150                 155                 160

Glu Ile Pro Ile Phe Arg Val Lys Pro Lys Asp Glu Glu Met Asp Asp
                165                 170                 175

Val Glu Val Lys Pro Pro Ser Pro Met Pro Tyr Asp Asp Tyr Asp Lys
            180                 185                 190

Pro Pro Val Val Phe Val Arg Ala Ala Pro Glu Asp Gly Val Pro Phe
        195                 200                 205

Val Phe Asp Arg Thr Gly Ala Leu Tyr Asp Leu Tyr Arg Ser Gly Leu
    210                 215                 220


<210> SEQ ID NO 23
<211> LENGTH: 939
<212> TYPE: DNA
<213> ORGANISM: Arabidopsis thaliana

<400> SEQUENCE: 23

atgggagaaa tgattgtttc aatggaccaa gatatccgac tggatacaac acgagcaaga      60

ttgtcaaacc ttctcaagag gcatcgagaa ttgtcagacc gtcttactag ggattctgat     120

aagacaatgt tagatcgctt aaacaaagaa tttgaagctg cacggagatc ccaaagtcag     180

gaagtcttct tagatgggga agagtggaat gatggtttgt tggccacatt aagggaacgg     240

gtgcatatgg aagctgacag aaaggcagat aacggtaatg caggtttttc actagtttgt     300

catcctgaag aacgaattac ttacagagtg ggaaataagg tgatatgttg cctagatgga     360

tcgagaattg gaatacagtt tgaaacatct actgcaggag aaacttacga ggtttaccac     420

tgtgtgcttg agagcaagtc gtttttggag aagatgattg tgcttgagca cacaattcct     480

ttctttttgc cgctaagtga cttggaaaat gatcttcttt tttcgaatgc taagaaattc     540

atcgataatg ttggggatct cctgcaagca tatgtggaca gaaaggaaca ggtccggctt     600

atcaaagagc tctttggaca tcagatcagt gagatttatc acagtcttcc ttaccacatg     660

attgaatttt ctatggatga ttgtgactgc aagttcgtgg tgagccttag atatggagat     720

cttctgtgtg aacttccgac aaaagtgaga attctagtat ggccaatgca tcatctgtcg     780

aagaaacagt gtacaagccc tggaagtcca gcaatccctg tgcgtttacc atttgccgag     840

gatgctttcc ggatccaatc actacctgaa gcatacgcag agattatgcc gaacatgccg     900

aatgaaattc ggcaattatt tcagactagt ccaagctag                            939
```

<210> SEQ ID NO 24
<211> LENGTH: 312
<212> TYPE: PRT
<213> ORGANISM: Arabidopsis thaliana

<400> SEQUENCE: 24

```
Met Gly Glu Met Ile Val Ser Met Asp Gln Asp Ile Arg Leu Asp Thr
1               5                   10                  15

Thr Arg Ala Arg Leu Ser Asn Leu Leu Lys Arg His Arg Glu Leu Ser
            20                  25                  30

Asp Arg Leu Thr Arg Asp Ser Asp Lys Thr Met Leu Asp Arg Leu Asn
        35                  40                  45

Lys Glu Phe Glu Ala Ala Arg Arg Ser Gln Ser Gln Glu Val Phe Leu
    50                  55                  60

Asp Gly Glu Glu Trp Asn Asp Gly Leu Leu Ala Thr Leu Arg Glu Arg
65                  70                  75                  80

Val His Met Glu Ala Asp Arg Lys Ala Asp Asn Gly Asn Ala Gly Phe
                85                  90                  95

Ser Leu Val Cys His Pro Glu Glu Arg Ile Thr Tyr Arg Val Gly Asn
            100                 105                 110

Lys Val Ile Cys Cys Leu Asp Gly Ser Arg Ile Gly Ile Gln Phe Glu
        115                 120                 125

Thr Ser Thr Ala Gly Glu Thr Tyr Glu Val Tyr His Cys Val Leu Glu
    130                 135                 140

Ser Lys Ser Phe Leu Glu Lys Met Ile Val Leu Glu His Thr Ile Pro
145                 150                 155                 160

Phe Phe Leu Pro Leu Ser Asp Leu Glu Asn Asp Leu Leu Phe Ser Asn
                165                 170                 175

Ala Lys Lys Phe Ile Asp Asn Val Gly Asp Leu Leu Gln Ala Tyr Val
            180                 185                 190

Asp Arg Lys Glu Gln Val Arg Leu Ile Lys Glu Leu Phe Gly His Gln
        195                 200                 205

Ile Ser Glu Ile Tyr His Ser Leu Pro Tyr His Met Ile Glu Phe Ser
    210                 215                 220

Met Asp Asp Cys Asp Cys Lys Phe Val Val Ser Leu Arg Tyr Gly Asp
225                 230                 235                 240

Leu Leu Cys Glu Leu Pro Thr Lys Val Arg Ile Leu Val Trp Pro Met
                245                 250                 255

His His Leu Ser Lys Lys Gln Cys Thr Ser Pro Gly Ser Pro Ala Ile
            260                 265                 270

Pro Val Arg Leu Pro Phe Ala Glu Asp Ala Phe Arg Ile Gln Ser Leu
        275                 280                 285

Pro Glu Ala Tyr Ala Glu Ile Met Pro Asn Met Pro Asn Glu Ile Arg
    290                 295                 300

Gln Leu Phe Gln Thr Ser Pro Ser
305                 310
```

<210> SEQ ID NO 25
<211> LENGTH: 633
<212> TYPE: DNA
<213> ORGANISM: Arabidopsis thaliana

<400> SEQUENCE: 25

```
atggagttct ctaccgccga ctttgaaagg cttatcatgt tcgaacatgc tcgcaaaaat     60

tctgaggctc agtacaagaa cgatcctctt gattccgaga atctgctgaa atggggtgga    120
```

```
gctttacttg aactttcaca gttccagcct attcctgaag ctaagctcat gttaaatgat    180

gctatttcca agttggaaga ggccttgaca ataaatccag ggaagcatca ggctctttgg    240

tgtattgcca acgcgtacac cgcccacgcg ttttatgttc acgatcctga agaagcaaaa    300

gagcactttg ataaagccac tgaatatttc cagagagcag aaaatgagga tccaggtaat    360

gacacatatc gcaagtcctt ggattcctca ctaaaggccc cggaactgca tatgcagttt    420

atgaatcaag gaatgggaca gcaaatacta ggtggaggag gaggaggagg tggaggagga    480

atggcttcat ctaatgttag ccagagtagt aagaagaaga agaggaacac tgaattcact    540

tatgatgtat gcggttggat aattctcgct tgtgggattg ttgcttgggt tggcatggca    600

aaatcccttg gccctccacc tcctgccaga tag                                 633
```

```
<210> SEQ ID NO 26
<211> LENGTH: 210
<212> TYPE: PRT
<213> ORGANISM: Arabidopsis thaliana

<400> SEQUENCE: 26

Met Glu Phe Ser Thr Ala Asp Phe Glu Arg Leu Ile Met Phe Glu His
1               5                   10                  15

Ala Arg Lys Asn Ser Glu Ala Gln Tyr Lys Asn Asp Pro Leu Asp Ser
            20                  25                  30

Glu Asn Leu Leu Lys Trp Gly Gly Ala Leu Leu Glu Leu Ser Gln Phe
        35                  40                  45

Gln Pro Ile Pro Glu Ala Lys Leu Met Leu Asn Asp Ala Ile Ser Lys
    50                  55                  60

Leu Glu Glu Ala Leu Thr Ile Asn Pro Gly Lys His Gln Ala Leu Trp
65                  70                  75                  80

Cys Ile Ala Asn Ala Tyr Thr Ala His Ala Phe Tyr Val His Asp Pro
                85                  90                  95

Glu Glu Ala Lys Glu His Phe Asp Lys Ala Thr Glu Tyr Phe Gln Arg
            100                 105                 110

Ala Glu Asn Glu Asp Pro Gly Asn Asp Thr Tyr Arg Lys Ser Leu Asp
        115                 120                 125

Ser Ser Leu Lys Ala Pro Glu Leu His Met Gln Phe Met Asn Gln Gly
    130                 135                 140

Met Gly Gln Gln Ile Leu Gly Gly Gly Gly Gly Gly Gly Gly Gly Gly
145                 150                 155                 160

Met Ala Ser Ser Asn Val Ser Gln Ser Ser Lys Lys Lys Lys Arg Asn
                165                 170                 175

Thr Glu Phe Thr Tyr Asp Val Cys Gly Trp Ile Ile Leu Ala Cys Gly
            180                 185                 190

Ile Val Ala Trp Val Gly Met Ala Lys Ser Leu Gly Pro Pro Pro Pro
        195                 200                 205

Ala Arg
    210
```

```
<210> SEQ ID NO 27
<211> LENGTH: 1812
<212> TYPE: DNA
<213> ORGANISM: Arabidopsis thaliana

<400> SEQUENCE: 27

atggcagctt cttcaactaa tgctcgtctc accaaccctc ctcgtctact ctccaaaccc     60

cgactttcac ctacctccgt cgccaatctc cgttttccag ccgccgattt ctccactcgc    120
```

```
ttctttgccg attcttcgtc cccgcggcta aggagtgtac cgtttccggt ggtattttcc    180

gatcaaaggc gccggcgaag catggaacct agcaatgtct atgtggcttc aaattccacg    240

gaaatggaga tcggaagtca tgatatcgtg aagaatccga gcttgatctg tgctccagtg    300

atggcggatt caatagacaa gatggtgatt gaaacgagta aagcccatga attgggtgca    360

gacttggttg aaattcgatt agattggcta aaggacttca atcctcttga ggatctaaaa    420

accattatta agaaatctcc tctacccact ttattcacct acagaccaaa atgggaaggt    480

ggtcagtatg aaggtgatga aaatgagaga cgggatgtgc ttcgtctggc catggagttg    540

ggagctgatt atattgatgt tgaacttcag gtggcaagtg agttcatcaa atctattgac    600

ggaaagaagc ctggaaagtt caaagtaatt gtttcatcgc acaactatca gaataccccct   660

tctgttgagg accttgatgg ccttgttgca agaatacaac agactggagc cgacattgtt    720

aagattgcta ctactgctgt ggacattgca gatgttgctc gcatgttcca tataacctca    780

aaagctcaag ttcccacaat tggacttgtt atgggtgaaa gaggtttgat gtctcggatt    840

ctttgttcga aatttggtgg ttatttgacc tttggcacct tagattctag taaagtttct    900

gcgccaggtc aaccaacgat caaggatctg ttggatcttt acaactttag aagaattggt    960

cctgacacaa aggtatatgg aattattggc aagcctgtca gccacagcaa atcacctatt   1020

gttcacaatc aagctttcaa atcagttgat tttaatggag tatatgtcca cctgttagtt   1080

gataatcttg taagcttttct tcaagcatac tcatcctctg atttcgctgg attcagctgt  1140

acaattccgc acaaagaagc tgcattgcaa tgttgtgatg aagttgatcc attggcaaag   1200

tctataggag ctgtgaacac tatactaagg agaaaaagtg acggaaagtt gttgggttac   1260

aacacagatt gtattggttc catttctgct attgaggatg gcctacgaag ttcaggtgat   1320

ccaagcagtg taccttcttc ttcttcgcca ttggccagta aaacagtggt ggttattggt   1380

gctggtggag caggcaaggc tcttgcttat ggtgcaaaag aaaagggggc caaagttgta   1440

attgctaatc gaacttacga acgagcacta gaactcgcag aagcaatagg aggcaaagcg   1500

ttatctctga cagatttaga taactatcac ccagaagatg gcatggtttt ggcaaacaca   1560

acatctatgg gtatgcaacc aaatgttgag gagactccaa tttctaagga tgcattgaag   1620

cactatgcac tggtctttga tgcggtatac actccgagaa tcaccagact gttgagggaa   1680

gcagaagaaa gtggagccat aactgtctca gggtcagaga tgtttgtcag gcaggcttac   1740

gagcagtttg agatcttcac cggtttaccc gctccaaagg aactctactg gcaaataatg   1800

tcaaagtact ag                                                       1812
```

<210> SEQ ID NO 28
<211> LENGTH: 603
<212> TYPE: PRT
<213> ORGANISM: Arabidopsis thaliana

<400> SEQUENCE: 28

```
Met Ala Ala Ser Ser Thr Asn Ala Arg Leu Thr Asn Pro Pro Arg Leu
1               5                   10                  15

Leu Ser Lys Pro Arg Leu Ser Pro Thr Ser Val Ala Asn Leu Arg Phe
            20                  25                  30

Pro Ala Ala Asp Phe Ser Thr Arg Phe Phe Ala Asp Ser Ser Ser Pro
        35                  40                  45

Arg Leu Arg Ser Val Pro Phe Pro Val Val Phe Ser Asp Gln Arg Arg
    50                  55                  60
```

```
Arg Arg Ser Met Glu Pro Ser Asn Val Tyr Val Ala Ser Asn Ser Thr
65                  70                  75                  80

Glu Met Glu Ile Gly Ser His Asp Ile Val Lys Asn Pro Ser Leu Ile
                85                  90                  95

Cys Ala Pro Val Met Ala Asp Ser Ile Asp Lys Met Val Ile Glu Thr
            100                 105                 110

Ser Lys Ala His Glu Leu Gly Ala Asp Leu Val Glu Ile Arg Leu Asp
        115                 120                 125

Trp Leu Lys Asp Phe Asn Pro Leu Glu Asp Leu Lys Thr Ile Ile Lys
    130                 135                 140

Lys Ser Pro Leu Pro Thr Leu Phe Thr Tyr Arg Pro Lys Trp Glu Gly
145                 150                 155                 160

Gly Gln Tyr Glu Gly Asp Glu Asn Glu Arg Arg Asp Val Leu Arg Leu
                165                 170                 175

Ala Met Glu Leu Gly Ala Asp Tyr Ile Asp Val Glu Leu Gln Val Ala
            180                 185                 190

Ser Glu Phe Ile Lys Ser Ile Asp Gly Lys Lys Pro Gly Lys Phe Lys
        195                 200                 205

Val Ile Val Ser Ser His Asn Tyr Gln Asn Thr Pro Ser Val Glu Asp
    210                 215                 220

Leu Asp Gly Leu Val Ala Arg Ile Gln Gln Thr Gly Ala Asp Ile Val
225                 230                 235                 240

Lys Ile Ala Thr Thr Ala Val Asp Ile Ala Asp Val Ala Arg Met Phe
                245                 250                 255

His Ile Thr Ser Lys Ala Gln Val Pro Thr Ile Gly Leu Val Met Gly
            260                 265                 270

Glu Arg Gly Leu Met Ser Arg Ile Leu Cys Ser Lys Phe Gly Gly Tyr
        275                 280                 285

Leu Thr Phe Gly Thr Leu Asp Ser Ser Lys Val Ser Ala Pro Gly Gln
    290                 295                 300

Pro Thr Ile Lys Asp Leu Leu Asp Leu Tyr Asn Phe Arg Arg Ile Gly
305                 310                 315                 320

Pro Asp Thr Lys Val Tyr Gly Ile Ile Gly Lys Pro Val Ser His Ser
                325                 330                 335

Lys Ser Pro Ile Val His Asn Gln Ala Phe Lys Ser Val Asp Phe Asn
            340                 345                 350

Gly Val Tyr Val His Leu Leu Val Asp Asn Leu Val Ser Phe Leu Gln
        355                 360                 365

Ala Tyr Ser Ser Ser Asp Phe Ala Gly Phe Ser Cys Thr Ile Pro His
    370                 375                 380

Lys Glu Ala Ala Leu Gln Cys Cys Asp Glu Val Asp Pro Leu Ala Lys
385                 390                 395                 400

Ser Ile Gly Ala Val Asn Thr Ile Leu Arg Arg Lys Ser Asp Gly Lys
                405                 410                 415

Leu Leu Gly Tyr Asn Thr Asp Cys Ile Gly Ser Ile Ser Ala Ile Glu
            420                 425                 430

Asp Gly Leu Arg Ser Ser Gly Asp Pro Ser Ser Val Pro Ser Ser Ser
        435                 440                 445

Ser Pro Leu Ala Ser Lys Thr Val Val Val Ile Gly Ala Gly Gly Ala
    450                 455                 460

Gly Lys Ala Leu Ala Tyr Gly Ala Lys Glu Lys Gly Ala Lys Val Val
465                 470                 475                 480

Ile Ala Asn Arg Thr Tyr Glu Arg Ala Leu Glu Leu Ala Glu Ala Ile
```

```
                485                 490                 495

Gly Gly Lys Ala Leu Ser Leu Thr Asp Leu Asp Asn Tyr His Pro Glu
            500                 505                 510

Asp Gly Met Val Leu Ala Asn Thr Thr Ser Met Gly Met Gln Pro Asn
        515                 520                 525

Val Glu Glu Thr Pro Ile Ser Lys Asp Ala Leu Lys His Tyr Ala Leu
    530                 535                 540

Val Phe Asp Ala Val Tyr Thr Pro Arg Ile Thr Arg Leu Leu Arg Glu
545                 550                 555                 560

Ala Glu Glu Ser Gly Ala Ile Thr Val Ser Gly Ser Glu Met Phe Val
                565                 570                 575

Arg Gln Ala Tyr Glu Gln Phe Glu Ile Phe Thr Gly Leu Pro Ala Pro
            580                 585                 590

Lys Glu Leu Tyr Trp Gln Ile Met Ser Lys Tyr
        595                 600


<210> SEQ ID NO 29
<211> LENGTH: 789
<212> TYPE: DNA
<213> ORGANISM: Zea mays

<400> SEQUENCE: 29

atggcggggc tctacgagaa gcagtcggag acgtacgcca agaagcgtcc gcagtacccc      60

aaggagtggt tctccatgct ggccagcctc accgcggggc accagcgcgc ctgggacgcc     120

gggtgtggca ccggccaggc cgccatcagc atggcggagc actacgagag cgtggtggcg     180

acggacgtga gcgaggggca gctccggcac gccaccgcgc acccgaaggt gcggtacctc     240

cacaccccgg agcacctctc ggaggacgag ctggtgtcgc tggtcggcgg cgagggctcc     300

ctggacctgg tcgtggtggc cacctccatc cactggttcg acgtcccgct cttctacgcc     360

gtcgtgagcc gcgccctgcg gaagcccggc ggcatgctcg ccgtgtgggg ctacaactac     420

gagatccacc cgttcgagga cgcgctgcac ggccagctct acccggccct gcggccgtac     480

ctggacccgc gggcgggact ggccatggag cggtacaggt ccctgccgtt cccgttcgag     540

cccgtcgggg tgggcgccga gggcgcgccc gccgacgtgg acatcgaggt ggagatgacg     600

ctggaggacc tggtcgggtt cctgaacacc ggctctgtcg tgaccacggc gagggccaag     660

ggcgtggacc tggaggcggt cacgagggcc gcgctgaagc gtgtggagga gcagtggggc     720

ggcgcgccca ccgtgccgag gaagctcgtg ttcaaggcgt tcatgctcgc cgggaggccc     780

aagtgctag                                                             789


<210> SEQ ID NO 30
<211> LENGTH: 262
<212> TYPE: PRT
<213> ORGANISM: Zea mays

<400> SEQUENCE: 30

Met Ala Gly Leu Tyr Glu Lys Gln Ser Glu Thr Tyr Ala Lys Lys Arg
1               5                   10                  15

Pro Gln Tyr Pro Lys Glu Trp Phe Ser Met Leu Ala Ser Leu Thr Ala
            20                  25                  30

Gly His Gln Arg Ala Trp Asp Ala Gly Cys Gly Thr Gly Gln Ala Ala
        35                  40                  45

Ile Ser Met Ala Glu His Tyr Glu Ser Val Val Ala Thr Asp Val Ser
    50                  55                  60
```

```
Glu Gly Gln Leu Arg His Ala Thr Ala His Pro Lys Val Arg Tyr Leu
65                  70                  75                  80

His Thr Pro Glu His Leu Ser Glu Asp Glu Leu Val Ser Leu Val Gly
                85                  90                  95

Gly Glu Gly Ser Leu Asp Leu Val Val Val Ala Thr Ser Ile His Trp
            100                 105                 110

Phe Asp Val Pro Leu Phe Tyr Ala Val Val Ser Arg Ala Leu Arg Lys
        115                 120                 125

Pro Gly Gly Met Leu Ala Val Trp Gly Tyr Asn Tyr Glu Ile His Pro
    130                 135                 140

Phe Glu Asp Ala Leu His Gly Gln Leu Tyr Pro Ala Leu Arg Pro Tyr
145                 150                 155                 160

Leu Asp Pro Arg Ala Gly Leu Ala Met Glu Arg Tyr Arg Ser Leu Pro
                165                 170                 175

Phe Pro Phe Glu Pro Val Gly Val Gly Ala Glu Gly Ala Pro Ala Asp
            180                 185                 190

Val Asp Ile Glu Val Glu Met Thr Leu Glu Asp Leu Val Gly Phe Leu
        195                 200                 205

Asn Thr Gly Ser Val Val Thr Thr Ala Arg Ala Lys Gly Val Asp Leu
    210                 215                 220

Glu Ala Val Thr Arg Ala Ala Leu Lys Arg Val Glu Glu Gln Trp Gly
225                 230                 235                 240

Gly Ala Pro Thr Val Pro Arg Lys Leu Val Phe Lys Ala Phe Met Leu
                245                 250                 255

Ala Gly Arg Pro Lys Cys
            260


<210> SEQ ID NO 31
<211> LENGTH: 648
<212> TYPE: DNA
<213> ORGANISM: Arabidopsis thaliana

<400> SEQUENCE: 31

atgggaatgg tttttggtaa aatcgctgta gagactccta aatacacggt gactaaatcc      60

ggtgacggtt atgagatccg tgaatatcca ccagcggttg cggcggaggt tacatacgat     120

gcgtcggagt tcaaaggtga taaagacgga ggctttcagc ttttggctaa gtacataggt     180

gtgtttggca aaccggagaa tgagaaaccg gagaaaattg ctatgactgc accggtgatc     240

actaaggaag gtgagaagat tgcgatgact gctccggtga ttactaagga gagtgagaag     300

attgagatga cttctccggt tgtaactaag gaaggtggtg gagaaggaag gaagaagttg     360

gtgacgatgc agtttttgtt gccgtcgatg tataagaagg cggaggaggc accacgtcca     420

acggatgaga gggttgtgat taaggaggaa ggagggagga agtatggtgt gattaagttt     480

agtggtatag cgtcggagag tgtggtgagt gagaaggtga agaagctgag tagtcatctt     540

gagaaagatg ggtttaagat caccggagat ttcgttcttg ctaggtataa tcctccatgg     600

acgttaccac cgtttaggac caatgaggtc atgattcctg ttgaatag                  648


<210> SEQ ID NO 32
<211> LENGTH: 215
<212> TYPE: PRT
<213> ORGANISM: Arabidopsis thaliana

<400> SEQUENCE: 32

Met Gly Met Val Phe Gly Lys Ile Ala Val Glu Thr Pro Lys Tyr Thr
1               5                   10                  15
```

```
Val Thr Lys Ser Gly Asp Gly Tyr Glu Ile Arg Glu Tyr Pro Pro Ala
            20                  25                  30

Val Ala Ala Glu Val Thr Tyr Asp Ala Ser Glu Phe Lys Gly Asp Lys
        35                  40                  45

Asp Gly Gly Phe Gln Leu Leu Ala Lys Tyr Ile Gly Val Phe Gly Lys
    50                  55                  60

Pro Glu Asn Glu Lys Pro Glu Lys Ile Ala Met Thr Ala Pro Val Ile
65                  70                  75                  80

Thr Lys Glu Gly Glu Lys Ile Ala Met Thr Ala Pro Val Ile Thr Lys
                85                  90                  95

Glu Ser Glu Lys Ile Glu Met Thr Ser Pro Val Val Thr Lys Glu Gly
            100                 105                 110

Gly Gly Glu Gly Arg Lys Lys Leu Val Thr Met Gln Phe Leu Leu Pro
        115                 120                 125

Ser Met Tyr Lys Lys Ala Glu Glu Ala Pro Arg Pro Thr Asp Glu Arg
    130                 135                 140

Val Val Ile Lys Glu Glu Gly Gly Arg Lys Tyr Gly Val Ile Lys Phe
145                 150                 155                 160

Ser Gly Ile Ala Ser Glu Ser Val Val Ser Glu Lys Val Lys Lys Leu
                165                 170                 175

Ser Ser His Leu Glu Lys Asp Gly Phe Lys Ile Thr Gly Asp Phe Val
            180                 185                 190

Leu Ala Arg Tyr Asn Pro Pro Trp Thr Leu Pro Pro Phe Arg Thr Asn
        195                 200                 205

Glu Val Met Ile Pro Val Glu
    210                 215

<210> SEQ ID NO 33
<211> LENGTH: 663
<212> TYPE: DNA
<213> ORGANISM: Sorghum bicolor

<400> SEQUENCE: 33

atggcctccg cgacgggggg ttcctcctcg gagatggcgg tggaccaccc gacggggccg      60

ggcgccgtgg agaagccgca attcgatgct ctgatgccga gtgagatgag cggcgggagg     120

ccccagttcc gaaaagtgac cgtgccgcag caccggttcg cgccgctcaa gcgatgctgg     180

atggaaatct acacgcccgt ttacgagcac atgaagatcg acatacgcat gaacctcaag     240

gcaaggaggg tggagctaaa gacaagacaa gatacaccag atgtgagcaa ccttcagaag     300

tgtgctgact ttgtgcatgc ttttatgctt gggtttgaca ttgctgatgc cgtcgccttg     360

ctgcgtcttg atgacctcta tgtggattcc tttgagatca aggacgtgaa gaccctgcga     420

ggggagcatc tgtcgcgtgc tattggccgc ctatcaggga aaggaggcaa gaccaagtat     480

gccattgaga actctaccag gacccgcatc gttatcgctg atacaaagat ccatatactt     540

ggatcctttg ttaacatcaa ggttgcgcgg gattcgcttt gcagtctcat cttgggttct     600

cctgctggca aagtgtattc gaagctaagg gctgtatcag ctaggttggc ggaaaggtat     660

tag                                                                   663

<210> SEQ ID NO 34
<211> LENGTH: 220
<212> TYPE: PRT
<213> ORGANISM: Sorghum bicolor

<400> SEQUENCE: 34
```

```
Met Ala Ser Ala Thr Gly Gly Ser Ser Ser Glu Met Ala Val Asp His
1               5                   10                  15

Pro Thr Gly Pro Gly Ala Val Glu Lys Pro Gln Phe Asp Ala Leu Met
            20                  25                  30

Pro Ser Glu Met Ser Gly Gly Arg Pro Gln Phe Arg Lys Val Thr Val
        35                  40                  45

Pro Gln His Arg Phe Ala Pro Leu Lys Arg Cys Trp Met Glu Ile Tyr
    50                  55                  60

Thr Pro Val Tyr Glu His Met Lys Ile Asp Ile Arg Met Asn Leu Lys
65                  70                  75                  80

Ala Arg Arg Val Glu Leu Lys Thr Arg Gln Asp Thr Pro Asp Val Ser
                85                  90                  95

Asn Leu Gln Lys Cys Ala Asp Phe Val His Ala Phe Met Leu Gly Phe
            100                 105                 110

Asp Ile Ala Asp Ala Val Ala Leu Leu Arg Leu Asp Asp Leu Tyr Val
        115                 120                 125

Asp Ser Phe Glu Ile Lys Asp Val Lys Thr Leu Arg Gly Glu His Leu
    130                 135                 140

Ser Arg Ala Ile Gly Arg Leu Ser Gly Lys Gly Gly Lys Thr Lys Tyr
145                 150                 155                 160

Ala Ile Glu Asn Ser Thr Arg Thr Arg Ile Val Ile Ala Asp Thr Lys
                165                 170                 175

Ile His Ile Leu Gly Ser Phe Val Asn Ile Lys Val Ala Arg Asp Ser
            180                 185                 190

Leu Cys Ser Leu Ile Leu Gly Ser Pro Ala Gly Lys Val Tyr Ser Lys
        195                 200                 205

Leu Arg Ala Val Ser Ala Arg Leu Ala Glu Arg Tyr
    210                 215                 220
```

<210> SEQ ID NO 35
<211> LENGTH: 564
<212> TYPE: DNA
<213> ORGANISM: Arabidopsis thaliana

<400> SEQUENCE: 35

```
atgagtcggc tcttgctacc taaacttttc tcaatctcta gaacacaggt tccagctgca      60

tcattgttca ataatctgta cagacgtcac aaacgttttg ttcattggac gagtaagatg     120

tcaacagata gtgttagatc atccacaact ggtggttctg cttctggagc tagaacattt     180

tgctccctcg cagatttatc aaccaaaaag tgtgtgccat gcaatgcgaa ggatctgcgc     240

gccatgaccg aacaaagtgc ccaagaccta cttcaaaagg ttgctggatg ggatttggcc     300

aatgacaatg atacattaaa gctgcatcgg tcatggaggg tgaaaagttt tacaaagggg     360

ctagatttct tccaacgtgt agctgatatc gctgaatcag aaggtcatca cccagatttg     420

catctggtcg gctggaataa tgtgaaaatt gagatatgga cacatgcgat aggtggtttg     480

acagaaaacg acttcattct tgctgctaag atcaacgagc tccaagtgga agatcttctg     540

aggaagaaga aagttgctaa gtag                                            564
```

<210> SEQ ID NO 36
<211> LENGTH: 187
<212> TYPE: PRT
<213> ORGANISM: Arabidopsis thaliana

<400> SEQUENCE: 36

```
Met Ser Arg Leu Leu Leu Pro Lys Leu Phe Ser Ile Ser Arg Thr Gln
1               5                   10                  15

Val Pro Ala Ala Ser Leu Phe Asn Asn Leu Tyr Arg Arg His Lys Arg
            20                  25                  30

Phe Val His Trp Thr Ser Lys Met Ser Thr Asp Ser Val Arg Ser Ser
        35                  40                  45

Thr Thr Gly Gly Ser Ala Ser Gly Ala Arg Thr Phe Cys Ser Leu Ala
    50                  55                  60

Asp Leu Ser Thr Lys Lys Cys Val Pro Cys Asn Ala Lys Asp Leu Arg
65                  70                  75                  80

Ala Met Thr Glu Gln Ser Ala Gln Asp Leu Leu Gln Lys Val Ala Gly
                85                  90                  95

Trp Asp Leu Ala Asn Asp Asn Asp Thr Leu Lys Leu His Arg Ser Trp
            100                 105                 110

Arg Val Lys Ser Phe Thr Lys Gly Leu Asp Phe Phe Gln Arg Val Ala
        115                 120                 125

Asp Ile Ala Glu Ser Glu Gly His His Pro Asp Leu His Leu Val Gly
    130                 135                 140

Trp Asn Asn Val Lys Ile Glu Ile Trp Thr His Ala Ile Gly Gly Leu
145                 150                 155                 160

Thr Glu Asn Asp Phe Ile Leu Ala Ala Lys Ile Asn Glu Leu Gln Val
                165                 170                 175

Glu Asp Leu Leu Arg Lys Lys Lys Val Ala Lys
            180                 185


<210> SEQ ID NO 37
<211> LENGTH: 1176
<212> TYPE: DNA
<213> ORGANISM: Arabidopsis thaliana

<400> SEQUENCE: 37

atggtgaaac tggagaactc gaggaaaccc gaaaaaattt cgaacaagaa catccccatg     60

tccgatttcg tggtcaatct ggatcatggt gatccaacgg cgtacgaaga atactggagg    120

aagatgggtg acaggtgtac ggtgacgata cgtggttgtg atctcatgag ttacttcagc    180

gacatgacga acttgtgttg gttccttgag ccagagcttg aagatgcgat caaggacttg    240

cacggtgttg ttggtaacgc tgcgacggag gatcggtaca tagtggttgg gaccggttcg    300

acgcagcttt gtcaagccgc cgtccacgca ctctcttcac tagccaggag tcaacctgtc    360

agcgtcgtcg ccgccgctcc tttttactcc acatatgtgg aggagacgac atatgttcgg    420

tcgggtatgt acaagtggga aggagacgca tggggtttcg acaaaaaggg tccgtacatc    480

gagctagtga cgtcacctaa taaccctgac ggaaccatca gagagacggt ggtgaaccgt    540

ccagacgacg acgaagccaa agtgatccat gactttgctt attactggcc ccactacact    600

cccatcactc gccgtcaaga ccatgacatc atgctcttca ctttctccaa gatcacaggc    660

cacgctgggt cccgtattgg gtgggcattg gtgaaggaca aggaggtagc taagaagatg    720

gttgagtata ttattgtgaa ctcgattggt gtgtctaagg agtcacaggt tcgaacagct    780

aagatactca acgttctaaa ggagacttgt aagagcgagt ccgagtctga gaatttcttc    840

aagtatggtc gtgagatgat gaagaatcgg tgggagaagc tacgtgaagt tgtgaaagag    900

agcgatgctt tcactcttcc caagtaccct gaagcatttt gcaactactt tggaaaatca    960

ctcgaatctt accctgcgtt tgcgtggcta gggacgaagg aagagacgga tctggtaagt   1020

gaattgagga gacacaaggt aatgagcaga gctggagagc gttgtggatc tgacaagaag   1080
```

```
catgtccgag tcagcatgct tagtcgtgaa gacgttttca atgtctttct cgagagactc   1140

gccaacatga agctcattaa aagcattgac ctttag                             1176


<210> SEQ ID NO 38
<211> LENGTH: 391
<212> TYPE: PRT
<213> ORGANISM: Arabidopsis thaliana

<400> SEQUENCE: 38

Met Val Lys Leu Glu Asn Ser Arg Lys Pro Glu Lys Ile Ser Asn Lys
1               5                   10                  15

Asn Ile Pro Met Ser Asp Phe Val Val Asn Leu Asp His Gly Asp Pro
            20                  25                  30

Thr Ala Tyr Glu Glu Tyr Trp Arg Lys Met Gly Asp Arg Cys Thr Val
        35                  40                  45

Thr Ile Arg Gly Cys Asp Leu Met Ser Tyr Phe Ser Asp Met Thr Asn
    50                  55                  60

Leu Cys Trp Phe Leu Glu Pro Glu Leu Glu Asp Ala Ile Lys Asp Leu
65                  70                  75                  80

His Gly Val Val Gly Asn Ala Ala Thr Glu Asp Arg Tyr Ile Val Val
                85                  90                  95

Gly Thr Gly Ser Thr Gln Leu Cys Gln Ala Ala Val His Ala Leu Ser
            100                 105                 110

Ser Leu Ala Arg Ser Gln Pro Val Ser Val Val Ala Ala Ala Pro Phe
        115                 120                 125

Tyr Ser Thr Tyr Val Glu Glu Thr Thr Tyr Val Arg Ser Gly Met Tyr
    130                 135                 140

Lys Trp Glu Gly Asp Ala Trp Gly Phe Asp Lys Lys Gly Pro Tyr Ile
145                 150                 155                 160

Glu Leu Val Thr Ser Pro Asn Asn Pro Asp Gly Thr Ile Arg Glu Thr
                165                 170                 175

Val Val Asn Arg Pro Asp Asp Asp Glu Ala Lys Val Ile His Asp Phe
            180                 185                 190

Ala Tyr Tyr Trp Pro His Tyr Thr Pro Ile Thr Arg Arg Gln Asp His
        195                 200                 205

Asp Ile Met Leu Phe Thr Phe Ser Lys Ile Thr Gly His Ala Gly Ser
    210                 215                 220

Arg Ile Gly Trp Ala Leu Val Lys Asp Lys Glu Val Ala Lys Lys Met
225                 230                 235                 240

Val Glu Tyr Ile Ile Val Asn Ser Ile Gly Val Ser Lys Glu Ser Gln
                245                 250                 255

Val Arg Thr Ala Lys Ile Leu Asn Val Leu Lys Glu Thr Cys Lys Ser
            260                 265                 270

Glu Ser Glu Ser Glu Asn Phe Phe Lys Tyr Gly Arg Glu Met Met Lys
        275                 280                 285

Asn Arg Trp Glu Lys Leu Arg Glu Val Val Lys Glu Ser Asp Ala Phe
    290                 295                 300

Thr Leu Pro Lys Tyr Pro Glu Ala Phe Cys Asn Tyr Phe Gly Lys Ser
305                 310                 315                 320

Leu Glu Ser Tyr Pro Ala Phe Ala Trp Leu Gly Thr Lys Glu Glu Thr
                325                 330                 335

Asp Leu Val Ser Glu Leu Arg Arg His Lys Val Met Ser Arg Ala Gly
            340                 345                 350
```

```
Glu Arg Cys Gly Ser Asp Lys Lys His Val Arg Val Ser Met Leu Ser
        355                 360                 365

Arg Glu Asp Val Phe Asn Val Phe Leu Glu Arg Leu Ala Asn Met Lys
    370                 375                 380

Leu Ile Lys Ser Ile Asp Leu
385                 390


<210> SEQ ID NO 39
<211> LENGTH: 2004
<212> TYPE: DNA
<213> ORGANISM: Zea mays

<400> SEQUENCE: 39

atggctggct ccgtagctcc ccacgctgtg gtcctcggtc ttctcctgct cgcggggctc     60

gcggcggcgc agagggcgac gacgccggct gcggcggccc ccgcgcccga ccccggctgc    120

aacggcatcc agctgaccta caacttcgtg gaccgcacca agatccggcc cttcgtcagc    180

gacaagaaca agcagcccta cgccttccgc gccaacgtca ccgtgctcaa ctccggcacc    240

cgcccgctca agtcctgggc ggcactcgtc acattcggct acggcgagat cctcgtcggc    300

gtcgacggcg ccgtgctcac gggcggcggc gacctgccgt acaacaccac ggaggacgcc    360

ggcaacgcca cctcgttctc cgggtacccg catacagacc tcctcacgcc catcgccacc    420

gccggggacc tgtcgcagat ccaggcctcc gtcggcatcg tcggcacgct cttcgccggg    480

cccggcccgt tcgtgccgct ccccaccgcg ctgtcgctgg acgacccggc ctacgcgtgc    540

ccggcggcga ccaacgtcac tgctcgggtg ctgtccacgt gctgcgtcct cacgccggag    600

gccgaggcca acgccactgc catcgacgcc aacaccaccg acccgaccaa ggatttcctg    660

ccgcgcggca ccggcgacct cgtcatcacc tacgatgtgc tccaggccta cccctccagc    720

taccttgcgc tcgtcacgct cgagaacaac gccaagctcg gccgcctcga caactggcgg    780

ctgtcgtggg agtggcggcg tggggagttc atctactcaa tgaaaggagc tcacccatca    840

gaggtggaca cctcgggctg tatctgtggg gcgcctgggc agtactacca gagccttgat    900

ttttcgcagg tgctcaattg tgaccgcaag ccggtgatcc ttgacctgcc cctgtcccgg    960

tacaacgaca ctcagattgg gaagattgac aattgctgca ggaatgggac aatcttgccc   1020

aagtccatgg acgaggcaca gtcgaaatct gcgttccaga tgcaagtttt caagatgcca   1080

ccagacctga accggactaa gctgttcccc cctgctaatt tcaagatcgt gggtgcatca   1140

tcgctgaacc cggactatgc ctgtggccag ccggtgcctg tcagcccaac cgcgttccca   1200

gacccgagcg ggcttgactc gacgacgctt gctgtggcaa catggcaggt ggtgtgcaac   1260

attaccacga caaagggggc caagcccaag tgttgtgtga ccttctcggc gtactacaac   1320

gactcagtga tcccctgcag cacctgcgct tgtgggtgcc ctgcaaacag gcgagggcca   1380

acgtgcagca ccaccgcaca atccatgctg ctgccaccgg aggcgctgct tgtgccattc   1440

gacaaccggt cacagaaggc gttggcgtgg gctgagctga agcattacaa tgtgccccgg   1500

ccgatgcctt gcggtgactt ttgtggcgtg agcatcaatt ggcatgtctc aacggactac   1560

aacaagggct ggagcgctcg ggtgacattg ttcaactggg aggatgtcga catggccaat   1620

tggtttgctg ccatcgtcat ggacaaggcg tatgacggct ttgagaaggc ttactcgttc   1680

aacggcaccg cagtgggcaa gaacacgatc tttatgcagg gtctggaggg gcttaattac   1740

ctggtgaagc agaccaacat gagtgggtcc gactaccttg ttcctggcaa gcaacagtca   1800

gtcctctcat tcaccaagaa gctgaccccg ggttaaatg ttgttgctgg agatggcttc    1860
```

```
ccaacaaagg tcttcttcaa tggcgacgaa tgcgctatgc cacagagaat tccgatcagc   1920

actggattca gcacccgtct cagcagtggc cttgctctgg ttccgttcct tgttgcttcg   1980

gctttcctat tgctccagca atag                                          2004


<210> SEQ ID NO 40
<211> LENGTH: 667
<212> TYPE: PRT
<213> ORGANISM: Zea mays

<400> SEQUENCE: 40

Met Ala Gly Ser Val Ala Pro His Ala Val Val Leu Gly Leu Leu Leu
1               5                   10                  15

Leu Ala Gly Leu Ala Ala Ala Gln Arg Ala Thr Thr Pro Ala Ala Ala
            20                  25                  30

Ala Pro Ala Pro Asp Pro Gly Cys Asn Gly Ile Gln Leu Thr Tyr Asn
        35                  40                  45

Phe Val Asp Arg Thr Lys Ile Arg Pro Phe Val Ser Asp Lys Asn Lys
    50                  55                  60

Gln Pro Tyr Ala Phe Arg Ala Asn Val Thr Val Leu Asn Ser Gly Thr
65                  70                  75                  80

Arg Pro Leu Lys Ser Trp Ala Ala Leu Val Thr Phe Gly Tyr Gly Glu
                85                  90                  95

Ile Leu Val Gly Val Asp Gly Ala Val Leu Thr Gly Gly Gly Asp Leu
            100                 105                 110

Pro Tyr Asn Thr Thr Glu Asp Ala Gly Asn Ala Thr Ser Phe Ser Gly
        115                 120                 125

Tyr Pro His Thr Asp Leu Leu Thr Pro Ile Ala Thr Ala Gly Asp Leu
    130                 135                 140

Ser Gln Ile Gln Ala Ser Val Gly Ile Val Gly Thr Leu Phe Ala Gly
145                 150                 155                 160

Pro Gly Pro Phe Val Pro Leu Pro Thr Ala Leu Ser Leu Asp Asp Pro
                165                 170                 175

Ala Tyr Ala Cys Pro Ala Ala Thr Asn Val Thr Ala Arg Val Leu Ser
            180                 185                 190

Thr Cys Cys Val Leu Thr Pro Glu Ala Glu Ala Asn Ala Thr Ala Ile
        195                 200                 205

Asp Ala Asn Thr Thr Asp Pro Thr Lys Asp Phe Leu Pro Arg Gly Thr
    210                 215                 220

Gly Asp Leu Val Ile Thr Tyr Asp Val Leu Gln Ala Tyr Pro Ser Ser
225                 230                 235                 240

Tyr Leu Ala Leu Val Thr Leu Glu Asn Asn Ala Lys Leu Gly Arg Leu
                245                 250                 255

Asp Asn Trp Arg Leu Ser Trp Glu Trp Arg Arg Gly Glu Phe Ile Tyr
            260                 265                 270

Ser Met Lys Gly Ala His Pro Ser Glu Val Asp Thr Ser Gly Cys Ile
        275                 280                 285

Cys Gly Ala Pro Gly Gln Tyr Tyr Gln Ser Leu Asp Phe Ser Gln Val
    290                 295                 300

Leu Asn Cys Asp Arg Lys Pro Val Ile Leu Asp Leu Pro Leu Ser Arg
305                 310                 315                 320

Tyr Asn Asp Thr Gln Ile Gly Lys Ile Asp Asn Cys Cys Arg Asn Gly
                325                 330                 335

Thr Ile Leu Pro Lys Ser Met Asp Glu Ala Gln Ser Lys Ser Ala Phe
            340                 345                 350
```

```
Gln Met Gln Val Phe Lys Met Pro Pro Asp Leu Asn Arg Thr Lys Leu
        355                 360                 365

Phe Pro Pro Ala Asn Phe Lys Ile Val Gly Ala Ser Ser Leu Asn Pro
    370                 375                 380

Asp Tyr Ala Cys Gly Gln Pro Val Pro Val Ser Pro Thr Ala Phe Pro
385                 390                 395                 400

Asp Pro Ser Gly Leu Asp Ser Thr Thr Leu Ala Val Ala Thr Trp Gln
                405                 410                 415

Val Val Cys Asn Ile Thr Thr Thr Lys Gly Ala Lys Pro Lys Cys Cys
            420                 425                 430

Val Thr Phe Ser Ala Tyr Tyr Asn Asp Ser Val Ile Pro Cys Ser Thr
        435                 440                 445

Cys Ala Cys Gly Cys Pro Ala Asn Arg Arg Gly Pro Thr Cys Ser Thr
    450                 455                 460

Thr Ala Gln Ser Met Leu Leu Pro Pro Glu Ala Leu Leu Val Pro Phe
465                 470                 475                 480

Asp Asn Arg Ser Gln Lys Ala Leu Ala Trp Ala Glu Leu Lys His Tyr
                485                 490                 495

Asn Val Pro Arg Pro Met Pro Cys Gly Asp Phe Cys Gly Val Ser Ile
            500                 505                 510

Asn Trp His Val Ser Thr Asp Tyr Asn Lys Gly Trp Ser Ala Arg Val
        515                 520                 525

Thr Leu Phe Asn Trp Glu Asp Val Asp Met Ala Asn Trp Phe Ala Ala
    530                 535                 540

Ile Val Met Asp Lys Ala Tyr Asp Gly Phe Glu Lys Ala Tyr Ser Phe
545                 550                 555                 560

Asn Gly Thr Ala Val Gly Lys Asn Thr Ile Phe Met Gln Gly Leu Glu
                565                 570                 575

Gly Leu Asn Tyr Leu Val Lys Gln Thr Asn Met Ser Gly Ser Asp Tyr
            580                 585                 590

Leu Val Pro Gly Lys Gln Gln Ser Val Leu Ser Phe Thr Lys Lys Leu
        595                 600                 605

Thr Pro Gly Leu Asn Val Val Ala Gly Asp Gly Phe Pro Thr Lys Val
    610                 615                 620

Phe Phe Asn Gly Asp Glu Cys Ala Met Pro Gln Arg Ile Pro Ile Ser
625                 630                 635                 640

Thr Gly Phe Ser Thr Arg Leu Ser Ser Gly Leu Ala Leu Val Pro Phe
                645                 650                 655

Leu Val Ala Ser Ala Phe Leu Leu Leu Gln Gln
            660                 665
```

```
<210> SEQ ID NO 41
<211> LENGTH: 2292
<212> TYPE: DNA
<213> ORGANISM: Saccharomyces cerevisiae

<400> SEQUENCE: 41

atgaacgata gccaaaactg cctacgacag agggaagaaa atagtcatct gaatcctgga      60

aatgacttcg gccaccacca gggtgcagaa tgtacgataa atcataacaa catgccacac     120

cgcaatgcat acacagaatc tacgaatgac acggaagcaa agtccatagt gatgtgcgac     180

gatcctaacg cataccaaat ttcctacaca aataatgagc cggcgggaga tggagctata     240

gaaaccacgt ccattctact atcgcaaccg ctgccgctgc gatcgaatgt gatgtctgtc     300
```

```
ttggtaggca tatttgttgc cgtggggggc ttcttgtttg ggtatgacac tggacttata    360

aacagtatca cggatatgcc gtatgttaaa acctacattg ctccgaacca ttcatatttc    420

accactagcc aaatagccat actcgtatca ttcctctccc taggaacatt tttcggtgcg    480

ttaatcgctc cctatatttc agattcatat ggtaggaagc caacaattat gtttagtacc    540

gctgttatct tttccatcgg aaactcatta caggtggcat ccggtggctt ggtgctatta    600

atcgtcggaa gagtgatctc aggtatcggg atcgggataa tctctgctgt ggttcctctt    660

tatcaagctg aagctgcgca gaagaacctt agaggtgcca tcatttccag ttatcagtgg    720

gctatcacta ttgggttact cgtgtccagt gcagtatcgc aaggaactca ttccaaaaat    780

ggcccgtctt catatagaat accaattggt ttgcagtacg tttggtcaag tattttagct    840

gtgggcatga tattccttcc agagagtcca agatattacg tcttgaagga tgaactcaat    900

aaagctgcaa aatcgttatc ctttttaaga ggcctcccga tcgaagatcc aagactctta    960

gaggagcttg ttgaaataaa agccacttac gattatgaag catcgttcgg cccgtcaaca   1020

cttttagatt gtttcaaaac aagtgaaaat agacccaaac agattttacg aatatttact   1080

ggtatcgcca tacaagcttt tcaacaggca tctggtatca attttatatt ctactatgga   1140

gttaattttt tcaacaacac aggggtggac aactcttact tggtttcttt tatcagctat   1200

gccgtcaacg tcgccttcag tataccgggt atgtatttag tggatcgaat tggtagaaga   1260

ccagtccttc ttgctggagg tgtcataatg gcaatagcaa atttagtcat tgccatcgtt   1320

ggtgtttccg agggaaaaac tgttgttgct agtaaaatta tgattgcttt tatatgcctt   1380

ttcattgctg cattttcggc gacatggggt ggtgtcgtgt gggtggtatc tgctgaactg   1440

tacccacttg gtgtcagatc gaaatgtacc gccatatgcg ctgccgcaaa ttggctagtt   1500

aatttcacct gtgccctgat tacaccttac attgttgatg tcggatcaca cacttcttca   1560

atggggccca aaatattctt catttggggc ggcttaaatg tcgtggccgt tatcgttgtt   1620

tatttcgctg tttatgaaac gaggggattg actttggaag agattgacga gttatttaga   1680

aaggccccaa atagcgtcat ttctagcaaa tggaacaaaa aaataaggaa aaggtgctta   1740

gcctttccca tttcacaaca aatagagatg aaaactaata tcaagaacgc tggaaagttg   1800

gacaacaaca acagtccaat tgtacaggat gacagccaca acataatcga tgtggatgga   1860

ttcttggaga accaaataca gtccaatgat catatgattg cggcggataa aggaagtggc   1920

tcgttagtaa acatcatcga tactgccccc ctaacatcta cagagtttaa acccgtggaa   1980

catccgccag taaattacgt cgacttgggg aatggtttgg gtctgaatac atacaataga   2040

ggtcctcctt ctatcatttc tgactctact gatgagttct atgaggaaaa tgactcctct   2100

tattacaata acaacactga acgaaatgga gctaacagcg tcaatacata tatggctcaa   2160

ctaatcaata gctcatctac tacaagcaac gacacatcgt tctctccatc acacaatagc   2220

aatgcaagaa cgtcctctaa ttggacgagt gacctcgcta gtaagcacag ccaatacact   2280

tccccccaat ag                                                       2292
```

```
<210> SEQ ID NO 42
<211> LENGTH: 763
<212> TYPE: PRT
<213> ORGANISM: Saccharomyces cerevisiae

<400> SEQUENCE: 42

Met Asn Asp Ser Gln Asn Cys Leu Arg Gln Arg Glu Glu Asn Ser His
1               5                   10                  15
```

```
Leu Asn Pro Gly Asn Asp Phe Gly His His Gln Gly Ala Glu Cys Thr
            20                  25                  30

Ile Asn His Asn Asn Met Pro His Arg Asn Ala Tyr Thr Glu Ser Thr
        35                  40                  45

Asn Asp Thr Glu Ala Lys Ser Ile Val Met Cys Asp Asp Pro Asn Ala
    50                  55                  60

Tyr Gln Ile Ser Tyr Thr Asn Asn Glu Pro Ala Gly Asp Gly Ala Ile
65                  70                  75                  80

Glu Thr Thr Ser Ile Leu Leu Ser Gln Pro Leu Pro Leu Arg Ser Asn
                85                  90                  95

Val Met Ser Val Leu Val Gly Ile Phe Val Ala Val Gly Gly Phe Leu
            100                 105                 110

Phe Gly Tyr Asp Thr Gly Leu Ile Asn Ser Ile Thr Asp Met Pro Tyr
        115                 120                 125

Val Lys Thr Tyr Ile Ala Pro Asn His Ser Tyr Phe Thr Thr Ser Gln
    130                 135                 140

Ile Ala Ile Leu Val Ser Phe Leu Ser Leu Gly Thr Phe Phe Gly Ala
145                 150                 155                 160

Leu Ile Ala Pro Tyr Ile Ser Asp Ser Tyr Gly Arg Lys Pro Thr Ile
                165                 170                 175

Met Phe Ser Thr Ala Val Ile Phe Ser Ile Gly Asn Ser Leu Gln Val
            180                 185                 190

Ala Ser Gly Gly Leu Val Leu Leu Ile Val Gly Arg Val Ile Ser Gly
        195                 200                 205

Ile Gly Ile Gly Ile Ile Ser Ala Val Val Pro Leu Tyr Gln Ala Glu
    210                 215                 220

Ala Ala Gln Lys Asn Leu Arg Gly Ala Ile Ile Ser Ser Tyr Gln Trp
225                 230                 235                 240

Ala Ile Thr Ile Gly Leu Leu Val Ser Ser Ala Val Ser Gln Gly Thr
                245                 250                 255

His Ser Lys Asn Gly Pro Ser Ser Tyr Arg Ile Pro Ile Gly Leu Gln
            260                 265                 270

Tyr Val Trp Ser Ser Ile Leu Ala Val Gly Met Ile Phe Leu Pro Glu
        275                 280                 285

Ser Pro Arg Tyr Tyr Val Leu Lys Asp Glu Leu Asn Lys Ala Ala Lys
    290                 295                 300

Ser Leu Ser Phe Leu Arg Gly Leu Pro Ile Glu Asp Pro Arg Leu Leu
305                 310                 315                 320

Glu Glu Leu Val Glu Ile Lys Ala Thr Tyr Asp Tyr Glu Ala Ser Phe
                325                 330                 335

Gly Pro Ser Thr Leu Leu Asp Cys Phe Lys Thr Ser Glu Asn Arg Pro
            340                 345                 350

Lys Gln Ile Leu Arg Ile Phe Thr Gly Ile Ala Ile Gln Ala Phe Gln
        355                 360                 365

Gln Ala Ser Gly Ile Asn Phe Ile Phe Tyr Tyr Gly Val Asn Phe Phe
    370                 375                 380

Asn Asn Thr Gly Val Asp Asn Ser Tyr Leu Val Ser Phe Ile Ser Tyr
385                 390                 395                 400

Ala Val Asn Val Ala Phe Ser Ile Pro Gly Met Tyr Leu Val Asp Arg
                405                 410                 415

Ile Gly Arg Arg Pro Val Leu Leu Ala Gly Gly Val Ile Met Ala Ile
            420                 425                 430

Ala Asn Leu Val Ile Ala Ile Val Gly Val Ser Glu Gly Lys Thr Val
```

```
        435                 440                 445

Val Ala Ser Lys Ile Met Ile Ala Phe Ile Cys Leu Phe Ile Ala Ala
    450                 455                 460

Phe Ser Ala Thr Trp Gly Gly Val Val Trp Val Val Ser Ala Glu Leu
465                 470                 475                 480

Tyr Pro Leu Gly Val Arg Ser Lys Cys Thr Ala Ile Cys Ala Ala Ala
                485                 490                 495

Asn Trp Leu Val Asn Phe Thr Cys Ala Leu Ile Thr Pro Tyr Ile Val
            500                 505                 510

Asp Val Gly Ser His Thr Ser Ser Met Gly Pro Lys Ile Phe Phe Ile
        515                 520                 525

Trp Gly Gly Leu Asn Val Val Ala Val Ile Val Val Tyr Phe Ala Val
    530                 535                 540

Tyr Glu Thr Arg Gly Leu Thr Leu Glu Glu Ile Asp Glu Leu Phe Arg
545                 550                 555                 560

Lys Ala Pro Asn Ser Val Ile Ser Ser Lys Trp Asn Lys Lys Ile Arg
                565                 570                 575

Lys Arg Cys Leu Ala Phe Pro Ile Ser Gln Gln Ile Glu Met Lys Thr
            580                 585                 590

Asn Ile Lys Asn Ala Gly Lys Leu Asp Asn Asn Asn Ser Pro Ile Val
        595                 600                 605

Gln Asp Asp Ser His Asn Ile Ile Asp Val Asp Gly Phe Leu Glu Asn
    610                 615                 620

Gln Ile Gln Ser Asn Asp His Met Ile Ala Ala Asp Lys Gly Ser Gly
625                 630                 635                 640

Ser Leu Val Asn Ile Ile Asp Thr Ala Pro Leu Thr Ser Thr Glu Phe
                645                 650                 655

Lys Pro Val Glu His Pro Pro Val Asn Tyr Val Asp Leu Gly Asn Gly
            660                 665                 670

Leu Gly Leu Asn Thr Tyr Asn Arg Gly Pro Pro Ser Ile Ile Ser Asp
        675                 680                 685

Ser Thr Asp Glu Phe Tyr Glu Glu Asn Asp Ser Ser Tyr Tyr Asn Asn
    690                 695                 700

Asn Thr Glu Arg Asn Gly Ala Asn Ser Val Asn Thr Tyr Met Ala Gln
705                 710                 715                 720

Leu Ile Asn Ser Ser Ser Thr Thr Ser Asn Asp Thr Ser Phe Ser Pro
                725                 730                 735

Ser His Asn Ser Asn Ala Arg Thr Ser Ser Asn Trp Thr Ser Asp Leu
            740                 745                 750

Ala Ser Lys His Ser Gln Tyr Thr Ser Pro Gln
        755                 760
```

```
<210> SEQ ID NO 43
<211> LENGTH: 609
<212> TYPE: DNA
<213> ORGANISM: Glycine max

<400> SEQUENCE: 43

atgtctaaca ccagcaacaa tgtcgctggg gtcgacaaca cgttcagaag aaaatttgat      60

cgagaagagt atctagaacg agcacgggag cgcgagagac aggaggagga gggtcgagcg     120

aaacctaaag ccaaaggtcc tcccgtgcag aggaagccct tgaaacatag agattatgaa     180

gtggaccttg aatcccgctt gggcaagact caggttgtta cgccggttgc accactaagt     240

cagcaggctg gatactactg ctcagtttgt gagtgtgtgg tgaaggactc tgcaaactac     300
```

```
ttggatcata ttaatggaaa gaaacatcaa agagccttgg gcatgtccat gcgagtagaa    360

cgtgcttctc tccaacaggt tcaggaacga tttgaagttc ttaagaagcg taaagatgtt    420

ggcagcttca cagagcaaga tcttgacgag cggattttaa aacagcagca agaggaggaa    480

gaaagaaagc gactgcgtcg agaaaagaaa aaagaaaaga aggagaaggc agttgaagaa    540

cctgaaattg atcctgatgt tgctgccatg atggggtttg gaggtttccg gtcatccaac    600

aagaaatag                                                            609
```

<210> SEQ ID NO 44
<211> LENGTH: 202
<212> TYPE: PRT
<213> ORGANISM: Glycine max

<400> SEQUENCE: 44

```
Met Ser Asn Thr Ser Asn Asn Val Ala Gly Val Asp Asn Thr Phe Arg
1               5                   10                  15

Arg Lys Phe Asp Arg Glu Glu Tyr Leu Glu Arg Ala Arg Glu Arg Glu
            20                  25                  30

Arg Gln Glu Glu Glu Gly Arg Ala Lys Pro Lys Ala Lys Gly Pro Pro
        35                  40                  45

Val Gln Arg Lys Pro Leu Lys His Arg Asp Tyr Glu Val Asp Leu Glu
    50                  55                  60

Ser Arg Leu Gly Lys Thr Gln Val Val Thr Pro Val Ala Pro Leu Ser
65                  70                  75                  80

Gln Gln Ala Gly Tyr Tyr Cys Ser Val Cys Glu Cys Val Val Lys Asp
                85                  90                  95

Ser Ala Asn Tyr Leu Asp His Ile Asn Gly Lys Lys His Gln Arg Ala
            100                 105                 110

Leu Gly Met Ser Met Arg Val Glu Arg Ala Ser Leu Gln Gln Val Gln
        115                 120                 125

Glu Arg Phe Glu Val Leu Lys Lys Arg Lys Asp Val Gly Ser Phe Thr
    130                 135                 140

Glu Gln Asp Leu Asp Glu Arg Ile Leu Lys Gln Gln Gln Glu Glu Glu
145                 150                 155                 160

Glu Arg Lys Arg Leu Arg Arg Glu Lys Lys Lys Glu Lys Lys Glu Lys
                165                 170                 175

Ala Val Glu Glu Pro Glu Ile Asp Pro Asp Val Ala Ala Met Met Gly
            180                 185                 190

Phe Gly Gly Phe Arg Ser Ser Asn Lys Lys
        195                 200
```

<210> SEQ ID NO 45
<211> LENGTH: 531
<212> TYPE: DNA
<213> ORGANISM: Arabidopsis thaliana

<400> SEQUENCE: 45

```
atgatgaaca gctgtggaat ccaacaaaac gcttttgaag agatgaggag aaacgccgcc     60

gtttctgatc ggagagacgc cgtgatttgt cctaaacctc gtcgtgttgg tgctcttaat    120

caccactctt ctcgatctct ccgttggcaa ctcaatcatc agatggaatt atgtgaatcg    180

aattcaggaa gtgagatttt ggatttcatc ctcacaaagg gtggtggtgg tggtggtgag    240

caagatcaga cgaggacggt gatgacgcca cctctgttct ttacagggtc acctccaagt    300

agagtttcta acccattaac aaaagattca ctttttcgag aagagcttct catggtggct    360
```

```
tctccgagtc catcgactcc acgagcaacc aaaccgcagc caccgtcttc tccaaggaac    420

ggtagttgtg ttatggcggc gacgagtttc gggaacaatc ctgtggttcg tgttgtgggg    480

tttgattgtg acagacgcag cagcaacagg agcatttcga ctcttgcata g             531


<210> SEQ ID NO 46
<211> LENGTH: 176
<212> TYPE: PRT
<213> ORGANISM: Arabidopsis thaliana

<400> SEQUENCE: 46

Met Met Asn Ser Cys Gly Ile Gln Gln Asn Ala Phe Glu Glu Met Arg
1               5                   10                  15

Arg Asn Ala Ala Val Ser Asp Arg Arg Asp Ala Val Ile Cys Pro Lys
            20                  25                  30

Pro Arg Arg Val Gly Ala Leu Asn His His Ser Ser Arg Ser Leu Arg
        35                  40                  45

Trp Gln Leu Asn His Gln Met Glu Leu Cys Glu Ser Asn Ser Gly Ser
    50                  55                  60

Glu Ile Leu Asp Phe Ile Leu Thr Lys Gly Gly Gly Gly Gly Gly Glu
65                  70                  75                  80

Gln Asp Gln Thr Arg Thr Val Met Thr Pro Pro Leu Phe Phe Thr Gly
                85                  90                  95

Ser Pro Pro Ser Arg Val Ser Asn Pro Leu Thr Lys Asp Ser Leu Phe
            100                 105                 110

Arg Glu Glu Leu Leu Met Val Ala Ser Pro Ser Pro Ser Thr Pro Arg
        115                 120                 125

Ala Thr Lys Pro Gln Pro Pro Ser Ser Pro Arg Asn Gly Ser Cys Val
    130                 135                 140

Met Ala Ala Thr Ser Phe Gly Asn Asn Pro Val Val Arg Val Val Gly
145                 150                 155                 160

Phe Asp Cys Asp Arg Arg Ser Ser Asn Arg Ser Ile Ser Thr Leu Ala
                165                 170                 175


<210> SEQ ID NO 47
<211> LENGTH: 1287
<212> TYPE: DNA
<213> ORGANISM: Arabidopsis thaliana

<400> SEQUENCE: 47

atgatgacga caacaaccaa tactatggct atgcttcaaa acctcgtctt ctctgttcca     60

atctctcgta tggtagttcg gcgtcactcc ctcgctacca ccttctccgc tgccgccaca    120

accgtcgtac cgtctcctaa accggtatca gccaaaccgg cgcgtactcc acacgtggac    180

tcacatgttc tcatcggaat gtcagagcct gagcttcaag agcttgctat caacctcggt    240

caagaaggat acagaggaaa gcagctccat catcttattt acaagagaaa ggttaataaa    300

gttgaagact ttagcaattt gccactgacg tttcgtaaag gacttgtgga tggtggattt    360

aaagtgggaa gatcacccat ttaccaaact gttactgcca ctgatggtac cattaagctt    420

ctgctaaagc ttgaagataa cctattgatc gaaactgttg gtataccagt tcaagatgat    480

gagaagggca taacgcgcct caccgcttgt gtctcttccc aggttggatg tccgcttcgt    540

tgttcgtttt gtgccacggg aaaaggaggc ttttcaagaa atctgcagcg ccatgaaatt    600

attgagcagg tgttggctat cgaggacgtg ttcaagcata gggtgacaaa tgtggttttc    660

atgggaatgg gtgagccgat gttgaaccta aagtcagtac ttgatgctca tcgttgtttg    720
```

```
aacaaggaca ttgaaatcgg acaacgaatg attacaatat cgactgtagg tgttccaaac    780

acaatcaaga agcttgcatc tcataagctt cagtcgacct tagctgtcag cttacatgcg    840

ccaaatcaga gcctcaggga gaaaattgta ccaagtgcca aggcttatcc gctggaagca    900

attatgaagg attgtcgtga ttacttccaa gaaacaaata gacgagtctc tttcgaatat    960

gcccttctag ctggagtcaa tgatcaagtt gagcatgcgg tggaacttgc agagctactc   1020

cgtgaatggg gtaaaactta tcacgtaaat ttgatacctt acaacccgat agagggatca   1080

gagtaccagc gaccttacaa gaaagcggtc ctagcgtttg cagctgcgtt ggagtcgcgt   1140

aagataacag caagcgtaag gcaaacaaga ggacttgatg caagtgctgc ttgtggtcag   1200

ctgaggaata agtttcagaa aagccctttg cttactgaga cggatagtca agagtctcag   1260

ccagatgcag aagctgtcgc ttgttag                                       1287
```

```
<210> SEQ ID NO 48
<211> LENGTH: 428
<212> TYPE: PRT
<213> ORGANISM: Arabidopsis thaliana

<400> SEQUENCE: 48

Met Met Thr Thr Thr Thr Asn Thr Met Ala Met Leu Gln Asn Leu Val
1               5                   10                  15

Phe Ser Val Pro Ile Ser Arg Met Val Val Arg Arg His Ser Leu Ala
            20                  25                  30

Thr Thr Phe Ser Ala Ala Ala Thr Thr Val Val Pro Ser Pro Lys Pro
        35                  40                  45

Val Ser Ala Lys Pro Ala Arg Thr Pro His Val Asp Ser His Val Leu
    50                  55                  60

Ile Gly Met Ser Glu Pro Glu Leu Gln Glu Leu Ala Ile Asn Leu Gly
65                  70                  75                  80

Gln Glu Gly Tyr Arg Gly Lys Gln Leu His His Leu Ile Tyr Lys Arg
                85                  90                  95

Lys Val Asn Lys Val Glu Asp Phe Ser Asn Leu Pro Leu Thr Phe Arg
            100                 105                 110

Lys Gly Leu Val Asp Gly Gly Phe Lys Val Gly Arg Ser Pro Ile Tyr
        115                 120                 125

Gln Thr Val Thr Ala Thr Asp Gly Thr Ile Lys Leu Leu Leu Lys Leu
    130                 135                 140

Glu Asp Asn Leu Leu Ile Glu Thr Val Gly Ile Pro Val Gln Asp Asp
145                 150                 155                 160

Glu Lys Gly Ile Thr Arg Leu Thr Ala Cys Val Ser Ser Gln Val Gly
                165                 170                 175

Cys Pro Leu Arg Cys Ser Phe Cys Ala Thr Gly Lys Gly Gly Phe Ser
            180                 185                 190

Arg Asn Leu Gln Arg His Glu Ile Ile Glu Gln Val Leu Ala Ile Glu
        195                 200                 205

Asp Val Phe Lys His Arg Val Thr Asn Val Val Phe Met Gly Met Gly
    210                 215                 220

Glu Pro Met Leu Asn Leu Lys Ser Val Leu Asp Ala His Arg Cys Leu
225                 230                 235                 240

Asn Lys Asp Ile Glu Ile Gly Gln Arg Met Ile Thr Ile Ser Thr Val
                245                 250                 255

Gly Val Pro Asn Thr Ile Lys Lys Leu Ala Ser His Lys Leu Gln Ser
            260                 265                 270
```

```
Thr Leu Ala Val Ser Leu His Ala Pro Asn Gln Ser Leu Arg Glu Lys
        275                 280                 285

Ile Val Pro Ser Ala Lys Ala Tyr Pro Leu Glu Ala Ile Met Lys Asp
    290                 295                 300

Cys Arg Asp Tyr Phe Gln Glu Thr Asn Arg Arg Val Ser Phe Glu Tyr
305                 310                 315                 320

Ala Leu Leu Ala Gly Val Asn Asp Gln Val Glu His Ala Val Glu Leu
                325                 330                 335

Ala Glu Leu Leu Arg Glu Trp Gly Lys Thr Tyr His Val Asn Leu Ile
            340                 345                 350

Pro Tyr Asn Pro Ile Glu Gly Ser Glu Tyr Gln Arg Pro Tyr Lys Lys
        355                 360                 365

Ala Val Leu Ala Phe Ala Ala Ala Leu Glu Ser Arg Lys Ile Thr Ala
    370                 375                 380

Ser Val Arg Gln Thr Arg Gly Leu Asp Ala Ser Ala Ala Cys Gly Gln
385                 390                 395                 400

Leu Arg Asn Lys Phe Gln Lys Ser Pro Leu Leu Thr Glu Thr Asp Ser
                405                 410                 415

Gln Glu Ser Gln Pro Asp Ala Glu Ala Val Ala Cys
            420                 425
```

<210> SEQ ID NO 49
<211> LENGTH: 1125
<212> TYPE: DNA
<213> ORGANISM: Arabidopsis thaliana

<400> SEQUENCE: 49

```
atgggatgtt tcggaccatc aaaggcttca agaacaagaa acaatgaaca tgacaagata     60

acacgacaaa acccctctca tcaacctcaa accatgagag ctgaagaagt tctgttgcag    120

attcctagat gtagagtcca tctcataggc gaatccgagg cggtggagct tgcctctggt    180

gatttcaagc tcgttaaggt ctcagacaac ggtgtaactc tagctatgat cgtgagaatc    240

ggacatgacc ttcagtggcc agtgattaga gatgagccag tggtaaaact tgacgcccgt    300

gattacctct tcactctccc ggttaaagac ggtgatccac ttagctacgg ggtcactttc    360

tctggcgatg acagagacgt agccctcgtg aacagtctga agttgcttga ccaattcttg    420

agtgagaatt cttgtttctc gtctacggct tcgagtaagg ttaacaatgg aatcgactgg    480

caagagtttg cgccgaggat tgaagattac aacaacgttg ttgctaaggc tattgctgga    540

ggaacaggac atatcattag aggaatcttt agtctcagta atgcttactc taaccaggtt    600

cacaagggag gcgacataat gattacaaag gctgaggaga gccagagaaa tggaagttac    660

aacaatggaa actccagtgg taatgagaag aaaaatggga tcaacacaca ccttcaacga    720

gtgaggaagc tgtcaaaggc gactgagaat ctgagcaaga cgatgttgaa tggtgcggga    780

gttgtgagcg gctctgtgat ggtccctatg atgaagtcga aaccagggat ggccttcttt    840

tcgatggttc caggggaggt cctcttagct tcacttgatg cccttaataa aatactagat    900

gcaactgaag ctgcagagag acaaactcta tctgcaacat ccagggctgc taccagaatg    960

gtcagtgaga ggtttggaga taacgcaggg gaggccaccg gagatgttct agcaacagcg   1020

ggccacgcag ctggaactgc ctggaatgtt ctcaagatcc gtaagacttt ctatccttca   1080

tcttctctta catcaggaat cgtcaaaaat gctccaagaa agtag                    1125
```

<210> SEQ ID NO 50

```
<211> LENGTH: 374
<212> TYPE: PRT
<213> ORGANISM: Arabidopsis thaliana

<400> SEQUENCE: 50

Met Gly Cys Phe Gly Pro Ser Lys Ala Ser Arg Thr Arg Asn Asn Glu
1               5                   10                  15

His Asp Lys Ile Thr Arg Gln Asn Pro Ser His Gln Pro Gln Thr Met
            20                  25                  30

Arg Ala Glu Glu Val Leu Leu Gln Ile Pro Arg Cys Arg Val His Leu
        35                  40                  45

Ile Gly Glu Ser Glu Ala Val Glu Leu Ala Ser Gly Asp Phe Lys Leu
    50                  55                  60

Val Lys Val Ser Asp Asn Gly Val Thr Leu Ala Met Ile Val Arg Ile
65                  70                  75                  80

Gly His Asp Leu Gln Trp Pro Val Ile Arg Asp Glu Pro Val Val Lys
                85                  90                  95

Leu Asp Ala Arg Asp Tyr Leu Phe Thr Leu Pro Val Lys Asp Gly Asp
            100                 105                 110

Pro Leu Ser Tyr Gly Val Thr Phe Ser Gly Asp Asp Arg Asp Val Ala
        115                 120                 125

Leu Val Asn Ser Leu Lys Leu Leu Asp Gln Phe Leu Ser Glu Asn Ser
    130                 135                 140

Cys Phe Ser Ser Thr Ala Ser Ser Lys Val Asn Asn Gly Ile Asp Trp
145                 150                 155                 160

Gln Glu Phe Ala Pro Arg Ile Glu Asp Tyr Asn Asn Val Val Ala Lys
                165                 170                 175

Ala Ile Ala Gly Gly Thr Gly His Ile Ile Arg Gly Ile Phe Ser Leu
            180                 185                 190

Ser Asn Ala Tyr Ser Asn Gln Val His Lys Gly Gly Asp Ile Met Ile
        195                 200                 205

Thr Lys Ala Glu Glu Ser Gln Arg Asn Gly Ser Tyr Asn Asn Gly Asn
    210                 215                 220

Ser Ser Gly Asn Glu Lys Lys Asn Gly Ile Asn Thr His Leu Gln Arg
225                 230                 235                 240

Val Arg Lys Leu Ser Lys Ala Thr Glu Asn Leu Ser Lys Thr Met Leu
                245                 250                 255

Asn Gly Ala Gly Val Val Ser Gly Ser Val Met Val Pro Met Met Lys
            260                 265                 270

Ser Lys Pro Gly Met Ala Phe Phe Ser Met Val Pro Gly Glu Val Leu
        275                 280                 285

Leu Ala Ser Leu Asp Ala Leu Asn Lys Ile Leu Asp Ala Thr Glu Ala
    290                 295                 300

Ala Glu Arg Gln Thr Leu Ser Ala Thr Ser Arg Ala Ala Thr Arg Met
305                 310                 315                 320

Val Ser Glu Arg Phe Gly Asp Asn Ala Gly Glu Ala Thr Gly Asp Val
                325                 330                 335

Leu Ala Thr Ala Gly His Ala Ala Gly Thr Ala Trp Asn Val Leu Lys
            340                 345                 350

Ile Arg Lys Thr Phe Tyr Pro Ser Ser Ser Leu Thr Ser Gly Ile Val
        355                 360                 365

Lys Asn Ala Pro Arg Lys
    370
```

<210> SEQ ID NO 51
<211> LENGTH: 2952
<212> TYPE: DNA
<213> ORGANISM: Arabidopsis thaliana

<400> SEQUENCE: 51

```
atggcaagcc cacataagcc gtggagggcg gagtatgcaa agtcgtcgag gtcttcatgt     60
aaaacttgca agtccgtcat taacaaggag aactttcgtc ttggaaagtt ggttcaatct    120
actcacttcg atggcatcat gcccatgtgg aaccatgctt cttgtatact aaagaagacg    180
aagcagataa aatcagttga tgatgttgaa ggcatagaat cacttcgttg ggaagatcag    240
caaaagatta gaaaatatgt cgaatctgga gcagggagta acacaagcac aagcacaggc    300
acaagcacga gcagtaccgc taataatgcc aaactagaat atgggattga agtgtcacaa    360
acttctcgtg ccggttgcag aaagtgtagc gaaaagatct tgaaaggaga ggtacgtata    420
ttctccaagc ctgaaggccc gggtaacaaa ggtttgatgt ggcatcacgc taaatgtttc    480
cttgaaatgt cttcctctac tgaactggaa agtttgtctg gatggagaag tataccagac    540
tcagaccaag aagctcttct tcccttagtg aagaaagctc tgccggcagc caaaactgag    600
acagcagaag cacgtcaaac aaattcaaga gcaggcacaa aacgaaaaaa tgattctgtt    660
gataacgaga agtcgaaact agcaaaaagt agttttgaca tgtctacaag tggtgcttta    720
caaccttgta gcaaagaaaa ggaaatggag gcccaaacta aggaattgtg ggacctgaag    780
gatgatctga aaaaatatgt aacatcagct gagttgcggg aaatgcttga agtaaatgaa    840
caaagtacaa gaggatctga acttgatctg cgtgataaat gtgctgatgg catgatgttt    900
ggcccactcg ctctctgccc aatgtgctct gggcatcttt ctttctccgg aggactttac    960
cgatgccatg gatacatctc agaatggagc aaatgttctc attccacttt ggatccagac   1020
cgcatcaaag ggaagtggaa aatccctgac gaaacagaaa atcaattcct tctgaagtgg   1080
aataagtctc aaaagagtgt gaagccaaaa cgtattctgc gtcctgtatt gtctggcgag   1140
acatctcagg gtcaaggttc taaagatgca actgactcct caaggagtga aaggctagca   1200
gatcttaaag tttcaattgc tggaaatact aaggaaaggc aaccatggaa gaagagaatt   1260
gaggaagctg gtgcagagtt tcatgctaat gttaaaaaag gtacaagctg tttggttgtt   1320
tgtggactga cagatatcag agacgctgaa atgagaaagg caaggaggat gaaagtggca   1380
atcgtgagag aggattattt ggttgattgt tttaaaaaac agaggaaact tccatttgac   1440
aagtacaaaa ttgaagacac tagtgagagc cttgtcactg ttaaagtaaa aggacgaagc   1500
gctgtgcatg aagcgtctgg cctccaagag cactgtcaca ttcttgaaga tgggaacagt   1560
atctataaca caactctgag catgtctgat ctctctaccg gtatcaatag ttattacata   1620
ctccagataa tccaagaaga taaaggttca gattgttacg tatttcgtaa atggggccga   1680
gttggaaatg aaaagattgg tggtaacaaa gtggaggaaa tgtcaaagtc tgatgcggtt   1740
cacgaattca aacgtctatt tcttgaaaaa accggaaaca catgggaatc ttgggaacaa   1800
aaaacgaatt tccagaaaca acctggaaaa tttctcccgt tggacattga ttatggagtt   1860
aataagcaag tagccaaaaa agagccattt cagaccagta gcaaccttgc tccatcatta   1920
atagaattga tgaagatgct tttgatgtg gaaacttaca gatctgcaat gatggagttc    1980
gagataaata tgtcagagat gccacttggg aagctcagca aacataatat acagaagggt   2040
tttgaggcat tgacggagat acagaggcta ttgactgaaa gcgacccccca gcctactatg   2100
aaagaaagct tgcttgttga tgctagtaac agatttttta ccatgatccc ttctattcat   2160
```

```
cctcatatta tccgagatga agatgacttt aagtcaaagg tgaaaatgct cgaggctctg   2220

caggatatcg aaatagcttc aagaatagtt ggctttgatg ttgatagcac cgaatctctt   2280

gatgataagt ataagaagct gcattgcgat atctcaccac ttcctcatga tagcgaagat   2340

tatcgattaa tcgagaagta tcttaacaca actcatgccc caacgcatac agagtggagt   2400

cttgagctag aggaagtttt tgctcttgaa agagaaggag agtttgataa atatgctccc   2460

cacagagaaa aacttggcaa taagatgctc ctatggcatg gttctcgatt aacgaatttt   2520

gttggaatat tgaaccaagg actgagaatt gcacctccag aagctcctgc tactggttac   2580

atgtttggaa aagggatata ctttgctgac cttgtcagta aaagtgctca gtactgctac   2640

acttgtaaga aaaatccggt gggtctaatg cttctgagtg aagttgcatt gggagaaata   2700

catgagctaa caaaagctaa gtatatggat aaacctccga gagggaaaca ctcgaccaaa   2760

gggctcggca agaaagtgcc tcaagattcc gagtttgcca agtggagagg tgatgtgact   2820

gttccctgtg gaaaacctgt ttcatcaaag gtcaaggctt ctgagcttat gtacaatgag   2880

tatatcgtct acgatacagc ccaggtgaag ttgcagttct tgttgaaagt aaggtttaag   2940

cacaagagat ag                                                        2952
```

<210> SEQ ID NO 52
<211> LENGTH: 983
<212> TYPE: PRT
<213> ORGANISM: Arabidopsis thaliana

<400> SEQUENCE: 52

```
Met Ala Ser Pro His Lys Pro Trp Arg Ala Glu Tyr Ala Lys Ser Ser
1               5                   10                  15

Arg Ser Ser Cys Lys Thr Cys Lys Ser Val Ile Asn Lys Glu Asn Phe
            20                  25                  30

Arg Leu Gly Lys Leu Val Gln Ser Thr His Phe Asp Gly Ile Met Pro
        35                  40                  45

Met Trp Asn His Ala Ser Cys Ile Leu Lys Lys Thr Lys Gln Ile Lys
    50                  55                  60

Ser Val Asp Asp Val Glu Gly Ile Glu Ser Leu Arg Trp Glu Asp Gln
65                  70                  75                  80

Gln Lys Ile Arg Lys Tyr Val Glu Ser Gly Ala Gly Ser Asn Thr Ser
                85                  90                  95

Thr Ser Thr Gly Thr Ser Thr Ser Ser Thr Ala Asn Asn Ala Lys Leu
            100                 105                 110

Glu Tyr Gly Ile Glu Val Ser Gln Thr Ser Arg Ala Gly Cys Arg Lys
        115                 120                 125

Cys Ser Glu Lys Ile Leu Lys Gly Glu Val Arg Ile Phe Ser Lys Pro
    130                 135                 140

Glu Gly Pro Gly Asn Lys Gly Leu Met Trp His His Ala Lys Cys Phe
145                 150                 155                 160

Leu Glu Met Ser Ser Ser Thr Glu Leu Glu Ser Leu Ser Gly Trp Arg
                165                 170                 175

Ser Ile Pro Asp Ser Asp Gln Glu Ala Leu Leu Pro Leu Val Lys Lys
            180                 185                 190

Ala Leu Pro Ala Ala Lys Thr Glu Thr Ala Glu Ala Arg Gln Thr Asn
        195                 200                 205

Ser Arg Ala Gly Thr Lys Arg Lys Asn Asp Ser Val Asp Asn Glu Lys
    210                 215                 220

Ser Lys Leu Ala Lys Ser Ser Phe Asp Met Ser Thr Ser Gly Ala Leu
```

```
225                 230                 235                 240

Gln Pro Cys Ser Lys Glu Lys Glu Met Glu Ala Gln Thr Lys Glu Leu
                245                 250                 255

Trp Asp Leu Lys Asp Asp Leu Lys Lys Tyr Val Thr Ser Ala Glu Leu
            260                 265                 270

Arg Glu Met Leu Glu Val Asn Glu Gln Ser Thr Arg Gly Ser Glu Leu
        275                 280                 285

Asp Leu Arg Asp Lys Cys Ala Asp Gly Met Met Phe Gly Pro Leu Ala
    290                 295                 300

Leu Cys Pro Met Cys Ser Gly His Leu Ser Phe Ser Gly Gly Leu Tyr
305                 310                 315                 320

Arg Cys His Gly Tyr Ile Ser Glu Trp Ser Lys Cys Ser His Ser Thr
                325                 330                 335

Leu Asp Pro Asp Arg Ile Lys Gly Lys Trp Lys Ile Pro Asp Glu Thr
            340                 345                 350

Glu Asn Gln Phe Leu Leu Lys Trp Asn Lys Ser Gln Lys Ser Val Lys
        355                 360                 365

Pro Lys Arg Ile Leu Arg Pro Val Leu Ser Gly Glu Thr Ser Gln Gly
    370                 375                 380

Gln Gly Ser Lys Asp Ala Thr Asp Ser Ser Arg Ser Glu Arg Leu Ala
385                 390                 395                 400

Asp Leu Lys Val Ser Ile Ala Gly Asn Thr Lys Glu Arg Gln Pro Trp
                405                 410                 415

Lys Lys Arg Ile Glu Glu Ala Gly Ala Glu Phe His Ala Asn Val Lys
            420                 425                 430

Lys Gly Thr Ser Cys Leu Val Val Cys Gly Leu Thr Asp Ile Arg Asp
        435                 440                 445

Ala Glu Met Arg Lys Ala Arg Arg Met Lys Val Ala Ile Val Arg Glu
    450                 455                 460

Asp Tyr Leu Val Asp Cys Phe Lys Lys Gln Arg Lys Leu Pro Phe Asp
465                 470                 475                 480

Lys Tyr Lys Ile Glu Asp Thr Ser Glu Ser Leu Val Thr Val Lys Val
                485                 490                 495

Lys Gly Arg Ser Ala Val His Glu Ala Ser Gly Leu Gln Glu His Cys
            500                 505                 510

His Ile Leu Glu Asp Gly Asn Ser Ile Tyr Asn Thr Thr Leu Ser Met
        515                 520                 525

Ser Asp Leu Ser Thr Gly Ile Asn Ser Tyr Tyr Ile Leu Gln Ile Ile
    530                 535                 540

Gln Glu Asp Lys Gly Ser Asp Cys Tyr Val Phe Arg Lys Trp Gly Arg
545                 550                 555                 560

Val Gly Asn Glu Lys Ile Gly Gly Asn Lys Val Glu Glu Met Ser Lys
                565                 570                 575

Ser Asp Ala Val His Glu Phe Lys Arg Leu Phe Leu Glu Lys Thr Gly
            580                 585                 590

Asn Thr Trp Glu Ser Trp Glu Gln Lys Thr Asn Phe Gln Lys Gln Pro
        595                 600                 605

Gly Lys Phe Leu Pro Leu Asp Ile Asp Tyr Gly Val Asn Lys Gln Val
    610                 615                 620

Ala Lys Lys Glu Pro Phe Gln Thr Ser Ser Asn Leu Ala Pro Ser Leu
625                 630                 635                 640

Ile Glu Leu Met Lys Met Leu Phe Asp Val Glu Thr Tyr Arg Ser Ala
                645                 650                 655
```

```
Met Met Glu Phe Glu Ile Asn Met Ser Glu Met Pro Leu Gly Lys Leu
            660                 665                 670

Ser Lys His Asn Ile Gln Lys Gly Phe Glu Ala Leu Thr Glu Ile Gln
        675                 680                 685

Arg Leu Leu Thr Glu Ser Asp Pro Gln Pro Thr Met Lys Glu Ser Leu
    690                 695                 700

Leu Val Asp Ala Ser Asn Arg Phe Phe Thr Met Ile Pro Ser Ile His
705                 710                 715                 720

Pro His Ile Ile Arg Asp Glu Asp Asp Phe Lys Ser Lys Val Lys Met
            725                 730                 735

Leu Glu Ala Leu Gln Asp Ile Glu Ile Ala Ser Arg Ile Val Gly Phe
            740                 745                 750

Asp Val Asp Ser Thr Glu Ser Leu Asp Asp Lys Tyr Lys Lys Leu His
        755                 760                 765

Cys Asp Ile Ser Pro Leu Pro His Asp Ser Glu Asp Tyr Arg Leu Ile
    770                 775                 780

Glu Lys Tyr Leu Asn Thr Thr His Ala Pro Thr His Thr Glu Trp Ser
785                 790                 795                 800

Leu Glu Leu Glu Glu Val Phe Ala Leu Glu Arg Glu Gly Glu Phe Asp
            805                 810                 815

Lys Tyr Ala Pro His Arg Glu Lys Leu Gly Asn Lys Met Leu Leu Trp
            820                 825                 830

His Gly Ser Arg Leu Thr Asn Phe Val Gly Ile Leu Asn Gln Gly Leu
        835                 840                 845

Arg Ile Ala Pro Pro Glu Ala Pro Ala Thr Gly Tyr Met Phe Gly Lys
    850                 855                 860

Gly Ile Tyr Phe Ala Asp Leu Val Ser Lys Ser Ala Gln Tyr Cys Tyr
865                 870                 875                 880

Thr Cys Lys Lys Asn Pro Val Gly Leu Met Leu Leu Ser Glu Val Ala
            885                 890                 895

Leu Gly Glu Ile His Glu Leu Thr Lys Ala Lys Tyr Met Asp Lys Pro
            900                 905                 910

Pro Arg Gly Lys His Ser Thr Lys Gly Leu Gly Lys Lys Val Pro Gln
        915                 920                 925

Asp Ser Glu Phe Ala Lys Trp Arg Gly Asp Val Thr Val Pro Cys Gly
    930                 935                 940

Lys Pro Val Ser Ser Lys Val Lys Ala Ser Glu Leu Met Tyr Asn Glu
945                 950                 955                 960

Tyr Ile Val Tyr Asp Thr Ala Gln Val Lys Leu Gln Phe Leu Leu Lys
            965                 970                 975

Val Arg Phe Lys His Lys Arg
            980
```

<210> SEQ ID NO 53
<211> LENGTH: 192
<212> TYPE: DNA
<213> ORGANISM: Gossypium hirsutum

<400> SEQUENCE: 53

```
atggctgaca agtgtggcaa ctgcgattgc gctgacaaga gccagtgtgt gaagaaagga      60

aacagcttgg tcattgagac tgaggagagc tacatcagca ccgtagtggt cgagcctctg     120

gcagagaacg atggcaagtg caagtgcgga actagctgca gctgcacaaa ctgcacatgt     180

ggcagtcact ag                                                         192
```

<210> SEQ ID NO 54
<211> LENGTH: 63
<212> TYPE: PRT
<213> ORGANISM: Gossypium hirsutum

<400> SEQUENCE: 54

```
Met Ala Asp Lys Cys Gly Asn Cys Asp Cys Ala Asp Lys Ser Gln Cys
1               5                   10                  15

Val Lys Lys Gly Asn Ser Leu Val Ile Glu Thr Glu Glu Ser Tyr Ile
            20                  25                  30

Ser Thr Val Val Val Glu Pro Leu Ala Glu Asn Asp Gly Lys Cys Lys
        35                  40                  45

Cys Gly Thr Ser Cys Ser Cys Thr Asn Cys Thr Cys Gly Ser His
    50                  55                  60
```

<210> SEQ ID NO 55
<211> LENGTH: 930
<212> TYPE: DNA
<213> ORGANISM: Triticum aestivum

<400> SEQUENCE: 55

```
atggcggctc tgctgatgcg taggctcgcc ggaacctacc gcggccgcgc gccgctggcc      60

gccgccgccg ttggcggggc cgcgctcttc tacgcctcgt cgaaccccac catcgcgcac     120

atggaggaga agggggaaga tgccgctgcc aaagttgctc ttaaccctga gaaatggtta     180

gaattcaagc tccaggagaa ggcaacagtt agtcatgatt cagagctatt cagattttcg     240

tttgacccat ctactaagct gggtctggat gttgcctcat gtctcgtaac aagggccccc     300

ataggtcagg aagtggaggg aaaaagaaaa tacgttattc gcccgtacac acctatctct     360

gacccagatt ctaaaggata tttcgaccta ttaatcaagg tttatcccga agggaaaatg     420

tctcagcatt ttgctaattt gaagccagga gatgttctcg aagtcaaagg gcccattgaa     480

aagctcagat atagcccaaa tatgaaaaga caaattggca tggttgctgg tggtactggc     540

ataacgccaa tgctgcaagt tgttagggcc atcctgaaaa accctgatga caacactcag     600

gtttccttga tctacgccaa tgtgtcacca gatgatatct tgctgaaaaa ggagttagat     660

agacttgcta gcagctatcc taatttcaag gtattttata cagtcgataa accatcaagt     720

gactggaggg gtggtgttgg ctacatatca aaggacatgg ttttgaaagg tttgccaggc     780

ccaggggagg attctcttat tcttgtttgt ggtcctcctg gaatgatgaa tcacatatct     840

ggagataagg caaaggatta ttcacagggc gaggtcactg gccttctcaa agatttagga     900

tacacggcag atatggtata caaattttag                                      930
```

<210> SEQ ID NO 56
<211> LENGTH: 309
<212> TYPE: PRT
<213> ORGANISM: Triticum aestivum

<400> SEQUENCE: 56

```
Met Ala Ala Leu Leu Met Arg Arg Leu Ala Gly Thr Tyr Arg Gly Arg
1               5                   10                  15

Ala Pro Leu Ala Ala Ala Ala Val Gly Gly Ala Ala Leu Phe Tyr Ala
            20                  25                  30

Ser Ser Asn Pro Thr Ile Ala His Met Glu Glu Lys Gly Glu Asp Ala
        35                  40                  45

Ala Ala Lys Val Ala Leu Asn Pro Glu Lys Trp Leu Glu Phe Lys Leu
```

```
    50                  55                  60

Gln Glu Lys Ala Thr Val Ser His Asp Ser Glu Leu Phe Arg Phe Ser
65                  70                  75                  80

Phe Asp Pro Ser Thr Lys Leu Gly Leu Asp Val Ala Ser Cys Leu Val
                85                  90                  95

Thr Arg Ala Pro Ile Gly Gln Glu Val Glu Gly Lys Arg Lys Tyr Val
            100                 105                 110

Ile Arg Pro Tyr Thr Pro Ile Ser Asp Pro Asp Ser Lys Gly Tyr Phe
        115                 120                 125

Asp Leu Leu Ile Lys Val Tyr Pro Glu Gly Lys Met Ser Gln His Phe
    130                 135                 140

Ala Asn Leu Lys Pro Gly Asp Val Leu Glu Val Lys Gly Pro Ile Glu
145                 150                 155                 160

Lys Leu Arg Tyr Ser Pro Asn Met Lys Arg Gln Ile Gly Met Val Ala
                165                 170                 175

Gly Gly Thr Gly Ile Thr Pro Met Leu Gln Val Val Arg Ala Ile Leu
            180                 185                 190

Lys Asn Pro Asp Asp Asn Thr Gln Val Ser Leu Ile Tyr Ala Asn Val
        195                 200                 205

Ser Pro Asp Asp Ile Leu Leu Lys Lys Glu Leu Asp Arg Leu Ala Ser
    210                 215                 220

Ser Tyr Pro Asn Phe Lys Val Phe Tyr Thr Val Asp Lys Pro Ser Ser
225                 230                 235                 240

Asp Trp Arg Gly Gly Val Gly Tyr Ile Ser Lys Asp Met Val Leu Lys
                245                 250                 255

Gly Leu Pro Gly Pro Gly Glu Asp Ser Leu Ile Leu Val Cys Gly Pro
            260                 265                 270

Pro Gly Met Met Asn His Ile Ser Gly Asp Lys Ala Lys Asp Tyr Ser
        275                 280                 285

Gln Gly Glu Val Thr Gly Leu Leu Lys Asp Leu Gly Tyr Thr Ala Asp
    290                 295                 300

Met Val Tyr Lys Phe
305
```

<210> SEQ ID NO 57
<211> LENGTH: 2199
<212> TYPE: DNA
<213> ORGANISM: Arabidopsis thaliana

<400> SEQUENCE: 57

```
atgagtaatc agaagaagag gaattttcag atagaggcgt ttaagcatcg agtcgttgtg     60

gatcccaaat acgctgataa aacttggcag attcttgagc gtgcgatcca tcagatttac    120

aatcaagatg ctagcggtct cagtttcgaa gaactttaca gaaatgcgta caacatggtc    180

ctgcacaagt ttggtgagaa gctatatact gggtttattg ctactatgac ttctcatctc    240

aaagaaaaat ccaagcttat cgaggcagct cagggagggt cgtttctaga agagcttaat    300

aagaaatgga atgagcacaa caaagcgtta gagatgattc gagacattct catgtatatg    360

gataggactt atattgagag caccaaaaag actcatgttc atccgatggg gcttaacttg    420

tggagggata atgttgtgca tttcactaag atacatacaa ggcttctaaa cactcttctt    480

gatctagtgc agaaggaacg gataggtgaa gttattgata gggggttgat gaggaatgtc    540

attaagatgt ttatggattt gggtgaatct gtgtatcagg aggattttga gaagccgttt    600

ttggatgcgt cttctgagtt ttataaggtt gagtctcagg agtttattga atcttgtgat    660
```

```
tgtggggact atctgaagaa atcagagaaa cgccttactg aagagataga gagggtagcg     720

cactacttag atgccaagag cgaagagaag attactagtg tggttgagaa agagatgatt     780

gccaaccaca tgcagagact ggttcacatg gagaactcag gtctggttaa tatgcttctg     840

aatgacaagt atgaggattt gggtagaatg tacaacttgt ttcgcagggt tactaatggt     900

cttgttactg tcagagacgt tatgacttcg catcttaggg agatgggaaa acaactggtt     960

actgatccgg aaaagtcaaa ggatccggtg gaatttgtac aacgtctatt ggatgagcgg    1020

gataaatatg acaaaatcat caacaccgca tttggcaatg ataaaacctt tcagaatgcc    1080

ctgaattctt cattcgagta tttcatcaac ttgaatgctc gttctcctga gtttatctcc    1140

ctgtttgttg atgacaagct acggaaagga cttaagggta tcaccgatgt ggatgttgag    1200

gttatccttg ataaagtgat gatgctgttc cgttatttac aagagaaaga tgtctttgag    1260

aagtactaca agcagcattt ggctaaaagg cttctctcag gcaaaactgt gtcagatgac    1320

gcagaaagga gtttaatagt gaaactaaag acagaatgtg gctatcagtt cacttcaaaa    1380

ttggaaggca tgttcactga catgaagact tcagaggaca caatgcgtgg gttttatggc    1440

agtcaccccg agctttcaga aggacctaca cttattgttc aggtacttac aactggttct    1500

tggccaacac agcctgcagt accttgtaat ctcccagctg aagtttcagt tctctgtgag    1560

aagttccgtt cttactacct tgggacacat accggtagaa gattgtcctg gcaaacaaac    1620

atgggcacag cagatatcaa agccatcttt ggaaagggtc agaaacatga actgaacgtg    1680

tcgactttcc agatgtgtgt tctcatgttg ttcaacaatt ctgatcgact cagctacaaa    1740

gagatcgaac aggctacaga aatcccggca gcagatctta aacgctgttt gcagtcgcta    1800

gcttgtgtaa agggcaaaaa cgtgataaag aaagaaccca tgagcaaaga catagggagag   1860

gaggatttgt tcgttgtgaa cgacaagttc actagcaagt tttacaaagt gaagatcgga    1920

actgtggttg cccaaaagga aacagaaccg gagaagcaag agacgagaca gagagtggag    1980

gaagacagaa aacctcagat tgaagcagcc atcgtaagga tcatgaagtc caggaaaata    2040

ctagaccaca acaacataat cgccgaggtg acgaaacagt tgcagccacg gttcctagct    2100

aatcccacgg agataaagaa gagaatcgag tcgctcattg aacgagattt cttggaaagg    2160

gatagtacag accggaaact ttaccgctat ctagcctag                           2199
```

<210> SEQ ID NO 58
<211> LENGTH: 732
<212> TYPE: PRT
<213> ORGANISM: Arabidopsis thaliana

<400> SEQUENCE: 58

```
Met Ser Asn Gln Lys Lys Arg Asn Phe Gln Ile Glu Ala Phe Lys His
1               5                   10                  15

Arg Val Val Val Asp Pro Lys Tyr Ala Asp Lys Thr Trp Gln Ile Leu
            20                  25                  30

Glu Arg Ala Ile His Gln Ile Tyr Asn Gln Asp Ala Ser Gly Leu Ser
        35                  40                  45

Phe Glu Glu Leu Tyr Arg Asn Ala Tyr Asn Met Val Leu His Lys Phe
    50                  55                  60

Gly Glu Lys Leu Tyr Thr Gly Phe Ile Ala Thr Met Thr Ser His Leu
65                  70                  75                  80

Lys Glu Lys Ser Lys Leu Ile Glu Ala Ala Gln Gly Gly Ser Phe Leu
                85                  90                  95
```

```
Glu Glu Leu Asn Lys Lys Trp Asn Glu His Asn Lys Ala Leu Glu Met
            100                 105                 110

Ile Arg Asp Ile Leu Met Tyr Met Asp Arg Thr Tyr Ile Glu Ser Thr
        115                 120                 125

Lys Lys Thr His Val His Pro Met Gly Leu Asn Leu Trp Arg Asp Asn
    130                 135                 140

Val Val His Phe Thr Lys Ile His Thr Arg Leu Leu Asn Thr Leu Leu
145                 150                 155                 160

Asp Leu Val Gln Lys Glu Arg Ile Gly Glu Val Ile Asp Arg Gly Leu
                165                 170                 175

Met Arg Asn Val Ile Lys Met Phe Met Asp Leu Gly Glu Ser Val Tyr
            180                 185                 190

Gln Glu Asp Phe Glu Lys Pro Phe Leu Asp Ala Ser Ser Glu Phe Tyr
        195                 200                 205

Lys Val Glu Ser Gln Glu Phe Ile Glu Ser Cys Asp Cys Gly Asp Tyr
    210                 215                 220

Leu Lys Lys Ser Glu Lys Arg Leu Thr Glu Glu Ile Glu Arg Val Ala
225                 230                 235                 240

His Tyr Leu Asp Ala Lys Ser Glu Glu Lys Ile Thr Ser Val Val Glu
                245                 250                 255

Lys Glu Met Ile Ala Asn His Met Gln Arg Leu Val His Met Glu Asn
            260                 265                 270

Ser Gly Leu Val Asn Met Leu Leu Asn Asp Lys Tyr Glu Asp Leu Gly
        275                 280                 285

Arg Met Tyr Asn Leu Phe Arg Arg Val Thr Asn Gly Leu Val Thr Val
    290                 295                 300

Arg Asp Val Met Thr Ser His Leu Arg Glu Met Gly Lys Gln Leu Val
305                 310                 315                 320

Thr Asp Pro Glu Lys Ser Lys Asp Pro Val Glu Phe Val Gln Arg Leu
                325                 330                 335

Leu Asp Glu Arg Asp Lys Tyr Asp Lys Ile Ile Asn Thr Ala Phe Gly
            340                 345                 350

Asn Asp Lys Thr Phe Gln Asn Ala Leu Asn Ser Ser Phe Glu Tyr Phe
        355                 360                 365

Ile Asn Leu Asn Ala Arg Ser Pro Glu Phe Ile Ser Leu Phe Val Asp
    370                 375                 380

Asp Lys Leu Arg Lys Gly Leu Lys Gly Ile Thr Asp Val Asp Val Glu
385                 390                 395                 400

Val Ile Leu Asp Lys Val Met Met Leu Phe Arg Tyr Leu Gln Glu Lys
                405                 410                 415

Asp Val Phe Glu Lys Tyr Tyr Lys Gln His Leu Ala Lys Arg Leu Leu
            420                 425                 430

Ser Gly Lys Thr Val Ser Asp Asp Ala Glu Arg Ser Leu Ile Val Lys
        435                 440                 445

Leu Lys Thr Glu Cys Gly Tyr Gln Phe Thr Ser Lys Leu Glu Gly Met
    450                 455                 460

Phe Thr Asp Met Lys Thr Ser Glu Asp Thr Met Arg Gly Phe Tyr Gly
465                 470                 475                 480

Ser His Pro Glu Leu Ser Glu Gly Pro Thr Leu Ile Val Gln Val Leu
                485                 490                 495

Thr Thr Gly Ser Trp Pro Thr Gln Pro Ala Val Pro Cys Asn Leu Pro
            500                 505                 510

Ala Glu Val Ser Val Leu Cys Glu Lys Phe Arg Ser Tyr Tyr Leu Gly
```

```
        515                 520                 525

Thr His Thr Gly Arg Arg Leu Ser Trp Gln Thr Asn Met Gly Thr Ala
    530                 535                 540

Asp Ile Lys Ala Ile Phe Gly Lys Gly Gln Lys His Glu Leu Asn Val
545                 550                 555                 560

Ser Thr Phe Gln Met Cys Val Leu Met Leu Phe Asn Asn Ser Asp Arg
                565                 570                 575

Leu Ser Tyr Lys Glu Ile Glu Gln Ala Thr Glu Ile Pro Ala Ala Asp
            580                 585                 590

Leu Lys Arg Cys Leu Gln Ser Leu Ala Cys Val Lys Gly Lys Asn Val
        595                 600                 605

Ile Lys Lys Glu Pro Met Ser Lys Asp Ile Gly Glu Glu Asp Leu Phe
    610                 615                 620

Val Val Asn Asp Lys Phe Thr Ser Lys Phe Tyr Lys Val Lys Ile Gly
625                 630                 635                 640

Thr Val Val Ala Gln Lys Glu Thr Glu Pro Glu Lys Gln Glu Thr Arg
                645                 650                 655

Gln Arg Val Glu Glu Asp Arg Lys Pro Gln Ile Glu Ala Ala Ile Val
            660                 665                 670

Arg Ile Met Lys Ser Arg Lys Ile Leu Asp His Asn Asn Ile Ile Ala
        675                 680                 685

Glu Val Thr Lys Gln Leu Gln Pro Arg Phe Leu Ala Asn Pro Thr Glu
    690                 695                 700

Ile Lys Lys Arg Ile Glu Ser Leu Ile Glu Arg Asp Phe Leu Glu Arg
705                 710                 715                 720

Asp Ser Thr Asp Arg Lys Leu Tyr Arg Tyr Leu Ala
                725                 730


<210> SEQ ID NO 59
<211> LENGTH: 168
<212> TYPE: PRT
<213> ORGANISM: Arabidopsis thaliana

<400> SEQUENCE: 59

Met Leu Val Tyr Gln Asp Leu Leu Thr Gly Asp Glu Leu Leu Ser Asp
1               5                   10                  15

Ser Phe Pro Tyr Lys Glu Ile Glu Asn Gly Ile Leu Trp Glu Val Glu
            20                  25                  30

Gly Lys Trp Val Thr Val Gly Ala Val Asp Val Asn Ile Gly Ala Asn
        35                  40                  45

Pro Ser Ala Glu Glu Gly Gly Glu Asp Glu Gly Val Asp Asp Ser Ala
    50                  55                  60

Gln Lys Val Val Asp Ile Val Asp Thr Phe Arg Leu Gln Glu Gln Pro
65                  70                  75                  80

Thr Tyr Asp Lys Lys Gly Phe Ile Ala Tyr Ile Lys Lys Tyr Ile Lys
                85                  90                  95

Leu Leu Thr Pro Lys Leu Ser Glu Glu Asp Gln Ala Val Phe Lys Lys
            100                 105                 110

Gly Ile Glu Gly Ala Thr Lys Phe Leu Leu Pro Arg Leu Ser Asp Phe
        115                 120                 125

Gln Phe Phe Val Gly Glu Gly Met His Asp Asp Ser Thr Leu Val Phe
    130                 135                 140

Ala Tyr Tyr Lys Glu Gly Ser Thr Asn Pro Thr Phe Leu Tyr Phe Ala
145                 150                 155                 160
```

```
His Gly Leu Lys Glu Val Lys Cys
                165


<210> SEQ ID NO 60
<211> LENGTH: 1161
<212> TYPE: PRT
<213> ORGANISM: Zea mays

<400> SEQUENCE: 60

Met Ala Ser Gly Ser Arg Ala Thr Pro Thr Arg Ser Pro Ser Ser Ala
1               5                   10                  15

Arg Pro Glu Ala Pro Arg His Ala His His His His His Ser Gln Ser
            20                  25                  30

Ser Gly Gly Ser Thr Ser Arg Ala Gly Gly Gly Ala Ala Ala Thr Glu
        35                  40                  45

Ser Val Ser Lys Ala Val Ala Gln Tyr Thr Leu Asp Ala Arg Leu His
    50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Ser Glu Gln Gln Ile Ala
                85                  90                  95

Ala Tyr Leu Ser Arg Ile Gln Arg Gly Gly His Ile Gln Pro Phe Gly
            100                 105                 110

Cys Thr Leu Ala Val Ala Asp Asp Ser Ser Phe Arg Leu Leu Ala Phe
        115                 120                 125

Ser Glu Asn Ser Pro Asp Leu Leu Asp Leu Ser Pro His His Ser Val
    130                 135                 140

Pro Ser Leu Asp Ser Ser Ala Pro Pro His Val Ser Leu Gly Ala Asp
145                 150                 155                 160

Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
            180                 185                 190

Arg Val Ser Ser Lys Pro Phe Tyr Ala Ile Leu His Arg Ile Asp Val
        195                 200                 205

Gly Val Val Ile Asp Leu Glu Pro Ala Arg Thr Glu Asp Pro Ala Leu
    210                 215                 220

Ser Ile Ala Gly Ala Val Gln Ser Gln Lys Leu Ala Val Arg Ala Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
            260                 265                 270

Val Tyr Arg Phe His Glu Asp Glu His Gly Glu Val Val Ala Glu Ser
        275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
                325                 330                 335

Gly Leu Ser Gln Pro Leu Cys Leu Val Gly Ser Thr Leu Arg Ala Pro
            340                 345                 350

His Gly Cys His Ala Gln Tyr Met Ala Asn Met Gly Ser Ile Ala Ser
        355                 360                 365
```

```
Leu Val Met Ala Val Ile Ile Ser Ser Gly Gly Asp Asp Glu Gln Thr
    370                 375                 380

Gly Arg Gly Gly Ile Ser Ser Ala Met Lys Leu Trp Gly Leu Val Val
385                 390                 395                 400

Cys His His Thr Ser Pro Arg Cys Ile Pro Phe Pro Leu Arg Tyr Ala
                405                 410                 415

Cys Glu Phe Leu Met Gln Ala Phe Gly Leu Gln Leu Asn Met Glu Leu
            420                 425                 430

Gln Leu Ala His Gln Leu Ser Glu Lys His Ile Leu Arg Thr Gln Thr
        435                 440                 445

Leu Leu Cys Asp Met Leu Leu Arg Asp Ser Pro Thr Gly Ile Val Thr
    450                 455                 460

Gln Ser Pro Ser Ile Met Asp Leu Val Lys Cys Asp Gly Ala Ala Leu
465                 470                 475                 480

Tyr Tyr His Gly Lys Tyr Tyr Pro Leu Gly Val Thr Pro Thr Glu Ser
                485                 490                 495

Gln Ile Lys Asp Ile Ile Glu Trp Leu Thr Val Phe His Gly Asp Ser
            500                 505                 510

Thr Gly Leu Ser Thr Asp Ser Leu Ala Asp Ala Gly Tyr Leu Gly Ala
        515                 520                 525

Ala Ala Leu Gly Glu Ala Val Cys Gly Met Ala Val Ala Tyr Ile Thr
    530                 535                 540

Pro Ser Asp Tyr Leu Phe Trp Phe Arg Ser His Thr Ala Lys Glu Ile
545                 550                 555                 560

Lys Trp Gly Gly Ala Lys His His Pro Glu Asp Lys Asp Asp Gly Gln
                565                 570                 575

Arg Met His Pro Arg Ser Ser Phe Lys Ala Phe Leu Glu Val Val Lys
            580                 585                 590

Ser Arg Ser Leu Pro Trp Glu Asn Ala Glu Met Asp Ala Ile His Ser
        595                 600                 605

Leu Gln Leu Ile Leu Arg Asp Ser Phe Arg Asp Ala Ala Glu Gly Thr
    610                 615                 620

Asn Asn Ser Lys Ala Ile Val Asn Gly Gln Val Gln Leu Arg Glu Leu
625                 630                 635                 640

Glu Leu Arg Gly Ile Asn Glu Leu Ser Ser Val Ala Arg Glu Met Val
                645                 650                 655

Arg Leu Ile Glu Thr Ala Thr Val Pro Ile Phe Ala Val Asp Thr Asp
            660                 665                 670

Gly Cys Ile Asn Gly Trp Asn Ala Lys Ile Ala Glu Leu Thr Gly Leu
        675                 680                 685

Ser Val Glu Glu Ala Met Gly Lys Ser Leu Val Asn Asp Leu Ile Phe
    690                 695                 700

Lys Glu Ser Glu Ala Thr Val Glu Lys Leu Leu Ser Arg Ala Leu Arg
705                 710                 715                 720

Gly Glu Glu Asp Lys Asn Val Glu Ile Lys Leu Lys Thr Phe Gly Ser
                725                 730                 735

Glu Gln Ser Lys Gly Pro Ile Phe Val Val Val Asn Ala Cys Ser Ser
            740                 745                 750

Arg Asp Tyr Thr Gln Asn Ile Val Gly Val Cys Phe Val Gly Gln Asp
        755                 760                 765

Val Thr Gly Gln Lys Val Val Met Asp Lys Phe Val Asn Ile Gln Gly
    770                 775                 780
```

```
Asp Tyr Lys Ala Ile Val His Asn Pro Asn Pro Leu Ile Pro Pro Ile
785                 790                 795                 800

Phe Ala Ser Asp Glu Asn Thr Ser Cys Ser Glu Trp Asn Thr Ala Met
                805                 810                 815

Glu Lys Leu Thr Gly Trp Ser Arg Gly Glu Val Val Gly Lys Phe Leu
            820                 825                 830

Ile Gly Glu Val Phe Gly Asn Cys Cys Arg Leu Lys Gly Pro Asp Ala
        835                 840                 845

Leu Thr Lys Phe Met Val Ile Ile His Asn Ala Ile Gly Gly Gln Asp
    850                 855                 860

Tyr Glu Lys Phe Pro Phe Ser Phe Phe Asp Lys Asn Gly Lys Tyr Val
865                 870                 875                 880

Gln Ala Leu Leu Thr Ala Asn Thr Arg Ser Lys Met Asp Gly Lys Ser
                885                 890                 895

Ile Gly Ala Phe Cys Phe Leu Gln Ile Ala Ser Thr Glu Ile Gln Gln
            900                 905                 910

Ala Phe Glu Ile Gln Arg Gln Gln Glu Lys Lys Cys Tyr Ala Arg Met
        915                 920                 925

Lys Glu Leu Ala Tyr Ile Cys Gln Glu Ile Lys Asn Pro Leu Ser Gly
    930                 935                 940

Ile Arg Phe Thr Asn Ser Leu Leu Gln Met Thr Asp Leu Asn Asp Asp
945                 950                 955                 960

Gln Arg Gln Phe Leu Glu Thr Ser Ser Ala Cys Glu Lys Gln Met Ser
                965                 970                 975

Lys Ile Val Lys Asp Ala Ser Leu Gln Ser Ile Glu Asp Gly Ser Leu
            980                 985                 990

Val Leu Glu Gln Ser Glu Phe Ser  Leu Gly Asp Val Met  Asn Ala Val
        995                 1000                1005

Val Ser  Gln Ala Met Leu Leu  Leu Arg Glu Arg Asp  Leu Gln Leu
    1010                1015                1020

Ile Arg  Asp Ile Pro Asp Glu  Ile Lys Asp Ala Ser  Ala Tyr Gly
    1025                1030                1035

Asp Gln  Cys Arg Ile Gln Gln  Val Leu Ala Asp Phe  Leu Leu Ser
    1040                1045                1050

Met Val  Arg Ser Ala Pro Ser  Glu Asn Gly Trp Val  Glu Ile Gln
    1055                1060                1065

Val Arg  Pro Asn Val Lys Gln  Asn Ser Asp Gly Thr  Asn Thr Glu
    1070                1075                1080

Leu Phe  Ile Phe Arg Phe Ala  Cys Pro Gly Glu Gly  Leu Pro Ala
    1085                1090                1095

Asp Val  Val Gln Asp Met Phe  Ser Asn Ser Gln Trp  Ser Thr Gln
    1100                1105                1110

Glu Gly  Val Gly Leu Ser Thr  Cys Arg Lys Ile Leu  Lys Leu Met
    1115                1120                1125

Gly Gly  Glu Val Gln Tyr Ile  Arg Glu Ser Glu Arg  Ser Phe Phe
    1130                1135                1140

Leu Ile  Val Leu Glu Gln Pro  Gln Pro Arg Pro Ala  Ala Gly Arg
    1145                1150                1155

Glu Ile  Val
    1160
```

<210> SEQ ID NO 61
<211> LENGTH: 783
<212> TYPE: PRT

```
<213> ORGANISM: Zea mays

<400> SEQUENCE: 61

Met Ala Ser Gly Ser Arg Ala Thr Pro Thr Arg Ser Pro Ser Ser Ala
1               5                   10                  15

Arg Pro Glu Ala Pro Arg His Ala His His His His His Ser Gln Ser
            20                  25                  30

Ser Gly Gly Ser Thr Ser Arg Ala Gly Gly Gly Ala Ala Ala Thr Glu
        35                  40                  45

Ser Val Ser Lys Ala Val Ala Gln Tyr Thr Leu Asp Ala Arg Leu His
    50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Ser Glu Gln Gln Ile Ala
                85                  90                  95

Ala Tyr Leu Ser Arg Ile Gln Arg Gly Gly His Ile Gln Pro Phe Gly
            100                 105                 110

Cys Thr Leu Ala Val Ala Asp Asp Ser Ser Phe Arg Leu Leu Ala Phe
        115                 120                 125

Ser Glu Asn Ser Pro Asp Leu Leu Asp Leu Ser Pro His His Ser Val
    130                 135                 140

Pro Ser Leu Asp Ser Ser Ala Pro Pro His Val Ser Leu Gly Ala Asp
145                 150                 155                 160

Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
            180                 185                 190

Arg Val Ser Ser Lys Pro Phe Tyr Ala Ile Leu His Arg Ile Asp Val
        195                 200                 205

Gly Val Val Ile Asp Leu Glu Pro Ala Arg Thr Glu Asp Pro Ala Leu
    210                 215                 220

Ser Ile Ala Gly Ala Val Gln Ser Gln Lys Leu Ala Val Arg Ala Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
            260                 265                 270

Val Tyr Arg Phe His Glu Asp Glu His Gly Glu Val Val Ala Glu Ser
        275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
                325                 330                 335

Gly Leu Ser Gln Pro Leu Cys Leu Val Gly Ser Thr Leu Arg Ala Pro
            340                 345                 350

His Gly Cys His Ala Gln Tyr Met Ala Asn Met Gly Ser Ile Ala Ser
        355                 360                 365

Leu Val Met Ala Val Ile Ile Ser Ser Gly Gly Asp Asp Glu Gln Thr
    370                 375                 380

Gly Arg Gly Gly Ile Ser Ser Ala Met Lys Leu Trp Gly Leu Val Val
385                 390                 395                 400
```

```
Cys His His Thr Ser Pro Arg Cys Ile Pro Phe Pro Leu Arg Tyr Ala
                405                 410                 415

Cys Glu Phe Leu Met Gln Ala Phe Gly Leu Gln Leu Asn Met Glu Leu
            420                 425                 430

Gln Leu Ala His Gln Leu Ser Glu Lys His Ile Leu Arg Thr Gln Thr
        435                 440                 445

Leu Leu Cys Asp Met Leu Leu Arg Asp Ser Pro Thr Gly Ile Val Thr
    450                 455                 460

Gln Ser Pro Ser Ile Met Asp Leu Val Lys Cys Asp Gly Ala Ala Leu
465                 470                 475                 480

Tyr Tyr His Gly Lys Tyr Tyr Pro Leu Gly Val Thr Pro Thr Glu Ser
                485                 490                 495

Gln Ile Lys Asp Ile Ile Glu Trp Leu Thr Val Phe His Gly Asp Ser
            500                 505                 510

Thr Gly Leu Ser Thr Asp Ser Leu Ala Asp Ala Gly Tyr Leu Gly Ala
        515                 520                 525

Ala Ala Leu Gly Glu Ala Val Cys Gly Met Ala Val Ala Tyr Ile Thr
    530                 535                 540

Pro Ser Asp Tyr Leu Phe Trp Phe Arg Ser His Thr Ala Lys Glu Ile
545                 550                 555                 560

Lys Trp Gly Gly Ala Lys His His Pro Glu Asp Lys Asp Asp Gly Gln
                565                 570                 575

Arg Met His Pro Arg Ser Ser Phe Lys Ala Phe Leu Glu Val Val Lys
            580                 585                 590

Ser Arg Ser Leu Pro Trp Glu Asn Ala Glu Met Asp Ala Ile His Ser
        595                 600                 605

Leu Gln Leu Ile Leu Arg Asp Ser Phe Arg Asp Ala Ala Glu Gly Thr
    610                 615                 620

Asn Asn Ser Lys Ala Ile Val Asn Gly Gln Val Gln Leu Arg Glu Leu
625                 630                 635                 640

Glu Leu Arg Gly Ile Asn Glu Leu Ser Ser Val Ala Arg Glu Met Val
                645                 650                 655

Arg Leu Ile Glu Thr Ala Thr Val Pro Ile Phe Ala Val Asp Thr Asp
            660                 665                 670

Gly Cys Ile Asn Gly Trp Asn Ala Lys Ile Ala Glu Leu Thr Gly Leu
        675                 680                 685

Ser Val Glu Glu Ala Met Gly Lys Ser Leu Val Asn Asp Leu Ile Phe
    690                 695                 700

Lys Glu Ser Glu Ala Thr Val Glu Lys Leu Leu Ser Arg Ala Leu Arg
705                 710                 715                 720

Gly Glu Glu Asp Lys Asn Val Glu Ile Lys Leu Lys Thr Phe Gly Ser
                725                 730                 735

Glu Gln Ser Lys Gly Pro Ile Phe Val Val Val Asn Ala Cys Ser Ser
            740                 745                 750

Arg Asp Tyr Thr Gln Asn Ile Val Gly Val Cys Phe Val Gly Gln Asp
        755                 760                 765

Val Thr Gly Gln Lys Val Val Met Asp Lys Phe Val Asn Ile Gln
    770                 775                 780
```

<210> SEQ ID NO 62
<211> LENGTH: 466
<212> TYPE: PRT
<213> ORGANISM: Arabidopsis lyrata

<400> SEQUENCE: 62

```
Met Met Lys Val Val Ser Pro Arg Thr Arg Ser Asp Ser Ile Thr Glu
1               5                   10                  15

Lys Val Phe Arg Arg Val Tyr Ser Asn Phe Asn Ile Ser Thr Val Glu
            20                  25                  30

Asp Glu Tyr Ile His Arg Gln Arg Ser Ser Asp Tyr Glu Lys Glu Ser
        35                  40                  45

Arg Leu Arg Lys Arg Gly Leu Glu Glu Lys Glu Glu Val Met Glu Met
    50                  55                  60

Glu Gln Met Gly Ala Glu Arg Ile Lys Thr Val Leu Ile Leu Met Ser
65                  70                  75                  80

Asp Thr Gly Gly Gly His Arg Ala Ser Ala Glu Ala Ile Arg Asp Ala
                85                  90                  95

Phe Lys Ile Glu Phe Gly Asp Asp Tyr Arg Ile Ile Ile Lys Asp Val
            100                 105                 110

Trp Lys Glu Tyr Thr Gly Trp Pro Leu Asn Asp Met Glu Arg Gln Tyr
        115                 120                 125

Lys Phe Met Val Lys His Val Gly Leu Trp Ser Val Ala Phe His Gly
    130                 135                 140

Thr Ser Pro Lys Trp Ile His Lys Ser Tyr Leu Ser Ala Leu Ala Ala
145                 150                 155                 160

Tyr Tyr Ala Lys Glu Ile Glu Ala Gly Leu Met Glu Tyr Lys Pro Asp
                165                 170                 175

Ile Ile Ile Ser Val His Pro Leu Met Gln His Ile Pro Leu Trp Val
            180                 185                 190

Met Lys Trp Gln Gly Leu His Lys Lys Val Ile Phe Val Thr Val Ile
        195                 200                 205

Thr Asp Leu Asn Thr Cys His Arg Thr Trp Phe His His Gly Val Ser
    210                 215                 220

Arg Cys Tyr Cys Pro Ser Lys Glu Val Ala Lys Arg Ala Leu Val Asp
225                 230                 235                 240

Gly Leu Asp Asp Ser Gln Ile Arg Val Phe Gly Leu Pro Val Arg Pro
                245                 250                 255

Ser Phe Pro Arg Thr Ile Ile Tyr Lys Asp Glu Leu Arg Arg Glu Leu
            260                 265                 270

Glu Ile Asp Leu Asn Leu Pro Ala Val Leu Leu Met Gly Gly Gly Glu
        275                 280                 285

Gly Met Gly Pro Val Gln Lys Thr Ala Leu Ala Leu Gly Asp Ala Leu
    290                 295                 300

Tyr Asn Ser Lys Glu Arg Asn Pro Ile Gly Gln Leu Ile Val Ile Cys
305                 310                 315                 320

Gly Arg Asn Lys Val Leu Ala Ser Ala Leu Ala Ser His Glu Trp Lys
                325                 330                 335

Ile Pro Val Lys Val Arg Gly Phe Glu Thr Gln Met Glu Lys Trp Met
            340                 345                 350

Gly Ala Cys Asp Cys Ile Ile Thr Lys Ala Gly Pro Gly Thr Ile Ala
        355                 360                 365

Glu Ala Leu Ile Cys Gly Leu Pro Ile Ile Leu Asn Asp Tyr Ile Pro
    370                 375                 380

Gly Gln Glu Lys Gly Asn Val Pro Tyr Val Val Asp Asn Gly Ala Gly
385                 390                 395                 400

Val Phe Thr Arg Ser Pro Lys Glu Thr Ala Lys Ile Val Ala Asn Trp
                405                 410                 415
```

```
Phe Ser Asn Asn Lys Glu Glu Leu Lys Lys Met Ser Glu Asn Ala Leu
            420                 425                 430

Lys Leu Ala Gln Pro Glu Ala Val Phe Asp Ile Val Lys Asp Ile His
        435                 440                 445

His Leu Ser Gln Gln Gln Gln Gln Arg Ile Pro Leu Phe Asn Asp Phe
    450                 455                 460

Ser Tyr
465


<210> SEQ ID NO 63
<211> LENGTH: 719
<212> TYPE: PRT
<213> ORGANISM: Arabidopsis lyrata

<400> SEQUENCE: 63

Met Asp Gly Ile Lys Leu Ser Phe Pro Pro Glu Ser Pro Pro Leu Ser
1               5                   10                  15

Val Ile Val Ala Leu Ser Leu Ser Ala Ser Pro Val Thr Ile Asp Ser
            20                  25                  30

Ser Ala Ser Val Thr Thr Val Pro Ser Phe Val Phe Ser Asp Gly Arg
        35                  40                  45

Lys Leu Ser Gly Thr Thr Val Leu Leu Arg Tyr Val Gly Arg Ser Ala
    50                  55                  60

Asn Thr Leu Pro Asp Phe Tyr Gly Asn Asn Ala Phe Asp Ser Ser Gln
65                  70                  75                  80

Ile Asp Glu Trp Val Asp Tyr Ala Ser Val Phe Ser Ser Gly Ser Glu
                85                  90                  95

Phe Glu Asn Ala Cys Gly Arg Val Asp Lys Tyr Leu Glu Ser Arg Thr
            100                 105                 110

Phe Leu Val Gly His Ser Leu Ser Ile Ala Asp Val Ala Ile Trp Ser
        115                 120                 125

Ala Leu Ala Gly Thr Gly Gln Arg Trp Glu Ser Leu Arg Lys Ser Lys
    130                 135                 140

Lys Tyr Gln Ser Leu Val Arg Trp Phe Asn Ser Ile Leu Asp Glu Tyr
145                 150                 155                 160

Ser Glu Leu Leu Asn Lys Val Leu Ala Thr Tyr Val Lys Lys Ser Ser
                165                 170                 175

Gly Lys Pro Val Ala Ala Pro Lys Ser Lys Asp Ser Gln Gln Ala Leu
            180                 185                 190

Lys Gly Asp Ala Gln Asp Lys Ser Lys Pro Glu Val Asp Leu Pro Glu
        195                 200                 205

Ala Glu Ile Gly Lys Val Arg Leu Arg Phe Ala Pro Glu Pro Ser Gly
    210                 215                 220

Tyr Leu His Ile Gly His Ala Lys Ala Ala Leu Leu Asn Lys Tyr Phe
225                 230                 235                 240

Ala Glu Arg Tyr Gln Gly Glu Val Ile Val Arg Phe Asp Asp Thr Asn
                245                 250                 255

Pro Ala Lys Glu Ser Asn Glu Phe Val Asp Asn Leu Val Lys Asp Ile
            260                 265                 270

Gly Thr Leu Gly Ile Lys Tyr Glu Arg Val Thr Tyr Thr Ser Asp Tyr
        275                 280                 285

Phe Pro Glu Leu Met Glu Met Ala Glu Lys Leu Met Arg Glu Gly Lys
    290                 295                 300

Ala Tyr Val Asp Asp Thr Pro Arg Glu Gln Met Gln Lys Glu Arg Met
305                 310                 315                 320
```

```
Asp Gly Ile Asp Ser Lys Cys Arg Asn His Ser Val Glu Glu Asn Leu
                325                 330                 335

Lys Leu Trp Lys Glu Met Ile Ala Gly Ser Glu Arg Gly Leu Gln Cys
            340                 345                 350

Cys Val Arg Gly Lys Phe Asn Met Gln Asp Pro Asn Lys Ala Met Arg
        355                 360                 365

Asp Pro Val Tyr Tyr Arg Cys Asn Pro Met Ser His His Arg Ile Gly
    370                 375                 380

Asp Lys Tyr Lys Ile Tyr Pro Thr Tyr Asp Phe Ala Cys Pro Phe Val
385                 390                 395                 400

Asp Ser Leu Glu Gly Ile Thr His Ala Leu Arg Ser Ser Glu Tyr His
                405                 410                 415

Asp Arg Asn Ala Gln Tyr Phe Lys Val Leu Glu Asp Met Gly Leu Arg
            420                 425                 430

Gln Val Gln Leu Tyr Glu Phe Ser Arg Leu Asn Leu Val Phe Thr Leu
        435                 440                 445

Leu Ser Lys Arg Lys Leu Leu Trp Phe Val Gln Thr Gly Leu Val Asp
    450                 455                 460

Gly Trp Asp Asp Pro Arg Phe Pro Thr Val Gln Gly Ile Val Arg Arg
465                 470                 475                 480

Gly Leu Lys Ile Glu Ala Leu Ile Gln Phe Ile Leu Glu Gln Gly Ala
                485                 490                 495

Ser Lys Asn Leu Asn Leu Met Glu Trp Asp Lys Leu Trp Ser Ile Asn
            500                 505                 510

Lys Arg Ile Ile Asp Pro Val Cys Pro Arg His Thr Ala Val Ile Ala
        515                 520                 525

Glu Arg Arg Val Leu Phe Thr Leu Thr Asp Gly Pro Asp Glu Pro Phe
    530                 535                 540

Val Arg Leu Ile Pro Lys His Lys Lys Phe Glu Gly Ala Gly Glu Lys
545                 550                 555                 560

Ala Thr Thr Phe Thr Lys Ser Ile Trp Ile Glu Glu Ala Asp Ala Ser
                565                 570                 575

Ala Ile Ser Val Gly Glu Glu Val Thr Leu Met Asp Trp Gly Asn Ala
            580                 585                 590

Ile Val Lys Glu Ile Thr Lys Asp Lys Glu Gly Arg Val Thr Ala Leu
        595                 600                 605

Ser Gly Val Leu Asn Leu Gln Gly Ser Val Lys Thr Thr Lys Leu Lys
    610                 615                 620

Leu Thr Trp Leu Pro Asp Thr Asn Glu Leu Val Asn Leu Thr Leu Thr
625                 630                 635                 640

Glu Phe Asp Tyr Leu Ile Thr Lys Lys Lys Leu Glu Asp Asp Asp Glu
                645                 650                 655

Val Ala Asp Phe Val Asn Pro Asn Thr Lys Lys Glu Thr Leu Ala Leu
            660                 665                 670

Gly Asp Ser Asn Met Arg Asn Leu Lys Cys Gly Asp Val Ile Gln Leu
        675                 680                 685

Glu Arg Lys Gly Tyr Phe Arg Cys Asp Val Pro Phe Val Lys Ser Ser
    690                 695                 700

Lys Pro Ile Val Leu Phe Ser Ile Pro Asp Gly Arg Ala Ala Lys
705                 710                 715
```

<210> SEQ ID NO 64
<211> LENGTH: 728

```
<212> TYPE: PRT
<213> ORGANISM: Arabidopsis thaliana

<400> SEQUENCE: 64

Met Asp Gly Met Lys Leu Ser Phe Pro Pro Glu Ser Pro Pro Leu Ser
1               5                   10                  15

Val Ile Val Ala Leu Ser Leu Ser Ala Ser Pro Val Thr Ile Asp Ser
            20                  25                  30

Ser Ala Ala Ala Thr Thr Val Pro Ser Phe Val Phe Ser Asp Gly Arg
        35                  40                  45

Lys Leu Asn Gly Ala Thr Val Leu Leu Arg Tyr Val Gly Arg Ser Ala
    50                  55                  60

Lys Lys Leu Pro Asp Phe Tyr Gly Asn Asn Ala Phe Asp Ser Ser Gln
65                  70                  75                  80

Val Ser Ile Leu Cys Ile Asn Met Lys Ile Asp Glu Trp Val Asp Tyr
                85                  90                  95

Ala Ser Val Phe Ser Ser Gly Ser Glu Phe Glu Asn Ala Cys Gly Arg
            100                 105                 110

Val Asp Lys Tyr Leu Glu Ser Ser Thr Phe Leu Val Gly His Ser Leu
        115                 120                 125

Ser Ile Ala Asp Val Ala Ile Trp Ser Ala Leu Ala Gly Thr Gly Gln
    130                 135                 140

Arg Trp Glu Ser Leu Arg Lys Ser Lys Lys Tyr Gln Ser Leu Val Arg
145                 150                 155                 160

Trp Phe Asn Ser Ile Leu Asp Glu Tyr Ser Glu Val Leu Asn Lys Val
                165                 170                 175

Leu Ala Thr Tyr Val Lys Lys Gly Ser Gly Lys Pro Val Ala Ala Pro
            180                 185                 190

Lys Ser Lys Asp Ser Gln Gln Ala Val Lys Gly Asp Gly Gln Asp Lys
        195                 200                 205

Gly Lys Pro Glu Val Asp Leu Pro Glu Ala Glu Ile Gly Lys Val Lys
    210                 215                 220

Leu Arg Phe Ala Pro Glu Pro Ser Gly Tyr Leu His Ile Gly His Ala
225                 230                 235                 240

Lys Ala Ala Leu Leu Asn Lys Tyr Phe Ala Glu Arg Tyr Gln Gly Glu
                245                 250                 255

Val Ile Val Arg Phe Asp Asp Thr Asn Pro Ala Lys Glu Ser Asn Glu
            260                 265                 270

Phe Val Asp Asn Leu Val Lys Asp Ile Gly Thr Leu Gly Ile Lys Tyr
        275                 280                 285

Glu Lys Val Thr Tyr Thr Ser Asp Tyr Phe Pro Glu Leu Met Asp Met
    290                 295                 300

Ala Glu Lys Leu Met Arg Glu Gly Lys Ala Tyr Val Asp Asp Thr Pro
305                 310                 315                 320

Arg Glu Gln Met Gln Lys Glu Arg Met Asp Gly Ile Asp Ser Lys Cys
                325                 330                 335

Arg Asn His Ser Val Glu Glu Asn Leu Lys Leu Trp Lys Glu Met Ile
            340                 345                 350

Ala Gly Ser Glu Arg Gly Leu Gln Cys Cys Val Arg Gly Lys Phe Asn
        355                 360                 365

Met Gln Asp Pro Asn Lys Ala Met Arg Asp Pro Val Tyr Tyr Arg Cys
    370                 375                 380

Asn Pro Met Ser His His Arg Ile Gly Asp Lys Tyr Lys Ile Tyr Pro
385                 390                 395                 400
```

```
Thr Tyr Asp Phe Ala Cys Pro Phe Val Asp Ser Leu Glu Gly Ile Thr
                405                 410                 415

His Ala Leu Arg Ser Ser Glu Tyr His Asp Arg Asn Ala Gln Tyr Phe
            420                 425                 430

Lys Val Leu Glu Asp Met Gly Leu Arg Gln Val Gln Leu Tyr Glu Phe
        435                 440                 445

Ser Arg Leu Asn Leu Val Phe Thr Leu Leu Ser Lys Arg Lys Leu Leu
    450                 455                 460

Trp Phe Val Gln Thr Gly Leu Val Asp Gly Trp Asp Asp Pro Arg Phe
465                 470                 475                 480

Pro Thr Val Gln Gly Ile Val Arg Arg Gly Leu Lys Ile Glu Ala Leu
                485                 490                 495

Ile Gln Phe Ile Leu Glu Gln Gly Ala Ser Lys Asn Leu Asn Leu Met
            500                 505                 510

Glu Trp Asp Lys Leu Trp Ser Ile Asn Lys Arg Ile Ile Asp Pro Val
        515                 520                 525

Cys Pro Arg His Thr Ala Val Val Ala Glu Arg Arg Val Leu Phe Thr
    530                 535                 540

Leu Thr Asp Gly Pro Asp Glu Pro Phe Val Arg Met Ile Pro Lys His
545                 550                 555                 560

Lys Lys Phe Glu Gly Ala Gly Glu Lys Ala Thr Thr Phe Thr Lys Ser
                565                 570                 575

Ile Trp Leu Glu Glu Ala Asp Ala Ser Ala Ile Ser Val Gly Glu Glu
            580                 585                 590

Val Thr Leu Met Asp Trp Gly Asn Ala Ile Val Lys Glu Ile Thr Lys
        595                 600                 605

Asp Glu Glu Gly Arg Val Thr Ala Leu Ser Gly Val Leu Asn Leu Gln
    610                 615                 620

Gly Ser Val Lys Thr Thr Lys Leu Lys Leu Thr Trp Leu Pro Asp Thr
625                 630                 635                 640

Asn Glu Leu Val Asn Leu Thr Leu Thr Glu Phe Asp Tyr Leu Ile Thr
                645                 650                 655

Lys Lys Lys Leu Glu Asp Asp Asp Glu Val Ala Asp Phe Val Asn Pro
            660                 665                 670

Asn Thr Lys Lys Glu Thr Leu Ala Leu Gly Asp Ser Asn Met Arg Asn
        675                 680                 685

Leu Lys Cys Gly Asp Val Ile Gln Leu Glu Arg Lys Gly Tyr Phe Arg
    690                 695                 700

Cys Asp Val Pro Phe Val Lys Ser Ser Lys Pro Ile Val Leu Phe Ser
705                 710                 715                 720

Ile Pro Asp Gly Arg Ala Ala Lys
                725
```

<210> SEQ ID NO 65
<211> LENGTH: 303
<212> TYPE: PRT
<213> ORGANISM: Arabidopsis lyrata

<400> SEQUENCE: 65

```
Met Val Thr Lys Thr Glu Glu Thr Gln Leu Asn Gln Leu Glu Asn Gln
1               5                   10                  15

Val Glu Asn Gly Gly Gly Gly Val Trp Glu Tyr Leu Cys Leu Val Arg
            20                  25                  30

Lys Leu Lys Val Arg Arg Ser Glu Ile Val Leu Lys His Gly Leu Ser
```

-continued

```
        35                  40                  45

Ile Leu Asn Asp Ser Gly Lys Arg Ser Ala Leu Gly Pro Asp Glu Trp
    50                  55                  60

Thr Leu Tyr Glu Gln Val Ala Ile Ala Ala Met Asp Cys Gln Ser Leu
65                  70                  75                  80

Gly Val Ala Gln Asn Cys Ile Lys Ala Leu Gln Lys Lys Phe Pro Glu
                85                  90                  95

Ser Lys Arg Val Gly Lys Leu Glu Ala Leu Leu Leu Glu Ala Lys Gly
            100                 105                 110

Met Trp Glu Glu Ala Glu Lys Ala Tyr Ser Ser Leu Leu Glu Asp Asn
        115                 120                 125

Pro Leu Asp Gln Val Ile His Lys Arg Lys Val Ala Met Ala Lys Ala
    130                 135                 140

Gln Gly Lys Pro Ser Leu Ala Ile Glu His Leu Asn Lys Tyr Leu Glu
145                 150                 155                 160

Val Phe Met Ala Asp His Asp Ala Trp Arg Glu Leu Ala Glu Ile Tyr
                165                 170                 175

Val Ser Leu Gln Met Tyr Lys Gln Ala Ala Phe Cys Tyr Glu Glu Leu
            180                 185                 190

Ile Leu Thr Gln Pro Thr Leu Pro Leu Tyr His Leu Ala Tyr Ala Asp
        195                 200                 205

Val Leu Tyr Thr Met Gly Gly Leu Glu Asn Leu Ile Ala Ala Arg Lys
    210                 215                 220

Tyr Tyr Ala Ala Thr Ile Asp Leu Thr Gly Gly Lys Ser Thr Arg Ala
225                 230                 235                 240

Leu Leu Gly Ile Cys Leu Cys Gly Ser Ala Ile Ala Gln Leu Ser Lys
                245                 250                 255

Gly Arg Asn Arg Glu Asp Lys Asp Met Ala Ala Pro Glu Leu Gln Ser
            260                 265                 270

Leu Ala Ala Thr Ala Leu Glu Arg Glu Tyr Lys Gln Lys Ala Pro Ala
        275                 280                 285

Lys Leu Asn Leu Leu Thr Cys Ala Leu Arg Asn Leu Lys Ile Ala
    290                 295                 300


<210> SEQ ID NO 66
<211> LENGTH: 299
<212> TYPE: PRT
<213> ORGANISM: Arabidopsis thaliana

<400> SEQUENCE: 66

Met Val Thr Lys Thr Glu Glu Ile Gln Leu Asn Gln Leu Glu Asn Gln
1               5                   10                  15

Val Glu Asn Gly Gly Gly Gly Val Trp Glu Tyr Leu Cys Leu Val Arg
            20                  25                  30

Lys Leu Lys Val Arg Arg Ser Glu Ile Val Leu Lys His Gly Leu Ser
        35                  40                  45

Ile Leu Asn Asp Ser Gly Lys Arg Ser Ala Leu Gly Pro Asp Glu Trp
    50                  55                  60

Thr Leu Tyr Glu Gln Val Ala Ile Ala Ala Met Asp Cys Gln Ser Leu
65                  70                  75                  80

Gly Val Ala Gln Val Leu Lys Lys Lys Phe Pro Glu Ser Lys Arg Val
                85                  90                  95

Gly Lys Leu Glu Ala Leu Leu Leu Glu Ala Lys Gly Met Trp Glu Glu
            100                 105                 110
```

```
Ala Glu Lys Ala Tyr Thr Ser Leu Leu Glu Asp Asn Pro Leu Asp Gln
        115                 120                 125

Val Ile His Lys Arg Lys Val Ala Met Ala Lys Ala Gln Gly Lys Ser
    130                 135                 140

Ser Leu Ala Ile Glu His Leu Asn Lys Tyr Leu Glu Val Phe Met Ala
145                 150                 155                 160

Asp His Asp Ala Trp Arg Glu Leu Ala Glu Ile Tyr Val Ser Leu Gln
                165                 170                 175

Met Tyr Lys Gln Ala Ala Phe Cys Tyr Glu Glu Leu Ile Leu Thr Gln
            180                 185                 190

Pro Thr Leu Pro Leu Tyr His Leu Ala Tyr Ala Asp Val Leu Tyr Thr
        195                 200                 205

Ile Gly Gly Leu Glu Asn Leu Ile Ala Ala Arg Lys Tyr Tyr Ala Ala
    210                 215                 220

Thr Ile Asp Leu Thr Gly Gly Lys Ser Thr Arg Ala Leu Leu Gly Ile
225                 230                 235                 240

Cys Leu Cys Gly Ser Ala Ile Ala Gln Ile Ser Lys Gly Arg Asn Lys
                245                 250                 255

Glu Asp Lys Asp Met Ala Ala Pro Glu Leu Gln Ser Leu Ala Ala Thr
            260                 265                 270

Ala Leu Glu Arg Glu Tyr Lys Gln Lys Ala Pro Ala Lys Leu Asn Leu
        275                 280                 285

Leu Thr Ser Ala Leu Arg Asn Leu Lys Ile Ala
    290                 295


<210> SEQ ID NO 67
<211> LENGTH: 712
<212> TYPE: PRT
<213> ORGANISM: Arabidopsis lyrata

<400> SEQUENCE: 67

Met Val Gly Gly Gly Ser Ser Ser Gly Gly Gly Gly Val Phe Arg Gly
1               5                   10                  15

Gly Gly Ser Gly Lys Gln Gln Arg Gly Phe Ser Leu Asn Pro Lys Asp
            20                  25                  30

Tyr Lys Leu Leu Glu Glu Ile Gly His Gly Ala Ser Ala Val Val Tyr
        35                  40                  45

Arg Ala Ile Tyr Leu Pro Thr Asn Glu Val Val Ala Ile Lys Cys Leu
    50                  55                  60

Asp Leu Asp Arg Cys Asn Ser Asn Leu Asp Asp Ile Arg Arg Glu Ser
65                  70                  75                  80

Gln Thr Met Ser Leu Ile Asp His Pro Asn Val Ile Lys Ser Phe Cys
                85                  90                  95

Ser Phe Ser Val Asp His Ser Leu Trp Val Val Met Pro Phe Met Ala
            100                 105                 110

Gln Gly Ser Cys Leu His Leu Met Lys Thr Ala Tyr Ser Asp Gly Phe
        115                 120                 125

Glu Glu Ser Ala Ile Cys Cys Val Leu Lys Glu Thr Leu Lys Ala Leu
    130                 135                 140

Asp Tyr Leu His Lys Gln Gly His Ile His Arg Asp Val Lys Ala Gly
145                 150                 155                 160

Asn Ile Leu Leu Asp Asp Ser Gly Glu Ile Lys Leu Gly Asp Phe Gly
                165                 170                 175

Val Ser Ala Cys Leu Phe Asp Asn Gly Asp Arg Arg Arg Ala Arg Asn
            180                 185                 190
```

```
Thr Phe Val Gly Thr Pro Cys Trp Met Ala Pro Glu Val Leu Gln Pro
        195                 200                 205

Gly Glu Gly Tyr Asn Ser Lys Ala Asp Ile Trp Ser Phe Gly Ile Thr
    210                 215                 220

Ala Leu Glu Leu Ala His Gly His Ala Pro Phe Ser Lys Tyr Pro Pro
225                 230                 235                 240

Met Lys Val Leu Leu Met Thr Ile Gln Asn Ala Pro Pro Gly Leu Asp
                245                 250                 255

Tyr Asp Arg Asp Lys Lys Phe Ser Lys Ser Phe Lys Glu Met Val Ala
            260                 265                 270

Met Cys Leu Val Lys Asp Gln Thr Lys Arg Pro Thr Ala Glu Lys Leu
        275                 280                 285

Leu Lys His Ser Cys Phe Lys His Thr Lys Pro Pro Glu Phe Tyr Val
    290                 295                 300

Lys Lys Leu Phe Ser Asp Leu Pro Pro Leu Trp Thr Arg Val Lys Ser
305                 310                 315                 320

Leu Gln Asp Lys Asp Ala Gln Gln Leu Ala Leu Lys Arg Met Ala Thr
                325                 330                 335

Ala Asp Glu Glu Ala Ile Ser Gln Ser Glu Tyr Gln Arg Gly Val Ser
            340                 345                 350

Ala Trp Asn Phe Asp Val Arg Asp Leu Lys Thr Gln Ala Ser Leu Leu
        355                 360                 365

Ile Asp Asp Asp Asp Leu Glu Glu Ser Lys Glu Asp Asp Glu Ile Leu
    370                 375                 380

Cys Ala Gln Phe Asn Lys Val Asn Asp Arg Val Gln Val Phe Asp Ser
385                 390                 395                 400

Leu Gln Leu Tyr Glu Thr Met Asn Glu Lys Glu Lys Val Ser Asn Thr
                405                 410                 415

Glu Val Glu Glu Pro Thr Cys Glu Glu Lys Phe Thr Phe Ile Thr Thr
            420                 425                 430

Ala Ser Ser Leu Glu Arg Met Ser Pro Asn Ser Glu His Asp Ile Pro
        435                 440                 445

Glu Ala Lys Val Lys Pro Val Arg Arg Gln Ser Gln Ser Gly Pro Leu
    450                 455                 460

Thr Ser Lys Thr Val Leu Cys His Ser Ala Ser Glu Lys Gly His Ile
465                 470                 475                 480

Phe Glu Arg Ser Glu Ser Glu Gln Gln Thr Ala Ser Thr Val Arg Arg
                485                 490                 495

Ala Pro Ser Phe Ser Gly Pro Leu Asn Leu Pro Thr Arg Ala Ser Ser
            500                 505                 510

Asn Ser Leu Ser Ala Pro Ile Lys Tyr Ser Gly Gly Phe Arg Asp Ser
        515                 520                 525

Leu Asp Asp Lys Ser Lys Ala Asn Leu Val Gln Lys Gly Arg Phe Ser
    530                 535                 540

Val Thr Ser Gly Asn Val Asp Leu Ala Lys Asp Val Pro Leu Ser Ile
545                 550                 555                 560

Val Pro Arg Arg Ser Pro Gln Ala Thr Pro Leu Arg Lys Ser Ala Ser
                565                 570                 575

Val Gly Asn Trp Ile Leu Glu Pro Lys Met Pro Thr Ala Gln Pro Gln
            580                 585                 590

Thr Ile Lys Glu His Ser Ser His Pro Thr Ser Ser Ser Ser Ser Leu
        595                 600                 605
```

```
Ile Val Pro Gln Leu Gln His Leu Phe Gln Gln Asn Ser Ile Gln Gln
    610                 615                 620

Asp Leu Ile Met Asn Leu Leu Asn Ser Ile Gln Pro Gly Glu Ala Thr
625                 630                 635                 640

Glu Gly Ser Gln Ser Gly Lys Leu Pro Pro Leu Pro Arg Ser Asp Ser
                645                 650                 655

Asn Gly Asn Val Glu Pro Val Ala Ser Glu Arg Glu Arg Leu Leu Leu
            660                 665                 670

Ser Ser Ile Ser Asp Leu Arg Ala Arg Leu Asp Asp Leu Thr Glu Glu
        675                 680                 685

Leu Asp Ile Glu Lys Ser Lys Tyr Ser Gln Leu Gln Gln Lys Leu Lys
    690                 695                 700

Ala Phe Thr Gly Arg Lys His Val
705                 710


<210> SEQ ID NO 68
<211> LENGTH: 563
<212> TYPE: PRT
<213> ORGANISM: Arabidopsis lyrata

<400> SEQUENCE: 68

Met Lys Glu Ser Phe Lys Val Cys Phe Cys Cys Val Arg Ser Phe Lys
1               5                   10                  15

Val Lys Ser Ser Glu Pro Pro Glu Glu Ile Lys Asn Leu Phe His Asp
            20                  25                  30

Tyr Ser Gln Asp Asp Arg Met Ser Ala Asp Glu Met Leu Arg Phe Val
        35                  40                  45

Ile Gln Val Gln Gly Glu Thr His Ala Asp Ile Asn Tyr Val Lys Asp
    50                  55                  60

Ile Phe His Arg Leu Lys His His Gly Val Phe His Pro Arg Gly Ile
65                  70                  75                  80

His Leu Glu Gly Phe Tyr Arg Tyr Leu Leu Ser Asp Phe Asn Ser Pro
                85                  90                  95

Leu Pro Val Thr Ser Glu Val Trp Gln Asp Met Asn Gln Pro Leu Ser
            100                 105                 110

His Tyr Phe Leu Tyr Thr Gly His Asn Ser Tyr Leu Thr Gly Asn Gln
        115                 120                 125

Leu Asn Ser Asn Ser Ser Ile Glu Pro Ile Val Lys Ala Leu Arg Lys
    130                 135                 140

Gly Val Arg Val Ile Glu Leu Asp Leu Trp Pro Asn Ser Ser Gly Lys
145                 150                 155                 160

Glu Ala Glu Val Arg His Gly Gly Thr Leu Thr Ser Cys Glu Asp Leu
                165                 170                 175

Gln Lys Cys Leu Asn Ala Val Lys Glu Asn Ala Phe Gln Val Ser Ala
            180                 185                 190

Tyr Pro Val Val Leu Thr Leu Glu Asp His Leu Thr Pro Asn Leu Gln
        195                 200                 205

Lys Lys Val Ala Lys Met Val Ser Lys Thr Phe Gly Gly Ser Leu Phe
    210                 215                 220

Gln Cys Thr Asp Glu Tyr Thr Glu Cys Phe Pro Ser Pro Glu Ser Leu
225                 230                 235                 240

Lys Asn Lys Ile Leu Ile Ser Thr Lys Pro Pro Lys Glu Tyr Leu Gln
                245                 250                 255

Thr Gln Val Ser Gln Gly Ser Thr Thr Asp Glu Ser Ile Lys Ala Lys
            260                 265                 270
```

```
Lys Ile Ala Asp Ala Glu Glu Gln Val Gln Glu Glu Asp Glu Glu Ser
        275                 280                 285

Val Ala Ile Glu Tyr Arg Asp Leu Ile Ser Ile His Ala Gly Asn Arg
    290                 295                 300

Lys Gly Gly Leu Lys Asn Cys Leu Asn Gly Asp Pro Asn Arg Val Ile
305                 310                 315                 320

Arg Leu Ser Met Ser Glu Gln Trp Leu Glu Thr Leu Ala Lys Thr Arg
                325                 330                 335

Gly Ser Asp Leu Val Lys Phe Thr Gln Arg Asn Leu Leu Arg Ile Phe
            340                 345                 350

Pro Lys Thr Thr Arg Phe Asp Ser Ser Asn Tyr Asp Pro Leu Val Gly
        355                 360                 365

Trp Ile His Gly Ala Gln Met Val Ala Phe Asn Met Gln Ser His Gly
    370                 375                 380

Arg Tyr Leu Trp Met Met Gln Gly Met Phe Lys Ala Asn Gly Gly Cys
385                 390                 395                 400

Gly Tyr Val Lys Lys Pro Asp Val Leu Leu Ser Asn Gly Pro Gly Gly
                405                 410                 415

Glu Ile Phe Asp Pro Cys Ser Gln Lys Leu Pro Ile Lys Thr Thr Leu
            420                 425                 430

Lys Val Lys Ile Tyr Thr Gly Glu Gly Trp Asn Met Asp Phe Pro Leu
        435                 440                 445

Asp His Phe Asp Arg Tyr Ser Pro Pro Asp Phe Tyr Ala Lys Ala Arg
    450                 455                 460

Val Gly Ile Ala Gly Val Pro Leu Asp Thr Ala Ser Tyr Arg Thr Glu
465                 470                 475                 480

Ile Asp Thr Asp Glu Trp Phe Pro Ile Trp Asp Lys Glu Phe Glu Phe
                485                 490                 495

Pro Leu Arg Val Pro Glu Leu Ala Ile Leu Cys Ile Thr Val Lys Asp
            500                 505                 510

Tyr Asp Ser Asn Thr Gln Asn Asp Phe Ala Gly Gln Thr Cys Leu Pro
        515                 520                 525

Leu Ser Glu Val Arg Pro Gly Ile Arg Ala Val Arg Leu His Asp Arg
    530                 535                 540

Ala Gly Glu Val Tyr Lys His Val Arg Leu Leu Met Arg Phe Val Leu
545                 550                 555                 560

Glu Pro Arg
```

<210> SEQ ID NO 69
<211> LENGTH: 561
<212> TYPE: PRT
<213> ORGANISM: Arabidopsis thaliana

<400> SEQUENCE: 69

```
Met Lys Glu Ser Phe Lys Val Cys Phe Cys Cys Val Arg Asn Phe Lys
1               5                   10                  15

Val Lys Ser Ser Glu Pro Pro Glu Glu Ile Lys Asn Leu Phe His Asp
            20                  25                  30

Tyr Ser Gln Asp Asp Arg Met Ser Ala Asp Glu Met Leu Arg Phe Val
        35                  40                  45

Ile Gln Val Gln Gly Glu Thr His Ala Asp Ile Asn Tyr Val Lys Asp
    50                  55                  60

Ile Phe His Arg Leu Lys His His Gly Val Phe His Pro Arg Gly Ile
65                  70                  75                  80
```

```
His Leu Glu Gly Phe Tyr Gly Tyr Leu Leu Ser Asp Phe Asn Ser Pro
                85                  90                  95

Leu Pro Leu Thr Arg Glu Val Trp Gln Asp Met Asn Gln Pro Leu Ser
            100                 105                 110

His Tyr Phe Leu Tyr Thr Gly His Asn Ser Tyr Leu Thr Gly Asn Gln
        115                 120                 125

Leu Asn Ser Asn Ser Ser Ile Glu Pro Ile Val Lys Ala Leu Arg Asn
    130                 135                 140

Gly Val Arg Val Ile Glu Leu Asp Leu Trp Pro Asn Ser Ser Gly Lys
145                 150                 155                 160

Glu Ala Glu Val Arg His Gly Gly Thr Leu Thr Ser Arg Glu Asp Leu
                165                 170                 175

Gln Lys Cys Leu Asn Val Val Lys Glu Asn Ala Phe Gln Val Ser Ala
            180                 185                 190

Tyr Pro Val Val Leu Thr Leu Glu Asp His Leu Thr Pro Ile Leu Gln
        195                 200                 205

Lys Lys Val Ala Lys Met Val Ser Lys Thr Phe Gly Gly Ser Leu Phe
    210                 215                 220

Gln Cys Thr Asp Glu Thr Thr Glu Cys Phe Pro Ser Pro Glu Ser Leu
225                 230                 235                 240

Lys Asn Lys Ile Leu Ile Ser Thr Lys Pro Pro Lys Glu Tyr Leu Gln
                245                 250                 255

Thr Gln Ile Ser Lys Gly Ser Thr Thr Asp Glu Ser Thr Arg Ala Lys
            260                 265                 270

Lys Ile Ser Asp Ala Glu Glu Gln Val Gln Glu Glu Asp Glu Glu Ser
        275                 280                 285

Val Ala Ile Glu Tyr Arg Asp Leu Ile Ser Ile His Ala Gly Asn Arg
    290                 295                 300

Lys Gly Gly Leu Lys Asn Cys Leu Asn Gly Asp Pro Asn Arg Val Ile
305                 310                 315                 320

Arg Leu Ser Met Ser Glu Gln Trp Leu Glu Thr Leu Ala Lys Thr Arg
                325                 330                 335

Gly Pro Asp Leu Val Lys Phe Thr Gln Arg Asn Leu Leu Arg Ile Phe
            340                 345                 350

Pro Lys Thr Thr Arg Phe Asp Ser Ser Asn Tyr Asp Pro Leu Val Gly
        355                 360                 365

Trp Ile His Gly Ala Gln Met Val Ala Phe Asn Met Gln Ser His Gly
    370                 375                 380

Arg Tyr Leu Trp Met Met Gln Gly Met Phe Lys Ala Asn Gly Gly Cys
385                 390                 395                 400

Gly Tyr Val Lys Lys Pro Asp Val Leu Leu Ser Asn Gly Pro Glu Gly
                405                 410                 415

Glu Ile Phe Asp Pro Cys Ser Gln Asn Leu Pro Ile Lys Thr Thr Leu
            420                 425                 430

Lys Val Lys Ile Tyr Thr Gly Glu Gly Trp Asn Met Asp Phe Pro Leu
        435                 440                 445

Asp His Phe Asp Arg Tyr Ser Pro Pro Asp Phe Tyr Ala Lys Val Gly
    450                 455                 460

Ile Ala Gly Val Pro Leu Asp Thr Ala Ser Tyr Arg Thr Glu Ile Asp
465                 470                 475                 480

Lys Asp Glu Trp Phe Pro Ile Trp Asp Lys Glu Phe Glu Phe Pro Leu
                485                 490                 495
```

```
Arg Val Pro Glu Leu Ser Leu Leu Cys Ile Thr Val Lys Asp Tyr Asp
            500                 505                 510

Ser Asn Thr Gln Asn Asp Phe Ala Gly Gln Thr Cys Phe Pro Leu Ser
        515                 520                 525

Glu Val Arg Pro Gly Ile Arg Ala Val Arg Leu His Asp Arg Ala Gly
    530                 535                 540

Glu Val Tyr Lys His Val Arg Leu Leu Met Arg Phe Val Leu Glu Pro
545                 550                 555                 560

Arg
```

<210> SEQ ID NO 70
<211> LENGTH: 178
<212> TYPE: PRT
<213> ORGANISM: Arabidopsis thaliana

<400> SEQUENCE: 70

```
Met Ala Thr His Ser Ser Phe Thr Ala Thr Thr Pro Leu Phe Leu Ile
1               5                   10                  15

Val Leu Leu Ser Leu Ser Ser Val Ser Val Leu Gly Ala Ser His His
            20                  25                  30

His Ala Thr Ala Pro Ala Pro Ser Val Asp Cys Ser Thr Leu Ile Leu
        35                  40                  45

Asn Met Ala Asp Cys Leu Ser Phe Val Ser Ser Gly Gly Thr Val Ala
    50                  55                  60

Lys Pro Glu Gly Thr Cys Cys Ser Gly Leu Lys Thr Val Leu Lys Ala
65                  70                  75                  80

Asp Ser Gln Cys Leu Cys Glu Ala Phe Lys Ser Ser Ala Ser Leu Gly
                85                  90                  95

Val Thr Leu Asn Ile Thr Lys Ala Ser Thr Leu Pro Ala Ala Cys Lys
            100                 105                 110

Leu His Ala Pro Ser Ile Ala Thr Cys Gly Leu Ser Val Ala Pro Ser
        115                 120                 125

Thr Ala Pro Gly Val Ala Ala Ala Gly Pro Glu Thr Ala Gly Phe Leu
    130                 135                 140

Ala Pro Asn Pro Ser Ser Gly Asn Asp Gly Ser Ser Leu Ile Pro Thr
145                 150                 155                 160

Ser Phe Thr Thr Val Leu Ser Ala Val Leu Phe Val Leu Phe Phe Ser
                165                 170                 175

Ser Ala
```

<210> SEQ ID NO 71
<211> LENGTH: 182
<212> TYPE: PRT
<213> ORGANISM: Arabidopsis thaliana

<400> SEQUENCE: 71

```
Met Ala Thr His Ser Ser Phe Thr Ala Thr Thr Pro Leu Phe Leu Ile
1               5                   10                  15

Val Leu Leu Ser Leu Ser Ser Val Ser Val Leu Gly Ala Ser His His
            20                  25                  30

His Ala Thr Ala Pro Ala Pro Ser Val Asp Cys Ser Ile Leu Ile Leu
        35                  40                  45

Asn Met Ala Asp Cys Leu Ser Phe Val Ser Ser Gly Gly Thr Val Ala
    50                  55                  60

Lys Pro Glu Gly Thr Cys Cys Ser Gly Leu Lys Thr Val Leu Lys Ala
65                  70                  75                  80
```

```
Asp Ser Gln Cys Leu Cys Glu Ala Phe Lys Ser Ser Ala Ser Leu Gly
                85                  90                  95

Val Thr Leu Asn Ile Thr Lys Ala Ser Thr Leu Pro Ala Ala Cys Lys
            100                 105                 110

Leu His Ala Pro Ser Ile Ala Thr Cys Gly Leu Ser Val Ala Pro Ser
        115                 120                 125

Thr Ala Pro Gly Leu Ala Pro Gly Val Ala Ala Ala Gly Pro Glu Thr
    130                 135                 140

Val Gly Phe Leu Ala Pro Asn Pro Ser Ser Gly Asn Asp Gly Ser Ser
145                 150                 155                 160

Leu Ile Pro Thr Ser Phe Thr Thr Val Leu Ser Ala Val Leu Phe Val
                165                 170                 175

Leu Phe Phe Ser Ser Ala
            180


<210> SEQ ID NO 72
<211> LENGTH: 1189
<212> TYPE: PRT
<213> ORGANISM: Arabidopsis thaliana

<400> SEQUENCE: 72

Met Glu Glu Asp Asp Glu Phe Gly Asp Leu Tyr Ser Asp Val Leu Gln
1               5                   10                  15

Pro Phe Gln Pro Pro Val Val Leu Pro Pro Pro Pro Pro Leu Pro His
            20                  25                  30

Arg Ser Ile Asp Leu Asn Leu Arg Ser Gln Asp Gln Asp Val Ser Glu
        35                  40                  45

Pro Asn Ser Ala Pro Ile Ser Arg Val Ser Asp Asn Asp Ala Val Lys
    50                  55                  60

Leu Ser Thr Gln Asp Ala Thr Arg Gln Ala Ile Val Asp Gly Gly Gly
65                  70                  75                  80

Asp Asp Lys Asp Met Ser Phe Asp Ile Glu Glu Pro Asp Ala Asp Ser
                85                  90                  95

Thr Pro Thr Ile Pro Gly Leu Phe Val Thr Gly Ala Leu Pro Gly Leu
            100                 105                 110

Ala Thr Asp Arg Gly Val Ser Gln Val Thr Thr Arg Ile Glu Gln Gln
        115                 120                 125

Val Gly Gly Gly Gly Asp Gly Gly Tyr Gly Gly Gln Gly Glu Gly Asp
    130                 135                 140

Asp Trp Asp Ser Asp Ser Glu Asp Asp Leu Gln Ile Val Leu Asn Asp
145                 150                 155                 160

Ser Ser Arg Asn Val Met Ile Gly Gly Ala Asp Arg Arg Ser Arg Met
                165                 170                 175

Gly Asp Asn Glu Asp Asp Asp Asp Glu Asp Asp Glu Asp Pro Leu Val
            180                 185                 190

Ile Val Ala Asp Thr Asp Pro Asn Gln Pro Met Glu Glu Gln Met Trp
        195                 200                 205

Gly Glu Asp Gly Leu Gln Gly Ile Glu Gly Asp Gly Lys Asp Gly Gly
    210                 215                 220

Glu Ala Gly Lys Gly Ser Gly Pro Gly Gly Ala Thr Gly Pro Pro Lys
225                 230                 235                 240

Ala Gly Tyr Ser Ser His Gly Tyr His Pro Phe His Ser Gln Phe Lys
                245                 250                 255

Tyr Val Arg Pro Gly Ala Ala Pro Ile Pro Gly Gly Ala Ala Ser Val
```

-continued

```
            260                 265                 270

Gly Gly Pro Ser Ser Gly Gln Val Arg Pro Pro Ala Asn Leu Gly Pro
        275                 280                 285

Met Ala Gly Arg Gly Arg Gly Asp Trp Arg Pro Leu Gly Met Arg Asn
    290                 295                 300

Ala Ser Ala Ala Gln Lys Gly Phe His Gln Pro Trp Gly Ser Asn Thr
305                 310                 315                 320

Ala Gly Arg Gly Leu Asp Phe Thr Leu Pro Ser His Lys Thr Ile Phe
                325                 330                 335

Glu Val Asp Ile Asp Ser Phe Glu Glu Lys Pro Trp Arg Tyr Pro Gly
            340                 345                 350

Val Glu Met Thr Asp Tyr Phe Asn Phe Gly Leu Asn Glu Glu Ser Trp
        355                 360                 365

Lys Asp Tyr Cys Lys Gln Leu Asp Gln His Arg Ile Gln Thr Thr Met
    370                 375                 380

Gln Ser Arg Ile Arg Val Tyr Glu Ser Gly Arg Thr Asp Gln Gly Tyr
385                 390                 395                 400

Asp Pro Asp Leu Pro Pro Glu Leu Ala Ala Ala Thr Gly Ala Gln Gly
                405                 410                 415

Val Pro Val Asp Ser Ser Asn Leu Val Lys Pro Asp Ser Val Gln Gly
            420                 425                 430

Asp Ser Ala Lys Val Pro Ala Asn Val Arg Pro Thr Leu Pro Pro Gly
        435                 440                 445

Arg Pro Ile Pro Val Glu Thr Gly Ser Gly Glu Arg Leu Pro Ser Ile
    450                 455                 460

Asp Thr Arg Ala Pro Arg Met Arg Asp Leu Asp Ala Ile Ile Glu Asp
465                 470                 475                 480

Ser His Glu Asp Glu Pro Ser Gly Glu Asn Gly Thr Asp Gln Ala Asp
                485                 490                 495

Ser Ser Leu Pro Gly Glu Asn Val Pro Val Glu Thr Ser Tyr Val Asn
            500                 505                 510

Asn Lys Arg Pro Asp Thr Glu Ser Ala Glu His Ser Pro Ala Gln Asp
        515                 520                 525

Glu Pro His Lys Asn Leu Leu Lys Lys Gln Asp Asp Glu Ile Ser Arg
    530                 535                 540

Ser Thr Asp Ser Gly Gln Ser Phe Arg Ser Ser Ser Pro Val Gly Asp
545                 550                 555                 560

Arg Gly Thr Arg Ser Ser Ser Val Asp Arg Glu Asp Val Gly Gly Glu
                565                 570                 575

Ala Gly Lys Asp Ala Glu Met Gly Glu Glu Leu Lys Met Ser Phe Thr
            580                 585                 590

Ser Pro Gln Ser Ala Val Gln Glu Asp Asp Gly Gly Glu Ser Lys Thr
        595                 600                 605

Glu Arg Ser Ser Glu Ser Ser Lys Ala Arg Ser Gly Ser His Arg Asp
    610                 615                 620

Phe Gln Gln Glu Glu Asp Val Ile Gln Asp Lys His Ser Ser Arg Pro
625                 630                 635                 640

Ala Asn Asn Arg Lys Gln Tyr Asp Asn Asn Ala Pro His Gln Ser Arg
                645                 650                 655

Lys Asn Gln Asp Arg Gly Lys Glu Met Glu Arg Thr Arg Ala Ala Ser
            660                 665                 670

Lys Gly Gly Arg Glu Asn Ser Asn Pro His Met Glu Leu Asp Ser Thr
        675                 680                 685
```

```
Tyr Ile Tyr Ser Ile Ala Ser Arg Glu Asp Phe Asp Lys Arg Lys Glu
    690                 695                 700

Arg Asp Val Asp Gly Ala Val Trp Arg Arg Lys Glu Asp Asp Pro Tyr
705                 710                 715                 720

Ser Arg Arg Gly Gly Asp Glu Gly Ser Arg Lys Arg Asp Arg Glu Asp
                725                 730                 735

Asp Pro Gly Phe Arg Gln Arg Gly Lys Met Arg Glu Asn Glu Ile Arg
            740                 745                 750

Ser Lys Asp Asp Gln Val Pro Ser Arg Lys His Met Asp Asp Ala Gly
        755                 760                 765

Met Arg Asn Ile Tyr Glu Pro Asp Asp His Ile Asn Lys Arg Arg Lys
    770                 775                 780

Asp Glu Glu Tyr Leu Arg Arg Ser Arg Pro Glu Lys Asn Glu Ile Ser
785                 790                 795                 800

Tyr Gly Gln Arg Glu Ser Met Ser Arg Val Lys Arg Glu Arg Asp Asp
                805                 810                 815

Arg Leu Glu His Gln Lys Arg Asp Val Gln His Lys Ile Arg Asp Asp
            820                 825                 830

Phe Asp Asp His Gly Ser Leu Arg Gln Arg Asp Asp Ile Tyr Met Gln
        835                 840                 845

Arg Asp Gly Asn Glu Arg Leu Arg Glu Arg Asp Val Leu Asp Lys Leu
    850                 855                 860

Lys Leu Pro His Glu Asp Gly Ile Ser Ala Arg Gly Arg Glu Arg Gln
865                 870                 875                 880

Val Ala Val Arg Gly His Arg Gly Ser Glu Asp Arg Ser Ser Arg Met
                885                 890                 895

Lys Asp Glu Tyr Lys Ala Ser Asp Lys Glu His Val Thr Lys Asp Thr
            900                 905                 910

Leu Arg His Ala Lys Gln Thr Lys Arg Arg Asp Tyr Pro Gly Glu Glu
        915                 920                 925

Ser Ser Ser His His Arg Gly His Glu Asp Phe Ser Ala Arg Thr Asp
    930                 935                 940

Asn Ile Val Asn Asn Glu Lys Lys Pro Arg Gln Glu Arg Thr Gly Ala
945                 950                 955                 960

Lys Ile Asp Lys Phe Ile Asp Thr Leu Asp Gly Gln Arg Leu Gln Asp
                965                 970                 975

Arg Lys His Lys Asp Ser Arg Arg Lys Ile Lys Glu Gln Arg Glu Gly
            980                 985                 990

Thr Glu Ser Leu Ser Lys Gln Gly  Glu Gln Asn Gly Ser  Ser Val Val
        995                 1000                1005

Thr Gly  Ser Lys Gly Thr Asn  Asp Ala Arg Asn Cys  Arg Ser Glu
    1010                1015                1020

Ile Pro  His Gln Pro Asn Thr  Ala Lys Arg His Lys  Glu Asn Ala
    1025                1030                1035

Ser Ser  Gly Asp Glu Ile His  Asp Ser Lys Arg Gly  Arg Thr Lys
    1040                1045                1050

Leu Glu  Arg Trp Ala Ser His  Lys Glu Arg Glu Asp  Ala Val Ser
    1055                1060                1065

Ala Lys  Ser Ser Ser Ile Ser  Ser Lys Leu Glu Glu  Lys Glu Asn
    1070                1075                1080

Asn Thr  Asn Gly Arg Leu Ser  Glu Pro Val His Gly  Ser Ile Gly
    1085                1090                1095
```

```
Lys Ser  Arg Asp Val Thr Glu  Glu Lys Ile Gly His  Asp Leu Ala
    1100                1105                1110

Asp Thr  Lys Asp Gly Ser Glu  Lys Gly Pro Gly Asp  Arg His Leu
    1115                1120                1125

Asp Thr  Val Glu Lys Leu Lys  Lys Arg Ser Glu Arg  Phe Lys Leu
    1130                1135                1140

Pro Met  Pro Thr Glu Lys Asp  Thr Thr Gly Val Lys  Lys Met Glu
    1145                1150                1155

Ser Glu  Thr Leu Pro Ser Ala  Lys Ile Glu Gly Pro  Val Asp Ser
    1160                1165                1170

Glu Val  Lys Ala Glu Arg Pro  Ala Arg Lys Arg Arg  Trp Thr Ser
    1175                1180                1185

Ser


<210> SEQ ID NO 73
<211> LENGTH: 1196
<212> TYPE: PRT
<213> ORGANISM: Arabidopsis thaliana

<400> SEQUENCE: 73

Met Glu Glu Asp Asp Glu Phe Gly Asp Leu Tyr Ser Asp Val Leu Gln
1               5                   10                  15

Pro Phe Gln Pro Pro Val Val Leu Pro Pro Pro Pro Pro Leu Pro His
            20                  25                  30

Arg Ser Ile Asp Leu Asn Leu Arg Ser Gln Asp Gln Asp Val Ser Glu
        35                  40                  45

Pro Asn Ser Ala Pro Ile Ser Arg Val Ser Asp Asn Asp Ala Val Lys
    50                  55                  60

Leu Ser Thr Gln Asp Ala Thr Arg Gln Ala Ile Val Asp Gly Gly Gly
65                  70                  75                  80

Asp Asp Lys Asp Met Ser Phe Asp Ile Glu Glu Pro Asp Ala Asp Ser
                85                  90                  95

Thr Pro Thr Ile Pro Gly Leu Phe Val Thr Gly Ala Leu Pro Gly Leu
            100                 105                 110

Ala Thr Asp Arg Gly Val Ser Gln Val Thr Thr Arg Ile Glu Gln Gln
        115                 120                 125

Val Gly Gly Gly Gly Asp Gly Gly Tyr Gly Gly Gln Gly Glu Gly Asp
    130                 135                 140

Asp Trp Asp Ser Asp Ser Glu Asp Asp Leu Gln Ile Val Leu Asn Asp
145                 150                 155                 160

Ser Ser Arg Asn Val Met Ile Gly Gly Ala Asp Arg Arg Ser Arg Met
                165                 170                 175

Gly Asp Asn Glu Asp Asp Asp Asp Glu Asp Asp Glu Asp Pro Leu Val
            180                 185                 190

Ile Val Ala Asp Thr Asp Pro Asn Gln Pro Met Glu Glu Gln Met Trp
        195                 200                 205

Gly Glu Asp Gly Leu Gln Gly Ile Glu Gly Asp Gly Lys Asp Gly Gly
    210                 215                 220

Glu Ala Gly Lys Gly Ser Gly Pro Gly Gly Ala Thr Gly Pro Pro Lys
225                 230                 235                 240

Ala Gly Tyr Ser Ser His Gly Tyr His Pro Phe His Ser Gln Phe Lys
                245                 250                 255

Tyr Val Arg Pro Gly Ala Ala Pro Ile Pro Gly Gly Ala Ala Ser Val
            260                 265                 270
```

```
Gly Gly Pro Ser Ser Gly Gln Val Arg Pro Pro Ala Asn Leu Gly Pro
        275                 280                 285

Met Ala Gly Arg Gly Arg Gly Asp Trp Arg Pro Leu Gly Met Arg Asn
    290                 295                 300

Ala Ser Ala Ala Gln Lys Gly Phe His Gln Pro Trp Gly Ser Asn Thr
305                 310                 315                 320

Ala Gly Arg Gly Leu Asp Phe Thr Leu Pro Ser His Lys Thr Ile Phe
                325                 330                 335

Glu Val Asp Ile Asp Ser Phe Glu Glu Lys Pro Trp Arg Tyr Pro Gly
            340                 345                 350

Val Glu Met Thr Asp Tyr Phe Asn Phe Gly Leu Asn Glu Glu Ser Trp
        355                 360                 365

Lys Asp Tyr Cys Lys Gln Leu Asp Gln His Arg Ile Gln Thr Thr Met
    370                 375                 380

Gln Ser Arg Ile Arg Val Tyr Glu Ser Gly Arg Thr Asp Gln Gly Tyr
385                 390                 395                 400

Asp Pro Asp Leu Pro Pro Glu Leu Ala Ala Ala Thr Gly Ala Gln Gly
                405                 410                 415

Val Pro Val Asp Ser Ser Asn Leu Val Lys Pro Asp Ser Val Gln Gly
            420                 425                 430

Asp Ser Ala Lys Val Pro Ala Asn Val Arg Pro Thr Leu Pro Pro Gly
        435                 440                 445

Arg Pro Ile Pro Val Glu Thr Gly Ser Gly Glu Arg Leu Pro Ser Ile
    450                 455                 460

Asp Thr Arg Ala Pro Arg Met Arg Asp Leu Asp Ala Ile Ile Glu Ile
465                 470                 475                 480

Val Cys Gln Asp Ser His Glu Asp Glu Pro Ser Gly Glu Asn Gly Thr
                485                 490                 495

Asp Gln Ala Asp Ser Ser Leu Pro Gly Glu Asn Val Pro Val Glu Thr
            500                 505                 510

Ser Tyr Val Asn Asn Lys Arg Pro Asp Thr Glu Ser Ala Glu His Ser
        515                 520                 525

Pro Ala Gln Asp Glu Pro His Lys Asn Leu Leu Lys Lys Gln Asp Asp
    530                 535                 540

Glu Ile Ser Arg Ser Thr Asp Ser Gly Gln Ser Phe Arg Ser Ser Ser
545                 550                 555                 560

Pro Val Gly Asp Arg Gly Thr Arg Ser Ser Ser Val Asp Arg Glu Asp
                565                 570                 575

Val Gly Gly Glu Ala Gly Lys Asp Ala Glu Met Gly Glu Glu Leu Lys
            580                 585                 590

Met Ser Phe Thr Ser Pro Gln Ser Ala Val Gln Glu Asp Asp Gly Gly
        595                 600                 605

Glu Ser Lys Thr Glu Arg Ser Ser Glu Ser Ser Lys Ala Arg Ser Gly
    610                 615                 620

Ser His Arg Asp Phe Gln Gln Glu Glu Asp Val Ile Gln Asp Lys His
625                 630                 635                 640

Ser Ser Arg Pro Ala Asn Asn Arg Lys Gln Tyr Asp Asn Asn Ala Pro
                645                 650                 655

His Gln Ser Arg Lys Asn Gln Asp Arg Gly Lys Glu Met Glu Arg Thr
            660                 665                 670

Arg Ala Ala Ser Lys Gly Gly Arg Glu Asn Ser Asn Pro His Met Glu
        675                 680                 685

Leu Asp Ser Thr Tyr Ile Tyr Ser Ile Ala Ser Arg Glu Asp Phe Asp
```

```
    690                 695                 700

Lys Arg Lys Glu Arg Asp Val Asp Gly Ala Val Trp Arg Arg Lys Glu
705                 710                 715                 720

Asp Asp Pro Tyr Ser Arg Arg Gly Gly Asp Glu Gly Ser Arg Lys Arg
                725                 730                 735

Asp Arg Glu Asp Asp Pro Gly Phe Arg Gln Arg Gly Lys Met Arg Glu
            740                 745                 750

Asn Glu Ile Arg Ser Lys Asp Asp Gln Val Pro Ser Arg Lys His Met
        755                 760                 765

Asp Asp Ala Gly Met Arg Asn Ile Tyr Glu Pro Asp Asp His Ile Asn
    770                 775                 780

Lys Arg Arg Lys Asp Glu Glu Tyr Leu Arg Arg Ser Arg Pro Glu Lys
785                 790                 795                 800

Asn Glu Ile Ser Tyr Gly Gln Arg Glu Ser Met Ser Arg Val Lys Arg
                805                 810                 815

Glu Arg Asp Asp Arg Leu Glu His Gln Lys Arg Asp Val Gln His Lys
            820                 825                 830

Ile Arg Asp Asp Phe Asp Asp His Gly Ser Leu Arg Gln Arg Asp Asp
        835                 840                 845

Ile Tyr Met Gln Arg Asp Gly Asn Glu Arg Leu Arg Glu Arg Asp Val
    850                 855                 860

Leu Asp Lys Leu Lys Leu Pro His Glu Asp Gly Ile Ser Ala Arg Gly
865                 870                 875                 880

Arg Glu Arg Gln Val Ala Val Arg Gly His Arg Gly Ser Glu Asp Arg
                885                 890                 895

Ser Ser Arg Met Lys Asp Glu Tyr Lys Ala Ser Asp Lys Glu His Val
            900                 905                 910

Thr Lys Asp Thr Leu Arg His Ala Lys Gln Thr Lys Arg Arg Asp Tyr
        915                 920                 925

Pro Gly Glu Glu Ser Ser Ser His His Arg Gly His Glu Asp Phe Ser
    930                 935                 940

Ala Arg Thr Asp Asn Ile Val Asn Asn Glu Lys Lys Pro Arg Gln Glu
945                 950                 955                 960

Arg Thr Gly Ala Lys Ile Asp Lys Phe Ile Asp Thr Leu Asp Gly Gln
                965                 970                 975

Arg Leu Gln Asp Arg Lys His Lys Asp Ser Arg Arg Lys Ile Lys Glu
            980                 985                 990

Gln Arg Glu Gly Thr Glu Ser Leu  Ser Lys Gln Gly Glu  Gln Asn Gly
        995                 1000                1005

Ser Ser  Val Val Thr Gly Ser  Lys Gly Thr Asn Asp  Ala Arg Asn
    1010                1015                1020

Cys Arg  Ser Glu Ile Pro His  Gln Pro Asn Thr Ala  Lys Arg His
    1025                1030                1035

Lys Glu  Asn Ala Ser Ser Gly  Asp Glu Ile His Asp  Ser Lys Arg
    1040                1045                1050

Gly Arg  Thr Lys Leu Glu Arg  Trp Ala Ser His Lys  Glu Arg Glu
    1055                1060                1065

Asp Ala  Val Ser Ala Lys Ser  Ser Ser Ile Ser Ser  Lys Leu Glu
    1070                1075                1080

Glu Lys  Glu Asn Asn Thr Asn  Gly Arg Leu Ser Glu  Pro Val His
    1085                1090                1095

Gly Ser  Ile Gly Lys Ser Arg  Asp Val Thr Glu Glu  Lys Ile Gly
    1100                1105                1110
```

```
His Asp  Leu Ala Asp Thr Lys  Asp Gly Ser Glu Lys  Gly Pro Gly
    1115                 1120                 1125

Asp Arg  His Leu Asp Thr Val  Glu Lys Leu Lys Lys  Arg Ser Glu
    1130                 1135                 1140

Arg Phe  Lys Leu Pro Met Pro  Thr Glu Lys Asp Thr  Thr Gly Val
    1145                 1150                 1155

Lys Lys  Met Glu Ser Glu Thr  Leu Pro Ser Ala Lys  Ile Glu Gly
    1160                 1165                 1170

Pro Val  Asp Ser Glu Gly Glu  Tyr Val Trp Asp Glu  Arg Ser Cys
    1175                 1180                 1185

Val Arg  Ile Gly Arg Glu Tyr  Ala
    1190                 1195


<210> SEQ ID NO 74
<211> LENGTH: 312
<212> TYPE: PRT
<213> ORGANISM: Arabidopsis thaliana

<400> SEQUENCE: 74

Met Gly Lys Met Ile Val Ser Met Asp Gln Asp Ile Arg Leu Asp Thr
1               5                   10                  15

Thr Arg Ala Arg Leu Ser Asn Leu Leu Lys Arg His Arg Glu Leu Ser
            20                  25                  30

Asp Arg Leu Thr Arg Asp Ser Asp Lys Thr Met Leu Asp Arg Leu Asn
        35                  40                  45

Lys Glu Phe Glu Ala Ala Arg Arg Ser Gln Ser Gln Glu Val Phe Leu
    50                  55                  60

Asp Gly Glu Glu Trp Asn Asp Gly Leu Leu Ala Thr Leu Arg Glu Arg
65                  70                  75                  80

Val His Met Glu Ala Asp Arg Lys Ala Asp Asn Gly Asn Ala Gly Phe
                85                  90                  95

Ser Leu Val Cys His Pro Glu Glu Arg Ile Thr Tyr Arg Val Gly Asn
            100                 105                 110

Lys Val Ile Cys Cys Leu Asp Gly Ser Arg Ile Gly Ile Gln Phe Glu
        115                 120                 125

Thr Ser Thr Ala Gly Glu Thr Tyr Glu Val Tyr His Cys Val Leu Glu
    130                 135                 140

Ser Lys Ser Phe Leu Glu Lys Met Ile Val Leu Glu His Thr Ile Pro
145                 150                 155                 160

Phe Phe Leu Pro Leu Ser Asp Leu Glu Asn Asp Leu Leu Phe Ser Asn
                165                 170                 175

Ala Lys Lys Phe Ile Asp Asn Val Gly Asp Leu Leu Gln Ala Tyr Val
            180                 185                 190

Asp Arg Lys Glu Gln Val Arg Leu Ile Lys Glu Leu Phe Gly His Gln
        195                 200                 205

Ile Ser Glu Ile Tyr His Ser Leu Pro Tyr His Met Ile Glu Phe Ser
    210                 215                 220

Met Asp Asp Cys Asp Cys Lys Phe Val Val Ser Leu Arg Tyr Gly Asp
225                 230                 235                 240

Leu Leu Cys Glu Leu Pro Thr Lys Val Arg Ile Leu Val Trp Pro Met
                245                 250                 255

His His Leu Ser Lys Lys Gln Cys Thr Ser Pro Gly Ser Pro Ala Ile
            260                 265                 270

Pro Val Arg Leu Pro Phe Ala Glu Asp Ala Phe Arg Ile Gln Ser Leu
```

275 280 285

Pro Glu Ala Tyr Ala Glu Ile Met Pro Asn Met Pro Asn Glu Ile Arg
290 295 300

Gln Leu Phe Gln Thr Ser Pro Ser
305 310

<210> SEQ ID NO 75
<211> LENGTH: 209
<212> TYPE: PRT
<213> ORGANISM: Arabidopsis thaliana

<400> SEQUENCE: 75

Met Glu Phe Ser Thr Ala Asp Phe Glu Arg Leu Ile Met Phe Glu His
1 5 10 15

Ala Arg Lys Asn Ser Glu Ala Gln Tyr Lys Asn Asp Pro Leu Asp Ser
20 25 30

Glu Asn Leu Leu Lys Trp Gly Gly Ala Leu Leu Glu Leu Ser Gln Phe
35 40 45

Gln Pro Ile Pro Glu Ala Lys Leu Met Leu Asn Asp Ala Ile Ser Lys
50 55 60

Leu Glu Glu Ala Leu Thr Ile Asn Pro Gly Lys His Gln Ala Leu Trp
65 70 75 80

Cys Ile Ala Asn Ala Tyr Thr Ala His Ala Phe Tyr Val His Asp Pro
85 90 95

Glu Glu Ala Lys Glu His Phe Asp Lys Ala Thr Glu Tyr Phe Gln Arg
100 105 110

Ala Glu Asn Glu Asp Pro Gly Asn Asp Thr Tyr Arg Lys Ser Leu Asp
115 120 125

Ser Ser Leu Lys Ala Pro Glu Leu His Met Gln Phe Met Asn Gln Gly
130 135 140

Met Gly Gln Gln Ile Leu Gly Gly Gly Gly Gly Gly Gly Gly Gly Gly
145 150 155 160

Met Ala Ser Ser Asn Val Ser Ser Ser Lys Lys Lys Lys Arg Asn Thr
165 170 175

Glu Phe Thr Tyr Asp Val Cys Gly Trp Ile Ile Leu Ala Cys Gly Ile
180 185 190

Val Ala Trp Val Gly Met Ala Lys Ser Leu Gly Pro Pro Pro Pro Ala
195 200 205

Arg

<210> SEQ ID NO 76
<211> LENGTH: 210
<212> TYPE: PRT
<213> ORGANISM: Arabidopsis thaliana

<400> SEQUENCE: 76

Met Glu Phe Ser Thr Ala Asp Phe Glu Arg Phe Ile Met Phe Glu His
1 5 10 15

Ala Arg Lys Asn Ser Glu Ala Gln Tyr Lys Asn Asp Pro Leu Asp Ser
20 25 30

Glu Asn Leu Leu Lys Trp Gly Gly Ala Leu Leu Glu Leu Ser Gln Phe
35 40 45

Gln Pro Ile Pro Glu Ala Lys Leu Met Leu Asn Asp Ala Ile Ser Lys
50 55 60

Leu Glu Glu Ala Leu Thr Ile Asn Pro Gly Lys His Gln Ala Leu Trp
65 70 75 80

```
Cys Ile Ala Asn Ala Tyr Thr Ala His Ala Phe Tyr Val His Asp Pro
                85                  90                  95

Glu Glu Ala Lys Glu His Phe Asp Lys Ala Thr Glu Tyr Phe Gln Arg
            100                 105                 110

Ala Glu Asn Glu Asp Pro Gly Asn Asp Thr Tyr Arg Lys Ser Leu Asp
        115                 120                 125

Ser Ser Leu Lys Ala Pro Glu Leu His Met Gln Phe Met Asn Gln Gly
    130                 135                 140

Met Gly Gln Gln Ile Leu Gly Gly Gly Gly Gly Gly Gly Gly Gly Gly
145                 150                 155                 160

Met Ala Ser Ser Asn Val Ser Gln Ser Ser Lys Lys Lys Lys Arg Asn
                165                 170                 175

Thr Glu Phe Thr Tyr Asp Val Cys Gly Trp Ile Ile Leu Ala Cys Gly
            180                 185                 190

Ile Val Ala Trp Val Gly Met Ala Lys Ser Leu Gly Pro Pro Pro Pro
        195                 200                 205

Ala Arg
    210


<210> SEQ ID NO 77
<211> LENGTH: 603
<212> TYPE: PRT
<213> ORGANISM: Arabidopsis thaliana

<400> SEQUENCE: 77

Met Ala Ala Ser Ser Thr Asn Ala Arg Leu Thr Asn Pro Pro Arg Leu
1               5                   10                  15

Leu Ser Lys Pro Arg Leu Ser Pro Thr Ser Val Ala Asn Leu Arg Phe
            20                  25                  30

Pro Ala Ala Asp Phe Ser Thr Arg Phe Phe Ala Asp Ser Ser Ser Pro
        35                  40                  45

Arg Leu Arg Ser Val Pro Phe Pro Val Val Phe Ser Asp Gln Arg Arg
    50                  55                  60

Arg Arg Ser Met Glu Pro Ser Asn Val Tyr Val Ala Ser Asn Ser Thr
65                  70                  75                  80

Glu Met Glu Ile Gly Ser His Asp Ile Val Lys Asn Pro Ser Leu Ile
                85                  90                  95

Cys Ala Pro Val Met Ala Asp Ser Ile Asp Lys Met Val Ile Glu Thr
            100                 105                 110

Ser Lys Ala His Glu Leu Gly Ala Asp Leu Val Glu Ile Arg Leu Asp
        115                 120                 125

Trp Leu Lys Asp Phe Asn Pro Leu Glu Asp Leu Lys Thr Ile Ile Lys
    130                 135                 140

Lys Ser Pro Leu Pro Thr Leu Phe Thr Tyr Arg Pro Lys Trp Glu Gly
145                 150                 155                 160

Gly Gln Tyr Glu Gly Asp Glu Asn Glu Arg Arg Asp Val Leu Arg Leu
                165                 170                 175

Ala Met Glu Leu Gly Ala Asp Tyr Ile Asp Val Glu Leu Gln Val Ala
            180                 185                 190

Ser Glu Phe Ile Lys Ser Ile Asp Gly Lys Lys Pro Gly Lys Phe Lys
        195                 200                 205

Val Ile Val Ser Ser His Asn Tyr Gln Asn Thr Pro Ser Val Glu Asp
    210                 215                 220

Leu Asp Gly Leu Val Ala Arg Ile Gln Gln Thr Gly Ala Asp Ile Val
```

```
225                 230                 235                 240

Lys Ile Ala Thr Thr Ala Val Asp Ile Ala Asp Val Ala Arg Met Phe
                245                 250                 255

His Ile Thr Ser Lys Ala Gln Val Pro Thr Ile Gly Leu Val Met Gly
            260                 265                 270

Glu Arg Gly Leu Met Ser Arg Ile Leu Cys Ser Lys Phe Gly Gly Tyr
        275                 280                 285

Leu Thr Phe Gly Thr Leu Asp Ser Ser Lys Val Ser Ala Pro Gly Gln
    290                 295                 300

Pro Thr Ile Lys Asp Leu Leu Asp Leu Tyr Asn Phe Arg Arg Ile Gly
305                 310                 315                 320

Pro Asp Thr Lys Val Tyr Gly Ile Ile Gly Lys Pro Val Ser His Ser
                325                 330                 335

Lys Ser Pro Ile Val His Asn Gln Ala Phe Lys Ser Val Asp Phe Asn
            340                 345                 350

Gly Val Tyr Val His Leu Leu Val Asp Asn Leu Val Ser Phe Leu Gln
        355                 360                 365

Ala Tyr Ser Ser Ser Asp Phe Ala Gly Phe Ser Cys Thr Ile Pro His
    370                 375                 380

Lys Glu Ala Ala Leu Gln Cys Cys Asp Glu Val Asp Pro Leu Ala Lys
385                 390                 395                 400

Ser Ile Gly Ala Val Asn Thr Ile Leu Arg Arg Lys Ser Asp Gly Lys
                405                 410                 415

Leu Leu Gly Tyr Asn Thr Asp Cys Ile Gly Ser Ile Ser Ala Ile Glu
            420                 425                 430

Asp Gly Leu Arg Ser Ser Gly Asp Pro Ser Ser Val Pro Ser Ser Ser
        435                 440                 445

Ser Pro Leu Ala Ser Lys Thr Val Val Val Ile Gly Ala Gly Gly Ala
    450                 455                 460

Gly Lys Ala Leu Ala Tyr Gly Ala Lys Glu Lys Gly Ala Lys Val Val
465                 470                 475                 480

Ile Ala Asn Arg Thr Tyr Glu Arg Ala Leu Glu Leu Ala Glu Ala Ile
                485                 490                 495

Gly Gly Lys Ala Leu Ser Leu Thr Asp Leu Asp Asn Tyr His Pro Glu
            500                 505                 510

Asp Gly Met Val Leu Ala Asn Thr Thr Ser Met Gly Met Gln Pro Asn
        515                 520                 525

Val Glu Glu Thr Pro Ile Ser Lys Asp Ala Leu Lys His Tyr Ala Leu
    530                 535                 540

Val Phe Asp Ala Val Tyr Thr Pro Arg Ile Thr Arg Gln Leu Arg Glu
545                 550                 555                 560

Ala Glu Glu Ser Gly Ala Ile Thr Val Ser Gly Ser Glu Met Phe Val
                565                 570                 575

Arg Gln Ala Tyr Glu Gln Phe Glu Ile Phe Thr Gly Leu Pro Ala Pro
            580                 585                 590

Lys Glu Leu Tyr Trp Gln Ile Met Ser Lys Tyr
        595                 600
```

<210> SEQ ID NO 78
<211> LENGTH: 220
<212> TYPE: PRT
<213> ORGANISM: Zea mays

<400> SEQUENCE: 78

```
Met Ala Ser Ala Thr Gly Val Ser Ser Ser Glu Met Ala Val Asp His
1               5                   10                  15

Ala Thr Gly Pro Gly Ala Val Asp Lys Pro Arg Phe Asp Ala Leu Thr
            20                  25                  30

Pro Asn Glu Met Ser Gly Gly Arg Pro Gln Phe Arg Lys Val Pro Val
        35                  40                  45

Pro Gln His Arg Phe Ala Pro Leu Lys Arg Cys Trp Met Glu Ile Tyr
    50                  55                  60

Thr Pro Val Tyr Glu His Met Lys Ile Asp Ile Arg Met Asn Leu Lys
65                  70                  75                  80

Ala Arg Arg Val Glu Leu Lys Thr Arg Gln Asp Thr Pro Asp Val Ser
                85                  90                  95

Asn Leu Gln Lys Cys Ala Asp Phe Val His Ala Phe Met Leu Gly Phe
            100                 105                 110

Asp Ile Ala Asp Ala Val Ala Leu Leu Arg Leu Asp Asp Leu Tyr Val
        115                 120                 125

Asp Ser Phe Glu Ile Lys Asp Val Lys Thr Leu Arg Gly Glu His Leu
    130                 135                 140

Ser Arg Ala Ile Gly Arg Leu Ser Gly Lys Gly Gly Lys Thr Lys Tyr
145                 150                 155                 160

Ala Ile Glu Asn Ser Thr Arg Thr Arg Ile Val Ile Ala Asp Thr Lys
                165                 170                 175

Ile His Ile Leu Gly Ser Phe Val Asn Ile Lys Val Ala Arg Asp Ser
            180                 185                 190

Leu Cys Ser Leu Ile Leu Gly Ser Pro Ala Gly Lys Val Tyr Ser Lys
        195                 200                 205

Leu Arg Ala Val Ser Ala Arg Leu Ala Glu Arg Tyr
    210                 215                 220


<210> SEQ ID NO 79
<211> LENGTH: 220
<212> TYPE: PRT
<213> ORGANISM: Zea mays

<400> SEQUENCE: 79

Met Ala Ser Ala Thr Gly Gly Ser Ser Ser Glu Met Ala Val Asp His
1               5                   10                  15

Ala Thr Gly Leu Gly Thr Val Glu Lys Pro Arg Phe Asp Ala Leu Met
            20                  25                  30

Pro Ser Glu Met Ser Gly Gly Arg Thr Gln Phe Arg Lys Val Thr Val
        35                  40                  45

Pro Gln His Arg Phe Ala Pro Leu Lys Arg Cys Trp Met Glu Ile Tyr
    50                  55                  60

Thr Pro Val Tyr Glu His Met Lys Ile Asp Ile Arg Met Asn Leu Lys
65                  70                  75                  80

Ala Arg Arg Val Glu Leu Lys Thr Arg Gln Asp Thr Pro Asp Val Ser
                85                  90                  95

Asn Leu Gln Lys Cys Ala Asp Phe Val His Ala Phe Met Leu Gly Phe
            100                 105                 110

Asp Ile Ala Asp Ala Val Ala Leu Leu Arg Leu Asp Asp Leu Tyr Val
        115                 120                 125

Asp Ser Phe Glu Ile Lys Asp Val Lys Thr Leu Arg Gly Glu His Leu
    130                 135                 140

Ser Arg Ala Ile Gly Arg Leu Ser Gly Lys Gly Gly Lys Thr Lys Tyr
145                 150                 155                 160
```

```
Ala Ile Glu Asn Ser Thr Arg Thr Arg Ile Val Ile Ala Asp Thr Lys
                165                 170                 175

Ile His Ile Leu Gly Ser Phe Val Asn Ile Lys Val Ala Arg Asp Ser
            180                 185                 190

Leu Cys Ser Leu Ile Leu Gly Ser Pro Ala Gly Lys Val Tyr Ser Lys
        195                 200                 205

Leu Arg Ala Val Ser Ala Arg Leu Ala Glu Arg Tyr
    210                 215                 220


<210> SEQ ID NO 80
<211> LENGTH: 220
<212> TYPE: PRT
<213> ORGANISM: Zea mays

<400> SEQUENCE: 80

Met Ala Ser Ala Thr Gly Gly Ser Ser Ser Glu Met Ala Val Asp His
1               5                   10                  15

Ala Thr Gly Leu Gly Thr Val Glu Lys Pro Arg Phe Asp Ala Leu Met
            20                  25                  30

Pro Ser Glu Met Ser Gly Gly Arg Thr Gln Phe Arg Lys Val Thr Val
        35                  40                  45

Pro Gln His Arg Phe Ala Pro Leu Lys Arg Cys Trp Met Glu Ile Tyr
    50                  55                  60

Thr Pro Val Tyr Glu His Met Lys Ile Asp Ile Arg Met Asn Leu Lys
65                  70                  75                  80

Ala Arg Arg Val Glu Leu Lys Thr Arg Gln Asp Thr Pro Asp Val Ser
                85                  90                  95

Asn Leu Gln Lys Cys Ala Asp Phe Val His Ala Phe Met Leu Gly Phe
            100                 105                 110

Asp Ile Ala Asp Ala Val Ala Leu Leu Arg Leu Asp Asp Leu Tyr Val
        115                 120                 125

Asp Ser Phe Lys Ile Lys Asp Val Lys Thr Leu Arg Gly Glu His Leu
    130                 135                 140

Ser Arg Ala Ile Gly Arg Leu Ser Gly Lys Gly Gly Lys Thr Lys Tyr
145                 150                 155                 160

Ala Ile Glu Asn Ser Thr Arg Thr Arg Ile Val Ile Ala Asp Thr Lys
                165                 170                 175

Ile His Ile Leu Gly Ser Phe Val Asn Ile Lys Val Ala Arg Asp Ser
            180                 185                 190

Leu Cys Ser Leu Ile Leu Gly Ser Pro Ala Gly Lys Val Tyr Ser Lys
        195                 200                 205

Leu Arg Ala Val Ser Ala Arg Leu Ala Glu Arg Tyr
    210                 215                 220


<210> SEQ ID NO 81
<211> LENGTH: 187
<212> TYPE: PRT
<213> ORGANISM: Arabidopsis thaliana

<400> SEQUENCE: 81

Met Ser Arg Leu Leu Leu Pro Lys Leu Phe Ser Ile Ser Arg Thr Gln
1               5                   10                  15

Val Pro Ala Ala Ser Leu Phe Asn Asn Leu Tyr Arg Arg His Lys Arg
            20                  25                  30

Phe Val His Trp Thr Ser Lys Met Ser Thr Asp Ser Val Arg Ser Ser
        35                  40                  45
```

```
Thr Thr Gly Gly Ser Ala Ser Gly Ala Arg Thr Phe Cys Ser Leu Ala
    50                  55                  60

Asp Leu Ser Thr Lys Lys Cys Val Pro Cys Asn Ala Lys Asp Leu Arg
65                  70                  75                  80

Ala Met Thr Glu Gln Ser Ala Gln Asp Leu Leu Gln Lys Val Ala Gly
                85                  90                  95

Trp Asp Leu Ala Asn Asp Asn Asp Thr Leu Lys Leu His Arg Ser Trp
            100                 105                 110

Arg Val Lys Ser Phe Thr Lys Gly Leu Asp Phe Phe Gln Arg Val Thr
        115                 120                 125

Asp Ile Ala Glu Ser Glu Gly His His Pro Asp Leu His Leu Val Gly
    130                 135                 140

Trp Asn Asn Val Lys Ile Glu Ile Trp Thr His Ala Ile Gly Gly Leu
145                 150                 155                 160

Thr Glu Asn Asp Phe Ile Leu Ala Ala Lys Ile Asn Glu Leu Gln Val
                165                 170                 175

Glu Asp Leu Leu Arg Lys Lys Lys Val Ala Lys
            180                 185


<210> SEQ ID NO 82
<211> LENGTH: 392
<212> TYPE: PRT
<213> ORGANISM: Arabidopsis lyrata

<400> SEQUENCE: 82

Met Val Lys Leu Glu Asn Pro Lys Lys Pro Glu Asn Val Ser Asn Lys
1               5                   10                  15

Asn Ile Pro Leu Ser Asp Phe Val Val Asn Leu Asp His Gly Asp Pro
            20                  25                  30

Thr Ala Tyr Glu Glu Tyr Trp Arg Lys Met Gly Asp Arg Cys Thr Val
        35                  40                  45

Thr Ile Arg Gly Cys Asp Leu Met Ser Tyr Phe Ser Asp Met Thr Asn
    50                  55                  60

Leu Cys Trp Phe Leu Glu Pro Glu Leu Glu Ala Ala Ile Lys Asp Leu
65                  70                  75                  80

His Gly Ala Val Gly Asn Ala Ala Thr Glu Asp Arg Tyr Ile Val Val
                85                  90                  95

Gly Thr Gly Ser Thr Gln Leu Cys Gln Ala Ala Val His Ala Leu Ser
            100                 105                 110

Ser Leu Ala Arg Thr Gln Pro Val Ser Val Val Ala Ala Ala Pro Phe
        115                 120                 125

Tyr Ser Thr Tyr Val Glu Glu Thr Thr Tyr Val Arg Ser Gly Met Tyr
    130                 135                 140

Lys Trp Glu Gly Asp Ala Trp Gly Phe Asp Lys Lys Gly Pro Tyr Ile
145                 150                 155                 160

Glu Leu Val Thr Ser Pro Asn Asn Pro Asp Gly Thr Ile Arg Glu Thr
                165                 170                 175

Val Val Asn Arg Pro Asp Asp Asp Glu Ala Lys Val Ile His Asp Phe
            180                 185                 190

Ala Tyr Tyr Trp Pro His Tyr Thr Pro Ile Thr Arg Arg Gln Asp His
        195                 200                 205

Asp Ile Met Leu Phe Thr Phe Ser Lys Ile Thr Gly His Ala Gly Ser
    210                 215                 220

Arg Ile Gly Trp Ala Leu Val Lys Asp Lys Glu Val Ala Lys Lys Met
```

```
225                 230                 235                 240

Val Glu Tyr Ile Ile Val Asn Ser Ile Gly Val Ser Lys Glu Ser Gln
                245                 250                 255

Val Arg Thr Ala Lys Ile Leu Lys Val Leu Lys Glu Thr Cys Asn Ser
            260                 265                 270

Glu Ser Asp Glu Ser Glu Asn Phe Phe Lys Tyr Gly Arg Lys Met Met
        275                 280                 285

Lys Asn Arg Trp Glu Lys Leu Arg Glu Val Val Lys Glu Ser Asp Ala
    290                 295                 300

Phe Thr Leu Pro Lys Tyr Pro Glu Ala Phe Cys Asn Tyr Phe Gly Lys
305                 310                 315                 320

Ser Leu Glu Ser Tyr Pro Ala Phe Ala Trp Leu Gly Thr Lys Glu Glu
                325                 330                 335

Thr Asp Leu Val Ser Glu Leu Arg Arg His Lys Val Met Cys Arg Ala
            340                 345                 350

Gly Glu Arg Cys Gly Ser Asp Lys Lys His Val Arg Val Ser Met Leu
        355                 360                 365

Ser Arg Glu Asp Val Phe Asn Val Phe Leu Glu Arg Leu Ala Asn Met
    370                 375                 380

Lys Leu Ile Lys Ser Ile Asp Leu
385                 390


<210> SEQ ID NO 83
<211> LENGTH: 391
<212> TYPE: PRT
<213> ORGANISM: Arabidopsis thaliana
<220> FEATURE:
<221> NAME/KEY: misc_feature
<222> LOCATION: (217)..(217)
<223> OTHER INFORMATION: Xaa can be any naturally occurring amino acid

<400> SEQUENCE: 83

Met Val Lys Leu Glu Asn Ser Arg Lys Pro Glu Lys Ile Ser Asn Lys
1               5                   10                  15

Asn Ile Pro Met Ser Asp Phe Val Val Asn Leu Asp His Gly Asp Pro
            20                  25                  30

Thr Ala Tyr Glu Glu Tyr Trp Arg Lys Met Gly Asp Arg Cys Thr Val
        35                  40                  45

Thr Ile Arg Gly Cys Asp Leu Met Ser Tyr Phe Ser Asp Met Thr Asn
    50                  55                  60

Leu Cys Trp Phe Leu Glu Pro Glu Leu Glu Asp Ala Ile Lys Asp Leu
65                  70                  75                  80

His Gly Val Val Gly Asn Ala Ala Thr Glu Asp Arg Tyr Ile Val Val
                85                  90                  95

Gly Thr Gly Ser Thr Gln Leu Cys Gln Ala Ala Val His Ala Leu Ser
            100                 105                 110

Ser Leu Ala Arg Ser Gln Pro Val Ser Val Val Ala Ala Ala Pro Phe
        115                 120                 125

Tyr Ser Thr Tyr Val Glu Glu Thr Thr Tyr Val Arg Ser Gly Met Tyr
    130                 135                 140

Lys Trp Glu Gly Asp Ala Trp Gly Phe Asp Lys Lys Gly Pro Tyr Ile
145                 150                 155                 160

Glu Leu Val Thr Ser Pro Asn Asn Pro Asp Gly Thr Ile Arg Glu Thr
                165                 170                 175

Val Val Asn Arg Pro Asp Asp Asp Glu Ala Lys Val Ile His Asp Phe
            180                 185                 190
```

Ala Tyr Tyr Trp Pro His Tyr Thr Pro Ile Thr Arg Arg Gln Asp His
195 200 205

Asp Ile Met Leu Phe Thr Phe Ser Xaa Ile Thr Gly His Ala Gly Ser
210 215 220

Arg Ile Gly Trp Ala Leu Val Lys Asp Lys Glu Val Ala Lys Lys Met
225 230 235 240

Val Glu Tyr Ile Ile Val Asn Ser Ile Gly Val Ser Lys Glu Ser Gln
245 250 255

Val Arg Thr Ala Lys Ile Leu Asn Val Leu Lys Glu Thr Cys Lys Ser
260 265 270

Glu Ser Glu Ser Glu Asn Phe Phe Lys Tyr Gly Arg Glu Met Met Lys
275 280 285

Asn Arg Trp Glu Lys Leu Arg Glu Val Val Lys Glu Ser Asp Ala Phe
290 295 300

Thr Leu Pro Lys Tyr Pro Glu Ala Phe Cys Asn Tyr Phe Gly Lys Ser
305 310 315 320

Leu Glu Ser Tyr Pro Ala Phe Ala Trp Leu Gly Thr Lys Glu Glu Thr
325 330 335

Asp Leu Val Ser Glu Leu Arg Arg His Lys Val Met Ser Arg Ala Gly
340 345 350

Glu Arg Cys Gly Ser Asp Lys Lys His Val Arg Val Ser Met Leu Ser
355 360 365

Arg Glu Asp Val Phe Asn Val Phe Leu Glu Arg Leu Ala Asn Met Lys
370 375 380

Leu Ile Lys Ser Ile Asp Leu
385 390

<210> SEQ ID NO 84
<211> LENGTH: 763
<212> TYPE: PRT
<213> ORGANISM: Saccharomyces cerevisiae YJM789

<400> SEQUENCE: 84

Met Asn Asp Ser Gln Asn Cys Leu Arg Gln Arg Glu Glu Asn Ser His
1 5 10 15

Leu Asn Pro Gly Asn Asp Phe Gly His His Gln Gly Ala Gly Cys Thr
20 25 30

Ile Asn His Asn Asn Met Pro His Arg Asn Ala Tyr Thr Glu Ser Thr
35 40 45

Asn Asp Thr Glu Ala Lys Ser Ile Val Met Cys Asp Asp Pro Asn Ala
50 55 60

Tyr Gln Ile Ser Tyr Thr Asn Asn Glu Pro Ala Gly Asp Gly Ala Ile
65 70 75 80

Glu Thr Thr Ser Ile Leu Leu Ser Gln Pro Leu Pro Leu Arg Ser Asn
85 90 95

Val Met Ser Val Leu Val Gly Ile Phe Val Ala Val Gly Gly Phe Leu
100 105 110

Phe Gly Tyr Asp Thr Gly Leu Ile Asn Ser Ile Thr Asp Met Pro Tyr
115 120 125

Val Lys Thr Tyr Ile Ala Pro Asn His Ser Tyr Phe Thr Thr Ser Gln
130 135 140

Ile Ala Ile Leu Val Ser Phe Leu Ser Leu Gly Thr Phe Phe Gly Ala
145 150 155 160

Leu Ile Ala Pro Tyr Ile Ser Asp Ser Tyr Gly Arg Lys Pro Thr Ile

```
                165                 170                 175

Met Phe Ser Thr Ala Val Ile Phe Ser Ile Gly Asn Ser Leu Gln Val
            180                 185                 190

Ala Ser Gly Gly Leu Val Leu Leu Ile Val Gly Arg Val Ile Ser Gly
        195                 200                 205

Ile Gly Ile Gly Ile Ile Ser Ala Val Val Pro Leu Tyr Gln Ala Glu
    210                 215                 220

Ala Ala Gln Lys Asn Leu Arg Gly Ala Ile Ile Ser Ser Tyr Gln Trp
225                 230                 235                 240

Ala Ile Thr Ile Gly Leu Leu Val Ser Ser Ala Val Ser Gln Gly Thr
                245                 250                 255

His Ser Lys Asn Gly Pro Ser Ser Tyr Arg Ile Pro Ile Gly Leu Gln
            260                 265                 270

Tyr Val Trp Ser Ser Ile Leu Ala Val Gly Met Ile Phe Leu Pro Glu
        275                 280                 285

Ser Pro Arg Tyr Tyr Val Leu Lys Asp Glu Leu Asn Lys Ala Ala Lys
    290                 295                 300

Ser Leu Ser Phe Leu Arg Gly Leu Pro Ile Glu Asp Pro Arg Leu Leu
305                 310                 315                 320

Glu Glu Leu Val Glu Ile Lys Ala Thr Tyr Asp Tyr Glu Ala Ser Phe
                325                 330                 335

Gly Pro Ser Thr Leu Leu Asp Cys Phe Lys Thr Ser Glu Asn Arg Pro
            340                 345                 350

Lys Gln Ile Leu Arg Ile Phe Thr Gly Ile Ala Ile Gln Ala Phe Gln
        355                 360                 365

Gln Ala Ser Gly Ile Asn Phe Ile Phe Tyr Tyr Gly Val Asn Phe Phe
    370                 375                 380

Asn Asn Thr Gly Val Asp Asn Ser Tyr Leu Val Ser Phe Ile Ser Tyr
385                 390                 395                 400

Ala Val Asn Val Ala Phe Ser Ile Pro Gly Met Tyr Leu Val Asp Arg
                405                 410                 415

Ile Gly Arg Arg Pro Val Leu Leu Ala Gly Gly Val Ile Met Ala Ile
            420                 425                 430

Ala Asn Leu Val Ile Ala Ile Val Gly Val Ser Glu Gly Lys Thr Val
        435                 440                 445

Val Ala Ser Lys Ile Met Ile Ala Phe Ile Cys Leu Phe Ile Ala Ala
    450                 455                 460

Phe Ser Ala Thr Trp Gly Gly Val Val Trp Val Val Ser Ala Glu Leu
465                 470                 475                 480

Tyr Pro Leu Gly Val Arg Ser Lys Cys Thr Ala Ile Cys Ala Ala Ala
                485                 490                 495

Asn Trp Leu Val Asn Phe Ile Cys Ala Leu Ile Thr Pro Tyr Ile Val
            500                 505                 510

Asp Val Gly Ser His Thr Ser Ser Met Gly Pro Lys Ile Phe Phe Ile
        515                 520                 525

Trp Gly Gly Leu Asn Val Val Ala Val Ile Ile Val Tyr Phe Ala Val
    530                 535                 540

Tyr Glu Thr Arg Gly Leu Thr Leu Glu Glu Ile Asp Glu Leu Phe Arg
545                 550                 555                 560

Lys Ala Pro Asn Ser Val Ile Ser Ser Lys Trp Asn Lys Lys Ile Arg
                565                 570                 575

Lys Arg Cys Leu Ala Phe Pro Ile Ser Gln Gln Ile Glu Met Lys Thr
            580                 585                 590
```

```
Asn Ile Lys Lys Ala Gly Lys Leu Asp Asn Asn Asn Ser Pro Ile Val
        595                 600                 605

Gln Asp Asp Ser His Asn Ile Ile Asp Val Asp Gly Phe Leu Glu Asn
    610                 615                 620

Gln Ile Gln Ser Asn Asp His Met Ile Ala Ala Asp Lys Gly Asn Gly
625                 630                 635                 640

Ser Leu Val Asn Ile Ile Asp Thr Ala Pro Leu Thr Ser Thr Glu Phe
                645                 650                 655

Lys Pro Val Glu His Pro Pro Val Asn Tyr Val Asp Leu Gly Asn Gly
            660                 665                 670

Leu Gly Leu Asn Thr Tyr Asn Arg Gly Pro Pro Ser Ile Ile Ser Asp
        675                 680                 685

Ser Thr Asp Glu Phe Tyr Glu Glu Asn Asp Ser Ser Tyr Tyr Asn Asn
    690                 695                 700

Asn Thr Glu Arg Asn Gly Ala Asn Ser Val Asn Thr Tyr Met Ala Gln
705                 710                 715                 720

Leu Ile Asn Ser Pro Ser Thr Thr Ser Asn Asp Thr Ser Phe Ser Pro
                725                 730                 735

Ser His Asn Ser Asn Ala Arg Thr Ser Ser Asn Trp Thr Ser Asp Leu
            740                 745                 750

Ala Ser Lys His Ser Gln Tyr Thr Ser Pro Gln
        755                 760


<210> SEQ ID NO 85
<211> LENGTH: 210
<212> TYPE: PRT
<213> ORGANISM: Glycine max

<400> SEQUENCE: 85

Met Ser Asn Thr Ser Asn Asn Val Ala Gly Val Asp Asn Thr Phe Arg
1               5                   10                  15

Arg Lys Phe Asp Arg Glu Glu Tyr Leu Glu Arg Ala Arg Glu Arg Glu
            20                  25                  30

Arg Gln Glu Glu Glu Gly Arg Ala Lys Pro Lys Ala Glu Gly Pro Pro
        35                  40                  45

Val Gln Arg Lys Pro Leu Lys His Arg Asp Tyr Glu Val Asp Leu Glu
    50                  55                  60

Ser Arg Leu Gly Lys Thr Gln Val Val Thr Pro Val Ala Pro Leu Ser
65                  70                  75                  80

Gln Gln Ala Gly Tyr Tyr Cys Ser Val Cys Glu Cys Val Val Lys Asp
                85                  90                  95

Ser Ala Asn Tyr Leu Asp His Ile Asn Gly Lys Lys His Gln Arg Ala
            100                 105                 110

Leu Gly Met Ser Met Arg Val Glu Arg Ala Ser Leu Gln Gln Val Gln
        115                 120                 125

Glu Arg Phe Glu Val Leu Lys Lys Arg Lys Asp Val Gly Ser Phe Thr
    130                 135                 140

Glu Gln Asp Leu Asp Glu Arg Ile Leu Lys Gln Gln Gln Glu Glu Glu
145                 150                 155                 160

Glu Arg Lys Arg Leu Arg Arg Glu Lys Lys Lys Glu Lys Lys Glu Lys
                165                 170                 175

Ala Val Glu Glu Pro Glu Ile Asp Pro Asp Val Ala Ala Met Met Gly
            180                 185                 190

Phe Gly Arg Phe Pro Gly His Pro Thr Arg Asn Asp Ser Ile Leu His
```

```
        195                 200                 205

Ala Glu
    210


<210> SEQ ID NO 86
<211> LENGTH: 419
<212> TYPE: PRT
<213> ORGANISM: Arabidopsis lyrata

<400> SEQUENCE: 86

Met Leu Gln Asn Leu Val Phe Ser Val Pro Ile Ser Arg Met Val Val
1               5                   10                  15

Arg Arg His Ser Leu Ala Ile Ala Ala Ala Thr Thr Val Val Pro
            20                  25                  30

Ser Pro Lys Pro Ala Ser Ala Lys Pro Ala Arg Thr Pro His Val Asp
        35                  40                  45

Ser His Val Leu Ile Gly Met Ser Glu Pro Glu Leu Gln Gln Leu Ala
    50                  55                  60

Ile Asn Leu Val Leu Ile Phe Gln Glu Gly Tyr Arg Gly Lys Gln Leu
65                  70                  75                  80

His His Leu Ile Tyr Lys Arg Lys Val Asn Lys Val Glu Asp Phe Ser
                85                  90                  95

Asn Leu Pro Gln Thr Phe Arg Lys Glu Leu Val Glu Gly Gly Phe Lys
            100                 105                 110

Val Gly Arg Ser Pro Ile Tyr Gln Thr Val Thr Ala Thr Asp Gly Thr
        115                 120                 125

Ile Lys Leu Leu Leu Lys Leu Glu Asp Asn Leu Leu Ile Glu Thr Val
    130                 135                 140

Gly Ile Pro Val Gln Asp Asp Glu Lys Gly Ile Thr Arg Leu Thr Ala
145                 150                 155                 160

Cys Val Ser Ser Gln Val Gly Cys Pro Leu Arg Cys Ser Phe Cys Ala
                165                 170                 175

Thr Gly Lys Gly Gly Phe Ser Arg Asn Leu Gln Arg His Glu Ile Ile
            180                 185                 190

Glu Gln Val Leu Ala Ile Glu Asp Val Phe Lys His Arg Val Thr Asn
        195                 200                 205

Val Val Phe Met Gly Met Gly Glu Pro Met Leu Asn Leu Lys Ser Val
    210                 215                 220

Leu Asp Ala His Arg Cys Leu Asn Lys Asp Ile Glu Ile Gly Gln Arg
225                 230                 235                 240

Met Ile Thr Ile Ser Thr Val Gly Val Pro Asn Thr Ile Lys Lys Leu
                245                 250                 255

Ala Ser His Lys Leu Gln Ser Thr Leu Ala Val Ser Leu His Ala Pro
            260                 265                 270

Asn Gln Ser Leu Arg Glu Lys Ile Val Pro Ser Ala Lys Ala Tyr Pro
        275                 280                 285

Leu Glu Ala Ile Met Lys Asp Cys Arg Asp Tyr Phe Gln Glu Thr Asn
    290                 295                 300

Arg Arg Val Ser Phe Glu Tyr Ala Leu Leu Ala Gly Val Asn Asp Gln
305                 310                 315                 320

Val Glu His Ala Val Glu Leu Ala Glu Leu Leu Arg Glu Trp Gly Lys
                325                 330                 335

Thr Tyr His Val Asn Leu Ile Pro Tyr Asn Pro Ile Glu Gly Ser Glu
            340                 345                 350
```

```
Tyr Lys Arg Pro Tyr Lys Lys Ala Val Leu Ala Phe Ala Ser Ala Leu
        355                 360                 365

Glu Ser Arg Lys Ile Thr Ala Ser Val Arg Gln Thr Arg Gly Leu Asp
    370                 375                 380

Ala Ser Ala Ala Cys Gly Gln Leu Arg Asn Lys Phe Gln Lys Ser Pro
385                 390                 395                 400

Leu Val Thr Glu Thr Asp Gly Gln Glu Ser Gln Pro Ala Ala Glu Ala
                405                 410                 415

Val Ser Cys


<210> SEQ ID NO 87
<211> LENGTH: 431
<212> TYPE: PRT
<213> ORGANISM: Arabidopsis thaliana

<400> SEQUENCE: 87

Met Met Thr Thr Thr Thr Asn Thr Met Ala Met Leu Gln Asn Leu Val
1               5                   10                  15

Phe Ser Val Pro Ile Ser Arg Met Val Val Arg Arg His Ser Leu Ala
            20                  25                  30

Thr Thr Phe Ser Ala Ala Ala Thr Thr Val Val Pro Ser Pro Lys Pro
        35                  40                  45

Val Ser Ala Lys Pro Ala Arg Thr Pro His Val Asp Ser His Val Leu
    50                  55                  60

Ile Gly Met Ser Glu Pro Glu Leu Gln Glu Leu Ala Ile Asn Leu Val
65                  70                  75                  80

Leu Ile Phe Gln Glu Gly Tyr Arg Gly Lys Gln Leu His His Leu Ile
                85                  90                  95

Tyr Lys Arg Lys Val Asn Lys Val Glu Asp Phe Ser Asn Leu Pro Leu
            100                 105                 110

Thr Phe Arg Lys Gly Leu Val Asp Gly Gly Phe Lys Val Gly Arg Ser
        115                 120                 125

Pro Ile Tyr Gln Thr Val Thr Ala Thr Asp Gly Thr Ile Lys Leu Leu
    130                 135                 140

Leu Lys Leu Glu Asp Asn Leu Leu Ile Glu Thr Val Gly Ile Pro Val
145                 150                 155                 160

Gln Asp Asp Glu Lys Gly Ile Thr Arg Leu Thr Ala Cys Val Ser Ser
                165                 170                 175

Gln Val Gly Cys Pro Leu Arg Cys Ser Phe Cys Ala Thr Gly Lys Gly
            180                 185                 190

Gly Phe Ser Arg Asn Leu Gln Arg His Glu Ile Ile Glu Gln Val Leu
        195                 200                 205

Ala Ile Glu Asp Val Phe Lys His Arg Val Thr Asn Val Val Phe Met
    210                 215                 220

Gly Met Gly Glu Pro Met Leu Asn Leu Lys Ser Val Leu Asp Ala His
225                 230                 235                 240

Arg Cys Leu Asn Lys Asp Ile Glu Ile Gly Gln Arg Met Ile Thr Ile
                245                 250                 255

Ser Thr Val Gly Val Pro Asn Thr Ile Lys Lys Leu Ala Ser His Lys
            260                 265                 270

Leu Gln Ser Thr Leu Ala Val Ser Leu His Ala Pro Asn Gln Ser Leu
        275                 280                 285

Arg Glu Lys Ile Val Pro Ser Ala Lys Ala Tyr Pro Leu Glu Ala Ile
    290                 295                 300
```

```
Met Lys Asp Cys Arg Asp Tyr Phe Gln Glu Thr Asn Arg Arg Val Ser
305                 310                 315                 320

Phe Glu Tyr Ala Leu Leu Ala Gly Val Asn Asp Gln Val Glu His Ala
                325                 330                 335

Val Glu Leu Ala Glu Leu Leu Arg Glu Trp Gly Lys Thr Tyr His Val
            340                 345                 350

Asn Leu Ile Pro Tyr Asn Pro Ile Glu Gly Ser Glu Tyr Gln Arg Pro
        355                 360                 365

Tyr Lys Lys Ala Val Leu Ala Phe Ala Ala Ala Leu Glu Ser Arg Lys
    370                 375                 380

Ile Thr Ala Ser Val Arg Gln Thr Arg Gly Leu Asp Ala Ser Ala Ala
385                 390                 395                 400

Cys Gly Gln Leu Arg Asn Lys Phe Gln Lys Ser Pro Leu Leu Thr Glu
                405                 410                 415

Thr Asp Ser Gln Glu Ser Gln Pro Asp Ala Glu Ala Val Ala Cys
            420                 425                 430


<210> SEQ ID NO 88
<211> LENGTH: 374
<212> TYPE: PRT
<213> ORGANISM: Arabidopsis lyrata

<400> SEQUENCE: 88

Met Gly Cys Phe Gly Pro Ser Lys Thr Ser Arg Thr Arg Asn His Glu
1               5                   10                  15

Lys Glu Thr Met Thr Arg Gln Asn Pro Ser Pro Gln Pro Gln Thr Met
            20                  25                  30

Arg Thr Glu Glu Val Leu Leu Gln Ile Pro Arg Cys Arg Val His Leu
        35                  40                  45

Ile Asp Glu Ser Glu Ala Val Glu Leu Ala Ser Gly Asp Phe Lys Leu
    50                  55                  60

Val Lys Val Ser Asp Asn Gly Val Thr Leu Ala Met Ile Val Arg Ile
65                  70                  75                  80

Gly His Asp Leu Gln Trp Pro Val Ile Arg Asp Glu Pro Val Val Lys
                85                  90                  95

Leu Asp Ala Arg Asp Tyr Leu Phe Thr Leu Pro Val Lys Asp Gly Asp
            100                 105                 110

Pro Leu Ser Tyr Gly Val Thr Phe Ser Gly Asp Asp Arg Asp Val Ala
        115                 120                 125

Leu Val Asn Ser Leu Lys Leu Leu Asp Gln Phe Leu Ser Glu Asn Ser
    130                 135                 140

Cys Phe Ser Ser Thr Ala Ser Ser Lys Val Asn Asn Gly Ile Asp Trp
145                 150                 155                 160

Gln Glu Phe Ala Pro Arg Ile Glu Asp Tyr Asn Asn Val Val Ala Lys
                165                 170                 175

Ala Ile Ala Gly Gly Thr Gly His Ile Ile Arg Gly Ile Phe Ser Leu
            180                 185                 190

Ser Asn Ala Tyr Ser Asn Gln Val His Lys Gly Gly Asp Ile Met Ile
        195                 200                 205

Thr Lys Ala Glu Glu Ser Gln Arg Asn Gly Gly Tyr Asn Asn Gly Asn
    210                 215                 220

Ser Ser Gly Asn Glu Lys Lys Asn Gly Ile Asn Thr Asn Leu Gln Arg
225                 230                 235                 240

Val Arg Lys Leu Ser Lys Ala Thr Glu Asn Leu Ser Arg Thr Met Leu
                245                 250                 255
```

```
Asn Gly Ala Gly Val Val Ser Gly Ser Val Met Val Pro Val Met Lys
            260                 265                 270

Ser Lys Pro Gly Met Ala Phe Phe Ser Met Val Pro Gly Glu Val Leu
        275                 280                 285

Leu Ala Ser Leu Asp Ala Leu Asn Lys Ile Leu Asp Ala Thr Glu Ala
    290                 295                 300

Ala Glu Arg Gln Thr Leu Ser Ala Thr Ser Arg Ala Ala Thr Arg Met
305                 310                 315                 320

Val Ser Glu Arg Phe Gly Glu Asn Ala Gly Glu Ala Thr Gly Asp Val
                325                 330                 335

Leu Ala Thr Ala Gly His Ala Ala Gly Thr Ala Trp Asn Val Leu Lys
            340                 345                 350

Ile Arg Lys Thr Phe Tyr Pro Ser Ser Ser Leu Thr Ser Gly Val Val
        355                 360                 365

Lys Asn Ala Pro Arg Lys
    370


<210> SEQ ID NO 89
<211> LENGTH: 979
<212> TYPE: PRT
<213> ORGANISM: Arabidopsis lyrata

<400> SEQUENCE: 89

Met Ala Ser Pro His Lys Pro Trp Arg Ala Glu Tyr Ala Lys Ser Ser
1               5                   10                  15

Arg Ser Ser Cys Lys Thr Cys Lys Ser Val Ile Asn Lys Glu Asn Phe
            20                  25                  30

Arg Leu Gly Lys Leu Val Gln Ser Thr His Phe Asp Gly Ile Met Pro
        35                  40                  45

Met Trp Asn His Ala Ser Cys Ile Leu Asn Lys Thr Lys Gln Ile Lys
    50                  55                  60

Ser Val Asp Asp Val Glu Gly Ile Glu Ser Leu Arg Trp Glu Asp Gln
65                  70                  75                  80

Gln Lys Ile Arg Lys Tyr Val Glu Ser Gly Ala Gly Asn Ser Thr Ser
                85                  90                  95

Thr Ser Lys Ser Ser Thr Ala Asn Asn Ala Lys Leu Glu Tyr Gly Ile
            100                 105                 110

Glu Val Ser Gln Thr Ser Arg Ala Gly Cys Arg Lys Cys Ser Glu Lys
        115                 120                 125

Ile Leu Lys Gly Glu Val Arg Ile Phe Ser Lys Pro Glu Gly Pro Gly
    130                 135                 140

Asn Lys Gly Leu Met Trp His His Ala Lys Cys Phe Leu Glu Met Ser
145                 150                 155                 160

Ser Ser Thr Glu Leu Glu Ser Leu Ser Gly Trp Arg Ser Ile Pro Asp
                165                 170                 175

Ala Asp Gln Glu Val Leu Leu Pro Leu Val Lys Lys Ala Leu Pro Val
            180                 185                 190

Ala Lys Thr Glu Thr Ala Glu Ala Arg Gln Thr Asn Ser Arg Ala Gly
        195                 200                 205

Thr Lys Arg Lys Asn Asp Ser Gly Asp Asn Glu Lys Ser Lys Leu Ala
    210                 215                 220

Lys Thr Ser Phe Asp Met Ser Thr Ser Gly Ala Leu Gln Pro Cys Ser
225                 230                 235                 240

Lys Glu Arg Glu Met Glu Ala Gln Thr Lys Glu Leu Trp Asp Leu Lys
```

```
                245                 250                 255

Asp Asp Leu Lys Lys Tyr Val Lys Ser Ala Glu Leu Arg Glu Met Leu
            260                 265                 270

Glu Val Asn Glu Gln Ser Thr Arg Gly Ser Glu Leu Asp Leu Arg Asp
        275                 280                 285

Lys Cys Ala Asp Gly Met Met Phe Gly Pro Leu Ala Leu Cys Pro Ile
    290                 295                 300

Cys Ser Gly His Leu Ser Phe Ser Gly Gly Leu Tyr Arg Cys His Gly
305                 310                 315                 320

Tyr Ile Ser Glu Trp Ser Lys Cys Ser His Ser Thr Leu Asp Pro Asp
                325                 330                 335

Arg Ile Lys Glu Lys Trp Lys Ile Pro Gly Glu Thr Glu Asn Gln Phe
            340                 345                 350

Leu Leu Lys Trp Asn Lys Ser Gln Asn Ser Val Lys Pro Lys Arg Ile
        355                 360                 365

Leu His Pro Val Ser Ser Gly Glu Thr Ser Gln Gly Gln Gly Ser Lys
    370                 375                 380

Asp Ala Thr Asp Ser Ser Arg Ser Glu Lys Leu Ala Asp Leu Lys Val
385                 390                 395                 400

Ser Ile Thr Gly Val Thr Lys Glu Arg Gln Ala Trp Lys Lys Arg Ile
                405                 410                 415

Glu Glu Ala Gly Gly Glu Phe His Ala Asn Val Lys Lys Gly Thr Ser
            420                 425                 430

Cys Leu Val Val Cys Gly Leu Thr Asp Ile Arg Asp Ala Glu Leu Arg
        435                 440                 445

Lys Ala Arg Arg Met Lys Val Ala Ile Val Arg Glu Asp Tyr Leu Val
    450                 455                 460

Asp Cys Phe Lys Lys Gln Arg Lys Leu Pro Phe Asp Lys Phe Lys Ile
465                 470                 475                 480

Glu Asp Thr Ser Glu Ser Leu Val Thr Val Lys Val Lys Gly Arg Ser
                485                 490                 495

Ala Val His Glu Ala Ser Gly Leu Gln Glu His Cys His Ile Leu Glu
            500                 505                 510

Asp Gly Asn Ser Ile Tyr Asn Thr Thr Leu Ser Met Ser Asp Leu Ser
        515                 520                 525

Thr Gly Ile Asn Ser Tyr Tyr Ile Leu Gln Ile Ile Gln Glu Asp Lys
    530                 535                 540

Gly Ser Asp Cys Tyr Val Phe Arg Lys Trp Gly Arg Val Gly Asn Glu
545                 550                 555                 560

Lys Ile Gly Gly Asn Lys Val Glu Glu Met Ser Lys Ser Asp Ala Val
                565                 570                 575

His Glu Phe Lys Arg Leu Phe Leu Glu Lys Thr Gly Asn Thr Trp Glu
            580                 585                 590

Ser Trp Glu Gln Lys Thr Asn Phe Gln Lys Gln Pro Gly Lys Phe Leu
        595                 600                 605

Pro Leu Asp Ile Asp Tyr Gly Val Asn Lys Gln Val Ala Lys Lys Glu
    610                 615                 620

Pro Cys Pro Ala Ser Ser Asn Leu Ala Pro Pro Leu Ile Glu Leu Met
625                 630                 635                 640

Lys Met Leu Phe Asp Val Glu Thr Tyr Arg Ser Ala Met Met Glu Phe
                645                 650                 655

Glu Ile Asn Met Ser Glu Met Pro Leu Gly Lys Leu Ser Lys His Asn
            660                 665                 670
```

Ile Gln Lys Gly Phe Glu Ala Leu Thr Glu Ile Gln Lys Leu Leu Thr
675 680 685

Glu Ser Asp Pro Gln Pro Ser Ile Lys Glu Ser Leu Leu Val Asp Ala
690 695 700

Ser Asn Arg Phe Phe Thr Met Ile Pro Ser Ile His Pro His Ile Ile
705 710 715 720

Arg Asp Glu Glu Asp Phe Lys Ser Lys Val Lys Met Leu Glu Ala Leu
725 730 735

Gln Asp Ile Glu Ile Ala Ser Arg Leu Val Gly Phe Asp Val Asp Ser
740 745 750

Thr Glu Ser Leu Asp Asp Lys Tyr Lys Lys Leu His Cys Asp Ile Ser
755 760 765

Pro Leu Pro His Asp Ser Glu Asp Tyr Arg Leu Ile Glu Lys Tyr Leu
770 775 780

Asn Thr Thr His Ala Pro Thr His Thr Glu Trp Ser Leu Glu Leu Glu
785 790 795 800

Glu Val Phe Ala Leu Glu Arg Glu Gly Glu Phe Asp Lys Tyr Ala Pro
805 810 815

His Arg Asp Lys Leu Gly Asn Lys Met Leu Leu Trp His Gly Ser Arg
820 825 830

Leu Thr Asn Phe Val Gly Ile Leu Asn Gln Gly Leu Arg Ile Ala Pro
835 840 845

Pro Glu Ala Pro Ala Thr Gly Tyr Met Phe Gly Lys Gly Ile Tyr Phe
850 855 860

Ala Asp Leu Val Ser Lys Ser Ala Gln Tyr Cys Tyr Thr Cys Lys Lys
865 870 875 880

Asn Pro Val Gly Leu Met Leu Leu Ser Glu Val Ala Leu Gly Glu Ile
885 890 895

His Glu Leu Thr Lys Ala Lys Tyr Met Asp Lys Pro Pro Lys Gly Lys
900 905 910

His Ser Thr Lys Gly Leu Gly Lys Lys Val Pro Gln Asp Ser Glu Phe
915 920 925

Ala Lys Trp Arg Gly Asp Val Thr Val Pro Cys Gly Lys Pro Val Ala
930 935 940

Ser Lys Val Lys Ala Ser Glu Leu Met Tyr Asn Glu Tyr Ile Val Tyr
945 950 955 960

Asn Thr Ala Gln Val Lys Leu Gln Phe Leu Leu Lys Val Arg Phe Lys
965 970 975

His Lys Arg

<210> SEQ ID NO 90
<211> LENGTH: 1009
<212> TYPE: PRT
<213> ORGANISM: Arabidopsis thaliana

<400> SEQUENCE: 90

Met Ala Ser Pro His Lys Pro Trp Arg Ala Glu Tyr Ala Lys Ser Ser
1 5 10 15

Arg Ser Ser Cys Lys Thr Cys Lys Ser Val Ile Asn Lys Glu Asn Phe
20 25 30

Arg Leu Gly Lys Leu Val Gln Ser Thr His Phe Asp Gly Ile Met Pro
35 40 45

Met Trp Asn His Ala Ser Cys Ile Leu Lys Lys Thr Lys Gln Ile Lys
50 55 60

```
Ser Val Asp Asp Val Glu Gly Ile Glu Ser Leu Arg Trp Glu Asp Gln
65                  70                  75                  80

Gln Lys Ile Arg Lys Tyr Val Glu Ser Gly Ala Gly Ser Asn Thr Ser
                85                  90                  95

Thr Ser Thr Gly Thr Ser Thr Ser Ser Thr Ala Asn Asn Ala Lys Leu
            100                 105                 110

Glu Tyr Gly Ile Glu Val Ser Gln Thr Ser Arg Ala Gly Cys Arg Lys
        115                 120                 125

Cys Ser Glu Lys Ile Leu Lys Gly Glu Val Arg Ile Phe Ser Lys Pro
    130                 135                 140

Glu Gly Pro Gly Asn Lys Gly Leu Met Trp His His Ala Lys Cys Phe
145                 150                 155                 160

Leu Glu Met Ser Ser Ser Thr Glu Leu Glu Ser Leu Ser Gly Trp Arg
                165                 170                 175

Ser Ile Pro Asp Ser Asp Gln Glu Ala Leu Leu Pro Leu Val Lys Lys
            180                 185                 190

Ala Leu Pro Ala Ala Lys Thr Gly Lys Ser Leu Lys Asp Pro Asp Leu
        195                 200                 205

Gln Tyr Phe Ser Leu Ile Phe Pro Leu Ile Tyr Phe Gly Pro Thr Gly
    210                 215                 220

Thr Glu Thr Ala Glu Ala Arg Gln Thr Asn Ser Arg Ala Gly Thr Lys
225                 230                 235                 240

Arg Lys Asn Asp Ser Val Asp Asn Glu Lys Ser Lys Leu Ala Lys Ser
                245                 250                 255

Ser Phe Asp Met Ser Thr Ser Gly Ala Leu Gln Pro Cys Ser Lys Glu
            260                 265                 270

Lys Glu Met Glu Ala Gln Thr Lys Glu Leu Trp Asp Leu Lys Asp Asp
        275                 280                 285

Leu Lys Lys Tyr Val Thr Ser Ala Glu Leu Arg Glu Met Leu Glu Val
    290                 295                 300

Asn Glu Gln Ser Thr Arg Gly Ser Glu Leu Asp Leu Arg Asp Lys Cys
305                 310                 315                 320

Ala Asp Gly Met Met Phe Gly Pro Leu Ala Leu Cys Pro Met Cys Ser
                325                 330                 335

Gly His Leu Ser Phe Ser Gly Gly Leu Tyr Arg Cys His Gly Tyr Ile
            340                 345                 350

Ser Glu Trp Ser Lys Cys Ser His Ser Thr Leu Asp Pro Asp Arg Ile
        355                 360                 365

Lys Gly Lys Trp Lys Ile Pro Asp Glu Thr Glu Asn Gln Phe Leu Leu
    370                 375                 380

Lys Trp Asn Lys Ser Gln Lys Ser Val Lys Pro Lys Arg Ile Leu Arg
385                 390                 395                 400

Pro Val Leu Ser Gly Glu Thr Ser Gln Gly Gln Gly Ser Lys Asp Ala
                405                 410                 415

Thr Asp Ser Ser Arg Ser Glu Arg Leu Ala Asp Leu Lys Val Ser Ile
            420                 425                 430

Ala Gly Asn Thr Lys Glu Arg Gln Pro Trp Lys Lys Arg Ile Glu Glu
        435                 440                 445

Ala Gly Ala Glu Phe His Ala Asn Val Lys Lys Gly Thr Ser Cys Leu
    450                 455                 460

Val Val Cys Gly Leu Thr Asp Ile Arg Asp Ala Glu Met Arg Lys Ala
465                 470                 475                 480
```

```
Arg Arg Met Lys Val Ala Ile Val Arg Glu Asp Tyr Leu Val Asp Cys
                485                 490                 495

Phe Lys Lys Gln Arg Lys Leu Pro Phe Asp Lys Tyr Lys Ile Glu Asp
            500                 505                 510

Thr Ser Glu Ser Leu Val Thr Val Lys Val Lys Gly Arg Ser Ala Val
        515                 520                 525

His Glu Ala Ser Gly Leu Gln Glu His Cys His Ile Leu Glu Asp Gly
    530                 535                 540

Asn Ser Ile Tyr Asn Thr Thr Leu Ser Met Ser Asp Leu Ser Thr Gly
545                 550                 555                 560

Ile Asn Ser Tyr Tyr Ile Leu Gln Ile Ile Gln Glu Asp Lys Gly Ser
                565                 570                 575

Asp Cys Tyr Val Phe Arg Lys Trp Gly Arg Val Gly Asn Glu Lys Ile
            580                 585                 590

Gly Gly Asn Lys Val Glu Glu Met Ser Lys Ser Asp Ala Val His Glu
        595                 600                 605

Phe Lys Arg Leu Phe Leu Glu Lys Thr Gly Asn Thr Trp Glu Ser Trp
    610                 615                 620

Glu Gln Lys Thr Asn Phe Gln Lys Gln Pro Gly Lys Phe Leu Pro Leu
625                 630                 635                 640

Asp Ile Asp Tyr Gly Val Asn Lys Gln Val Ala Lys Lys Glu Pro Phe
                645                 650                 655

Gln Thr Ser Ser Asn Leu Ala Pro Ser Leu Ile Glu Leu Met Lys Met
            660                 665                 670

Leu Phe Asp Val Glu Thr Tyr Arg Ser Ala Met Met Glu Phe Glu Ile
        675                 680                 685

Asn Met Ser Glu Met Pro Leu Gly Lys Leu Ser Lys His Asn Ile Gln
    690                 695                 700

Lys Gly Phe Glu Ala Leu Thr Glu Ile Gln Arg Leu Leu Thr Glu Ser
705                 710                 715                 720

Asp Pro Gln Pro Thr Met Lys Glu Ser Leu Leu Val Asp Ala Ser Asn
                725                 730                 735

Arg Phe Phe Thr Met Ile Pro Ser Ile His Pro His Ile Ile Arg Asp
            740                 745                 750

Glu Asp Asp Phe Lys Ser Lys Val Lys Met Leu Glu Ala Leu Gln Asp
        755                 760                 765

Ile Glu Ile Ala Ser Arg Ile Val Gly Phe Asp Val Asp Ser Thr Glu
    770                 775                 780

Ser Leu Asp Asp Lys Tyr Lys Lys Leu His Cys Asp Ile Ser Pro Leu
785                 790                 795                 800

Pro His Asp Ser Glu Asp Tyr Arg Leu Ile Glu Lys Tyr Leu Asn Thr
                805                 810                 815

Thr His Ala Pro Thr His Thr Glu Trp Ser Leu Glu Leu Glu Glu Val
            820                 825                 830

Phe Ala Leu Glu Arg Glu Gly Glu Phe Asp Lys Tyr Ala Pro His Arg
        835                 840                 845

Glu Lys Leu Gly Asn Lys Met Leu Leu Trp His Gly Ser Arg Leu Thr
    850                 855                 860

Asn Phe Val Gly Ile Leu Asn Gln Gly Leu Arg Ile Ala Pro Pro Glu
865                 870                 875                 880

Ala Pro Ala Thr Gly Tyr Met Phe Gly Lys Gly Ile Tyr Phe Ala Asp
                885                 890                 895

Leu Val Ser Lys Ser Ala Gln Tyr Cys Tyr Thr Cys Lys Lys Asn Pro
```

```
            900                 905                 910

Val Gly Leu Met Leu Leu Ser Glu Val Ala Leu Gly Glu Ile His Glu
        915                 920                 925

Leu Thr Lys Ala Lys Tyr Met Asp Lys Pro Pro Arg Gly Lys His Ser
    930                 935                 940

Thr Lys Gly Leu Gly Lys Lys Val Pro Gln Asp Ser Glu Phe Ala Lys
945                 950                 955                 960

Trp Arg Gly Asp Val Thr Val Pro Cys Gly Lys Pro Val Ser Ser Lys
                965                 970                 975

Val Lys Ala Ser Glu Leu Met Tyr Asn Glu Tyr Ile Val Tyr Asp Thr
            980                 985                 990

Ala Gln Val Lys Leu Gln Phe Leu  Leu Lys Val Arg Phe  Lys His Lys
        995                 1000                1005

Arg


<210> SEQ ID NO 91
<211> LENGTH: 732
<212> TYPE: PRT
<213> ORGANISM: Arabidopsis thaliana

<400> SEQUENCE: 91

Met Ser Asn Gln Lys Lys Arg Asn Phe Gln Ile Glu Ala Phe Lys His
1               5                   10                  15

Arg Val Val Val Asp Pro Lys Tyr Ala Asp Lys Thr Trp Gln Ile Leu
            20                  25                  30

Glu Arg Ala Ile His Gln Ile Tyr Asn Gln Asp Ala Ser Gly Leu Ser
        35                  40                  45

Phe Glu Glu Leu Tyr Arg Asn Ala Tyr Asn Met Val Leu His Lys Phe
    50                  55                  60

Gly Glu Lys Leu Tyr Thr Gly Phe Ile Ala Thr Met Thr Ser His Leu
65                  70                  75                  80

Lys Glu Lys Ser Lys Leu Ile Glu Ala Ala Gln Gly Gly Ser Phe Leu
                85                  90                  95

Glu Glu Leu Asn Lys Lys Trp Asn Glu His Asn Lys Ala Leu Glu Met
            100                 105                 110

Ile Arg Asp Ile Leu Met Tyr Met Asp Arg Thr Tyr Ile Glu Ser Thr
        115                 120                 125

Lys Lys Thr His Val His Pro Met Gly Leu Asn Leu Trp Arg Asp Asn
    130                 135                 140

Val Val His Phe Thr Lys Ile His Thr Arg Leu Leu Asn Thr Leu Leu
145                 150                 155                 160

Asp Leu Val Gln Lys Glu Arg Ile Gly Glu Val Ile Asp Arg Gly Leu
                165                 170                 175

Met Arg Asn Val Ile Lys Met Phe Met Asp Leu Gly Glu Ser Val Tyr
            180                 185                 190

Gln Glu Asp Phe Glu Lys Pro Phe Leu Asp Ala Ser Ser Glu Phe Tyr
        195                 200                 205

Lys Val Glu Ser Gln Glu Phe Ile Glu Ser Cys Asp Cys Gly Asp Tyr
    210                 215                 220

Leu Lys Lys Ser Glu Lys Arg Leu Thr Glu Glu Ile Glu Arg Val Ala
225                 230                 235                 240

His Tyr Leu Asp Ala Lys Ser Glu Glu Lys Ile Thr Ser Val Val Glu
                245                 250                 255

Lys Glu Met Ile Ala Asn His Met Gln Arg Leu Val His Met Glu Asn
```

```
            260                 265                 270

Ser Gly Leu Val Asn Met Leu Leu Asn Asp Lys Tyr Glu Asp Leu Gly
        275                 280                 285

Arg Met Tyr Asn Leu Phe Arg Arg Val Thr Asn Gly Leu Val Thr Val
    290                 295                 300

Arg Asp Val Met Thr Ser His Leu Arg Glu Met Gly Lys Gln Leu Val
305                 310                 315                 320

Thr Asp Pro Glu Lys Ser Lys Asp Pro Val Glu Phe Val Gln Arg Leu
                325                 330                 335

Leu Asp Glu Arg Asp Lys Tyr Asp Lys Ile Ile Asn Thr Ala Phe Gly
            340                 345                 350

Asn Asp Lys Thr Phe Gln Asn Ala Leu Asn Ser Ser Phe Glu Tyr Phe
        355                 360                 365

Ile Asn Leu Asn Ala Arg Ser Pro Glu Phe Ile Ser Leu Phe Val Asp
    370                 375                 380

Asp Lys Leu Arg Lys Gly Leu Lys Gly Ile Thr Asp Val Asp Val Glu
385                 390                 395                 400

Val Ile Leu Asp Lys Val Met Met Leu Phe Arg Tyr Leu Gln Glu Lys
                405                 410                 415

Asp Val Phe Glu Lys Tyr Tyr Lys Gln His Leu Ala Lys Arg Leu Leu
            420                 425                 430

Ser Gly Lys Thr Val Ser Asp Asp Ala Glu Arg Ser Leu Ile Val Lys
        435                 440                 445

Leu Lys Thr Glu Cys Gly Tyr Gln Phe Ile Ser Lys Leu Glu Gly Met
    450                 455                 460

Phe Thr Asp Met Lys Thr Ser Glu Asp Thr Met Arg Gly Phe Tyr Gly
465                 470                 475                 480

Ser His Pro Glu Leu Ser Glu Gly Pro Thr Leu Ile Val Gln Val Leu
                485                 490                 495

Thr Thr Gly Ser Trp Pro Thr Gln Pro Ala Val Pro Cys Asn Leu Pro
            500                 505                 510

Ala Glu Val Ser Val Leu Cys Glu Lys Phe Arg Ser Tyr Tyr Leu Gly
        515                 520                 525

Thr His Thr Gly Arg Arg Leu Ser Trp Gln Thr Asn Met Gly Thr Ala
    530                 535                 540

Asp Ile Lys Ala Ile Phe Gly Lys Gly Gln Lys His Glu Leu Asn Val
545                 550                 555                 560

Ser Thr Phe Gln Met Cys Val Leu Met Leu Phe Asn Asn Ser Asp Arg
                565                 570                 575

Leu Ser Tyr Lys Glu Ile Glu Gln Ala Thr Glu Ile Pro Ala Ala Asp
            580                 585                 590

Leu Lys Arg Cys Leu Gln Ser Leu Ala Cys Val Lys Gly Lys Asn Val
        595                 600                 605

Ile Lys Lys Glu Pro Met Ser Lys Asp Ile Gly Glu Glu Asp Leu Phe
    610                 615                 620

Val Val Asn Asp Lys Phe Thr Ser Lys Phe Tyr Lys Val Lys Ile Gly
625                 630                 635                 640

Thr Val Val Ala Gln Lys Glu Thr Glu Pro Glu Lys Gln Glu Thr Arg
                645                 650                 655

Gln Arg Val Glu Glu Asp Arg Lys Pro Gln Ile Glu Ala Ala Ile Val
            660                 665                 670

Arg Ile Met Lys Ser Arg Lys Ile Leu Asp His Asn Asn Ile Ile Ala
        675                 680                 685
```

```
Glu Val Thr Lys Gln Leu Gln Pro Arg Phe Leu Ala Asn Pro Thr Glu
    690                 695                 700

Ile Lys Lys Arg Ile Glu Ser Leu Ile Glu Arg Asp Phe Leu Glu Arg
705                 710                 715                 720

Asp Ser Thr Asp Arg Lys Leu Tyr Arg Tyr Leu Ala
                725                 730


<210> SEQ ID NO 92
<211> LENGTH: 732
<212> TYPE: PRT
<213> ORGANISM: Arabidopsis lyrata

<400> SEQUENCE: 92

Met Ser Asn Gln Lys Lys Arg Asn Phe Gln Ile Glu Ala Phe Lys His
1               5                   10                  15

Arg Val Val Val Asp Pro Lys Tyr Ala Asp Lys Thr Trp Gln Ile Leu
            20                  25                  30

Glu Arg Ala Ile His Gln Ile Tyr Asn Gln Asp Ala Ser Gly Leu Ser
        35                  40                  45

Phe Glu Glu Leu Tyr Arg Asn Ala Tyr Asn Met Val Leu His Lys Phe
    50                  55                  60

Gly Glu Lys Leu Tyr Thr Gly Phe Ile Ala Thr Met Thr Ser His Leu
65                  70                  75                  80

Lys Glu Lys Ser Lys Leu Ile Glu Ala Ala Gln Gly Gly Ser Phe Leu
                85                  90                  95

Glu Glu Leu Asn Lys Lys Trp Asn Glu His Asn Lys Ala Leu Glu Met
            100                 105                 110

Ile Arg Asp Ile Leu Met Tyr Met Asp Arg Thr Tyr Ile Glu Ser Thr
        115                 120                 125

Lys Lys Thr His Val His Pro Met Gly Leu Asn Leu Trp Arg Asp Asn
    130                 135                 140

Val Val His Phe Thr Lys Ile His Thr Arg Leu Leu Asn Thr Leu Leu
145                 150                 155                 160

Asp Leu Val Gln Lys Glu Arg Thr Gly Glu Val Ile Asp Arg Gly Leu
                165                 170                 175

Met Arg Asn Val Ile Lys Met Phe Met Asp Leu Gly Glu Ser Val Tyr
            180                 185                 190

Gln Glu Asp Phe Glu Lys Pro Phe Leu Asp Ala Ser Ser Glu Phe Tyr
        195                 200                 205

Lys Val Glu Ser Gln Glu Phe Ile Glu Ser Cys Asp Cys Gly Asp Tyr
    210                 215                 220

Leu Lys Lys Ala Glu Lys Arg Leu Thr Glu Glu Ile Glu Arg Val Ala
225                 230                 235                 240

His Tyr Leu Asp Ala Lys Ser Glu Glu Lys Ile Thr Ser Val Val Glu
                245                 250                 255

Lys Glu Met Ile Ala Asn His Met Gln Arg Leu Val His Met Glu Asn
            260                 265                 270

Ser Gly Leu Val Asn Met Leu Leu Asn Asp Lys Tyr Asp Asp Leu Gly
        275                 280                 285

Arg Met Tyr Asn Leu Phe Arg Arg Val Thr Asn Gly Leu Val Thr Val
    290                 295                 300

Arg Asp Val Met Thr Ser His Leu Arg Glu Met Gly Lys Gln Leu Val
305                 310                 315                 320

Thr Asp Pro Glu Lys Ser Lys Asp Pro Val Glu Phe Val Gln Arg Leu
```

```
                325                 330                 335

Leu Asp Glu Arg Asp Lys Tyr Asp Lys Ile Ile Ser Thr Ala Phe Gly
            340                 345                 350

Asn Asp Lys Thr Phe Gln Asn Ala Leu Asn Ser Ser Phe Glu Tyr Phe
        355                 360                 365

Ile Asn Leu Asn Ala Arg Ser Pro Glu Phe Ile Ser Leu Phe Val Asp
    370                 375                 380

Asp Lys Leu Arg Lys Gly Leu Lys Gly Ile Ala Asp Val Asp Val Glu
385                 390                 395                 400

Val Ile Leu Asp Lys Val Met Met Leu Phe Arg Tyr Leu Gln Glu Lys
                405                 410                 415

Asp Val Phe Glu Lys Tyr Tyr Lys Gln His Leu Ala Lys Arg Leu Leu
            420                 425                 430

Ser Gly Lys Thr Val Ser Asp Glu Ala Glu Arg Ser Leu Ile Val Lys
        435                 440                 445

Leu Lys Thr Glu Cys Gly Tyr Gln Phe Thr Ser Lys Leu Glu Gly Met
    450                 455                 460

Phe Thr Asp Met Lys Thr Ser Glu Asp Thr Met Arg Gly Phe Tyr Gly
465                 470                 475                 480

Ser His Pro Glu Leu Ser Glu Gly Pro Thr Leu Ile Val Gln Val Leu
                485                 490                 495

Thr Thr Gly Ser Trp Pro Thr Gln Pro Ala Val Pro Cys Asn Leu Pro
            500                 505                 510

Ala Glu Val Ser Val Leu Cys Glu Lys Phe Arg Ser Tyr Tyr Leu Gly
        515                 520                 525

Thr His Thr Gly Arg Arg Leu Ser Trp Gln Thr Asn Met Gly Thr Ala
    530                 535                 540

Asp Ile Lys Ala Ile Phe Gly Lys Gly Gln Lys His Glu Leu Asn Val
545                 550                 555                 560

Ser Thr Phe Gln Met Cys Val Leu Met Leu Phe Asn Asn Ser Asp Arg
                565                 570                 575

Leu Ser Tyr Lys Glu Ile Glu Gln Ala Thr Glu Ile Pro Ala Ala Asp
            580                 585                 590

Leu Lys Arg Cys Leu Gln Ser Leu Ala Cys Val Lys Gly Lys Asn Val
        595                 600                 605

Ile Lys Lys Glu Pro Met Ser Lys Asp Ile Gly Glu Glu Asp Ser Phe
    610                 615                 620

Val Val Asn Asp Lys Phe Thr Ser Lys Phe Tyr Lys Val Lys Ile Gly
625                 630                 635                 640

Thr Val Val Ala Gln Lys Glu Thr Glu Pro Glu Lys Gln Glu Thr Arg
                645                 650                 655

Gln Arg Val Glu Glu Asp Arg Lys Pro Gln Ile Glu Ala Ala Ile Val
            660                 665                 670

Arg Ile Met Lys Ser Arg Lys Ile Leu Asp His Asn Asn Ile Ile Ala
        675                 680                 685

Glu Val Thr Lys Gln Leu Gln Pro Arg Phe Leu Ala Asn Pro Thr Glu
    690                 695                 700

Ile Lys Lys Arg Ile Glu Ser Leu Ile Glu Arg Asp Phe Leu Glu Arg
705                 710                 715                 720

Asp Ser Thr Asp Arg Lys Leu Tyr Arg Tyr Leu Ala
                725                 730
```

<210> SEQ ID NO 93

<211> LENGTH: 640
<212> TYPE: DNA
<213> ORGANISM: Zea mays

<400> SEQUENCE: 93

```
cctcaaagag gcagccatgg ctccacataa aagcgcccaa tgggagctcc ctcttctccc     60

cccacgcccc tccccctctt gataagccca cgtcggcggc aggggggcg gccgccaggc    120

ttgctatagc tggtccatgg caccatacat gtaagcacgc acacaggcac acacacacac    180

gcacgcaatg atctacgtat ctagcagcag cttatcatgt cgtcatcatg catgcatggc    240

cgacggaggt cgtcatctta tctgggagcg tgtgtgtctt ggcaatggga agctgcatgc    300

gcctctcggg cgtcggcgcg tcggcgccta gctgtagggc ggcgtgccat agagctgcct    360

cctgccgctc acaccatgct gttgacgagg actgatggtg gccatggcct ctcggcgtcg    420

gtggcggcgg cgccggcgcc gagttttacc tctctactaa ggtagggcaa cttgtatcct    480

ttggcaattg ttctcatcta tctgggtctg tctgttggct gcccggtgac ggtatacggt    540

gatgttctaa tagtactcaa ttggtcttgg atcggagttc atgctacggc tcctctgtta    600

tatattacac ggctgacggc tcctccttat taatgtgtac                        640
```

<210> SEQ ID NO 94
<211> LENGTH: 640
<212> TYPE: DNA
<213> ORGANISM: Artificial sequence
<220> FEATURE:
<223> OTHER INFORMATION: Zea mays miR399 47862C decoy with a synthetic miR172 binding site substituted for miR399 binding site

<400> SEQUENCE: 94

```
cctcaaagag gcagccatgg ctccacataa aagcgcccaa tgggagctcc ctcttctccc     60

cccacgcccc tccccctctt gataagccca cgtcggcggc aggggggcg gccgccaggc    120

ttgctatagc tggtccatgg caccatacat gtaagcacgc acacaggcac acacacacac    180

gcacgcaatg atctacgtat ctagcagcag cttatcatgt cgtcatcatg catgcatggc    240

cgacggaggt cgtcatctta tctgggagcg tgtgtgtctt ggcaatggga agctgcatgc    300

gcctctcggg cgtcggcgcg tcggcgccta gctgtagggc ggcgtgccat agagctgcct    360

cctgccgctc acaccatgct gttgacgagg actgatggtg gccatggcct ctcggcgtcg    420

gtggcggcgg cgccggcgcc gagttttacc tctctactaa ggctgcagca tcactatcaa    480

gattctattg ttctcatcta tctgggtctg tctgttggct gcccggtgac ggtatacggt    540

gatgttctaa tagtactcaa ttggtcttgg atcggagttc atgctacggc tcctctgtta    600

tatattacac ggctgacggc tcctccttat taatgtgtac                        640
```

<210> SEQ ID NO 95
<211> LENGTH: 640
<212> TYPE: DNA
<213> ORGANISM: Artificial sequence
<220> FEATURE:
<223> OTHER INFORMATION: Zea mays miR399 47862C decoy with a synthetic miR166 binding site substituted for miR399 binding site.

<400> SEQUENCE: 95

```
cctcaaagag gcagccatgg ctccacataa aagcgcccaa tgggagctcc ctcttctccc     60

cccacgcccc tccccctctt gataagccca cgtcggcggc aggggggcg gccgccaggc    120

ttgctatagc tggtccatgg caccatacat gtaagcacgc acacaggcac acacacacac    180

gcacgcaatg atctacgtat ctagcagcag cttatcatgt cgtcatcatg catgcatggc    240
```

```
cgacggaggt cgtcatctta tctgggagcg tgtgtgtctt ggcaatggga agctgcatgc    300

gcctctcggg cgtcggcgcg tcggcgccta gctgtagggc ggcgtgccat agagctgcct    360

cctgccgctc acaccatgct gttgacgagg actgatggtg gccatggcct ctcggcgtcg    420

gtggcggcgg cgccggcgcc gagttttacc tctctactaa ggcgggaatg aagctacctg    480

gtccgaattg ttctcatcta tctgggtctg tctgttggct gcccggtgac ggtatacggt    540

gatgttctaa tagtactcaa ttggtcttgg atcggagttc atgctacggc tcctctgtta    600

tatattacac ggctgacggc tcctccttat taatgtgtac                         640
```

```
<210> SEQ ID NO 96
<211> LENGTH: 640
<212> TYPE: DNA
<213> ORGANISM: Artificial sequence
<220> FEATURE:
<223> OTHER INFORMATION: Zea mays miR399 47862C decoy with a synthetic
      miR444 binding site substituted for miR399 binding site.

<400> SEQUENCE: 96

cctcaaagag gcagccatgg ctccacataa aagcgcccaa tgggagctcc ctcttctccc     60

cccacgcccc tccccctctt gataagccca cgtcggcggc aggggggcg gccgccaggc    120

ttgctatagc tggtccatgg caccatacat gtaagcacgc acacaggcac acacacacac    180

gcacgcaatg atctacgtat ctagcagcag cttatcatgt cgtcatcatg catgcatggc    240

cgacggaggt cgtcatctta tctgggagcg tgtgtgtctt ggcaatggga agctgcatgc    300

gcctctcggg cgtcggcgcg tcggcgccta gctgtagggc ggcgtgccat agagctgcct    360

cctgccgctc acaccatgct gttgacgagg actgatggtg gccatggcct ctcggcgtcg    420

gtggcggcgg cgccggcgcc gagttttacc tctctactaa ggccagcaag cttctagagg    480

cagcaaattg ttctcatcta tctgggtctg tctgttggct gcccggtgac ggtatacggt    540

gatgttctaa tagtactcaa ttggtcttgg atcggagttc atgctacggc tcctctgtta    600

tatattacac ggctgacggc tcctccttat taatgtgtac                         640
```

```
<210> SEQ ID NO 97
<211> LENGTH: 640
<212> TYPE: DNA
<213> ORGANISM: Artificial sequence
<220> FEATURE:
<223> OTHER INFORMATION: Zea mays miR399 47862C decoy with a synthetic
      miR172e binding site substituted for miR399 binding site.

<400> SEQUENCE: 97

cctcaaagag gcagccatgg ctccacataa aagcgcccaa tgggagctcc ctcttctccc     60

cccacgcccc tccccctctt gataagccca cgtcggcggc aggggggcg gccgccaggc    120

ttgctatagc tggtccatgg caccatacat gtaagcacgc acacaggcac acacacacac    180

gcacgcaatg atctacgtat ctagcagcag cttatcatgt cgtcatcatg catgcatggc    240

cgacggaggt cgtcatctta tctgggagcg tgtgtgtctt ggcaatggga agctgcatgc    300

gcctctcggg cgtcggcgcg tcggcgccta gctgtagggc ggcgtgccat agagctgcct    360

cctgccgctc acaccatgct gttgacgagg actgatggtg gccatggcct ctcggcgtcg    420

gtggcggcgg cgccggcgcc gagttttacc tctctactaa ggttgcagca tcactatcaa    480

gattccattg ttctcatcta tctgggtctg tctgttggct gcccggtgac ggtatacggt    540

gatgttctaa tagtactcaa ttggtcttgg atcggagttc atgctacggc tcctctgtta    600
```

tatattacac ggctgacggc tcctccttat taatgtgtac 640

<210> SEQ ID NO 98
<211> LENGTH: 641
<212> TYPE: DNA
<213> ORGANISM: Artificial sequence
<220> FEATURE:
<223> OTHER INFORMATION: Zea mays miR399 47862C decoy with a synthetic miR393 binding site substituted for the miR399 binding site.

<400> SEQUENCE: 98
cctcaaagag gcagccatgg ctccacataa aagcgcccaa tgggagctcc ctcttctccc 60
cccacgcccc tccccctctt gataagccca cgtcggcggc aggggggcg gccgccaggc 120 ttgctatagc tggtccatgg caccatacat gtaagcacgc acacaggcac acacacacac 180
gcacgcaatg atctacgtat ctagcagcag cttatcatgt cgtcatcatg catgcatggc 240
cgacggaggt cgtcatctta tctgggagcg tgtgtgtctt ggcaatggga agctgcatgc 300
gcctctcggg cgtcggcgcg tcggcgccta gctgtagggc ggcgtgccat agagctgcct 360
cctgccgctc acaccatgct gttgacgagg actgatggtg gccatggcct ctcggcgtcg 420
gtggcggcgg cgccggcgcc gagttttacc tctctactaa ggtgatcaat gcgactatcc 480
ctttggaatt gttctcatct atctgggtct gtctgttggc tgcccggtga cggtatacgg 540
tgatgttcta atagtactca attggtcttg gatcggagtt catgctacgg ctcctctgtt 600
atatattaca cggctgacgg ctcctcctta ttaatgtgta c 641

<210> SEQ ID NO 99
<211> LENGTH: 640
<212> TYPE: DNA
<213> ORGANISM: Artificial sequence
<220> FEATURE:
<223> OTHER INFORMATION: Zea mays miR399 47862C decoy with a synthetic miR397 binding site substituted for the naturally occurring miR399 binding site.

<400> SEQUENCE: 99
cctcaaagag gcagccatgg ctccacataa aagcgcccaa tgggagctcc ctcttctccc 60
cccacgcccc tccccctctt gataagccca cgtcggcggc aggggggcg gccgccaggc 120 ttgctatagc tggtccatgg caccatacat gtaagcacgc acacaggcac acacacacac 180
gcacgcaatg atctacgtat ctagcagcag cttatcatgt cgtcatcatg catgcatggc 240
cgacggaggt cgtcatctta tctgggagcg tgtgtgtctt ggcaatggga agctgcatgc 300
gcctctcggg cgtcggcgcg tcggcgccta gctgtagggc ggcgtgccat agagctgcct 360
cctgccgctc acaccatgct gttgacgagg actgatggtg gccatggcct ctcggcgtcg 420
gtggcggcgg cgccggcgcc gagttttacc tctctactaa gggatcaacg ctgcagcact 480
caatgaattg ttctcatcta tctgggtctg tctgttggct gcccggtgac ggtatacggt 540
gatgttctaa tagtactcaa ttggtcttgg atcggagttc atgctacggc tcctctgtta 600
tatattacac ggctgacggc tcctccttat taatgtgtac 640

<210> SEQ ID NO 100
<211> LENGTH: 24
<212> TYPE: DNA
<213> ORGANISM: Zea mays

<400> SEQUENCE: 100
tagggcaact tgtatccttt ggca 24

<210> SEQ ID NO 101
<211> LENGTH: 24
<212> TYPE: DNA
<213> ORGANISM: Artificial sequence
<220> FEATURE:
<223> OTHER INFORMATION: synthetic miR172 binding site.

<400> SEQUENCE: 101
ctgcagcatc actatcaaga ttct 24

<210> SEQ ID NO 102
<211> LENGTH: 24
<212> TYPE: DNA
<213> ORGANISM: Artificial sequence
<220> FEATURE:
<223> OTHER INFORMATION: synthetic miR166 binding site.

<400> SEQUENCE: 102
cgggaatgaa gctacctggt ccga 24

<210> SEQ ID NO 103
<211> LENGTH: 24
<212> TYPE: DNA
<213> ORGANISM: Artificial sequence
<220> FEATURE:
<223> OTHER INFORMATION: synthetic miR444 binding site.

<400> SEQUENCE: 103
ccagcaagct tctagaggca gcaa 24

<210> SEQ ID NO 104
<211> LENGTH: 24
<212> TYPE: DNA
<213> ORGANISM: Artificial sequence
<220> FEATURE:
<223> OTHER INFORMATION: synthetic miR172e binding site.

<400> SEQUENCE: 104
ttgcagcatc actatcaaga ttcc 24

<210> SEQ ID NO 105
<211> LENGTH: 25
<212> TYPE: DNA
<213> ORGANISM: Artificial sequence
<220> FEATURE:
<223> OTHER INFORMATION: synthetic miR393 binding site.

<400> SEQUENCE: 105
tgatcaatgc gactatccct ttgga 25

<210> SEQ ID NO 106
<211> LENGTH: 24
<212> TYPE: DNA
<213> ORGANISM: Artificial sequence
<220> FEATURE:
<223> OTHER INFORMATION: synthetic miR397 binding site.

<400> SEQUENCE: 106
gatcaacgct gcagcactca atga 24

<210> SEQ ID NO 107
<211> LENGTH: 1461
<212> TYPE: DNA
<213> ORGANISM: Glycine max

<400> SEQUENCE: 107

```
atgttagatc ttaatctcaa tgcggagtgg accgattcgt ttagtaacgg tgagtcgccg     60
ttaccgttag agaagtttcc agacggtttg aggaaccaaa tggccgagtc agggacttcg    120
aattcctccg tggtgaatgc ggacgggtcc agtaacggcg gcggcgacga ggactcggac    180
tccacacgag ctgctgatga cgtgtacacc actttcaatt tcgatatcct taaagtcgaa    240
ggcgcgaacg gcttcgtaac gaaggagctc tttccggtga tgagtgaagg agctaaagga    300
cacgctacgt cgtcgttttc agggacgaat ggtttcgtgg atctctcgtt cgatggcgat    360
ggagggaaca ctagtgagat gaagatgctt cagcctcaga atcagaatca gactcaaacg    420
cgaactcaga cacagcaacc agcgaaaaag agtaggagag gaccgaggtc tcgaagctcg    480
caatacagag ggttactttt ttacagaagg acgggaagat gggaatcgca tatctgggat    540
tgcgggaaac aagtctattt gggtggattt gacacggctc atgctgctgc cagagcctat    600
gatcgagccg ctattaagtt caggggagtt gatgctgata tcaatttcaa tctgagtgat    660
tatgaggatg accttaaaca gatgcagaat ttgtccaagg aggaattcgt acatatactg    720
cgtcgccaaa gtactggttt ctcaagagga agctctaaat accgaggagt aacactccac    780
aagtgtggcc ggtgggaagc tcgaatggga caatttcttg gcaaaaagta tatatatctt    840
ggactattcg acagcgaagt agaagctgca agggcttatg acaaggcagc tatcaaatgc    900
aacggaaggg aagcagtgac caactttgag ccaagtactt atgaaggaga gctgaaatct    960
gcagccatta atgaaggagg cagtcagaat cttgatctca atttgggcat agcaacccca   1020
ggacctccca aagaaaattg gggcaactt cagttcccct ccttcccta caatacacat   1080
ggtggaagaa gttcaatgat ggaaaccaat gttagttctg gaattggtaa tccatctttg   1140
aaaaggatgg ttgcaactga agatcgtcct tcattatgga atggcatgtc tcctaatttc   1200
tttcccaatg gggaaagagc agagagaatc ggcgttgatc cttcaaacgg actccccaac   1260
tgggcgtggc aaacacatgg ccaggtcaat gctaccccag taccaacgtt ctctgctgca   1320
gcatcatcag gattctcaat ttcagctacc tttccatcgg ctgccatctt tccaacaagt   1380
tctatgaact caattcccca gagtctctgt tttacttcat ccagcatgcc tacccgcaat   1440
gcatctgaat attattacta g                                             1461
```

```
<210> SEQ ID NO 108
<211> LENGTH: 486
<212> TYPE: PRT
<213> ORGANISM: Glycine max

<400> SEQUENCE: 108

Met Leu Asp Leu Asn Leu Asn Ala Glu Trp Thr Asp Ser Phe Ser Asn
1               5                   10                  15

Gly Glu Ser Pro Leu Pro Leu Glu Lys Phe Pro Asp Gly Leu Arg Asn
            20                  25                  30

Gln Met Ala Glu Ser Gly Thr Ser Asn Ser Ser Val Val Asn Ala Asp
        35                  40                  45

Gly Ser Ser Asn Gly Gly Gly Asp Glu Asp Ser Asp Ser Thr Arg Ala
    50                  55                  60

Ala Asp Asp Val Tyr Thr Thr Phe Asn Phe Asp Ile Leu Lys Val Glu
65                  70                  75                  80

Gly Ala Asn Gly Phe Val Thr Lys Glu Leu Phe Pro Val Met Ser Glu
                85                  90                  95

Gly Ala Lys Gly His Ala Thr Ser Ser Phe Ser Gly Thr Asn Gly Phe
            100                 105                 110
```

```
Val Asp Leu Ser Phe Asp Gly Asp Gly Gly Asn Thr Ser Glu Met Lys
        115                 120                 125

Met Leu Gln Pro Gln Asn Gln Asn Gln Thr Gln Thr Arg Thr Gln Thr
    130                 135                 140

Gln Gln Pro Ala Lys Lys Ser Arg Arg Gly Pro Arg Ser Arg Ser Ser
145                 150                 155                 160

Gln Tyr Arg Gly Val Thr Phe Tyr Arg Arg Thr Gly Arg Trp Glu Ser
                165                 170                 175

His Ile Trp Asp Cys Gly Lys Gln Val Tyr Leu Gly Gly Phe Asp Thr
            180                 185                 190

Ala His Ala Ala Ala Arg Ala Tyr Asp Arg Ala Ala Ile Lys Phe Arg
        195                 200                 205

Gly Val Asp Ala Asp Ile Asn Phe Asn Leu Ser Asp Tyr Glu Asp Asp
    210                 215                 220

Leu Lys Gln Met Gln Asn Leu Ser Lys Glu Glu Phe Val His Ile Leu
225                 230                 235                 240

Arg Arg Gln Ser Thr Gly Phe Ser Arg Gly Ser Ser Lys Tyr Arg Gly
                245                 250                 255

Val Thr Leu His Lys Cys Gly Arg Trp Glu Ala Arg Met Gly Gln Phe
            260                 265                 270

Leu Gly Lys Lys Tyr Ile Tyr Leu Gly Leu Phe Asp Ser Glu Val Glu
        275                 280                 285

Ala Ala Arg Ala Tyr Asp Lys Ala Ala Ile Lys Cys Asn Gly Arg Glu
    290                 295                 300

Ala Val Thr Asn Phe Glu Pro Ser Thr Tyr Glu Gly Glu Leu Lys Ser
305                 310                 315                 320

Ala Ala Ile Asn Glu Gly Gly Ser Gln Asn Leu Asp Leu Asn Leu Gly
                325                 330                 335

Ile Ala Thr Pro Gly Pro Pro Lys Glu Asn Trp Gly Gln Leu Gln Phe
            340                 345                 350

Pro Ser Phe Pro Tyr Asn Thr His Gly Gly Arg Ser Ser Met Met Glu
        355                 360                 365

Thr Asn Val Ser Ser Gly Ile Gly Asn Pro Ser Leu Lys Arg Met Val
    370                 375                 380

Ala Thr Glu Asp Arg Pro Ser Leu Trp Asn Gly Met Ser Pro Asn Phe
385                 390                 395                 400

Phe Pro Asn Gly Glu Arg Ala Glu Arg Ile Gly Val Asp Pro Ser Asn
                405                 410                 415

Gly Leu Pro Asn Trp Ala Trp Gln Thr His Gly Gln Val Asn Ala Thr
            420                 425                 430

Pro Val Pro Thr Phe Ser Ala Ala Ala Ser Ser Gly Phe Ser Ile Ser
        435                 440                 445

Ala Thr Phe Pro Ser Ala Ala Ile Phe Pro Thr Ser Ser Met Asn Ser
    450                 455                 460

Ile Pro Gln Ser Leu Cys Phe Thr Ser Ser Ser Met Pro Thr Arg Asn
465                 470                 475                 480

Ala Ser Glu Tyr Tyr Tyr
                485
```

<210> SEQ ID NO 109
<211> LENGTH: 2565
<212> TYPE: DNA
<213> ORGANISM: Zea mays

<400> SEQUENCE: 109

```
atggcgagca gcagggggag gctgaggctc tccccgcgcg cggcggcgcc gcagctggac     60
gcgggcaagt acgtgcggta cacggcggag caggtggatg cgctggagct tgcctacggc    120
gagtgcccca agcccagctc gctgcgccgg cagcagctca tccgggactg cgccgtcctc    180
accaacgtcg agcccaggca gatcaaggtc tggttccaga accgcagatg ccgggagaag    240
cagcggaggg agtcctctcg tctgcagacc gtcaaccgga agctgggtgc catgaacaag    300
ctgttgatgg aggagaacga ccggctgcag aagcaggtgt cccgtctcgt cttcgacaac    360
gggtatatga agaatcggct ccacagtcct tctgtagcca ccaccgacac aagctgcgag    420
tctgtggtga caagtggtca gcacaagcag cagcaaaacc cagcagttct gcatcctcca    480
caaagggatg cgaacaaccc agcaggtcta ctcgctattg ctgaggagac attggcggag    540
ttcatgtcca aggcgaccgg aactgctgtc aactgggtgc agatggttgg gatgaagcct    600
ggtccggatt ccgttggaat catcgctgtt tcgcacaact gcagcggcgt agcagcacga    660
gcttgcggcc ttgtgagcct cgagcccaca aaggttgccg agatccttaa ggatcgcgca    720
tcgtggtatc gcgattgtcg gcgtgttgat atcctccatg ttatccctac gggtaacggt    780
ggaacgattg agctgatcta tatgcagact tatgcactga caactctggc ggaaccgcgc    840
gacttttgga cactacgata cactagtggt cttgacgatg gcagtcttgt gatctgcgaa    900
aggtcattga cccactccac tggaggtcct tctggaccta aaactccaga ttttataaga    960
gctgaggtgc ttcctagtgg ttatctgatt cgaccttgtg atgggggagg ttccatgatt   1020
tacattgtgg atcatgttga tctgaatgct tgtagtgtcc ctgaggttct tcgaccgctc   1080
tatgaatctc ctaagatact ggcacaaaag atgactgctg cggcgttgcg tcacattagg   1140
caaattgcac acgaatcaag tggtgaaacg ccctatggtg ctgggcgaca gccagctgtt   1200
ctcagaactt tcagtcaaag gctcagcaga ggcttcaatg atgctgtgag tggctttcca   1260
gacgatggct ggtcttcttt gttgagcagt gatggtgctg aggatatttc aattacaatc   1320
aactcatctc caaacaaact tattgggtct gatgtcagcc cttccccatt cttttctgcc   1380
atggggggcg gcatcatgtg cgcaaaagcg tcaatgctac tgcagaatgt gccacctgct   1440
ctacttgtgc gatttttgag ggagcatcgc tctgaatggg ctgaccctgg tgttgatgct   1500
tattccgctg cctctctgag ggccaaccca tataatgttc cgggtttaag ggctggtggg   1560
tttatgggca accaggttat actacccctt gcacgcaccg tggagcatga agagtgcttg   1620
gaggttattc gacttcaagg acatggcttt agccatgacg aggttcttat gtccccggat   1680
atgtttcttc tgcagttgtg cagcggcatc gatgaggatg cgccgggtgc ttgtgcacag   1740
cttgtcttcg ctcctatcga tgaatctttt gctgacgatg caccgttgct accctctggc   1800
ttccgtgtga taccgcttga tgctaagacg gatgtgccat ctgccacacg tacccttgac   1860
cttgcttctg cgctcgaggt cggatcaggc ggaggtctgt gtgctttaag cgatagcggg   1920
tcaggcacgc gcagcacgag gtcggtcctg accatcgcct tccagttctc gttcgagaac   1980
cacctccgcg agagcgtggc agcgatggcc aggcagtatg tcagggcagt gatggcgatc   2040
gtgcagaggg tggccatggc gatttctccc tctcgccttg gcccgcatgt cgaactgaag   2100
catccgccag gctctcccga ggcactcgca ctagcttcgt ggattggcag gagctacagg   2160
gcgcacactg gaacggagat ccgctggtcg gacactgaag acgcggcggg ctctccccctg   2220
acgctgttct ggaagcacag cgacgccata atctgctgct ctctaaagcc ggctttcaca   2280
ctcaagttcg ccaacagcgc cggcttcgac atactggaga cgacggtcgc gaacgtccag   2340
```

```
gacctgcagc tggaggcggt ccttgatgac gggggacaga aggccctggt cgcacagctc   2400

cccaagatca tgctgcaggg cctggcgtac ctccccggcg gcgtgtgcag gtcgagcatg   2460

gggcggcagg cgtcgtacga gcaggcggtg gcgtggaagg tggtgggcga cgacggcgcg   2520

ccgcagtgcc tggcgctcat gttcgtcaac tggaccttca tctga                   2565
```

<210> SEQ ID NO 110
<211> LENGTH: 854
<212> TYPE: PRT
<213> ORGANISM: Zea mays

<400> SEQUENCE: 110

```
Met Ala Ser Ser Arg Gly Arg Leu Arg Leu Ser Pro Arg Ala Ala Ala
1               5                   10                  15

Pro Gln Leu Asp Ala Gly Lys Tyr Val Arg Tyr Thr Ala Glu Gln Val
            20                  25                  30

Asp Ala Leu Glu Leu Ala Tyr Gly Glu Cys Pro Lys Pro Ser Ser Leu
        35                  40                  45

Arg Arg Gln Gln Leu Ile Arg Asp Cys Ala Val Leu Thr Asn Val Glu
    50                  55                  60

Pro Arg Gln Ile Lys Val Trp Phe Gln Asn Arg Arg Cys Arg Glu Lys
65                  70                  75                  80

Gln Arg Arg Glu Ser Ser Arg Leu Gln Thr Val Asn Arg Lys Leu Gly
                85                  90                  95

Ala Met Asn Lys Leu Leu Met Glu Glu Asn Asp Arg Leu Gln Lys Gln
            100                 105                 110

Val Ser Arg Leu Val Phe Asp Asn Gly Tyr Met Lys Asn Arg Leu His
        115                 120                 125

Ser Pro Ser Val Ala Thr Thr Asp Thr Ser Cys Glu Ser Val Val Thr
    130                 135                 140

Ser Gly Gln His Lys Gln Gln Gln Asn Pro Ala Val Leu His Pro Pro
145                 150                 155                 160

Gln Arg Asp Ala Asn Asn Pro Ala Gly Leu Leu Ala Ile Ala Glu Glu
                165                 170                 175

Thr Leu Ala Glu Phe Met Ser Lys Ala Thr Gly Thr Ala Val Asn Trp
            180                 185                 190

Val Gln Met Val Gly Met Lys Pro Gly Pro Asp Ser Val Gly Ile Ile
        195                 200                 205

Ala Val Ser His Asn Cys Ser Gly Val Ala Ala Arg Ala Cys Gly Leu
    210                 215                 220

Val Ser Leu Glu Pro Thr Lys Val Ala Glu Ile Leu Lys Asp Arg Ala
225                 230                 235                 240

Ser Trp Tyr Arg Asp Cys Arg Arg Val Asp Ile Leu His Val Ile Pro
                245                 250                 255

Thr Gly Asn Gly Gly Thr Ile Glu Leu Ile Tyr Met Gln Thr Tyr Ala
            260                 265                 270

Leu Thr Thr Leu Ala Glu Pro Arg Asp Phe Trp Thr Leu Arg Tyr Thr
        275                 280                 285

Ser Gly Leu Asp Asp Gly Ser Leu Val Ile Cys Glu Arg Ser Leu Thr
    290                 295                 300

His Ser Thr Gly Gly Pro Ser Gly Pro Lys Thr Pro Asp Phe Ile Arg
305                 310                 315                 320

Ala Glu Val Leu Pro Ser Gly Tyr Leu Ile Arg Pro Cys Asp Gly Gly
                325                 330                 335
```

```
Gly Ser Met Ile Tyr Ile Val Asp His Val Asp Leu Asn Ala Cys Ser
            340                 345                 350

Val Pro Glu Val Leu Arg Pro Leu Tyr Glu Ser Pro Lys Ile Leu Ala
        355                 360                 365

Gln Lys Met Thr Ala Ala Ala Leu Arg His Ile Arg Gln Ile Ala His
    370                 375                 380

Glu Ser Ser Gly Glu Thr Pro Tyr Gly Ala Gly Arg Gln Pro Ala Val
385                 390                 395                 400

Leu Arg Thr Phe Ser Gln Arg Leu Ser Arg Gly Phe Asn Asp Ala Val
                405                 410                 415

Ser Gly Phe Pro Asp Asp Gly Trp Ser Ser Leu Leu Ser Ser Asp Gly
            420                 425                 430

Ala Glu Asp Ile Ser Ile Thr Ile Asn Ser Ser Pro Asn Lys Leu Ile
        435                 440                 445

Gly Ser Asp Val Ser Pro Ser Pro Phe Phe Ser Ala Met Gly Gly Gly
    450                 455                 460

Ile Met Cys Ala Lys Ala Ser Met Leu Leu Gln Asn Val Pro Pro Ala
465                 470                 475                 480

Leu Leu Val Arg Phe Leu Arg Glu His Arg Ser Glu Trp Ala Asp Pro
                485                 490                 495

Gly Val Asp Ala Tyr Ser Ala Ala Ser Leu Arg Ala Asn Pro Tyr Asn
            500                 505                 510

Val Pro Gly Leu Arg Ala Gly Gly Phe Met Gly Asn Gln Val Ile Leu
        515                 520                 525

Pro Leu Ala Arg Thr Val Glu His Glu Glu Cys Leu Glu Val Ile Arg
    530                 535                 540

Leu Gln Gly His Gly Phe Ser His Asp Glu Val Leu Met Ser Pro Asp
545                 550                 555                 560

Met Phe Leu Leu Gln Leu Cys Ser Gly Ile Asp Glu Asp Ala Pro Gly
                565                 570                 575

Ala Cys Ala Gln Leu Val Phe Ala Pro Ile Asp Glu Ser Phe Ala Asp
            580                 585                 590

Asp Ala Pro Leu Leu Pro Ser Gly Phe Arg Val Ile Pro Leu Asp Ala
        595                 600                 605

Lys Thr Asp Val Pro Ser Ala Thr Arg Thr Leu Asp Leu Ala Ser Ala
    610                 615                 620

Leu Glu Val Gly Ser Gly Gly Gly Leu Cys Ala Leu Ser Asp Ser Gly
625                 630                 635                 640

Ser Gly Thr Arg Ser Thr Arg Ser Val Leu Thr Ile Ala Phe Gln Phe
                645                 650                 655

Ser Phe Glu Asn His Leu Arg Glu Ser Val Ala Ala Met Ala Arg Gln
            660                 665                 670

Tyr Val Arg Ala Val Met Ala Ile Val Gln Arg Val Ala Met Ala Ile
        675                 680                 685

Ser Pro Ser Arg Leu Gly Pro His Val Glu Leu Lys His Pro Pro Gly
    690                 695                 700

Ser Pro Glu Ala Leu Ala Leu Ala Ser Trp Ile Gly Arg Ser Tyr Arg
705                 710                 715                 720

Ala His Thr Gly Thr Glu Ile Arg Trp Ser Asp Thr Glu Asp Ala Ala
                725                 730                 735

Gly Ser Pro Leu Thr Leu Phe Trp Lys His Ser Asp Ala Ile Ile Cys
            740                 745                 750
```

```
Cys Ser Leu Lys Pro Ala Phe Thr Leu Lys Phe Ala Asn Ser Ala Gly
        755                 760                 765

Phe Asp Ile Leu Glu Thr Thr Val Ala Asn Val Gln Asp Leu Gln Leu
    770                 775                 780

Glu Ala Val Leu Asp Asp Gly Gly Gln Lys Ala Leu Val Ala Gln Leu
785                 790                 795                 800

Pro Lys Ile Met Leu Gln Gly Leu Ala Tyr Leu Pro Gly Gly Val Cys
                805                 810                 815

Arg Ser Ser Met Gly Arg Gln Ala Ser Tyr Glu Gln Ala Val Ala Trp
            820                 825                 830

Lys Val Val Gly Asp Asp Gly Ala Pro Gln Cys Leu Ala Leu Met Phe
        835                 840                 845

Val Asn Trp Thr Phe Ile
    850


<210> SEQ ID NO 111
<211> LENGTH: 681
<212> TYPE: DNA
<213> ORGANISM: Oryza sativa

<400> SEQUENCE: 111

atggggagag ggaagattgc catcaagagg atcgacaaca cgatgaaccg gcaggtgacc      60

ttctcgaagc ggcgcggcgg gctgatgaag aaggcccggg agctggccat cctctgcgac     120

gccgacgtcg gcctcattgt cttctcctgc accggccgcc tctacgactt ctccagctca     180

agcatgaaat caataataga gcggtaccag gaggcaggag aggagcattg tcggttgctg     240

aacccaatgt cagaggctaa gttttggcag cgggaggtta caactttgag gcagcaagtg     300

caaaacttac accacaacaa caggcaactt ttgggagagg aaatctccaa cttcacagtt     360

agagatctgc agcttctcca gaaccaagtt gagatgagcc tacattccat aagaaataaa     420

aaggatcaac ttttggcaga ggagattcta aaactcaatg aaaaggggtc tcttgttcaa     480

aaggagaaca gtgaacttcg caagaagttc aacattgctc atcaacgcaa catagaatta     540

cacaagaagc ttaactctgg agaaagcacg tcaagtgagc aagttaccag aagctcaaag     600

gatcccggag aatcgagtac accccgtgat tcacgtgtgt gtattgacct tgaattgagt     660

caaaaagaag ttgaagatga a                                               681


<210> SEQ ID NO 112
<211> LENGTH: 228
<212> TYPE: PRT
<213> ORGANISM: Oryza sativa
<220> FEATURE:
<221> NAME/KEY: misc_feature
<222> LOCATION: (228)..(228)
<223> OTHER INFORMATION: Xaa can be any naturally occurring amino acid

<400> SEQUENCE: 112

Met Gly Arg Gly Lys Ile Ala Ile Lys Arg Ile Asp Asn Thr Met Asn
1               5                   10                  15

Arg Gln Val Thr Phe Ser Lys Arg Arg Gly Gly Leu Met Lys Lys Ala
            20                  25                  30

Arg Glu Leu Ala Ile Leu Cys Asp Ala Asp Val Gly Leu Ile Val Phe
        35                  40                  45

Ser Cys Thr Gly Arg Leu Tyr Asp Phe Ser Ser Ser Ser Met Lys Ser
    50                  55                  60

Ile Ile Glu Arg Tyr Gln Glu Ala Gly Glu Glu His Cys Arg Leu Leu
65                  70                  75                  80
```

```
Asn Pro Met Ser Glu Ala Lys Phe Trp Gln Arg Glu Val Thr Thr Leu
                85                  90                  95

Arg Gln Gln Val Gln Asn Leu His His Asn Asn Arg Gln Leu Leu Gly
            100                 105                 110

Glu Glu Ile Ser Asn Phe Thr Val Arg Asp Leu Gln Leu Leu Gln Asn
        115                 120                 125

Gln Val Glu Met Ser Leu His Ser Ile Arg Asn Lys Lys Asp Gln Leu
    130                 135                 140

Leu Ala Glu Glu Ile Leu Lys Leu Asn Glu Lys Gly Ser Leu Val Gln
145                 150                 155                 160

Lys Glu Asn Ser Glu Leu Arg Lys Lys Phe Asn Ile Ala His Gln Arg
                165                 170                 175

Asn Ile Glu Leu His Lys Lys Leu Asn Ser Gly Glu Ser Thr Ser Ser
            180                 185                 190

Glu Gln Val Thr Arg Ser Ser Lys Asp Pro Gly Glu Ser Ser Thr Pro
        195                 200                 205

Arg Asp Ser Arg Val Cys Ile Asp Leu Glu Leu Ser Gln Lys Glu Val
    210                 215                 220

Glu Asp Glu Xaa
225


<210> SEQ ID NO 113
<211> LENGTH: 2013
<212> TYPE: DNA
<213> ORGANISM: Glycine max

<400> SEQUENCE: 113

gtggctagcc agcaagggag aattgaagct attggaatag agagctcaaa aggggtaacc      60

atatggcagc gtttggtatt caaatcatgc tattgctggc agctttcttg cttccactat     120

ctgtggaagc tatggttcgc cactacaagt tcaatgtggt gcaaaagaat accacaagat     180

tgggttcaac caagcccatt gttaccataa atggaaagtt cccaggtccc accatctatg     240

caagggaaga tgacactgtt ctggttaagg tagtcaacca ggtcaagtac aatgtcagca     300

tccattggca tggggtgaga caattgagaa caggttgggc tgatgggcca gcatacataa     360

cccagtgtcc aattctaccg agccaggcct atgtctacaa ctttactctt acaggccaga     420

gaggcacact ttggtggcat gcacatatcc tctggcttag ggccactgtc catggtgcct     480

tggtcatctt gcccaagctt ggagttcctt accctttccc caaaccaaat atggaacaag     540

ttatcatatt gagtgaatgg tggaaatcag atactgaggc tgtaataaat gaagctttga     600

aatctggttt ggctccaaat gcctctgatg ctcacacaat caacggccat ccaggaccta     660

tccaaggcta tgcttcacaa ggaggatata agttggatgt tcaaccagga aagacctact     720

tgctaagaat catcaatgct gcactcaatg aagagctctt ctttaaaatt gctgggcatg     780

aactcactgt tgttgaggtt gatgcagttt acacaaaacc tttgaaaact gataccattg     840

tcatagcacc tggccaaacc acaaatgtgc ttctaacaac caaacatgca actggcaaat     900

acttggttgc agcctctcct ttcatggatg ctcctattgc agttgacaac aagactgcca     960

ctgccacttt acactatcta ggcacccttg gttccaccat caccaccctc acttccatgc    1020

ctcctaaaaa tgcaacacca gttgccacca ctttcatcga ctctctccga agcttaaact    1080

ccaaagagca tcctgctaga gtccctttaa agattgatca taacttgctc ttcacagtta    1140

gccttggtgt caacccttgt gctacttgtg tgaataatag cagggtggta gcagatatca    1200
```

```
acaatgttac ctttgtgatg cctaaaattt ctcttcttca agcacatttc ttcaagatca   1260

agggagtttt caccgacgat ttccccggaa atcctcctgt ggtgtataac ttcacaggga   1320

cacaaccatc aaatttgaag accatgaaag gcacaagggt ctatagactt gcttacaatt   1380

ccacagttca attggtcttg caagatactg gaatgataac acctgagaac catcctattc   1440

atctccatgg cttcaacttt tttgtggttg gtaggggaca agggaatttc aaccccacaa   1500

aagaccccaa gaaatttaac cttgtagatc ctgtggagag aaatacagtt ggagtcccgg   1560

ctggggggtg gactgctatt agattcaggg ctgacaatcc aggtgtctgg tttatgcatt   1620

gccacttgga aattcataca acatggggac tgaagatggc ttttgttgtg gacaacggta   1680

aaggaccaaa tgaatcttta ttaccacctc caactgacct acccaagtgt tgagaaaatt   1740

actaagtata tgcacaatga ggaaggagaa acatataaag agaagtatat atgccaaagg   1800

gaggagaaat caaggctttc atagagtaaa gaaaggagaa gatgctcaga gtggaataag   1860

atcagatgac cagttgccat gtatttttct aatttccttt ttcatcattc ttttgtatat   1920

tgtttgtact ctcatcattc tccttcttga atgatatttt tggcattaat tatgcatata   1980

aatgtcaatc aaaattttaa ggatttttaa gcc                                2013
```

<210> SEQ ID NO 114
<211> LENGTH: 556
<212> TYPE: PRT
<213> ORGANISM: Glycine max

<400> SEQUENCE: 114

```
Met Ala Ala Phe Gly Ile Gln Ile Met Leu Leu Leu Ala Ala Phe Leu
1               5                   10                  15

Leu Pro Leu Ser Val Glu Ala Met Val Arg His Tyr Lys Phe Asn Val
            20                  25                  30

Val Gln Lys Asn Thr Thr Arg Leu Gly Ser Thr Lys Pro Ile Val Thr
        35                  40                  45

Ile Asn Gly Lys Phe Pro Gly Pro Thr Ile Tyr Ala Arg Glu Asp Asp
    50                  55                  60

Thr Val Leu Val Lys Val Val Asn Gln Val Lys Tyr Asn Val Ser Ile
65                  70                  75                  80

His Trp His Gly Val Arg Gln Leu Arg Thr Gly Trp Ala Asp Gly Pro
                85                  90                  95

Ala Tyr Ile Thr Gln Cys Pro Ile Leu Pro Ser Gln Ala Tyr Val Tyr
            100                 105                 110

Asn Phe Thr Leu Thr Gly Gln Arg Gly Thr Leu Trp Trp His Ala His
        115                 120                 125

Ile Leu Trp Leu Arg Ala Thr Val His Gly Ala Leu Val Ile Leu Pro
    130                 135                 140

Lys Leu Gly Val Pro Tyr Pro Phe Pro Lys Pro Asn Met Glu Gln Val
145                 150                 155                 160

Ile Ile Leu Ser Glu Trp Trp Lys Ser Asp Thr Glu Ala Val Ile Asn
                165                 170                 175

Glu Ala Leu Lys Ser Gly Leu Ala Pro Asn Ala Ser Asp Ala His Thr
            180                 185                 190

Ile Asn Gly His Pro Gly Pro Ile Gln Gly Tyr Ala Ser Gln Gly Gly
        195                 200                 205

Tyr Lys Leu Asp Val Gln Pro Gly Lys Thr Tyr Leu Leu Arg Ile Ile
    210                 215                 220

Asn Ala Ala Leu Asn Glu Glu Leu Phe Phe Lys Ile Ala Gly His Glu
```

```
225                 230                 235                 240

Leu Thr Val Val Glu Val Asp Ala Val Tyr Thr Lys Pro Leu Lys Thr
                245                 250                 255

Asp Thr Ile Val Ile Ala Pro Gly Gln Thr Thr Asn Val Leu Leu Thr
            260                 265                 270

Thr Lys His Ala Thr Gly Lys Tyr Leu Val Ala Ala Ser Pro Phe Met
        275                 280                 285

Asp Ala Pro Ile Ala Val Asp Asn Lys Thr Ala Thr Ala Thr Leu His
    290                 295                 300

Tyr Leu Gly Thr Leu Gly Ser Thr Ile Thr Thr Leu Thr Ser Met Pro
305                 310                 315                 320

Pro Lys Asn Ala Thr Pro Val Ala Thr Thr Phe Ile Asp Ser Leu Arg
                325                 330                 335

Ser Leu Asn Ser Lys Glu His Pro Ala Arg Val Pro Leu Lys Ile Asp
            340                 345                 350

His Asn Leu Leu Phe Thr Val Ser Leu Gly Val Asn Pro Cys Ala Thr
        355                 360                 365

Cys Val Asn Asn Ser Arg Val Val Ala Asp Ile Asn Asn Val Thr Phe
    370                 375                 380

Val Met Pro Lys Ile Ser Leu Leu Gln Ala His Phe Phe Lys Ile Lys
385                 390                 395                 400

Gly Val Phe Thr Asp Asp Phe Pro Gly Asn Pro Pro Val Val Tyr Asn
                405                 410                 415

Phe Thr Gly Thr Gln Pro Ser Asn Leu Lys Thr Met Lys Gly Thr Arg
            420                 425                 430

Val Tyr Arg Leu Ala Tyr Asn Ser Thr Val Gln Leu Val Leu Gln Asp
        435                 440                 445

Thr Gly Met Ile Thr Pro Glu Asn His Pro Ile His Leu His Gly Phe
    450                 455                 460

Asn Phe Phe Val Val Gly Arg Gly Gln Gly Asn Phe Asn Pro Thr Lys
465                 470                 475                 480

Asp Pro Lys Lys Phe Asn Leu Val Asp Pro Val Glu Arg Asn Thr Val
                485                 490                 495

Gly Val Pro Ala Gly Gly Trp Thr Ala Ile Arg Phe Arg Ala Asp Asn
            500                 505                 510

Pro Gly Val Trp Phe Met His Cys His Leu Glu Ile His Thr Thr Trp
        515                 520                 525

Gly Leu Lys Met Ala Phe Val Val Asp Asn Gly Lys Gly Pro Asn Glu
    530                 535                 540

Ser Leu Leu Pro Pro Pro Thr Asp Leu Pro Lys Cys
545                 550                 555
```

<210> SEQ ID NO 115
<211> LENGTH: 3483
<212> TYPE: DNA
<213> ORGANISM: Zea mays

<400> SEQUENCE: 115

```
atggcgtcgg gcagccgcgc cacgcccacg cgctccccct cctccgcgcg gcccgaggcg      60

ccgcgtcacg cgcaccacca ccaccactcc cagtcgtcgg gcgggagcac gtcccgcgcg     120

ggcgggggag ccgcggccac ggagtcggtc tccaaggccg tcgcccagta caccctagac     180

gcgcgcctac acgcggtgtt cgagcaatcg ggcgcgtcgg gccgcagctt cgactactcc     240

caatcgctgc gcgcgccgcc cacgccgtcc tccgagcagc agatcgccgc ctacctctcc     300
```

```
cgcatccagc gcggcggcca catccagccc ttcggctgca cgctcgctgt tgccgacgac    360
tcctccttcc gcctcctcgc cttctccgag aactccccg acctgctcga cctgtcgcct    420
caccactccg ttccctcgct ggactcctct gcgccgcccc acgtttccct gggtgccgac    480
gcgcgcctcc tcttctcccc ctcgtccgcg gtcctcctag agcgcgcctt cgccgcgcgc    540
gagatctcgc tgctcaaccc gatatggatc cactccaggg tctcctccaa gccgttctac    600
gccatcctcc accgcatcga cgtcggcgtc gtcatcgacc tcgagcccgc ccgcaccgag    660
gaccccgctc tctccatcgc cggtgcagtc cagtcccaga aactggcggt ccgcaccatc    720
tcccgcctcc aggcgctacc cggcggggac gtcaagcttc tctgcgacac agtcgtggag    780
catgttcgcg agctcacggg ttatgaccgt gtcatggtgt acaggttcca tgaagacgag    840
cacggggaag ttgtcgccga gagccggcgc gacaaccttg agccttacct cggattgcat    900
tatcccgcca cagatatccc ccaggcgtcg cgcttcctgt tccggcagaa ccgcgtgcga    960
atgattgccg attgccatgc caccccggtg agagttattc aagatcctgg gctgtcgcag   1020
cctctgtgtt tggtaggctc cacgctacgc gctccacacg ggtgtcatgc acagtacatg   1080
gcgaacatgg ggtcaattgc gtcgcttgtt atggcagtca tcattagcag tggcggtgac   1140
gatgagcaaa caggtcgggg tggcatctcc tcggcaatga agttgtgggg gttagtggtg   1200
tgccaccata catcaccacg gtgtatccct tttccattga ggtatgcttg cgagtttctc   1260
atgcaggtat ttgggttgca gctcaacatg gagttgcagc ttgcgcacca gctgtcagag   1320
aagcacattc tgcgaactca gacgctattg tgtgacatgc tactacgaga ttcaccaact   1380
ggcatcgtca cgcagagccc cagcatcatg gaccttgtga agtgcgacgg ggctgcactg   1440
tattatcatg ggaaatacta tccattgggt gtcactccca ctgagtctca gattaaggat   1500
atcatcgagt ggttgacggt gtttcatggg gactcaacag ggctcagcac agatagcctg   1560
gctgatgcag gctaccttgg tgctgctgca ctaggggagg ctgtgtgtgg aatggcggtg   1620
gcttatatta caccgagtga ttacttgttt tggtttcggt cacacacagc taaagagatc   1680
aaatggggtg gcgcaaagca tcaccctgag gataaggatg atggtcagag gatgcaccca   1740
cggtcgtcat tcaaggcatt tcttgaagtg gttaaaagca gaagcctacc atgggagaat   1800
gcagaaatgg acgcaataca ttccttgcag ctcatattgc gtgactcctt cagggatgct   1860
gcagagggca ccaacaactc aaaagccatt gtcaatggac aagttcagct tcgggagcta   1920
gaattgcggg ggataaatga gcttagttcc gtagcaagag agatggttcg gttgatagag   1980
acagcaacag tacccatatt tgcagtagat actgatgggt gtataaatgg ttggaatgca   2040
aagattgctg agttgacagg gctttcagtt gaggaggcaa tgggcaaatc tctggtaaat   2100
gatcttatct tcaaggaatc tgaggcgaca gttgaaaaac tactctcacg agctttaaga   2160
ggtgaagaca aaaatgtgga gataaagctg aagacatttg ggtcagagca atctaaggga   2220
ccaatatttg ttgttgtcaa tgcttgttct agtagagatt acacacaaaa tattgttggt   2280
gtctgttttg ttggacaaga tgtcacagga caaaaggtgg tcatggataa atttgttaac   2340
atacaagggg actacaaagc tattgtacac aatcctaatc ctctgatacc accaattttt   2400
gcatcagatg agaacacttc ttgttcagaa tggaatacag ccatggaaaa acttacagga   2460
tggtcgagag gtgaagttgt tggtaagttt cttattggag aggtgtttgg aaattgttgt   2520
cgactcaagg gcccagatgc attgacaaaa ttcatggtta ttattcacaa cgctatagga   2580
gggcaggatt atgagaagtt ccctttttca ttttttgaca agaatggaaa gtatgtgcag   2640
```

```
gccttattga ccgccaatac aaggagcaaa atggatggta aatccattgg agccttttgt   2700

ttcctgcaga ttgcaagcgc tgaaatacag caagccattg agattcagag acaacaagaa   2760

aagaagtgtt acgcaaggat gaaagaattg gcctatattt gccaggagat aaagaatcct   2820

cttagtggca tccgatttac caactctctg ttgcagatga ctgatttaaa tgatgaccag   2880

aggcagttcc ttgaaactag ctctgcttgt gagaaacaga tgtccaagat tgttaaggac   2940

gccagtctcc aaagtatcga ggacggctct ttggtgcttg agcaaagtga gttttctctt   3000

ggagacgtta tgaatgctgt tgtcagccaa gcaatgttat tgttgagaga gagggattta   3060

caacttattc gggacatccc tgatgaaatc aaggatgcgt cagcgtatgg tgatcaatgt   3120

agaattcaac aagttttggc tgacttcttg ctaagcatgg tgcggtctgc tccatccgag   3180

aatggttggg tagaaataca agtcagacca aatgtaaaac agaattctga tggaacaaat   3240

acagaacttt tcatattcag gtttgcctgc cctggtgagg gcctccctgc tgacgtcgtc   3300

caggatatgt tcagcaattc ccaatggtca acacaagaag gcgtaggact aagcacatgc   3360

aggaagatcc tcaaattgat gggtggcgag gtccaataca tcagagagtc agagcggagt   3420

ttcttcctca tcgtcctcga gcagccccaa cctcgtccag cagctggtag agaaatcgtc   3480

tag                                                                 3483
```

<210> SEQ ID NO 116
<211> LENGTH: 1160
<212> TYPE: PRT
<213> ORGANISM: Zea mays

<400> SEQUENCE: 116

```
Met Ala Ser Gly Ser Arg Ala Thr Pro Thr Arg Ser Pro Ser Ser Ala
1               5                   10                  15

Arg Pro Glu Ala Pro Arg His Ala His His His His His Ser Gln Ser
            20                  25                  30

Ser Gly Gly Ser Thr Ser Arg Ala Gly Gly Gly Ala Ala Ala Thr Glu
        35                  40                  45

Ser Val Ser Lys Ala Val Ala Gln Tyr Thr Leu Asp Ala Arg Leu His
    50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Ser Glu Gln Gln Ile Ala
                85                  90                  95

Ala Tyr Leu Ser Arg Ile Gln Arg Gly Gly His Ile Gln Pro Phe Gly
            100                 105                 110

Cys Thr Leu Ala Val Ala Asp Asp Ser Ser Phe Arg Leu Leu Ala Phe
        115                 120                 125

Ser Glu Asn Ser Pro Asp Leu Leu Asp Leu Ser Pro His His Ser Val
    130                 135                 140

Pro Ser Leu Asp Ser Ser Ala Pro Pro His Val Ser Leu Gly Ala Asp
145                 150                 155                 160

Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
            180                 185                 190

Arg Val Ser Ser Lys Pro Phe Tyr Ala Ile Leu His Arg Ile Asp Val
        195                 200                 205

Gly Val Val Ile Asp Leu Glu Pro Ala Arg Thr Glu Asp Pro Ala Leu
    210                 215                 220
```

```
Ser Ile Ala Gly Ala Val Gln Ser Gln Lys Leu Ala Val Arg Thr Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
            260                 265                 270

Val Tyr Arg Phe His Glu Asp Glu His Gly Glu Val Val Ala Glu Ser
        275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
                325                 330                 335

Gly Leu Ser Gln Pro Leu Cys Leu Val Gly Ser Thr Leu Arg Ala Pro
            340                 345                 350

His Gly Cys His Ala Gln Tyr Met Ala Asn Met Gly Ser Ile Ala Ser
        355                 360                 365

Leu Val Met Ala Val Ile Ile Ser Ser Gly Gly Asp Asp Glu Gln Thr
    370                 375                 380

Gly Arg Gly Gly Ile Ser Ser Ala Met Lys Leu Trp Gly Leu Val Val
385                 390                 395                 400

Cys His His Thr Ser Pro Arg Cys Ile Pro Phe Pro Leu Arg Tyr Ala
                405                 410                 415

Cys Glu Phe Leu Met Gln Val Phe Gly Leu Gln Leu Asn Met Glu Leu
            420                 425                 430

Gln Leu Ala His Gln Leu Ser Glu Lys His Ile Leu Arg Thr Gln Thr
        435                 440                 445

Leu Leu Cys Asp Met Leu Leu Arg Asp Ser Pro Thr Gly Ile Val Thr
    450                 455                 460

Gln Ser Pro Ser Ile Met Asp Leu Val Lys Cys Asp Gly Ala Ala Leu
465                 470                 475                 480

Tyr Tyr His Gly Lys Tyr Tyr Pro Leu Gly Val Thr Pro Thr Glu Ser
                485                 490                 495

Gln Ile Lys Asp Ile Ile Glu Trp Leu Thr Val Phe His Gly Asp Ser
            500                 505                 510

Thr Gly Leu Ser Thr Asp Ser Leu Ala Asp Ala Gly Tyr Leu Gly Ala
        515                 520                 525

Ala Ala Leu Gly Glu Ala Val Cys Gly Met Ala Val Ala Tyr Ile Thr
    530                 535                 540

Pro Ser Asp Tyr Leu Phe Trp Phe Arg Ser His Thr Ala Lys Glu Ile
545                 550                 555                 560

Lys Trp Gly Gly Ala Lys His His Pro Glu Asp Lys Asp Asp Gly Gln
                565                 570                 575

Arg Met His Pro Arg Ser Ser Phe Lys Ala Phe Leu Glu Val Val Lys
            580                 585                 590

Ser Arg Ser Leu Pro Trp Glu Asn Ala Glu Met Asp Ala Ile His Ser
        595                 600                 605

Leu Gln Leu Ile Leu Arg Asp Ser Phe Arg Asp Ala Ala Glu Gly Thr
    610                 615                 620

Asn Asn Ser Lys Ala Ile Val Asn Gly Gln Val Gln Leu Arg Glu Leu
625                 630                 635                 640
```

```
Glu Leu Arg Gly Ile Asn Glu Leu Ser Ser Val Ala Arg Glu Met Val
            645                 650                 655

Arg Leu Ile Glu Thr Ala Thr Val Pro Ile Phe Ala Val Asp Thr Asp
            660                 665                 670

Gly Cys Ile Asn Gly Trp Asn Ala Lys Ile Ala Glu Leu Thr Gly Leu
        675                 680                 685

Ser Val Glu Glu Ala Met Gly Lys Ser Leu Val Asn Asp Leu Ile Phe
    690                 695                 700

Lys Glu Ser Glu Ala Thr Val Glu Lys Leu Leu Ser Arg Ala Leu Arg
705                 710                 715                 720

Gly Glu Asp Lys Asn Val Glu Ile Lys Leu Lys Thr Phe Gly Ser Glu
            725                 730                 735

Gln Ser Lys Gly Pro Ile Phe Val Val Val Asn Ala Cys Ser Ser Arg
            740                 745                 750

Asp Tyr Thr Gln Asn Ile Val Gly Val Cys Phe Val Gly Gln Asp Val
        755                 760                 765

Thr Gly Gln Lys Val Val Met Asp Lys Phe Val Asn Ile Gln Gly Asp
    770                 775                 780

Tyr Lys Ala Ile Val His Asn Pro Asn Pro Leu Ile Pro Pro Ile Phe
785                 790                 795                 800

Ala Ser Asp Glu Asn Thr Ser Cys Ser Glu Trp Asn Thr Ala Met Glu
            805                 810                 815

Lys Leu Thr Gly Trp Ser Arg Gly Glu Val Val Gly Lys Phe Leu Ile
            820                 825                 830

Gly Glu Val Phe Gly Asn Cys Cys Arg Leu Lys Gly Pro Asp Ala Leu
        835                 840                 845

Thr Lys Phe Met Val Ile Ile His Asn Ala Ile Gly Gly Gln Asp Tyr
    850                 855                 860

Glu Lys Phe Pro Phe Ser Phe Phe Asp Lys Asn Gly Lys Tyr Val Gln
865                 870                 875                 880

Ala Leu Leu Thr Ala Asn Thr Arg Ser Lys Met Asp Gly Lys Ser Ile
            885                 890                 895

Gly Ala Phe Cys Phe Leu Gln Ile Ala Ser Ala Glu Ile Gln Gln Ala
            900                 905                 910

Ile Glu Ile Gln Arg Gln Gln Glu Lys Lys Cys Tyr Ala Arg Met Lys
        915                 920                 925

Glu Leu Ala Tyr Ile Cys Gln Glu Ile Lys Asn Pro Leu Ser Gly Ile
    930                 935                 940

Arg Phe Thr Asn Ser Leu Leu Gln Met Thr Asp Leu Asn Asp Asp Gln
945                 950                 955                 960

Arg Gln Phe Leu Glu Thr Ser Ser Ala Cys Glu Lys Gln Met Ser Lys
            965                 970                 975

Ile Val Lys Asp Ala Ser Leu Gln Ser Ile Glu Asp Gly Ser Leu Val
            980                 985                 990

Leu Glu Gln Ser Glu Phe Ser Leu  Gly Asp Val Met Asn  Ala Val Val
        995                 1000                 1005

Ser Gln  Ala Met Leu Leu Leu  Arg Glu Arg Asp Leu  Gln Leu Ile
    1010                 1015                 1020

Arg Asp  Ile Pro Asp Glu Ile  Lys Asp Ala Ser Ala  Tyr Gly Asp
    1025                 1030                 1035

Gln Cys  Arg Ile Gln Gln Val  Leu Ala Asp Phe Leu  Leu Ser Met
    1040                 1045                 1050

Val Arg  Ser Ala Pro Ser Glu  Asn Gly Trp Val Glu  Ile Gln Val
```

-continued

```
    1055                1060                1065

Arg Pro  Asn Val Lys Gln Asn  Ser Asp Gly Thr Asn  Thr Glu Leu
    1070                1075                1080

Phe Ile  Phe Arg Phe Ala Cys  Pro Gly Glu Gly Leu  Pro Ala Asp
    1085                1090                1095

Val Val  Gln Asp Met Phe Ser  Asn Ser Gln Trp Ser  Thr Gln Glu
    1100                1105                1110

Gly Val  Gly Leu Ser Thr Cys  Arg Lys Ile Leu Lys  Leu Met Gly
    1115                1120                1125

Gly Glu  Val Gln Tyr Ile Arg  Glu Ser Glu Arg Ser  Phe Phe Leu
    1130                1135                1140

Ile Val  Leu Glu Gln Pro Gln  Pro Arg Pro Ala Ala  Gly Arg Glu
    1145                1150                1155

Ile Val
    1160
```

TRANSGENIC PLANTS WITH ENHANCED TRAITS

CROSS REFERENCE TO RELATED APPLICATIONS

This application is a Continuation of U.S. Patent Application No. 15/027,777 filed on Apr. 7, 2016, which claims benefit to U.S. National Stage filing under 35 U.S.C. § 371 of International Application No. PCT/US2014/059253 filed on Oct. 2014, which claims benefit and priority to U.S. Provisional Application No. 61/932,899 filed on 29 Jan. 2014 and U.S. Provisional Application No. 61/887,545 filed on 7 Oct. 2013, which are incorporated herein by reference.

INCORPORATION OF SEQUENCE LISTING

The sequence list file name "P34445US03_SL.txt", which is 372,483 bytes (measured in MS-WINDOWS) and was created on Aug. 13, 2019, is filed herewith and incorporated herein by reference in its entirety.

FIELD OF The INVENTION

Disclosed herein are plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

In one aspect, the disclosure provides a plant comprising a recombinant DNA molecule comprising a polynucleotide encoding a polypeptide, wherein the nucleotide sequence of the polynucleotide is selected from the group consisting of: a) a nucleotide sequence as set forth in SEQ ID NO: 1, 3, 5, 7, 9, 11, 13, 15, 17, 19, 21 ,23, 25, 27, 29, 31, 33, 35, 37, 39, 41, 43, 45, 47, 49, 51, 53, 55, 57 or 115; b) a nucleotide sequence encoding a protein, said protein having an amino acid sequence as set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 59-92 or 116; c) a nucleotide sequence with at least 90%, at least 91%, at least 92%, at least 93%, at least 94%, at least 95%, at least 96%, at least 97%, at least 98% or at least 99% identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 115; and d) a nucleotide sequence encoding a protein with at least 90%, at least 91%, at least 92%, at least 93%, at least 94%, at least 95%, at least 96%, at least 97%, at least 98% or at least 99% identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 59-92 or 116; wherein the plant has an enhanced trait as compared to a control plant.

In another aspect, the disclosure provides a plant comprising a recombinant DNA molecule of the disclosure, wherein the enhanced trait is selected from the group consisting of increased yield, increased nitrogen use efficiency, and increased water use efficiency.

In another aspect, the disclosure provides a plant comprising a recombinant DNA molecule of the disclosure, wherein the plant has at least one phenotype selected from the group consisting of anthocyanin, biomass, canopy area, chlorophyll score, plant height, water applied, water content and water use efficiency that is altered for said plant as compared to a control plant.

In another aspect, the disclosure provides a plant comprising a recombinant DNA molecule of the disclosure, wherein the promoter is selected from the group consisting of a constitutive, inducible, tissue specific, diurnally regulated, tissue enhanced, and cell specific promoter.

In another aspect, the disclosure provides a plant comprising a recombinant DNA molecule of the disclosure, wherein the plant is a progeny, a propagule, or a field crop.

In another aspect, the disclosure provides a plant comprising a recombinant DNA molecule of the disclosure, wherein the field crop is selected from the group consisting of corn, soybean, cotton, canola, rice, barley, oat, wheat, turf grass, alfalfa, sugar beet, sunflower, quinoa and sugar cane.

In another aspect, the disclosure provides a plant comprising a recombinant DNA molecule of the disclosure, wherein the propagule is selected from the group consisting of a cell, pollen, ovule, flower, embryo, leaf, root, stem, shoot, meristem, grain and seed.

In another aspect, the disclosure provides a plant comprising a recombinant DNA molecule of the disclosure, wherein the plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, bromegrass plant, *Miscanthus* plant, pampas grass plant, switchgrass (*Panicum*) plant, and/or teosinte plant, or is a member of the family Alliaceae, onion plant, leek plant, garlic plant; or wherein the plant is a dicot plant or is a member of the family Amaranthaceae, spinach plant, quinoa plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, papaya plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, eucalyptus plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, or spruce plant.

In another aspect, the disclosure provides a method for producing a plant comprising: introducing into a plant cell a recombinant DNA molecule comprising a polynucleotide encoding a polypeptide and growing a plant from the plant cell. In this aspect, the polynucleotide comprises a polynucleotide sequence selected from the group consisting of: a) a nucleotide sequence as set forth as SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 115; b) a nucleotide sequence encoding a protein comprising an amino acid sequence as set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 59-92 or 116; c) a nucleotide sequence with at least 90%, at least 91%, at least 92%, at least 93%, at least 94%, at least 95%, at least 96%, at least 97%, at least 98% or at least 99% identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 115; and d) a nucleotide sequence encoding a protein with at least 90%, at least 91%, at least 92%, at least 93%, at least 94%, at least 95%, at least 96%, at least 97%, at least 98% or at least 99% identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 59-92 or 116. In another aspect, the method further comprises the step of selecting a plant with an enhanced trait as compared to a control plant, wherein the enhanced trait is selected from increased yield, increased nitrogen use efficiency, and increased water use efficiency as compared to a control plant.

In another aspect, the disclosure provides a method for producing a plant comprising: introducing into a plant cell a recombinant DNA molecule of the present disclosure, growing a plant from the plant cell and selecting a plant with a phenotype selected from the group consisting of anthocyanin, biomass, canopy area, chlorophyll score, plant height, water applied, water content and water use efficiency, wherein the phenotype for the plant is altered as compared to a control plant.

In another aspect, the disclosure provides a method for increasing yield, increasing nitrogen use efficiency, or increasing water use efficiency in a plant comprising: crossing a plant comprising a recombinant DNA molecule of the present invention with itself, a second plant from the same plant line, a wild type plant, or a second plant from a different line of plants to produce a seed; growing the seed to produce a plurality of progeny plants; and selecting a progeny plant with increased yield, increased nitrogen use efficiency, or increased water use efficiency.

In another aspect, the disclosure provides a recombinant DNA molecule comprising a heterologous promoter operably linked lo a polynucleotide that is transcribed into a non-coding miRNA molecule. In this aspect, the non-coding miRNA molecule is selected from the group consisting of a) a non-coding miRNA molecule which, when present in a plant, provides an altered level of a protein as compared to a control plant, wherein said protein is selected from the group consisting of: a phosphate transporter protein, an APETALA2-like transcription factor, an ANR1 MADS-box protein, an E3 ligase SCF complex F-box protein, a HOS1 protein, a bHLH transcription factor, a diphenol oxidase protein, and the polypeptides set forth in SEQ ID NO: 108, 110, 112 and 114; b) a non-coding miRNA molecule which, when present in a plant, interferes with the functioning of one or more species of an endogenous miRNA selected from the group consisting of: miR399, miR172, miR166, miR166, miR444, miR393 and miR397; c) a non-coding miRNA molecule comprising a miRNA binding site sequence as set forth in SEQ ID NOs: 100-106; and d) a non-coding miRNA molecule comprising a miRNA polynucleotide sequence as set forth in SEQ ID NOs: 93-99. Also in this aspect, the promoter is selected from the group consisting of a constitutive promoter, a developmental promoter, a tissue enhanced promoter, a tissue preferred promoter, a tissue specific promoter, a cell type-specific promoter, an inducible promoter and a diurnal promoter. In a further aspect, when the recombinant DNA molecule is present in a plant, the plant exhibits an altered phenotype or an enhanced trait as compared to a control plant.

In another aspect, the disclosure provides a plant comprising a recombinant DNA molecule comprising a heterologous promoter functional in plant cells operably linked to a polynucleotide that is transcribed into a non-coding miRNA molecule. In this aspect, the non-coding miRNA molecule is selected from the group consisting of: a) a non-coding miRNA molecule wherein, when present in a plant, the plant exhibits an altered level of a target protein, wherein the target protein is selected from the group consisting of: a phosphate transporter protein, an APETALA2-like transcription factor, an ANR1 MADS-box protein, an E3 ligase SCF complex F-box protein, a HOS1 protein, a bHLH transcription factor, a diphenol oxidase proteinligase, and the polypeptides set forth in SEQ ID NO: 108, 110, 112 and 114; b) a non-coding miRNA molecule which, when present in a plant, interferes with the functioning of one or more species of an endogenous miRNA selected from the group consisting of: miR399, miR172, miR166, miR166, miR444, miR393 and miR397; c) a non-coding miRNA molecule comprising a miRNA binding site sequence as set forth in SEQ ID NOs: 100-106; and d) a non-coding miRNA molecule comprising a miRNA polynucleotide sequence as set forth in SEQ ID NOs: 93-99. Also in this aspect, the heterologous promoter is selected from the group consisting of a constitutive promoter, a developmental promoter, a tissue enhanced promoter, a tissue preferred promoter, a tissue specific promoter, a cell type-specific promoter, an inducible promoter and a diurnal promoter. Also in this aspect, the plant has an enhanced trait as compared to a control plant.

In another aspect, the disclosure provides a method for producing a plant comprising: introducing into a plant cell a recombinant DNA molecule comprising a heterologous promoter functional in plant cells and operably linked to a polynucleotide that is transcribed into a non-coding miRNA molecule as provided by the disclosure, and growing a plant from the plant cell, wherein the plants exhibit an altered level of a target protein selected from the group consisting of: a phosphate transporter protein, an APETALA2-like transcription factor, an ANR1 MADS-box protein, an E3 ligase SCF complex F-box protein, a HOS1 protein, a bHLH transcription factor, a diphenol oxidase proteinligase, and the polypeptides set forth in SEQ ID NO: 108, 110, 112 and 114.

In another aspect, the disclosure provides a method for producing a plant comprising: introducing into a plant cell a recombinant DNA molecule comprising a heterologous promoter functional in plant cells operably linked to a polynucleotide that is transcribed into a non-coding miRNA molecule as provided in the disclosure, and growing a plant from the plant cell, wherein the non-coding miRNA molecule interferes with the functioning of one or more endogenous miRNA molecules selected from the group consisting of: miR399, miR172, miR166, miR166, miR444, miR393 and miR397.

In another aspect, the disclosure provides a method for producing a plant comprising: introducing into a plant cell a recombinant DNA molecule comprising a heterologous promoter functional in plant cells operably linked to a polynucleotide that is transcribed into a non-coding miRNA molecule, and growing a plant from the plant cell, wherein the non-coding miRNA molecule comprises a miRNA binding site poly nucleotide sequence as set forth in SEQ ID NOs: 100-106.

In another aspect, the disclosure provides a method for producing a plant comprising: introducing into a plant cell a recombinant DNA molecule comprising a heterologous promoter functional in plant cells operably linked to a polynucleotide that is transcribed into a non-coding miRNA molecule, and growing a plant from the plant cell, wherein the non-coding miRNA molecule comprises a non-coding miRNA polynucleotide sequence as set forth in SEQ ID NOs: 93-99.

DETAILED DESCRIPTION OF THE INVENTION

In the attached sequence listing:

SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57 and 115 are nucleotide sequences of the coding strand of the DNA constructs used in the recombinant DNA imparting an enhanced trait in plants, each representing a coding sequence for a protein.

SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58 and 116 are amino acid sequences of the cognate proteins of the DNA molecules with nucleotide sequences 1, 3, 5, 7, 9, 11, 13, 15, 17, 19, 21, 23, 25, 27,29, 31, 33, 35, 37, 39, 41, 43, 45, 47, 49, 51, 53, 55, 57 and 115.

SEQ ID NOs: 59-92 are amino acid sequences of proteins homologous to the proteins with amino acid sequences 2, 4, 6, 8, 10, 12, 14, 16, 18, 20, 22, 24, 26, 28, 30, 32, 34, 36, 38, 40, 42, 44, 46, 48, 50, 52, 54, 56, 58 and 116.

SEQ ID NOs: 93, 94, 95, 96, 97, 98 and 99 are nucleotide sequences of the coding strand of DNA molecules used in the recombinant DNA imparting an enhanced trait or altered phenotype in plants, each representing a miRNA decoy.

SEQ ID NOs: 100, 101, 102, 103, 104, 105 and 106 are nucleotide sequences corresponding to the miRNA binding sites of the miRNA decoys with nucleotide sequences 93, 94, 95, 96, 97, 98 and 99.

SEQ ID NOs: 108, 110, 112 and 114 are amino acid sequences corresponding to proteins that are down-regulated by endogenous miR172, miR166, miR444 and miR397, respectively. SEQ ID NOs: 107, 109, 111 and 113 are polynucleotides sequences encoding those proteins.

As used herein, the term "expression" refers to the production of a polynucleotide or a protein by a plant, plant cell or plant tissue which can give rise to an altered phenotype or enhanced trait. Expression can also refer to the process by which information from a gene is used in the synthesis of functional gene products, which may include but are not limited to other polynucleotides or proteins which may serve, e.g., an enzymatic, structural or regulatory function. Gene products having a regulatory function include but are not limited to elements that affect the occurrence or level of transcription or translation of a target protein. In some cases, the expression product is a non-coding functional RNA.

"Modulation" of expression refers to the process of effecting either overexpression or suppression of a polynucleotide or a protein.

The term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. In alternate non-limiting embodiments, the target protein or target polynucleotide is one the suppression of which can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby effect the altered phenotype or enhanced trait indirectly.

Suppression can be applied using numerous approaches. Non limiting examples include: suppressing an endogenous gene(s) or a subset of genes in a pathway, suppressing one or more mutation that has resulted in decreased activity of a protein, suppressing the production of an inhibitory agent, to elevate, reducing or eliminating the level of substrate that an enzyme requires for activity, producing a new protein, activating a normally silent gene; or accumulating a product that does not normally increase under natural conditions.

Conversely, the term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides or polypeptides under the control of a promoter, examples of which include but are not limited to endogenous promoters, heterologous promoters, inducible promoters and tissue specific promoters. In one exemplary embodiment, the promoter is a constitutive promoter, for example, the cauliflower mosaic virus 35S transcription initiation region. Thus, depending on the promoter used, overexpression can occur throughout a plant, in specific tissues of the plant, or in the presence or absence of different inducing or inducible agents, such as hormones or environmental signals.

Small RNAs that regulate protein expression include miRNAs and ta-siRNAs. A miRNA is a small (typically about 21 nucleotide) RNA that has the ability to modulate the expression of a target gene by binding to a messenger RNA encoding a target protein at specific "miRNA binding sites" to form a RNA duplex, leading to destabilization of the target protein messenger RNA or to translational inhibition of the target protein messenger RNA, and ultimately resulting in suppression of the target protein.

Recombinant DNA constructs can be used to modify the activity of native miRNAs by a variety of means. By increasing the expression of a miRNA, e.g. temporally or spatially, the modulation of expression of a native target gene can be enhanced. An alternative gene suppression approach for suppressing the expression of a target protein can include the use of a recombinant DNA construct that produces a synthetic miRNA that is designed to bind to a native or synthetic miRNA recognition site on messenger RNA for the target protein. By reducing the expression of a miRNA, the modulation of a native target gene can be diminished resulting in enhanced expression of the target protein. More specifically, the expression of a target protein can be enhanced by suppression of the activity of the miRNA that binds to a recognition site in the messenger RNA that is transcribed from the native gene for the target protein. Several types of recombinant DNA constructs can be designed to suppress the activity of a miRNA.

For example, a recombinant DNA construct that produces an abundance of RNA with the miRNA recognition site can be used as a decoy for the native miRNA allowing endogenous messenger RNA with the miRNA recognition site to be translated to the target protein without interference from native miRNA. A recombinant DNA construct that produces RNA with a modified miRNA recognition site, e.g. with nucleotides at positions 10 and/or 11 in a 21mer miRNA recognition site which are unpaired with respect to the native miRNA, can be used to sequester natively expressed miRNA thereby reducing the cleavage that normally occurs when miRNA binds to a recognition site. The unpaired nucleotides can be produced e.g. through additional nucleotides between positions 10 and 11 or through substitutions of the nucleotides at positions 10 and 11.

Naturally occurring or endogenous decoys exist which include one or more miRNA binding sites. A "miRNA decoy" is defined herein as a sequence that can be recognized and bound by an endogenous mature miRNA resulting in base-pairing between the miRNA decoy sequence and the endogenous mature miRNA, thereby forming a stable RNA duplex that is not cleaved because of the presence of mismatches between the miRNA decoy sequence and the mature miRNA.

Rules for predicting endogenous microRNA decoy sequences have been developed. In general, these rules define (1) mismatches that are required, and (2) mismatches that are permitted but not required. Mismatches include canonical mismatches (e.g., G-A, C-U, C-A) as well as G::U wobble pairs and indels (nucleotide insertions or deletions). These rules may be applied to design synthetic decoys.

With respect to constructing synthetic decoys, required mismatches include: (a) at least 1 mismatch between the miRNA decoy sequence and the endogenous mature miRNA at positions 9, 10, or 11 of the endogenous mature miRNA, or alternatively, (b) 1, 2, 3, 4, or 5 insertions (i.e., extra nucleotides) at a position in the miRNA decoy sequence corresponding to positions 9, 10, or 11 of the endogenous mature miRNA. In preferred embodiments, there exists either (a) at least 1 mismatch between the miRNA decoy sequence and the endogenous mature miRNA at positions 10 and/or 11 of the endogenous mature miRNA, or (b) at least 1 insertion in the miRNA decoy sequence between the nucleotides at positions corresponding to positions 10 and/or 11 of the endogenous mature miRNA. In exemplary embodiments, there can be 2, 3, 4, 5, 6, 7, 8, 9, or 10 insertions.

Mismatches that are permitted, but not required, include: (a) 0, 1, or 2 mismatches between the miRNA decoy sequence and the endogenous mature miRNA at positions 1, 2, 3, 4, 5, 6, 7, 8, and 9 of the endogenous mature miRNA, and (b) 0, 1, 2, or 3 mismatches between the miRNA decoy sequence and the endogenous mature miRNA at positions 12 through the last position of the endogenous mature miRNA (i.e., at position 21 of a 21-nucleotide mature miRNA), wherein each of the mismatches at positions 12 through the last position of the endogenous mature miRNA is adjacent to at least one complementary base-pair (i.e., so that there is not more than 2 contiguous mismatches at positions 12 through the last position of the endogenous mature miRNA). In preferred embodiments, there exist no mismatches (i.e., there are all complementary base-pairs) at positions 1, 2, 3, 4, 5, 6, 7, and 8 of the endogenous mature miRNA.

Decoy constructs may include but are not limited to DNA sequences that are transcribed into (i) naturally occurring decoys containing one or more naturally occurring miRNA binding sites specific for miRNA families, (ii) synthetic decoys constructed using a naturally occurring non-coding RNA "scaffolding" and one or more binding sites, i.e., naturally occurring decoys in which the one or more naturally occurring binding sites are substituted or supplemented with one or more synthetic miRNA binding sites, (iii) synthetic decoys wherein a miRNA binding site, which may be naturally occurring or synthetic, is introduced into the 3'-untranslated region of a coding mRNA, or (iv) decoys which are chimeras of any of the preceding decoys.

The construction and description of recombinant DNA constructs to modulate small non-coding RNA activities arc disclosed in US Patent Application Publication US 2009/0070898 A1, and US Patent Application Publication US2011/0296555 A1, both of which are incorporated herein by reference. In particular, with respect to US 2009/0070898 A1, see e.g. paragraphs 182 to 186 and Example 11 at paragraphs 290 to 297.

Combinatorial regulation is a further feature of miRNA mediated overexpression. Multiple families of miRNA molecules are known, each of which can encompass multiple species of miRNA molecules. A given miRNA family may have multiple different mRNA targets; conversely, a given target can be targeted by multiple miRNA families. Another feature of endogenous miRNA-mediated overexpression is that expression of individual miRNA families is in some cases cell-type or tissue-specific, or varies temporally, developmentally or in response to environmental stimuli. Hence expression of particular miRNA families can overlap in time, spatially, developmentally or according to growth conditions, resulting in varied patterns of target protein expression.

Hence, it is possible to produce plants with desirable altered phenotypes or enhanced traits by selectively interfering with the expression pattern or function of specific miRNA families that suppress target proteins associated with those phenotypes or traits.

Thus, in one embodiment, a target protein can be overexpressed by interfering with the endogenous activities of these small inhibitory RNA molecules, which can be accomplished by several ways. One non-limiting example is to reduce the expression of a miRNA, by which the modulation of a native target gene can be diminished and consequently enhancing expression of the target protein. Yet another embodiment of the present invention for overexpressing a target protein is, to modify the native miRNA recognition site in the mRNA encoding the protein to render it resistant to the binding of cognate miRNA which regulates the native gene. Yet another non-limiting example is to express a miRNA "decoy" constructed as described above.

Thus exemplary embodiments include plants transformed with a recombinant DNA molecule encoding at least one polynucleotide sequence transcribed into a mature miRNA decoy that recognizes and binds at least one miRNA species, wherein the polynucleotide has a sequence selected from the group consisting of SEQ ID NOs 93-99, and wherein the plants exhibit an altered phenotype or an enhanced trait or both.

Further exemplary embodiments of the disclosure include a plant transformed with a recombinant DNA molecule encoding as least one polynucleotide sequence transcribed into a mature miRNA decoy that recognizes and binds at least one miRNA species, wherein the polynucleotide comprises at least one miRNA binding site having a sequence selected from the group consisting of SEQ ID NOs: 100-106 and wherein the plants exhibit an altered phenotype or an enhanced trait or both.

Further exemplary embodiments include plants transformed with a recombinant DNA molecule encoding a heterologous promoter operably linked to at least one polynucleotide sequence transcribed into a mature miRNA decoy that recognizes and binds at least one miRNA species, wherein the promoter is a constitutive promoter, a developmental promoter, a tissue enhanced promoter, a tissue preferred promoter, a tissue specific promoter, a cell type-specific promoter, an inducible promoter or a diurnal promoter.

Further exemplary embodiments include a method of producing plants exhibiting an altered phenotype or an enhanced trait or both by transforming the plants with recombinant DNA constructs encoding a least one polynucleotide sequence transcribed into a mature miRNA decoy that recognizes and binds at least one miRNA species, wherein the polynucleotide has a sequence selected from the group consisting of SEQ ID NOs: 93-99, and wherein the plants exhibit an altered phenotype or an enhanced trait or both.

Further exemplary embodiments of the disclosure include a method of producing plants exhibiting an altered phenotype or an enhanced trait or both by transforming the plants with recombinant DNA constructs encoding a least one polynucleotide sequence transcribed into a mature miRNA decoy that recognizes and binds at least one miRNA species, wherein the polynucleotide comprises at least one miRNA binding site having sequence selected from the group consisting of SEQ ID NOs: 100-106.

Further exemplary embodiments include a method of producing plants exhibiting an altered phenotype or an enhanced trait or both by transforming the plants with a recombinant DNA molecule encoding a heterologous promoter operably linked to at least one polynucleotide sequence transcribed into a mature miRNA decoy that recognizes and binds at least one miRNA species, wherein the promoter is a constitutive promoter, a developmental promoter, a tissue enhanced promoter, a tissue preferred promoter, a tissue specific promoter, a cell type-specific promoter, an inducible promoter or a diurnal promoter.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant cell" means a plant cell that is transformed with stably-integrated, recombinant DNA, for example, by *Agrobacterium*-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein a "control plant" means a plant that does not contain the recombinant DNA of the present disclosure that imparts an enhanced trait or altered phenotype. A control plant is used to identify and select a transgenic plant that has an enhanced trait or altered phenotype. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of drought tolerance, increased water use efficiency, cold tolerance, increased nitrogen use efficiency and increased yield as shown in Tables 9-16, and altered phenotypes as shown in Tables 4-8. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in a modified trait. Therefore, the trait modification observed entails a change of the normal distribution and magnitude of the trait in the plants as compared to a control plant.

The present disclosure relates to a plant with improved economically important characteristics, more specifically increased yield. More specifically the present disclosure relates to a plant comprising a polynucleotide of this disclosure, wherein the plant has increased yield as compared to a control plant. Many plants of this disclosure exhibited increased yield as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), seed production and more. Root development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear, weight per kernel, ear number, fresh or dry ear biomass (weight), kernel rows per ear and kernels per row.

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having increased yield; performance of the method gives plants increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, aleurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by producing a plant comprising a polynucleic acid sequence of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA molecule, transgenic plants can be prepared by crossing a first plant having a stably integrated recombinant DNA molecule with a second plant lacking the DNA. For example, recombinant DNA can be introduced into a first plant line that is amenable to transformation to produce a transgenic plant which can be crossed with a second plant line to introgress the recombinant DNA into the second plant line.

A transgenic plant transformed with a recombinant DNA molecule and having the polynucleotide of this disclosure provides the enhanced trait of increased yield compared to a control plant. Genetic markers associated with recombinant DNA can produce transgenic progeny that is homozygous for the desired recombinant DNA. Progeny plants carrying DNA for both parental traits can be back crossed into a parent line multiple times, for example usually 6 to 8 generations, to produce a progeny plant with substantially the same genotype as the one original transgenic parental line but having the recombinant DNA of the other transgenic parental line. The team "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used interchangeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of Water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, oligonucleotide, nucleotide, or any fragment thereof. In many instances, a polynucleotide encodes a polypeptide (or protein) or a domain or fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such enrichment is not the result of a natural response of a wild type plant. Alternatively, or additionally, the isolated polypeptide is separated from other cellular components, with which it is typically associated, for example, by any of the various protein purification methods.

As used herein, a "functional fragment" refers to a portion of a polypeptide provided herein which retains full or partial molecular, physiological or biochemical function of the full length polypeptide. A functional fragment often contains the domain(s), such as Pfam domains (see below), identified in the polypeptide provided in the sequence listing.

A "DNA construct" as used in the present disclosure comprises at least one expression cassette having a promoter operable in plant cells and a polynucleotide of the present disclosure. DNA constructs can be used as a means of delivering recombinant DNA molecules to a plant cell in order to effect stable integration of the recombinant molecule into the plant cell genome. In one embodiment, the polynucleotide can encode a protein or variant of a protein or fragment of a protein that is functionally defined to maintain activity in transgenic host cells including plant cells, plant parts, explants and whole plants. In another embodiment, the polynucleotide can encode a non-coding RNA that interferes with the functioning of endogenous classes of small RNAs that regulate expression, including but not limited to taRNAs, siRNAs and miRNAs. Recombinant DNA constructs are assembled using methods known to persons of ordinary skill in the art and typically comprise a promoter operably linked to DNA, the expression of which provides the enhanced agronomic trait.

Other construct components can include additional regulatory elements, such as 5' leaders and introns for enhancing transcription, 3' untranslated regions (such as polyadenylation signals and sites), and DNA for transit or targeting or signal peptides.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from common ancestral genes by speciation and encode proteins retain the same function, but do not include paralogs, i.e., genes that are related by duplication but have evolved to encode proteins with different functions. Homologous genes include naturally occurring alleles and artificially-created variants.

Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about 80%, at least about 85%, at least about 90%, at least about 92%, at least about 94%, at least about 95%, at least about 96%, at least about 97%, at least about 98%, at least about 99%, or even at least about 99.5% identity over the full length of a protein or its corresponding nucleotide sequence identified as being associated with imparting an enhanced trait or altered phenotype when expressed in plant cells. In one aspect of the disclosure homolog proteins have at least about 80%, at least about 85%, at least about 90%, at least about 92%, at least about 94%, at least about 95%, at least about 96%, at least about 97%, at least about 98%, at least about 99%, or at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query emails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

"Pfam" is a large collection of multiple sequence alignments and hidden Markov models covering many common protein families, for example, Pfam version 27.0 (March 2013) contains alignments and models for 14381 protein families and uses UniProtKB as its reference sequence databases. See *The Pfam protein families database*: M. Punta, P. C. Coggill, R. Y. Eberhardt, J. Mistry, J. Tate, C. Boursnell, N. Pang. K. Forslund, G. Ceric, J. Clements, A. Heger, L. Holm, E. L. L. Sonnhammer, S. R. Eddy, A. Bateman, R. D. Finn Nucleic Acids Research (2012) Database Issue 40:D290-D30, which is incorporated herein by reference in its entirety. The Pfam database is currently maintained and updated by the Pfam Consortium. The alignments represent some evolutionary conserved structure that has implications for the protein's function. Profile hidden Markov models (profile HMMs) built from the protein family alignments are useful for automatically recognizing that a new protein belongs to an existing protein family even if the homology by alignment appears to be low.

Protein domains are identified by querying the amino acid sequence of a protein against Hidden Markov Models which characterize protein family domains ("Pfam domains") using HMMER software, which is available from the Pfam Consortium and is available through the Howard Hughes Medical Institute's Janelia Farm website. A protein domain meeting the gathering cutoff for the alignment of a particular Pfam domain is considered to contain the Pfam domain.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly and broadly defined domains, leading to identification of overlapping domains on some proteins. A Pfam domain module is characterized by non-overlapping domains. Where there is overlap, the domain having a function that is more closely associated with the function of the protein (based on the B value of the Pfam match) is selected.

Once one DNA is identified as encoding a protein which imparts an enhanced trait when expressed in transgenic plants, other DNA encoding proteins with the same Pfam domain module are identified by querying the amino acid sequence of protein encoded by the candidate DNA against the Hidden Markov Models which characterizes the Pfam domains using HMMER software. Candidate proteins meeting the same Pfam domain module are in the protein family and have cognate DNA that is useful in constructing recombinant DNA for the use in the plant cells of this disclosure. Hidden Markov Model databases for the use with HMMER software in identifying DNA expressing protein with a common Pfam domain module for recombinant DNA in the plant cells of this disclosure are included in the computer program listing in this application.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

Sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) *Transgenic Res.* 6(2):157-166, globulin I as disclosed by Belanger et al (1991) *Genetics* 129:863-872, glutelin I as disclosed by Russell (1997) supra, and peroxiredoxin antioxidant (Per1) as disclosed by Stacy et al. (1996) *Plant Mol Biol.* 31(6):1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule. As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For description of the transit peptide region of an Arabidopsis EPSPS gene in the present disclosure, see Klee. H. J. Et al (*MGG* (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or an herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvylshikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011)), bialaphos or phosphinothricin or derivatives (e.g., phosphinothricin acetyltransferase (bar) tolerance to phosphinothricin or glufosinate (U.S. Pat. Nos. 5,646,024; 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a nontranslated RNA, in the sense or antisense direction, a microRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutetin gene, a rice lactate dehydrogenase gene and a rice beta-tubulin gene, all of which are disclosed in US Patent Application Publication 2002/0192813 A1; and the pea (*Pisum sativum*) ribulose biphosphate carboxylase gene (rbs 3'), and 3' elements from the genes within the host plant.

As used herein "operably linked" means the association of two or more DNA fragments in a recombinant DNA molecule so that the function of one, for example, protein-encoding DNA, is controlled by the other, for example, a promoter.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtl) described in Misawa et al, (1993) *Plant J.* 4:833-840 and in Misawa et al. (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in US Patent Application Publication 2003/010609 A1 for imparting N-amino methyl phosphorite acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506,599; 5,986,175 and US Patent Application Publication 2003/0150017 A1. Plant Cell Transformation Methods Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365.807 (rice). *Agrobacterium*-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice). US Patent Application Publication 2004/0087030 A1 (cotton), and US Patent Application Publication 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA molecule, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of protein-encoding DNA ("genes") as recombinant DNA for production of transgenic plants with enhanced traits, the elements of Table 1 are described by reference to:

PEP SEQ ID NO" which identifies an amino acid sequence.

"."NUC SEQ ID NO" which identifies a DNA sequence.

"Gene ID" which refers to an arbitrary identifier.

"Protein Name" which is a common name for the protein encoded by the recombinant DNA.

TABLE 1

Protein sequences

| NUC SEQ ID NO | PEP SEQ ID NO | Gene ID | Protein Name |
|---|---|---|---|
| 1 | 2 | TRDX3-1 | Translationally controlled tumor protein homolog |
| 3 | 4 | TRDX3-2 | Phytochrome B1 containing Histidine kinase-like ATPases |
| 5 | 6 | TRDX3-3 | unknown protein |
| 7 | 8 | TRDX3-4 | monogalactosyl-diacylglycerol (MGDG) synthase type C protein |
| 9 | 10 | TRDX3-5 | putative GluRS (glutamate-tRNA ligase) |
| 11 | 12 | TRDX3-6 | prenylyltransferase-like protein |
| 13 | 14 | TRDX3-7 | protein kinase family protein |
| 15 | 16 | TRDX3-8 | PLC1 (Phosphoinositide phospholipase C 1) |
| 17 | 18 | TRDX3-9 | Non-specific lipid-transfer protein-like protein |
| 19 | 20 | TRDX3-10 | ATFIP1 (Factor Interacting with PolyA polymerase) |
| 21 | 22 | TRDX3-11 | cysteine protease inhibitor |
| 23 | 24 | TRDX3-12 | hypothetical protein containing Cenp-O kinetochore centromere component domain |
| 25 | 26 | TRDX3-13 | TOM20-2 (Translocase Outer Membrane 20-2) |
| 27 | 28 | TRDX3-14 | 3-dehydroquinate dehydratase/shikimate dehydrogenase |
| 29 | 30 | TRDX3-15 | unknown protein |
| 31 | 32 | TRDX3-16 | SOUL family putative heme binding protein 1 |
| 33 | 34 | TRDX3-17 | Nob1 containing a predicted RNA-binding protein (contains KH domains) domain |
| 35 | 36 | TRDX3-18 | PCD (Pterin-4a-carbinolamine dehydratases) |
| 37 | 38 | TRDX3-19 | WEI8 (weak ethylene insensitive 8) gene encoding Trpytophan (Trp) aminotransferase |
| 39 | 40 | TRDX3-20 | RTH3 (root hairless 3) containing domain of COBRA-like protein |
| 41 | 42 | TRDX3-21 | RGT2 (Restores Glucose Transport 2) |
| 43 | 44 | TRDX3-22 | a protein of unknown function containing U1 zinc finger domain (zf-U1) |
| 45 | 46 | TRDX3-23 | RING-H2 finger protein ATL4E |
| 47 | 48 | TRDX3-24 | radical SAM domain-containing protein |
| 49 | 50 | TRDX3-25 | senescence-associated protein |
| 51 | 52 | TRDX3-26 | ATPARP2 (POLY(ADP-RIBOSE) POLYMERASE 2 |
| 53 | 54 | TRDX3-27 | MT3a Metallothionein 3a |
| 55 | 56 | TRDX3-28 | Cytochrome B5 reductase |
| 57 | 58 | TRDX3-29 | CUL3 (Cullin 3) containing cullin family domain |
| 115 | 116 | TRDX3-37 | corn phyt: 2 |

Table 2 provides a list of miRNA decoy elements as recombinant DNA for production of transgenic plants with enhanced traits. The elements of Table 2 are described by reference to:

"Decoy Element NUC SEQ ID NO:" which identifies a decoy element nucleotide sequence.

"Decoy Element miRNA binding site NUC SEQ ID NO:" which identifies the miRNA binding site of the decoy element.

"Decoy Element ID:" which is an arbitrary identifier.

"Target miRNA Name" which identifies a target miRNA for binding by the decoy.

"Target Protein Name" which identifies the target protein which bind the target miRNA.

"Target Protein NUC SEQ ID NO:" which identifies the nucleotide sequence encoding the target protein of the target miRNA "Target Protein PEP SEQ ID NO:" which identifies the amino acid sequence of the target protein of the target miRNA screening for the trait in a greenhouse or field trial or by screening for a surrogate trait. Such analyses can be directed to detecting changes in the chemical composition, biomass, physiological property, or morphology of the plant. Changes in chemical compositions such as nutritional composition of grain can be detected by analysis of the seed composition and content of protein, free amino acids, oil free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

TABLE 2

Decoy Elements

| Decoy Element ID | Decoy Element (NUC) SEQ ID NO: | Decoy Element miRNA binding site (NUC) SEQ ID NO: | Target miRNA Name | Target Protein Names | Target Protein NUCSEQ ID NO: | Target Protein PEP SEQ ID NO: |
|---|---|---|---|---|---|---|
| TRDX3-30 | 93 | 100 | miR399 | Phosphate transporter | | |
| TRDX3-31 | 94 | 101 | miR172 | APETALA2-like transcription factor | 107 | 108 |
| TRDX3-32 | 95 | 102 | miR166 | Revoluta | 109 | 110 |
| TRDX3-33 | 96 | 103 | miR444 | ANR1 MADS-box protein | 111 | 112 |
| TRDX3-34 | 97 | 104 | miR172e | APETALA2-like transcription factor | | |
| TRDX3-35 | 98 | 105 | miR393 | HOSI: E3 ligase SCF complex F-box protein bHLH transcription factor | | |
| TRDX3-36 | 99 | 106 | miR397 | diphenol oxidase | 113 | 114 |

Selection Methods for Transgenic Plants with Enhanced Traits

Within a population of transgenic plants each regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Transgenic plums having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield are identified by screening using progenies of the transgenic plants over multiple locations for several years with plants grown under optimal production management practices and maximum weed and pest control. Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, quinoa and sugar cane plants.

Example 1. Corn Transformation

This example illustrates transformation methods in producing a transgenic corn plant cell, seed, and plant having altered phenotypes as shown in Tables 4-6, or an enhanced trait, for example, increased water use efficiency as shown in Tables 15-16, increased yield as shown in Tables 11-12, and increased nitrogen use efficiency as shown in Tables 9-10.

For *Agrobacterium*-mediated transformation of corn embryo cells corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown *Agrobacterium* cells, and incubated at room temperature with *Agrobacterium* for 5-20 minutes. Inoculated immature embryos were then co-cultured with *Agrobacterium* for 1 to 3 days at 23° C. in the dark. Co-cultured embryos were transferred to selection media and cultured for approximately two weeks to allow embryogenic callus to develop. Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1 or with recombinant DNA from Table 2 that is transcribed into a non-coding miRNA. Progeny transgenic plants and seeds of the transformed plants were screened for the presence and single copy of the inserted gene, and for increased water use efficiency, increased yield, increased nitrogen use efficiency, and altered phenotypes as shown in Tables 4-6. From each group of multiple events of transgenic plants with a specific recombinant DNA from Table 1 or Table 2, the event(s) that showed increased yield, increased water use efficiency, increased nitrogen use efficiency, and altered phenotypes was (were) identified.

Example 2. Soybean Transformation

This example illustrates plant transformation in producing a transgenic soybean plant cell, seed, and plant having altered phenotypes as shown in Tables 7-8, or an enhanced trait, for example, increased water use efficiency or drought tolerance and increased yield as shown in Tables 13-14.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA from the genes identified in Table 1 or recombinant DNA transcribed into a miRNA decoy identified in Table 2. Progeny transgenic plants and seed of the transformed plant cells were screened for the presence and single copy of the inserted gene, and for increased water use efficiency, increased yield, increased nitrogen use efficiency, and altered phenotypes as shown in Tables 6-7.

Example 3. Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent publication No. US20110135161 (filed on Nov. 10, 2010), which is incorporated by reference herein in its entirety.

Screening and Identification of Transgenic Corn Plants for Altered Phenotypes Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific condition as shown in Table 3.

TABLE 3

Description of the 3 AGH screens for corn plants.

| Screen | Description | Germination phase (5 days) | Screen specific phase (22 days) |
|---|---|---|---|
| Non-stress | well watered<br>sufficient nitrogen | 55% VWC<br>water | 55% VWC<br>8 mM nitrogen |
| Water deficit | limited watered<br>sufficient nitrogen | 55% VWC<br>water | 30% VWC<br>8 mM nitrogen |
| Nitrogen deficit | well watered<br>low nitrogen | 55% VWC<br>water | 55% VWC<br>2 mM nitrogen |

Water deficit is defined as a specific Volumetric Water Content (VWC) that is lower than the VWC of non-stress plant. For example, a non-stressed plant might be maintained at 55% VWC and the VWC for a water-deficit assay might be defined around 30% VWC as shown in Table 3. Data were collected using visible light and hyperspectral imaging as well as direct measurement of pot weight and amount of water and nutrient applied to individual plants on a daily basis.

Nitrogen deficit is defined in part as a specific mM concentration of nitrogen that is lower than the nitrogen concentration of non-stress plants. For example, a non-stress plant might be maintained at 8 mM nitrogen while the nitrogen concentration applied in a nitrogen-deficit assay might be maintained at a concentration of 2 mM.

Eight parameters were measured for each screen. The visible light color imaging based measurements are: biomass, canopy area and plant height. Biomass (B) is defined as estimated shoot fresh weight (g) of the plant obtained from images acquired from multiple angles of view. Canopy Area (Can) is defined as area of leaf as seen in top-down image ($mm^2$). Plant Height (H) refers to the distance from the top of the pot to the highest point of the plant derived from side image (mm). Anthocyanin score, chlorophyll score and water content score are hyperspectral imaging based parameters. Anthocyanin Score (An) is an estimate of anthocyanin in the leaf canopy obtained from a top-down hyperspectral image. Chlorophyll Score (Chl) is a measurement of chlorophyll in the leaf canopy obtained from a top-down hyperspectral image. Water Content Score (WC) is a measurement of water in the leaf canopy obtained from a top-down hyperspectral image. Water Use Efficiency (WUE) is derived from the grams of plant biomass per liter of water added. Water Applied (WA) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 4-6 are summaries of transgenic corn plants comprising the disclosed recombinant DNA molecules with altered phenotypes under non stress, nitrogen deficit, and water deficit conditions, respectively.

"+" denotes an increase in the tested parameter at $p \le 0.1$; whereas "−" denotes a decrease in the tested parameter at $p \le 0.1$. The numbers in parenthesis show penetrance of the altered phenotypes, where the denominators represent total number of transgenic events tested for a given parameter in a specific screen, and the numerators represent the number of events showing a particular altered phenotype. For example, 5 transgenic plants were screened for water use efficiency score in the non-stress screen for TRDX3-3 and 1 of the 5 tested showed increased water use efficiency at $p \le 0.1$.

TABLE 4

Summary of transgenic corn plants with altered phenotypes in AGH non-stress screens

| | Non-Stress | | | | | | | |
|---|---|---|---|---|---|---|---|---|
| Gene_ID | An | B | Can | Chl | H | WA | WC | WUE |
| TRDX3-3 | — | +1/5 | −1/5 | — | — | +1/5 | — | +1/5 |
| TRDX3-4 | — | −3/5 | −4/5 | — | −3/5 | −5/5 | — | −1/5 |
| TRDX3-6 | −4/5 | −4/5 | −1/5 | −1/5 | −3/5 | −3/5 | −3/5 | −2/5 |
| TRDX3-7 | — | −2/5 | −1/5 | +1/5 | −1/5 | −4/5 | — | −1/5 |
| TRDX3-12 | — | −1/5 | — | +1/5 | −1/5 | — | — | −1/5 |
| TRDX3-13 | — | +1/5 | — | — | — | −1/5 | +1/5 | +2/5 |
| TRDX3-16 | — | −1/5 | — | — | — | — | — | −1/5 |
| TRDX3-20 | −1/5 | — | −2/5 | — | — | −1/5 | — | — |
| TRDX3-21 | −1/4 | — | +2/4 | — | — | +2/4 | — | — |
| TRDX3-25 | — | +1/5 | — | — | — | — | — | +1/5 |
| TRDX3-28 | — | +2/5 | +1/5 | +1/5 | +1/5 | +4/5 | +1/5 | +1/5 |
| TRDX3-29 | — | −1/5 | −2/5 | +1/5 | −3/5 | −1/5 | +1/5 | −1/5 |
| TRDX3-35 | — | −1/5 | — | — | — | −1/5 | — | −2/5 |

TABLE 5

Summary of transgenic corn plants with altered phenotypes in AGH nitrogen-deficit screens

| | Nitrogen Deficit | | | | | | | |
|---|---|---|---|---|---|---|---|---|
| Gene_ID | An | B | Can | Chl | H | WA | WC | WUE |
| TRDX3-3 | — | +1/5 | +1/5 | +1/5 | −1/5 | +1/5 | — | — |
| TRDX3-4 | — | −2/5 | −1/5 | −1/5 | +1/5 | −3/5 | — | — |
| TRDX3-6 | — | — | −1/5 | — | — | — | — | +2/5 |
| TRDX3-7 | −2/5 | −1/5 | −1/5 | +1/5 | — | −4/5 | — | — |
| TRDX3-12 | −1/5 | −2/5 | — | — | −1/5 | −4/5 | — | −1/5 |
| TRDX3-13 | −1/5 | −1/5 | — | +1/5 | — | — | — | −1/5 |

TABLE 5-continued

Summary of transgenic corn plants with altered phenotypes in AGH nitrogen-deficit screens

| | Nitrogen Deficit | | | | | | | |
|---|---|---|---|---|---|---|---|---|
| Gene_ID | An | B | Can | Chl | H | WA | WC | WUE |
| TRDX3-16 | +1/5 | −3/5 | −1/5 | +3/5 | −1/5 | −4/5 | −4/5 | — |
| TRDX3-20 | — | −2/5 | −2/5 | +1/5 | −1/5 | −1/5 | — | −1/5 |
| TRDX3-21 | −1/5 | +1/5 | +2/5 | +1/5 | −1/5 | — | +1/5 | +1/5 |
| TRDX3-24 | −1/5 | — | +3/5 | — | — | +3/5 | — | — |
| TRDX3-28 | −1/5 | +4/5 | +1/5 | — | +1/5 | −1/5 | +1/5 | +1/5 |
| TRDX3-29 | — | −1/1 | −1/1 | — | −1/1 | — | — | −1/1 |
| TRDX3-35 | +1/5 | −2/5 | −2/5 | +3/5 | −2/5 | −2/5 | — | −2/5 |

TABLE 6

Summary of transgenic corn plants with altered phenotypes in AGH water-deficit screens

| | Water Deficit | | | | | | | |
|---|---|---|---|---|---|---|---|---|
| Gene ID | An | B | Can | Chl | H | WA | WC | WUE |
| TRDX3-3 | — | +1/5 | — | — | −2/5 | −1/5 | +2/5 | −1/5 |
| TRDX3-4 | — | +2/5 | +1/5 | +1/5 | +1/5 | +3/5 | +1/5 | — |
| TRDX3-6 | −2/5 | — | — | — | −1/5 | — | — | — |
| TRDX3-7 | +2/5 | −3/5 | −4/5 | −2/5 | −3/5 | −4/5 | −2/5 | −2/5 |
| TRDX3-12 | — | — | −1/5 | −1/5 | −1/5 | +4/5 | — | — |
| TRDX3-13 | — | +2/5 | +1/5 | −1/5 | +2/5 | +4/5 | — | +1/5 |
| TRDX3-16 | — | +2/5 | — | +3/5 | — | +3/5 | — | — |
| TRDX3-20 | — | — | −1/5 | — | — | −1/5 | — | −1/5 |
| TRDX3-21 | −1/5 | — | +1/5 | +1/5 | — | — | −1/5 | −1/5 |
| TRDX3-24 | — | — | — | −2/5 | — | +1/5 | −1/5 | — |
| TRDX3-28 | +2/5 | +1/5 | +2/5 | +1/5 | +1/5 | +2/5 | — | +1/5 |
| TRDX3-35 | — | −2/5 | — | −2/5 | — | −1/5 | −2/5 | −2/5 |

Screening and Identification of Transgenic Soybean Plants for Altered Phenotypes Soybean plants were tested in 2 screens in AGH under non-stress and water deficit stress conditions. For non-stress screen, the plants were kept under constant VWC of 55% throughout the screen length of 27 days. For water deficit screen, the VWC was kept at 55% for the first 12 days after sowing, followed by gradual dry down at a rate of 0.025 VWC per day, followed by water recovery to 55% VWC at 25 days after sowing.

Water deficit is defined as a specific Volumetric Water Content (VWC) that is lower than the VWC of non-stress plant. For example, a non-stressed plant might be maintained at 55% VWC and water-deficit assay might be defined around 30% VWC as shown in Table 3. Data were collected using visible light and hyperspectral imaging as well as direct measurement of pot weight and amount of water and nutrient applied to individual plants on a daily basis.

Eight parameters were measured for each screen. The visible light color imaging based measurements are: biomass, canopy area and plant height. Biomass (B) is defined as estimated shoot fresh weight (g) of the plant obtained from images acquired from multiple angles of view. Canopy Area (Can) is defined as area of leaf as seen in top-down image ($mm^2$). Plant Height (H) refers to the distance from the top of the pot to the highest point of the plant derived from side image (mm)—Chlorophyll score—is a hyperspectral imaging based parameter. Chlorophyll Score (Chl) is a measurement of chlorophyll in the leaf canopy obtained from a top-down hyperspectral image. Water Use Efficiency (WUE) is derived from the grams of plant biomass per liter of water added. Wafer Applied (WA) is a direct measurement of water added to a pot (pot with no hole) during the course of an experiment.

These physiological screen runs were set up so that tested transgenic lines were compared to a control line. The collected data were analyzed against the control using % delta and/or certain p-value cutoff. Tables 7-8 are summaries of transgenic soybean plants comprising the disclosed recombinant DNA molecules with altered phenotypes. "+" denotes an increase in the tested parameter at $p \leq 0.1$; whereas "−" denotes a decrease in the tested parameter at $p \leq 0.1$. The numbers in parenthesis show penetrance of the altered phenotypes, where the denominators represent total number of transgenic plants tested for a given parameter in a specific screen, and the numerators represent the number of transgenic plants showing a particular phenotype. For example, 5 transgenic plants were screened for biomass in the non-stress screen for TRDX3-26. Of the 5 tested, 2 showed a decrease in biomass at $p \leq 0.1$.

TABLE 7

Summary of transgenic soybean plants with altered phenotypes in AGH non-stress screens

| | Non-Stress | | | | | | | |
|---|---|---|---|---|---|---|---|---|
| Gene_ID | An | B | Can | Chl | H | WA | WC | WUE |
| TRDX3-26 | — | −2/5 | −3/5 | −2/5 | −2/5 | −2/5 | — | −1/5 |
| TRDX3-22 | — | +3/5 | +1/5 | +2/5 | +3/5 | +2/5 | — | +3/5 |
| TRDX3-27 | — | — | — | +1/5 | — | −1/5 | — | — |

TABLE 8

Summary of transgenic soybean plants with altered phenotypes in AGH water deficit screens

| | Water Deficit | | | | | | | |
|---|---|---|---|---|---|---|---|---|
| Gene_ID | An | B | Can | Chl | H | WA | WC | WUE |
| TRDX3-26 | — | — | — | — | −1/5 | — | — | — |
| TRDX3-22 | — | +1/5 | +1/5 | — | — | −1/5 | — | +1/5 |
| TRDX3-27 | — | — | — | — | +1/5 | — | — | — |

Example 4. Phenotypic Evaluation of Transgenic Corn Plants for Increased Nitrogen Use Efficiency Corn Nitrogen field efficacy trials were conducted to identify genes and miRNA decoy elements that can improve nitrogen use efficiency under nitrogen limiting conditions leading to increased yield performance as compared to non transgenic controls. A yield increase in corn can be manifested as one or more of the following: an increase in the number of ears per plant, an increase in the number of rows, number of kernels per row, kernel weight, thousand kernel weight, fresh or dry ear length/diameter/biomass (weight), increase in the seed filling rate (which is the number of filled seeds divided by the total number of seeds and multiplied by 100), among others. For the Nitrogen field trial results shown in Table 9, each field was planted under nitrogen limiting condition (60 lbs/acre) and the corn ear weight or yield was compared to control plants to measure the yield increases.

Table 9 provides a list of protein encoding DNA or polynucleotide sequences ("genes") for producing transgenic corn plant with increased nitrogen use efficiency as compared to a control plant. Polynucleotide sequences in constructs with at least one event showing significant yield or ear weight increase across multiple locations at p≤0.2 are included. The elements of Table 9 are described by reference to:

"SEQ ID NO: polynucleotide" which identifies a nucleotide sequence.

"SEQ ID NO: polypeptide" which identifies an amino acid sequence.

"Gene ID" which refers to an arbitrary identifier.

"NUE results" which refers to the sequence in a construct with at least one event showing significant yield increase at p≤0.2 across locations. The first number refers to the number of events with significant yield or ear weight increase, whereas the second number refers to the total number of events tested for each sequence in the construct. The numbers are listed for each construct separately when more than one construct was used in the trials.

TABLE 9

Recombinant DNA for increased nitrogen use efficiency in corn

| SEQ ID NO: Polynucleotide | SEQ ID NO: Polypeptide | Gene ID | NUE Results |
|---|---|---|---|
| 5 | 6 | TRDX3-3 | 2/12 |
| 7 | 8 | TRDX3-4 | 3/16 |
| 11 | 12 | TRDX3-6 | 2/13 |
| 13 | 14 | TRDX3-7 | Construct 1: 4/14<br>Construct 2: 1/7 |
| 15 | 16 | TRDX3-8 | 1/8 |
| 17 | 18 | TRDX3-9 | 1/13 |
| 25 | 26 | TRDX3-13 | 1/5 |
| 27 | 28 | TRDX3-14 | 3/13 |
| 33 | 34 | TRDX3-17 | 2/13 |
| 35 | 36 | TRDX3-18 | 3/14 |
| 37 | 38 | TRDX3-19 | 4/13 |
| 45 | 46 | TRDX3-23 | 2/13 |
| 47 | 48 | TRDX3-24 | 1/8 |
| 49 | 50 | TRDX3-25 | 5/20 |

Table 10 provides a list of miRNA decoy elements provided as recombinant DNA for production of transgenic corn plants with increased nitrogen use efficiency. The elements of Table 10 are described by reference to:

"Decoy Element (NUC) SEQ ID NO:" which identities a decoy element nucleotide sequence from.

"Decoy Element ID:" which is an arbitrary identifier.

"Target miRNA Name" which identifies a target miRNA for binding by the decoy.

"Protein Name (PEP)" which identifies the amino acid sequence of a protein which binds miR166.

"NUE results" which refers to the sequence in a construct with at least one event showing significant yield increase at p≤0.2 across locations. The first number refers to the number of events with significant yield or ear weight increase, whereas the second number refers to the total number of events tested for each sequence in the construct.

TABLE 10

Recombinant DNA for miRNA decoy elements for increased nitrogen use efficiency in corn

| Decoy Element (NUC) SEQ ID NO | Decoy Element ID | Target miRNA Name | Protein Name | Protein (PEP) SEQ ID NO | Broad Acre Yield Results |
|---|---|---|---|---|---|
| 95 | TRDX3-32 | miR166 | Revoluta | 110 | 2/16 |

Example 5. Phenotypic Evaluation of Transgenic Plants for Increased Yield

This example illustrates selection and identification pf transgenic plants for increased yield in both dicotyledonous and monocotyledonous plants with primary examples presented for corn and soybean in Tables 11-12 and 13-14 respectively. Polynucleotide sequences in constructs with at least one event that resulted in significant yield increase across locations at p≤0.2 are included.

Selection of Transgenic Wants with Enhanced Agronomic Trait(s): Increased Yield

Effective selection of increased and/or enhanced yielding transgenic plants uses hybrid progenies of the transgenic plants for corn, cotton, and canola, or inbred progenies of transgenic plants for soybean plants plant such as corn, cotton, canola, or inbred plant such as soy, canola and cotton over multiple locations with plants grown under optimal production management practices. An exemplary target for improved yield is a 2% to 10% increase in yield as compared to yield produced by plants grown from seed of a control plant. Selection methods can be applied in multiple and diverse geographic locations, for example up to 16 or more locations, over one or more planting seasons, for example at least two planting seasons, to statistically distinguish yield improvement from natural environmental effects.

Increased Yield in Corn

Table 11 provides a list of protein encoding DNA or polynucleotide sequences ("genes") in the production of transgenic corn plants with increased yield as compared to a control plant. The elements of Table 11 are described by reference to:

"Gene (NUC) SEQ ID NO:" which identifies a nucleotide sequence.

"Gene (PEP) SEQ ID NO:" polypeptide" which identifies an amino acid sequence.

"Gene identifier" which refers to an arbitrary identifier.

"Broad acre yield results" refers to the sequence in a construct with at least one event showing significant yield increase at p≤0.2 across locations. The first number refers to the number of events with significant yield increase, whereas the second number refers to the total number of events tested for each sequence in a construct.

TABLE 11

Recombinant DNA for increased yield in corn

| Gene (NUC) SEQ ID NO: | Gene (PEP) SEQ ID NO: | Gene ID | Broad Acre Yield Results |
|---|---|---|---|
| 1 | 2 | TRDX3-1 | 1/5 |
| 3 | 4 | TRDX3-2 | 1/8 |
| 9 | 10 | TRDX3-5 | 1/13 |
| 21 | 22 | TRDX3-11 | 2/16 |
| 25 | 26 | TRDX3-13 | 1/6 |
| 29 | 30 | TRDX3-15 | 5/16 |
| 31 | 32 | TRDX3-16 | 5/30 |
| 35 | 36 | TRDX3-18 | 1/6 |
| 41 | 42 | TRDX3-21 | 2/20 |
| 55 | 56 | TRDX3-28 | 2/22 |
| 57 | 58 | TRDX3-29 | 1/8 |

Table 12 provides a list of miRNA decoy elements provided as recombinant DNA for production of transgenic corn plants with increased yield. The elements of Table 12 are described by reference to:

"Decoy Element (NUC) SEQ ID NO:" which identities a nucleic acid sequence.

"Decoy Element Identifier" which is an arbitrary identifier.

"Target miRNA Name" which identifies a target miRNA for binding by the decoy.

"Protein name" which identifies a gene down-regulated by the target miRNA.

"Broad acre yield results" refers to the sequence in a construct with at least one event showing significant yield increase at p≤0.2 across locations. The first number refers to the number of events with significant yield increase, whereas the second number refers to the total number of events tested for each sequence in a construct.

TABLE 12

Recombinant DNA for miRNA decoys for increased yield in corn

| Decoy Element (NUC) SEQ ID NO: | Decoy Element Identifier | Target miRNA Name | Protein Name | Broad Acre Yield Results |
|---|---|---|---|---|
| 93 | TRDX3-30 | miR399 | Phosphate transporter | 1/18 |
| 95 | TRDX3-32 | miR172 | APETALA2-like transcription factor | 1/18 |
| 97 | TRDX3-34 | miR172e | APETALA2-like transcription factor | 3/18 |
| 98 | TRDX3-35 | miR393 | HOS1; E3 ligase SCF complex F-box protein; bHLH transcription factor | 1/22 |

Increased Yield in Soybean

A yield increase in soybean can be manifested as one or more of the following: an increase in pods per plant, pods per acre, seeds per plant, seeds per pod, weight per seed, weight per pod, pods per node, number of nodes, and the number of internodes per plant.

Table 13 provides a list of protein encoding DNA or polynucleotide sequences used ("genes") in the production of transgenic soybean plants with increased yield as compared to a control plant. The elements of Table 13 are described by reference to:

"Gene (NUC) SEQ ID NO:" which identifies a nucleotide sequence

"Gene (PEP) SEQ ID NO:" which identifies an amino acid sequence.

"Gene identifier" which refers to an arbitrary identifier.

"Broad acre yield results" which refers to the sequence in a construct with at least one event showing significant yield increase at p≤0.2 across locations. The first number refers to the number of events with significant yield increase, whereas the second number refers to the total number of events tested for each sequence in a construct.

TABLE 13

Recombinant DNA for increased yield in soybean

| Gene (NUC) SEQ ID NO: | Gene (PEP) SEQ ID NO: | Gene Identifier | Broad Acre Yield Results |
|---|---|---|---|
| 43 | 44 | TRDX3-22 | 3/16 |
| 51 | 52 | TRDX3-26 | 3/16 |
| 53 | 54 | TRDX3-27 | 3/15 |

Table 14 provides a list of miRNA decoy elements provided as recombinant DNA for production of transgenic corn plants with increased yield. The elements of Table 14 are described by reference to:

"Decoy Element (NUC) SEQ ID NO:" which identifies a decoy element nucleotide sequence.

"Decoy Element ID:" which identifies a decoy element sequence.

"Target miRNA Name" which identifies a target miRNA for binding by the decoy.

"Protein name" which identifies amino acid sequences of proteins which bind the target miRNA.

"Protein (PEP) SEQ ID NO" which identifies an amino acid sequence.

"Broad acre yield results" refers to the sequence in a construct with at least one event showing significant yield increase at p≤0.2 across locations. The first number refers to the number of events with significant yield increase, whereas the second number refers to the total number of events tested for each sequence in a construct.

TABLE 14

Recombinant DNA miRNA decoys for increased yield in soybean

| Decoy Element (NUC) SEQ ID NO | Decoy Element ID | Target miRNA Name | Protein Name | Protein (PEP) SEQ ID NO: | Broad Acre Yield Results |
|---|---|---|---|---|---|
| 94 | TRDX3-31 | miR172 | APETALA-2-like transcription factor | | 2/12 |
| 99 | TRDX3-36 | miR397 | diphenol dioxidase | 114 | 1/10 |

Example 6. Phenotypic Evaluation of Corn for Increased Water Use Efficiency

Corn field trials were conducted to identify genes that can improve water use efficiency under water limiting conditions leading to increased yield performance as compared to non transgenic controls. A yield increase in corn can be manifested as one or more of the following: an increase in the number of ears per plant, an increase in the number of rows, number of kernels per row, kernel weight, thousand kernel weight, fresh or dry ear length/diameter/biomass (weight), increase in the seed filling rate (which is the number of filled seeds divided by the total number of seeds and multiplied by 100), among others. The water use efficiency trials for results shown in Table 15 were conducted under managed water limiting conditions, and the corn ear weight or yield was compared to control plants to measure the yield increases.

Table 15 provides a list of protein encoding DNA or polynucleotide sequences ("genes") for producing transgenic corn plant with increased water use efficiency as compared to a control plant. Polynucleotide sequences in constructs with at least one event showing significant yield or ear weight increase across multiple locations at p≤0.2 are included. The elements of Table 15 are described by reference to:

"SEQ ID NO: polynucleotide" which identifies a nucleotide sequence.

"SEQ ID NO: polypeptide" which identifies an amino acid sequence.

"Gene identifier" which refers to an arbitrary identifier.

"WUE results" which refers to the sequence in a construct with at least one event showing significant yield increase at p≤0.2 across locations. The first number refers to the number of events with significant yield or car weight increase, whereas the second number refers to the total number of events tested for each sequence in the construct.

TABLE 15

Recombinant DNA for Increased Water Use Efficiency in Corn

| SEQ ID NO: Polynucleotide | SEQ ID NO: Polypeptide | Gene Identifier | WUE Results |
|---|---|---|---|
| 7 | 8 | TRDX3-4 | 2/16 |
| 11 | 12 | TRDX3-6 | 2/8 |
| 13 | 14 | TRDX3-7 | 2/7 |
| 19 | 20 | TRDX3-10 | 3/16 |
| 23 | 24 | TRDX3-12 | 3/14 |
| 33 | 34 | TRDX3-17 | 4/13 |
| 35 | 36 | TRDX3-18 | 1/8 |
| 39 | 40 | TRDX3-20 | 3/13 |
| 45 | 46 | TRDX3-23 | 2/6 |
| 49 | 50 | TRDX3-25 | 1/5 |

Table 16 provides a list of miRNA decoy elements provided as recombinant DNA for production of transgenic corn plants with increased water use efficiency. The elements of Table 16 are described by reference to:

"Decoy Element (NUC) SEQ ID NO:" which identifies a decoy element nucleotide sequence.

"Decoy Element ID:" which is an arbitrary identifier.

"Target miRNA Name" which identities a target miRNA for binding by the decoy.

"Protein name" which identities amino acid sequences of proteins which bind the target miRNA.

"Gene (PEP) SEQ ID NO" which identities an amino acid sequence.

TABLE 16

Recombinant DNA miRNA Decoys for Increased Water Use Efficiency in Corn

| Decoy Element (NUC) SEQ ID NO: | Decoy Element ID | Target miRNA Name | Protein Name | Protein (PEP) SEQ ID NO | Broad Acre Yield Results |
|---|---|---|---|---|---|
| 95 | TRDX3-32 | miR166 | Revoluta | 110 | 1/8 |
| 96 | TRDX3-33 | miR444 | ANR1 MADS-box protein | 112 | 1/8 |
| 97 | TRDX3-34 | miR172e | APETALA2-like transcription factor | | 4/8 |

Example 7. Homolog Identification

This example illustrates the identification of homologs of proteins encoded by the DNA identified in Table 1 which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The AH Protein Database was queried using amino acid sequences provided in Table 1 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over 95% of the length of the polypeptide sequences provided in Table 1 are reported below in Table 17 with the SEQ ID NO of the original query sequence and the identified homologs.

TABLE 17

Protein sequences and their homologs

| Polypeptide SEQ ID NO (PEP) | Homolog SEQ ID NOs (PEP) |
|---|---|
| 2 | 59 |
| 4 | 61 |
| 8 | 62 |
| 10 | 63, 64 |
| 12 | 65, 66 |
| 14 | 67 |
| 16 | 68, 69 |
| 18 | 70, 71 |
| 20 | 72, 73 |
| 24 | 74 |
| 26 | 75, 76 |
| 28 | 77 |

TABLE 17-continued

| Protein sequences and their homologs | |
|---|---|
| Polypeptide SEQ ID NO (PEP) | Homolog SEQ ID NOs (PEP) |
| 34 | 78, 79, 80 |
| 36 | 81 |
| 38 | 82, 83 |
| 42 | 84 |
| 44 | 85 |
| 48 | 86, 87 |
| 50 | 88 |
| 52 | 89, 90 |
| 58 | 91, 92 |
| 116 | 60 |

Example 8. Identification of Protein Domains and Domain Modules by Pfam Analysis This example illustrates the identification of domain and domain module by Pfam analysis.

The amino acid sequences of the expressed proteins that are shown to be associated with an enhanced trait were analyzed for Pfam protein family against the current Pfam collection of multiple sequence alignments and hidden Markov models using the HMMER software and Pfam databases (version 27.0). The Pfam protein domains and modules for the proteins of SEQ ID NOs: 2, 4, 6, 8, 10, 12, 14, 16, 18, 20, 22, 24, 26, 28, 30, 32, 34, 36, 38, 40, 42, 44, 48, 50, 52, 54, 56 and 58 are shown in Tables 18, 19 and 20. The Hidden Markov model databases for the identified patent families are also available from the Pfam consortium allowing identification of other homologous proteins and their cognate encoding DNA to enable the full breadth of the invention for a person of ordinary skill in the art. Certain proteins are identified by a single Pfam domain and others by multiple Pfam domains. The function of the identified Pfam domains in proteins providing an enhanced trait in plants was verified by searching identified homologs for the conservation of the identified Pfam domains. The HMM score values for the identified Pfam domains in sequences from Table 1 are reported below in Table 18.

TABLE 18

| Pfam Domains and Their Locations on Proteins Associated with Enhanced Traits | | | | | |
|---|---|---|---|---|---|
| PEP SEQ ID NO | Pfam domain name | Begin | Stop | HMM Score | E-value |
| 2 | TCTP | 1 | 165 | 208.1 | 5.30E−66 |
| 4 | PAS_2 | 97 | 217 | 135.0 | 8.90E−43 |
| 4 | GAF | 253 | 432 | 135.0 | 1.00E−42 |
| 4 | PHY | 443 | 620 | 232.0 | 1.70E−72 |
| 4 | PAS | 654 | 769 | 93.2 | 5.30E−30 |
| 4 | PAS | 785 | 904 | 68.4 | 2.80E−22 |
| 4 | HisKA | 930 | 989 | 38.1 | 7.10E−13 |
| 4 | HATPase_c | 1039 | 1139 | 36.3 | 2.40E−12 |
| 6 | FmdA_AmdA | 9 | 295 | 363 | 8.40E−113 |
| 8 | MGDG_synth | 86 | 254 | 205.2 | 2.10E−64 |

TABLE 18-continued

| Pfam Domains and Their Locations on Proteins Associated with Enhanced Traits | | | | | |
|---|---|---|---|---|---|
| PEP SEQ ID NO | Pfam domain name | Begin | Stop | HMM Score | E-value |
| 8 | Glyco_tran_28_C | 312 | 404 | 35.1 | 3.30E−12 |
| 10 | GST_C_3 | 75 | 156 | 38.5 | 4.70E−13 |
| 10 | tRNA-synt_1c | 213 | 516 | 324.4 | 1.90E−100 |
| 10 | tRNA-synt_1c_C | 520 | 697 | 128.7 | 6.90E−41 |
| 12 | TPR_11 | 104 | 160 | 18.1 | 1.40E−06 |
| 12 | TPR_11 | 167 | 228 | 24.1 | 1.90E−08 |
| 14 | Pkinase | 33 | 293 | 215.9 | 1.40E−67 |
| 16 | EF-hand_like | 25 | 101 | 59.3 | 7.50E−20 |
| 16 | PI-PLC-X | 107 | 249 | 148.5 | 2.20E−47 |
| 16 | PI-PLC-Y | 322 | 409 | 95.1 | 7.00E−31 |
| 16 | C2 | 432 | 524 | 51.6 | 1.60E−17 |
| 18 | LTP_2 | 28 | 121 | 54.4 | 2.10E−18 |
| 20 | Fip1 | 336 | 379 | 74.4 | 1.90E−25 |
| 22 | Cystatin | 83 | 136 | 12.0 | 1.20E−05 |
| 24 | CENP-O | 123 | 200 | 59.7 | 1.60E−20 |
| 26 | TOM20_plant | 8 | 201 | 328.4 | 6.70E−102 |
| 28 | DHquinase_I | 97 | 315 | 260.5 | 1.60E−80 |
| 28 | Shikimate_dh_N | 328 | 408 | 95.2 | 2.40E−30 |
| 28 | Shikimate_DH | 449 | 548 | 61.1 | 1.50E−19 |
| 30 | Methyltransf_11 | 39 | 134 | 36.2 | 4.60E−12 |
| 32 | SOUL | 10 | 215 | 196.1 | 2.20E−62 |
| 34 | KH_1 | 128 | 173 | 28.9 | 8.40E−11 |
| 36 | Pterin_4a | 80 | 174 | 103.2 | 3.00E−34 |
| 38 | Alliinase_C | 25 | 383 | 565.1 | 1.20E−173 |
| 40 | CBM_2 | 68 | 97 | 9.2 | 0.00016 |
| 40 | COBRA | 164 | 191 | 1.6 | 0.027 |
| 40 | COBRA | 241 | 422 | 217.4 | 1.30E−68 |
| 40 | CBM_2 | 512 | 547 | 2.7 | 0.017 |
| 42 | Sugar_tr | 103 | 559 | 427.0 | 9.50E−132 |
| 44 | zf-met | 85 | 109 | 27.3 | 5.60E−10 |
| 48 | Radical_SAM | 175 | 338 | 50.3 | 5.90E−17 |
| 50 | Senescence | 177 | 356 | 168.2 | 9.00E−54 |
| 52 | zf-PARP | 11 | 88 | 83.3 | 4.80E−27 |
| 52 | zf-PARP | 117 | 186 | 68.0 | 3.00E−22 |
| 52 | PADR1 | 290 | 343 | 72.8 | 4.90E−24 |
| 52 | BRCT | 399 | 471 | 21.9 | 6.60E−08 |
| 52 | WGR | 519 | 600 | 58.9 | 1.60E−19 |
| 52 | PARP_reg | 634 | 765 | 115.3 | 6.90E−37 |
| 52 | PARP | 767 | 979 | 262.0 | 1.40E−81 |
| 54 | Metallothio | 5 | 19 | 7.6 | 0.00044 |
| 54 | Metallothio | 43 | 62 | 16.1 | 9.60E−07 |
| 56 | FAD_binding_6 | 62 | 164 | 79.2 | 3.9E−26 |
| 56 | NAD_binding_1 | 174 | 279 | 97.0 | 1.80E−31 |
| 58 | Cullin | 29 | 631 | 640.5 | 5.00E−196 |
| 58 | Cullin_Nedd8 | 659 | 725 | 92.4 | 2.20E−30 |

TABLE 19

Pfam Domain Modules and Their Positions

| PEP SEQ ID NO | Pfam Domain Module | Position |
|---|---|---|
| 4 | PAS_2::GAF::PHY::PAS::HisKA::HATPase_c | 97-217::253-432::443-620::654-769, 785-904::930-989::1039-1139 |
| 8 | MGDG_synth::Glyco_tran_28_C | 86-254::312-404 |
| 10 | GST_C_3::tRNA-synt_1c::tRNA-synt_1c_C | 75-156::215-516::520-697 |
| 12 | TPR_11::TPR_11 | 104-160, 167-228 |
| 16 | EF-hand_like::PI-PLC-X::PI-PLC-Y::C2 | 25-101::107-249::322-409:: 432-524 |
| | HMGL-like::LeuA_dimer | 84-366::459-604 |
| 28 | DHquinase_I::Shikimate_dh_N::Shikimate_DH | 97-315::328-408::449-548 |
| 40 | CBM_2::COBRA::CBM_2 | 68-97::164-191, 241-422::512-547 |
| 46 | Lung_7-TM_R::zf-RING_2 | 24-64::110-153 |
| 52 | zf-PARP::PADR1::BRCT::WGR::PARP_reg::PARP | 11-88, 117, 186::290-343::399-471::519-600::634-765::767-979 |
| 54 | Metallothio:: Metallothio | 5-19, 43-62 |
| 56 | FAD_binding_6[1]::NAD_binding_1 | 62-164::174-279 |
| 58 | Cullin[1]::Cullin_Nedd8 | 29-631::659-725 |

TABLE 20

Pfam Domain Properties

| PEP SEQ ID NO | Pfam domain name | Accession number | Gathering cutoff | Domain description |
|---|---|---|---|---|
| 2 | TCTP | PF00838 | 20.8 | Translationally controlled tumour protein |
| 4 | GAF | PF01590 | 20.9 | GAF domain |
| 4 | HATPase_c | PF02518 | 21.3 | Histidine kinase-, DNA gyrase B-, and HSP90-like ATPase |
| 4 | HisKA | PF00512 | 22.4 | His Kinase A (phospho-acceptor) domain |
| 4 | PAS | PF00989 | 22.6 | PAS fold |
| 4 | PAS_2 | PF08446 | 14.0 | PAS fold |
| 4 | PHY | PF00360 | 18.0 | Phytochrome region |
| 6 | FmdA_AmdA | PF03069 | 19.5 | Acetamidase/Formamidase family |
| 8 | Glyco_tran_28_C | PF04101 | 21.0 | Glycosyltransferase family 28 C-terminal domain |
| 8 | MGDG_synth | PF06925 | 20.9 | Monogalactosyldiacylglycerol (MGDG) synthase |
| 10 | GST_C_3 | PF14497 | 27.0 | Glutathione S-transferase, C-terminal domain |
| 10 | tRNA-synt_1c | PF00749 | 19.8 | tRNA synthetases class I (E and Q), catalytic domain |
| 10 | tRNA-synt_1c_C | PF03950 | 21.0 | tRNA synthetases class I (E and Q), anti-codon binding domain |
| 12 | TPR_11 | PF13414 | 26.8 | TPR repeat |
| 14 | Pkinase | PF00069 | 20.4 | Protein kinase domain |
| 16 | C2 | PF00168 | 4.5 | C2 domain |
| 16 | EF-hand_like | PF09279 | 20.9 | Phosphoinositide-specific phospholipase C, efhand-like |
| 16 | PI-PLC-X | PF00388 | 22.1 | Phosphatidylinositol-specific phospholipase C, X domain |
| 16 | PI-PLC-Y | PF00387 | 20.2 | Phosphatidylinositol-specific phospholipase C, Y domain |
| 18 | LTP_2 | PF14368 | 22.0 | Probable lipid transfer |
| 20 | Fip1 | PF05182 | 22.7 | Fip1 motif |
| 22 | Cystatin | PF00031 | 20.9 | Cystatin domain |
| 24 | CENP-O | PF09496 | 19.6 | Cenp-O kinetochore centromere component |
| 26 | TOM20_plant | PF06552 | 20.6 | Plant specific mitochondrial import receptor subunit TOM20 |
| 28 | DHquinase_I | PF01487 | 20.7 | Type I 3-dehydroquinase |
| 28 | Shikimate_DH | PF01488 | 24.3 | Shikimate/quinate 5-dehydrogenase |
| 28 | Shikimate_dh_N | PF08501 | 21.3 | Shikimate dehydrogenase substrate binding domain |
| 30 | Methyltransf_11 | PF08241 | 21.2 | Methyltransferase domain |
| 32 | SOUL | PF04832 | 21.2 | SOUL heme-binding protein |
| 34 | KH_1 | PF00013 | 20.2 | KH domain |
| 36 | Pterin_4a | PF01329 | 20.8 | Pterin_4a |

TABLE 20-continued

| Pfam Domain Properties | | | | |
|---|---|---|---|---|
| PEP SEQ ID NO | Pfam domain name | Accession number | Gathering cutoff | Domain description |
| 38 | Allinase_C | | | Allinase |
| 40 | CBM_2 | PF00553 | 21.1 | Cellulose binding domain |
| 40 | COBRA | PF04833 | 19.0 | COBRA-like protein |
| 42 | Sugar_tr | PF00083 | 20.7 | Sugar (and other) transporter |
| 44 | zf-met | PF12874 | 13.3 | Zinc-finger of C2H2 type |
| 46 | Lung_7-TM_R | PF06814 | 25.2 | Lung seven transmembrane receptor |
| 46 | zf-RING_2 | PF13639 | 27.0 | Ring finger domain |
| 48 | Radical_SAM | PF04055 | 29.4 | Radical SAM superfamily |
| 50 | Senescence | PF06911 | 21.6 | Senescence-associated protein |
| 54 | Metallothio | PF00131 | 20.6 | Metallothionein |

Example 9. Construction of miRNA Decoys

This example illustrates monocot and dicot plant transformation to produce recombinant DNA molecules useful for stable integration into plant chromosomes in the nuclei of plant cells to provide transgenic plants having enhanced traits by suppressing the activity of miRNAs.

The recombinant DNA molecules of SEQ ID NOs: 94, 95, 96, 97, 98 and 99 were constructed as follows.

Synthetic miRNA binding site sequences capable of hybridizing, respectively, miR172, miR166, miR444, miR172e, miR393 and miR397 species under physiological conditions were constructed by modifying naturally occurring miRNA binding sites. Specifically, the binding site sequences were constructed by inserting three nucleotides between nucleotides 10 and 11 of the polynucleotide sequences encoding naturally occurring binding sites specific For miR172, miR166, miR444, miR172e, miR393 and miR397, and in some cases by adding additional nucleotides at either the 5' or the 3' end of the naturally occurring biding site sequences. These modifications gave synthetic binding sites having polynucleotide sequences as set forth in SEQ ID NOs: 101-106.

The synthetic decoys were then constructed using the naturally occurring *Zea mays* miR399_47862C decoy of SEQ ID NO: 93 as a scaffolding. The native miR399 binding site of SEQ ID NO: 100 was removed and substituted with one of the synthetic miRNA binding sites set forth in SEQ ID NOs 101-106, to give a recombinant DNA of, respectively, SEQ ID NO: 94-99.

Transformation vectors, each comprising a heterologous promoter operably linked to a polynucleotide encoding either the decoy of naturally occurring miR399 from *Zea mays* as set forth in SEQ ID NO: 93 or a synthetic decoy as set forth in SEQ ID NOs: 94-99 were then constructed by methods known in the art and used to transform plant cells, from which transgenic plants were produced as described above. The transgenic plants were then tested for altered phenotypes and enhanced traits, again as described above.

Similarly, recombinant DNA molecules comprising polynucleotide sequences transcribed into non-coding miRNA decoys are constructed as above, by using other native decoy sequences as a scaffolding, and using binding site sequences which bind some or all of other miRNA families that are naturally occurring or are derived from naturally occurring sites.

We claim:

1. A transgenic corn plant comprising a recombinant DNA molecule comprising a heterologous promoter operably linked to a polynucleotide having a nucleotide sequence encoding a polypeptide, wherein the nucleotide sequence of the polynucleotide is selected from the group consisting of:

(a) a nucleotide sequence having at least 95% nucleotide sequence identity to the nucleotide sequence as set forth in SEQ ID NO: 29 and encoding a polypeptide comprising an amino acid sequence having at least 95% amino acid sequence identity to the amino acid sequence as set forth in SEQ ID NO: 30; and (b) a nucleotide sequence encoding a polypeptide comprising an amino acid sequence having at least 95% amino acid sequence identity to the amino acid sequence as set forth in SEQ ID NO: 30;

wherein expression of said polypeptide in said transgenic corn plant imparts increased broad acre yield as compared to a control corn plant lacking said recombinant DNA molecule and grown under identical growth conditions.

2. The transgenic corn plant of claim 1, wherein said transgenic corn plant has at least one phenotype selected from the group consisting of increased biomass, increased canopy area, increased plant height, decreased amount of water applied, increased plant water content and increased water use efficiency as compared to said control corn plant.

3. The transgenic corn plant of claim 1, wherein the heterologous promoter is selected from the group consisting of a constitutive promoter, an inducible promoter, a tissue specific promoter, a diurnally regulated promoter, a tissue enhanced promoter, and a plant cell specific promoter.

4. The transgenic corn plant of claim 1, wherein said transgenic corn plant is a progeny, a propagule, or a field crop plant, and wherein said progeny, said propagule, or said field crop plant comprises said recombinant DNA molecule.

5. The transgenic corn plant of claim 4, wherein said propagule is selected from the group consisting of a cell, pollen, ovule, flower, embryo, leaf, root, stem, shoot, meristem and grain.

6. A method for producing a corn plant comprising: transforming a corn plant cell with a recombinant DNA molecule comprising a polynucleotide having a nucleotide sequence encoding a polypeptide, wherein the polynucleotide comprises a nucleotide sequence selected from the group consisting of:

(a) a nucleotide sequence having at least 90% nucleotide sequence identity to the nucleotide sequence as set forth in SEQ ID NO: 29 and encoding a polypeptide comprising an amino acid sequence having at least 95% amino acid sequence identity to the amino acid sequence as set forth in SEQ ID NO: 30; and (b) a nucleotide sequence encoding a protein polypeptide comprising an amino acid sequence having at least 95% amino acid sequence identity to the amino acid sequence as set forth in SEQ ID NO: 30;

and growing a transformed corn plant expressing said polypeptide from said transformed corn plant cell.

7. The method of claim 6, further comprising selecting a transformed corn plant with an enhanced trait as compared to a control corn plant lacking said recombinant DNA and grown under identical growth conditions, and wherein said enhanced trait is selected from increased yield, increased nitrogen use efficiency, and increased water use efficiency as compared to a said corn control plant.

8. The method of claim 6, further comprising selecting a transformed corn plant with a phenotype selected from the group consisting of increased biomass, increased canopy area, increased plant height, decreased amount of water applied, and increased water content as compared to a corn control plant lacking said recombinant DNA and grown under identical growth conditions.

9. A method for increasing yield, increasing nitrogen use efficiency, or increasing water use efficiency in a corn plant comprising:

crossing the transgenic corn plant of claim 1 with itself, a second transgenic corn plant from the same transgenic corn plant line, a wild type corn plant, or a second corn plant from a different line of corn plants to produce a transgenic corn seed;

growing said transgenic corn seed to produce a plurality of progeny transgenic corn plants; and selecting a progeny transgenic corn plant with increased yield, increased nitrogen use efficiency, or increased water use efficiency, wherein said progeny transgenic corn plant comprises said recombinant DNA molecule and expresses said polypeptide.

10. The transgenic corn plant of claim 1, wherein the nucleotide sequence of the polynucleotide has at least 99% nucleotide sequence identity to the nucleotide sequence as set forth in SEQ ID NO: 29.

11. The transgenic corn plant of claim 1, wherein the nucleotide sequence of the polynucleotide encodes a polypeptide comprising an amino acid sequence haying at least 99% amino acid sequence identity to the amino acid sequence as set forth in SEQ ID NO: 30.

12. The transgenic corn plant of claim 1, wherein the nucleotide sequence of the polynucleotide has 100% nucleotide sequence identity to the nucleotide sequence as set forth in SEQ ID NO: 29.

13. The transgenic corn plant of claim 1, wherein the nucleotide sequence of the polynucleotide encodes a polypeptide comprising an amino acid sequence having 100% amino acid sequence identity to the amino acid sequence as set forth in SEQ ID NO: 30.

* * * * *